US011224649B2

(12) United States Patent
Kraemer-Kuehl et al.

(10) Patent No.: US 11,224,649 B2
(45) Date of Patent: Jan. 18, 2022

(54) 4/91 IBV VACCINE WITH HETEROLOGOUS SPIKE PROTEIN

(71) Applicant: Boehringer Ingelheim Vetmedica GmbH, Ingelheim am Rhein (DE)

(72) Inventors: Annika Kraemer-Kuehl, Seesen (DE); Hans-Christian Philipp, Hemmingen (DE)

(73) Assignee: Boehringer Ingelheim Vetmedica GmbH, Ingelheim Am Rhein (DE)

( * ) Notice: Subject to any disclaimer, the term of this patent is extended or adjusted under 35 U.S.C. 154(b) by 13 days.

(21) Appl. No.: 16/665,434

(22) Filed: Oct. 28, 2019

(65) Prior Publication Data

US 2020/0129613 A1 Apr. 30, 2020

(30) Foreign Application Priority Data

Oct. 31, 2018 (EP) .................................... 18203626

(51) Int. Cl.

*A61K 39/215* (2006.01)
*A61P 31/14* (2006.01)
*C12N 7/00* (2006.01)
*A61K 39/00* (2006.01)

(52) U.S. Cl.

CPC ............ *A61K 39/215* (2013.01); *A61P 31/14* (2018.01); *C12N 7/00* (2013.01); *A61K 2039/5256* (2013.01); *A61K 2039/552* (2013.01); *C12N 2770/20021* (2013.01); *C12N 2770/20022* (2013.01); *C12N 2770/20034* (2013.01); *C12N 2770/20071* (2013.01)

(58) Field of Classification Search

CPC .......... A61K 39/215; A61K 2039/5256; A61K 2039/552; A61K 2039/5254; A61K 2039/54; A61K 39/12; A61P 31/14; A61P 31/12; C12N 7/00; C12N 2770/20021; C12N 2770/20022; C12N 2770/20034; C12N 2770/20071; C07K 14/005

See application file for complete search history.

(56) References Cited

U.S. PATENT DOCUMENTS 5,750,113 A * 5/1998 Cook .................... A61K 39/12 424/222.1
2007/0154489 A1* 7/2007 Cavanagh ............ A61K 39/215 424/199.1
2011/0097353 A1* 4/2011 Sellers ..................... C12N 7/00 424/186.1
2012/0177675 A1* 7/2012 Britton .................... A61P 31/16 424/186.1
2016/0030550 A1* 2/2016 Toro Guzman ......... A61P 31/14 424/214.1
2019/0046634 A1* 2/2019 van Santen ............ A61K 39/12

FOREIGN PATENT DOCUMENTS

WO WO-0100234 A2 * 1/2001 .......... A61K 39/265
WO 2004078203 A2 9/2004

OTHER PUBLICATIONS

Cavanagh D, Picault JP, Gough R, Hess M, Mawditt K, Britton P. Variation in the spike protein of the 793/B type of infectious bronchitis virus, in the field and during alternate passage in chickens and embryonated eggs. Avian Pathol. Feb. 2005;34(1):20-5. (Year: 2005).*
Britton P, Evans S, Dove B, Davies M, Casais R, Cavanagh D. Generation of a recombinant avian coronavirus infectious bronchitis virus using transient dominant selection. J Virol Methods. Feb. 2005;123(2):203-11. (Year: 2005).*
Kalokhoran AY, Ghalyanchilangeroudi A, Hosseini H, Madadgar O, Karimi V, Hashemzadeh M, Hesari P, Zabihi Petroudi MT, Najafi H. Co-circulation of three clusters of 793/B-like avian infectious bronchitis virus genotypes in Iranian chicken flocks. Arch Virol. Oct. 2017;162(10):3183-3189. Epub Jul. 8, 2017.*
Rohaim MA, El Naggar RF, Abdelsabour MA, Mohamed MHA, El-Sabagh IM, Munir M. Evolutionary Analysis of Infectious Bronchitis Virus Reveals Marked Genetic Diversity and Recombination Events. Genes (Basel). May 29, 2020;11(6):605.*
Zhang T, Han Z, Xu Q, Wang Q, Gao M, Wu W, Shao Y, Li H, Kong X, Liu S. Serotype shift of a 793/B genotype infectious bronchitis coronavirus by natural recombination. Infect Genet Evol. Jun. 2015;32:377-87. Epub Apr. 3, 2015.*
Casais R, Thiel V, Siddell SG, Cavanagh D, Britton P. Reverse genetics system for the avian coronavirus infectious bronchitis virus. J Virol. Dec. 2001;75(24):12359-69. (Year: 2001).*
Shimazaki Y, Horiuchi T, Harada M, Tanimura C, Seki Y, Kuroda Y, Yagyu K, Nakamura S, Suzuki S. Isolation of 4/91 type of infectious bronchitis virus as a new variant in Japan and efficacy of vaccination against 4/91 type field isolate. Avian Dis. Dec. 2008;52(4):618-22. (Year: 2008).*
Ellis, Samantha, et al. "Recombinant infectious bronchitis viruses expressing chimeric spike glycoproteins induce partial protective immunity against homologous challenge despite limited replication in vivo." Journal of virology 92.23 (2018): e01473-18.

(Continued)

*Primary Examiner* — Rachel B Gill
(74) *Attorney, Agent, or Firm* — Jamie L. Graham

(57) ABSTRACT

The present invention relates i.a. to a 4/91 IBV (infectious bronchitis virus) encoding for a heterologous S (spike) protein or fragment thereof. Further, the present invention relates to an immunogenic composition comprising said 4/91 IBV encoding for a heterologous S (spike) protein or fragment thereof. Furthermore, the present invention relates to methods for immunizing a subject comprising administering to such subject the immunogenic composition of the present invention. Moreover, the present invention relates to methods of treating or preventing clinical signs caused by IBV in a subject of need, the method comprising administering to the subject a therapeutically effective amount of an immunogenic composition according to the present invention.

17 Claims, 2 Drawing Sheets

Specification includes a Sequence Listing.

(56) References Cited

OTHER PUBLICATIONS

Zhou, Yingshun, et al. "The establishment and characteristics of cell-adapted IBV strain H120." Archives of virology 161.11 (2016): 3179-3187.

Wei, Yan-Quan, et al. "Development and characterization of a recombinant infectious bronchitis virus expressing the actodomain region of S1 gene of H120 strain." Applied microbiology and biotechnology 98.4 (2014): 1727-1735.

Armesto, Maria, et al. "A recombinant avian infectious bronchitis virus expressing a heterologous spike gene belonging to the 4/91 serotype." PLoS One 6.8 (2011): e24352.

Hodgson, Teri, et al. "Recombinant infectious bronchitis coronavirus Beaudette with the spike protein gene of the pathogenic M41 strain remains attenuated but induces protective immunity." Journal of virology 78.24 (2004): 13804-13811.

Casais, Rosa, et al. "Recombinant avian infectious bronchitis virus expressing a heterologous spike gene demonstrates that the spike protein is a determinant of cell tropism." Journal of virology 77.16 (2003): 9084-9089.

Bickerton, Erica, Giulia Dowgier, and Paul Britton. "Recombinant infectious bronchitis viruses expressing heterologous S1 subunits: potential for a new generation of vaccines that replicate in Vero cells." Journal of General Virology 99.12 (2018): 1681-1685.

Valastro, Viviana, et al. "S1 gene-based phylogeny of infectious bronchitis virus: an attempt to harmonize virus classification." Infection, Genetics and Evolution 39 (2016): 349-364.

Shan, Dan, et al. "Effects of hypervariable regions in spike protein on pathogenicity, tropism, and serotypes of infectious bronchitis virus." Virus research 250 (2018): 104-113.

Zhou, Ying Shun, et al. "Establishment of reverse genetics system for infectious bronchitis virus attenuated vaccine strain H120" Veterinary microbiology 162.1 (2013): 53-61.

* cited by examiner

SEQUENCE LISTING

```
<160> NUMBER OF SEQ ID NOS: 61

<210> SEQ ID NO 1
<211> LENGTH: 27659
<212> TYPE: DNA
<213> ORGANISM: Avian infectious bronchitis virus

<400> SEQUENCE: 1

acttaagtgt gatataaata tatatcatac atactagcct tgtgctagat ttccaactta     60
```

```
acaaaacgga cttaaatacc tacagttggt ccctataggt gttccattgc agtgcacttt    120
agtgccctgg atggcacctg gccacctgtc aggtttttgt tattaaaata atattgttgc    180
tggtatcact gcttgttttg ccgtgtctca ctttatacat ccgttgcttg ggctacctag    240
tatccagcgt cctactggcg ttgtggtcgg ttcgagtgcg aagaacctct ggttcatcta    300
gcggtacgcg ggtgtgtgga agtagcgctt cagacgtacc ggttctgttg cgtgaaatac    360
ggggtcacct ccccccacat acctctaagg gcttttgagc ctagcgttgg gctacgttct    420
cgcacaaggt cggctatacg gcgtttgtag ggggtagtgc caaacaaccc ctgaggtgac    480
aggttctggt ggtgtttagt gagcagacat acaatagaca gtgacaacat ggcttcaagc    540
ctaaaacagg gagtatctcc caaaccaagg gatgtcattc ttgttgccaa agacattccc    600
gaacaactcc gtgacgcttt gtttttctat acgtcacata aacccaagga ttacgctgaa    660
gcctttgccc ttaggcagaa gtttgaccgt aatctgcaga ctgggaagca gtttaaattt    720
gaaactgtgt gtggtctctt cctcttgaag ggagttgaca aaataacacc tggtgtccca    780
gcaaaagttt taaaagccag ttctaagttg gcagatttag aaggcatttt tggtgtctct    840
ccttttgcac ggaagtaccg tgatctgttg aaaacagcat gccagtggtc tcttacagta    900
gatacactgg atgctcgtgc acaaactctt gatgaaattt ttaaccccac tgaaatactt    960
tggcttcagg tggctgcaaa aattcaagtt tcagctatgg caatgcgcag gcttgttgga   1020
gaagtaactg caaaagtcat ggatgctctt ggctctaatt tgagtgctct tttcaaattt   1080
gttagagaac aaatagtcag aatctttcaa aaggcactgg ctatttttga agatgtgagt   1140
gaattaccac agcgtattgc agcacttaag atggcctttg ccaagattgc taagtcaatt   1200
actgttgtgg ttgtggaaag aactctagtt gttagagagt tcgcaggaac ttgtcttgca   1260
agcatcaatg gtgctgttgc aaaattcttc gaagaacttc caaatggctt tatgggttct   1320
aaaatttca caacattggc cttctttaaa gaagcagctg tgaaaattgt ggaaaatata   1380
ccaaatgcac caagaggtac tagaggtttt gaggtcgttg gcaatgccaa aggtacacaa   1440
gttattgtgc gtggcatgcg aaatgactta acgctgcttg accaaaaagc tgacattcct   1500
gttgagaaag aaggttggtc tgcaattttt gaaggacatc tttgctatgt ctttaagagc   1560
ggtgaccgtt tttatgcggc acctctttct ggaaattttg cattgcatga tgtacattgt   1620
tgtgagcgtg ttgtctgtct gtctgatggt gtaacaccgg agataaatga tggactcatt   1680
ctagcagcaa tttattcatc tgttagtgtt tcagaactcg tggcagcact taaaaagggc   1740
gaaccattta agttcttggg gcataaattt gtgtacgcga aggacgcagc agtgtcgttt   1800
actttagcga aggctgccac tattgcagat gtactgaagc tgtttcaatc agctcgtgtg   1860
caagcggaag atgtgtggtc tgcatttact gaaaagtctt ttaatttctg gaaactcgca   1920
tatggaaaag tgcgtaatct tgaagaagtt gtgaagactc atttttgtaa agctcaaatg   1980
tcacttatcg ttctagtagc agtgcttgga gaaggtgttt ggcatattgc ttctcaggtc   2040
atctacaaat taggtggtct ttttactaaa gttgttgact tttgtgaaaa acactggaaa   2100
ggtttttgtg tacagttgaa gaaggctaag ctcattgtga ctgaaaatct ttgtgttctt   2160
aagggagtgg cacagcattg ttttcaacta ttgctggatg caatacattc tttgtatatg   2220
agttttaaga agtgtgcact tggtagaatt catggagact tactcttctg gaaagggggt   2280
gtacacaaaa ttgttcaaga tggcgatgaa gtttggtttg acgccattga tagtattgat   2340
gttgaagatc tgggtgttgt caaagaaaaa cctatagatt ttgaggtttg tgatgacgta   2400
```

```
acacttccag aaaatcaacc cggtcatatg gttcaaatcg aggatgacgg aaagaactat   2460
atgttcttcc gcttcaaaaa ggatgagaat atttattata caccaatgtc tcaacttggt   2520
gcaattaatg tagtttgcaa agcaggcggc aaaaccgtta cctttggaga cattacagtg   2580
aaagaaatac cgccacctga tgtcgtgcct attaaggtta gcatagagtg ttgtggtgag   2640
ccatggaata caatcttcaa gaaagcttat aaagagccca ttgaagttga gacagacctc   2700
acagttgaac aattgctctc tgtgatttat gagaaaatgt gtgacgacct caaactgttt   2760
ccagaggcac ctgagcctcc accatttgag aatgttgccc ttgttgataa gaacggtaaa   2820
gatttggatt gcataaaatc atgccacctt atctaccgtg attgtgagag cgatgatgac   2880
atcgaggaag aagatgctga agagtgtgac accgattcag ctgatgctga agcatgtgac   2940
acagcctcag agtgtgaaga agaggacgag gatactaaag tgttggctct tatacaagac   3000
ccagcaagta ataaataccc tcttccactt gatgatgatt atagcgtcta taatggatgt   3060
attgttcata gagacgctct tgatgtagtg aatctaccat ctggcgaaga aacttttgtt   3120
gttaataact gttttgaggg agctattaaa ccactcccac agaaagttat tgatgttcta   3180
ggtgactggg gcgaggctgt tgatgcacaa gaacaattgt gtcaacagga atctacccaa   3240
gtcacacttg agaaaccagt tgagggtcct actggtattt gtcacgtaat ggctgaacaa   3300
gctgttgttg atgaacagga ggtagtttct gtatttgaag aaaagtctga ggttattgtt   3360
tacacacctg cagatctgga agttgttaaa gaaacagcag gagaacttga tgagttcatt   3420
ctcatctttg atgtccctaa agaagaagtt gtgtctcaag agaaagataa gccacaggtt   3480
gagcaagagc ctactcaagt tgttaaacca caacgtgaga agaaggctaa aaagttcaga   3540
gttaaaccat ctacatgtga aaagcccaaa tttttggagt acaaaacatg tgtgggtgat   3600
ctgactgttg taattgctaa ggcattggat gagtttaaag agttctgcat tgtaaacgct   3660
gcaaatgaac atatgtctca tggtggtggc gttgcgaaag caattgcaga cttctgtgga   3720
cctgattttg tggaatattg tgaggcctat gttaagaaac atgggccaca acagagactt   3780
gttacacctt cgtttgtcaa gggcattcaa tgtgtgaaca atgttgtggg acctcgtcat   3840
ggagacagca acttgcgtga gaaactcgtt gttgcttaca agaatgttct tgtggatggc   3900
gtcttcaact atgtagtgcc agttctctct tcagggattt ttggtgtgga ttttaaaatg   3960
tcaatagacg caatgcgtga agcctttgat ggttgcgaca tacgcatcct tttgttttct   4020
ctgagtcaag aacacatcga ctattttgat gtaacttgca agcagaagac aatttatctt   4080
acggaggatg gtgttaaata ccgctccgtt gttgtaaaac ctggcgactc attgagtcaa   4140
tttggacagg tttttgctaa aaataaggca gtctttacag ctgatgatgt tgaggataaa   4200
gaaatcctct tcgttcctac tactgacaag actgttcttg attattatca tttagatgcg   4260
caaaagtatg tgatatattt acaagctctt gcgcagaaat gggatgttca atatagggac   4320
aattttattg cattagagtg gcgtgatgga aattgctggg ttagttcagc aatagtgctc   4380
cttcaggctg ctaaggtaaa gtttagaggt tttcttgcag aagcatgggc taagtttttg   4440
ggtggtgatc ccactgattt tgtggcctgg tgttatgcaa gttgcaatgc taaagttggt   4500
gagttttcag atgctaattg gctcttggct aatctggcag aacattttga tgcagattac   4560
acgaatgcac ttcttaagaa gcgcgtatca tgtaactgcg gtgttaagag ttatgagctt   4620
aggggtcttg aagcttgcat tcaaccagta agggcaccta accttctaca ttttaagaca   4680
caatattcaa attgcccaac ctgtggcgca aatagtacgg atgaagtaat agaagcttca   4740
ttaccttact tattgctctt tgctaccgat ggtcctgcta cagttgattg tgatgaaaat   4800
```

```
gctgtaggga ctgttgtttt cattgggtct actaatagtg gacactgtta tacacaagcc   4860
atgggtaagg cttttgataa tcttgctaaa gatagaaaat ttggaaagaa gtcgccttac   4920
attacagcaa tgtacacacg cttctccctt aagagtgaaa accctttgcc tgtcaagcag   4980
agccagggta aaactaaagt agtaaaagaa gatgtttcta atctagcaac aagttcaaaa   5040
gtcagttttg atgatcttac tgactttgag cagtggtatg atagcaacat ctatgaaagt   5100
cttaaagtgc aggaaacgcc tgataattct gatgggtatg tgtcatttac aacaaaagaa   5160
gattctaagt tgccactgac acttaaagtt agaggtatta aatcagttgt tgattttagg   5220
tcgaaggatg gtttcactta caaattaata cctgatattg atgaaaattc aaaagcacca   5280
atttactatc cagtcttgga ctctattagt cttaaggcaa tatgggtgga aggtggtgct   5340
aattttgttg ttgggcatcc aaattattat agtaaatctc tccgcattcc tactttttgg   5400
gaaagtgcag agagttttgt taaaatgggt gataaagttg atggtgtaac tatgggcctt   5460
tggcgtgcag agcatcttaa caaacctaat cttgagaaaa ttttcaacat tgctaagaaa   5520
gctattgttg gatctagtgt tgttactacg caatgtggta aagtaattag taaggcggct   5580
acattcattg ctgataaaat aggtgggggt gtagttcgca acattataga tagaattaag   5640
ggtctttgtg ggtttacacg tggcattttt gaaagaaaat tgtctccaca attcataaaa   5700
acacttatat tcttcttctt ctactttata aaggctagtg ctaagggttt agttgctagc   5760
tataagaatg tgttatgtaa ggtggtattc gctactttat ttatagtgtg gtttatatat   5820
acaagtaatc cagtagtgtt tactggaaca cgtatgttag acttcctatt tgagggttct   5880
ttgtgtggtc cttataatga ctacggtaaa gattcttttg atgtgttacg ctattgtgga   5940
gatgatttta cttgtcgtgt gtgtttacat gacagagact ctctacattt gtataaacat   6000
gcttatagca tagaacagat ttataaagct gcaagttctg gcattgtttt taattggaat   6060
tggctttatt tggtctttct aattttattt gttaagccag tggcaggttt tgttattatt   6120
tgctattgtg ttaagttttt agtgttgagt tcaactgtgc tccaaactgg tgtaggtttt   6180
ctagactggt ttattcaaac agtttttact cactttaatt ttatgggtgc aggtttctat   6240
ttctggctct tttataaatt gtacatacag gttcatcata tactgtattg taaggatata   6300
acatgtgaag tgtgtaagag agttgcacgc agtaacaggc atggggttag tgttgttgtt   6360
ggtggacgca agcaaattgt gcatgtgtac actaactctg gttacaactt ttgtaagaga   6420
cataattggt attgtaggaa ttgtgatgta tatggtcacc aaaacacatt tatgtctcct   6480
gaagttgctg gtgagctgtc tgaaaagctt aaacgccatg ttaaacctac agcacatgct   6540
taccacgttg tggatgaggc ttgcgtagtt gatgattttg ttaacttaaa atacaaagct   6600
gcaactcctg gtaaggatgg tgcacctcct gcagttaaat gtttcagtgt tacagatttc   6660
ttgaagaaag ctgtttttct taaggatgcg ctgaaatgtg aacaaatatc taatgatggt   6720
tttatagtgt gtaatacgca gagtgcgcat gctttagagg aagcaaagaa tgcagccatc   6780
tattatgcgc aatacctgtg taaacctata cttatactcg accaggcact ctaccagaat   6840
ttaatagtgg aacctgtatc gaagagcgtt gtcaacaaag tgtgtgacat tttgtctagg   6900
ataatttctg tagatactgc atctttggat tataaagcag gtacagttcg tgatgccttg   6960
ctgtctgtta ctaaagatga agaagctgta gatatggcta tcttctgtca taatcatgaa   7020
gttgaatata caggtgatgg ttttactaat gttataccgt catatggtat agaccctgat   7080
aaattaacac ctcgtgatag agggtttttg ataaatgcag atgcttctgt tgctaactta   7140
```

-continued

```
agagttaaaa atgctccgcc ggtagtatgg aagttttctg atcttattaa gttgtctgac   7200

agttgtctta aatatttaat ctcagcaact gtcaagtcag ggtctcgttt ctttataaca   7260

agatctggtg ctaaacaaat tttttcctgt agtactcaga aattgttggt agagaaaaag   7320

gctggtggtg tcattagtgg tacctttaat tggtttaaga gttgttgtaa atggctcttg   7380

atcttctatg tgctttttac attgtgttgt ttgggttgtt atcatatgga gacgaataaa   7440

agttttgttc atcctatgta tgatgttaac tctacaatgc atgttgaagg ctttaaggtt   7500

atagataaag gtgttattag agacattgta ccagaggatg cttgtttctc taataagttt   7560

gctaactttg atgcattttg gggtaaacca tatgtgaata gtagagactg tccaattgtt   7620

acagcagtca tagatggcgc tggaacaata gcagctggtg ttcctggttt tgtagactgg   7680

gttcttgatg gtgttatgtt tgtacacatg acacaaacag aaagaaaacc ctggtacatt   7740

cccacgtggt ttaacagaga aattgttggt tacactcagg attcaattat tactgaaggt   7800

agtttttata catctatagc gttgttttct gctaggtgtt tatacttaac agccagtaat   7860

acaccgcaat tgtattgttt taatggtgat aatgatgctc ctggagcctt accatttggt   7920

agtattgttc ctcataaggt ctacttccaa ccaaatggtg ttaggcttgt agttccacaa   7980

caaatactac acacacccta catagtgaag tttgtttcag acagctattg tagaggtagt   8040

gtatgtgagt atactaaacc aggttactgt gtgtcattga actcacagtg ggttttgttt   8100

aatgatgaat acacaagcaa acctggcgtt ttctgtggtt ctactgttag agaacttatg   8160

tttaatatgg ttaatacatt ctttactggt gtcaatccta atatttatat gcaactagca   8220

actatgtttt tgatactagt tgttgttgtt ttaatttttg caatggttat aaagtttcaa   8280

ggtgttttta aagcttatgc gaccattgtt tttacaataa tgttagtttg ggttgttaat   8340

gcatttgttt tgtgtgtaca tagttataac agtgttttag ctgttatatt attggtaatc   8400

tattgttatg catcattggt tacaagtcgt aatactgcta taataatgca ttgttggctt   8460

gtgtttacct ttggtttaat tgtacccata tggttggcgt gttgctacct ggcatttgtt   8520

ttatatatgt acacaccatt gtttttctgg tgttacggta ctactaaaaa tactcgtaaa   8580

ttgtatgatg gcaacgagtt tgttggtagt tatgatcttg ctgcgaagag cacttttgtt   8640

attcgcggtc ctgaatttgt taagcttacg aacgagatag gtgataagtt tgaacactat   8700

ctctcagcgt atgctagact taaatactac tcaggcactg gcagtgaaca agattacttg   8760

caagcctgtc gtgcatggtt agcttatgct ttggaccagt atagaaatag tggtgtggaa   8820

attgtgtata ctccaccacg ttactctatt ggtgttagta gattacaggc tggttttaag   8880

aaactagttt ctcctagtag tgctgttgaa aggtgcattg ttagtgtctc ttatagaggt   8940

aataagctta atggactgtg gctaggtgat actatctact gtccgcgaca tgttctaggc   9000

aagttttcag gcgatcaatg gagtgatgta cttaatcttg ctaataatca tgagtttgag   9060

gttgtaactc aaaatggtgt tactttgaat gttgttagta gacggttgag aggcgcagtt   9120

ttaattttac aaactgctgt cgccaatgct gacactccta agtataagtt tgttaaagct   9180

aattgtggag atagtttcac aattgcttgt tcttatggtg gtacagttgt gggactctac   9240

cctgttacta tgcgttctaa tggtactatt agagcgtctt tccttgcagg agcttgtggc   9300

tcagttggtt ttaatataga aaagggtgta gttaatttct tttatatgca ccatcttgag   9360

ttacctaatg cattacacac cggaactgac ctagcgggtg acttctatgg tggttatgtg   9420

gatgaagagg ttgcacaaag ggtgccacca gataatttag ttactaacaa tattgtagca   9480

tggctttatg cagcaattat tagtgttaaa gagagtagct tctcactgcc taaatggttg   9540
```

-continued

```
gagagtacta ctgccagtgt tgaagattat aataagtggg ctggtgataa tggttttaca   9600
ccattttcta ctagtactgc tattactaaa ttaagtgcta taacgggagt tgatgtttgt   9660
aaactccttc gcactattat ggtaaaaagt agtcaatggg gtagtgatcc catttttagga  9720
caatacaatt ttgaagatga attgacacct gagtctgtct ttaatcaggt tggcggtgtt   9780
agattacagt cttctattgt aagaagagcc acatcttggt tttggagtag atgtgtgtta   9840
gcttgcttct tgtttgtgtt gtgtgctgta gttttgttta cggcagtacc acttagatat   9900
tatttacatg cagctgttat tttgttagtg gctgtacttt ttatttcttt tactgttaaa   9960
catgttatgg catatatgga tacttttcta ttgccgacat tggttacagt tattattgga  10020
gtttgtgctg aagttccttt catatacaat actctaatta gtcaagttat tattttctta  10080
agtcaatggt atgatcctgt agtttttgat actatagtac catggatgtt gttgccatta  10140
gtgttgtaca ctgcttttaa gtgtgtacaa ggttgctata tgaattcgtt caatacttcg  10200
ttgttaatgc tgtaccagtt tatgaagtta ggttttgtta tttatacctc ttctaacact  10260
cttactgcat atacagaagg taattgggag ttattctttg agttggttca cactactgtg  10320
ttggctaatg ttagtagtaa ttccttaatt ggtttaattg tctttaagtg tgctaagtgg  10380
atgttgtatt attgtaatgc aacatacttt aacaattatg ttttaatggc agttatggtt  10440
aatggcatag gctggctttg cacttgttac tttggattgt attggtggat taataaggtt  10500
tttggtttaa ccttaggtaa atacaatttt aaagtttcag tagaccaata taggtatatg  10560
tgtctgcata agatagaccc ccctaaaact gtgtgggaag tcttttcgac aaatatactt  10620
atacaaggga ttggtggtga ccgtgtgttg cctattgcta cagttcaatc taaattgagt  10680
gatgtaaagt gtacaactgt tgtgttaatg caacttttga ctaagcttaa tgttgaagca  10740
aattcaaaaa tgcatgctta tcttgttgag ttacacaata aaatcctcgc atctgatgat  10800
gttggagagt gcatggataa tttattgggt atgcttatta cactattttg tatagattct  10860
actattgatt taggtgagta ttgtgatgat atacttaaga ggtcaactgt attacaatca  10920
gttactcaag agttttcaca catacccctct tatgctgaat atgaaagagc taagaatctt  10980
tatgaaaagg ttttagctga ttctaaaaat ggtggtgtaa cacagcaaga gcttgctgca  11040
tatcgtaaag ctgccaatat tgcaaagtca gtttttgata gagatttggc tgttcaaaag  11100
aagttagaca gcatggcaga acgtgctatg acaacaatgt ataaagaggc gcgtgtaact  11160
gatagacgag caaaattagt ctcatcacta catgcgttac ttttttcaat gcttaagaaa  11220
atagattctg aaaagcttaa tgtcttattt gatcaggcta gtagtggtgt tgtacctcta  11280
gctactgttc caattgtttg tagtaataag cttaccccttg tagtaccaga tccagaaact  11340
tgggtcaagt gtgtggaagg tatgcatgtt acatattcaa cagttgtttg gaatatagat  11400
actgttattg atgctgatgg tacagaggta catccaactt ctacaggtag tggattgaca  11460
tactgtataa gtggtgccaa tatagcatgg cctttaaagg ttaacttgac taggaatggg  11520
cataataagg ttgatgttgc tttgcagaat aatgagctta tgcctcatgg tgtaaaaaca  11580
aaggcttgcg tagcaggtgt ggatcaagca cattgtagcg tagagtctaa atgttattat  11640
acaaatatta gtggcaattc agttgtagct gccattactt cttcaaatcc aaatctgaaa  11700
gtagcttcat tttgaacga ggcaggcaat cagatttatg tagacttaga cccaccatgc  11760
aaatttggca tgaaggtggg tgacaaggtt gaggttgttt acttgtattt tataaagaat  11820
acaaggtcga ttgttagggg tatggtactt ggtgctatat ctaatgttgt tgtcttacag  11880
```

```
tctaaagggc atgaaacaga ggaagtggat gctgttggca ttctttcact ttgttctttt  11940
gcagtagatc ctgcagacac gtattgtaaa tatgtggcag caggtaatca acctctaggt  12000
aactgtgtta aaatgttgac agttcataat ggtagtggct ttgctataac atcgaagcca  12060
agtccaactc ctgatcagga ttcctacgga ggagcttctg tgtgtctcta ttgtagggca  12120
cacatagcac atcctggtgg tgcaggaaat ttagatgggc gttgtcaatt taaaggttcc  12180
tttgtgcaaa taccaactat ggagaaagac cctgttggat tctgtctacg taataaggtt  12240
tgcactgtct gtcaatgttg gattggttat ggatgtcagt gcgatgcact tagacaacca  12300
aaaccttctg ttcaatcagc tgccaatgta gctgatttcg ataagaatta tttaaacggg  12360
tacggggtag cagtgaggct cggctgatac cccttgctag tggatgtgat cctgatgttg  12420
tgaagcgagc ctttgatgtt tgtaataagg aatcagccgg tatgtttcgt aatttgaagc  12480
gtaactgtgc gcggttccaa gaagtacgtg atactgaaga tggaagtctt gagtattgtg  12540
attcattctt cgtggttaaa caaaccactc ctagtaatta tgaacatgag aaagcttgtt  12600
atgaagactt aaagtcagaa gtgacggctg accatgattt ctttgtgttc aataagaaca  12660
tttataatat tagtaggcaa cgtcttacta agtatactat gatggatttt tgctatgctt  12720
tgaggcattt tgacccaaag gactgcgaag ttcttaaaga aatacttgtc acttatggtt  12780
gtatagaaga ttatcaccct aagtggtttg aagagaataa ggattggtac gacccaatag  12840
aaaacccaaa atattatgcc atgttggcta aaatggggcc tattgtacga cgtgctttat  12900
tgaatgctat tgagttcgga aaccttatgg ttgagaaagg ttatgttggt gtagttacac  12960
ttgacaacca agatcttaat ggcaaatttt atgactttgg tgattttcag aaaacagcac  13020
ttggtgctgg ggttcctatt tttgatacat attattccta catgatgccc atcatagcca  13080
tgacggatgc tttagcacct gaaaggtatt ttgaatatga tgtgcataag ggttataagt  13140
cttatgatct tctcaagtat gattatactg aggagaaaca agatttgttt cagaagtact  13200
ttaagtattg ggaccaggag taccatccta actgccgtga ctgtagtgat gacaggtgtt  13260
tgatacattg tgcaaacttc aacatattgt tttctacatt gataccacag acttcttttg  13320
gtaatttgtg tagaaaagtg tttgttgatg gtgtaccttt tatagctact tgtggctatc  13380
attctaaaga acttggtgtt attatgaatc aagataacac catgtcgttt tcaaaaatgg  13440
gtttaagtca actcatgcag tttgttggag accctgcctt gttagtggga acatccaata  13500
atttagtcga tcttagaacg tcttgtttta gtgtttgtgc attagcgtct ggtattactc  13560
atcaaacggt aaaaccgggt cactttaaca aggatttcta tgattttgca gagaaggccg  13620
gtatgtttaa agagggttct tctataccac ttaaacattt cttctaccca caaactggta  13680
atgctgctat aaacgattat gattactatc gttataacag gcctaccatg tttgatatac  13740
gtcaacttct attttgttta gaagtgactt ctaaatactt tgactgttat gaaggcggct  13800
gtataccagc aagccaagtt gtagttaata atttagataa gagtgcaggc tacccattta  13860
ataaatttgg aaaagctcgc ctctattatg aaatgagtct agatgaacag gaccaactct  13920
ttgagagtac aaagaagaat gtcctgccta ctataactca aatgaattta aaatatgcca  13980
tatccgcgaa aaatagagcg cgtacagtgg caggtgtgtc tatcctttct actatgacta  14040
ataggcaatt tcatcagaag attcttaagt ctatagttaa cactagaaat gctcctgtag  14100
ttattggaac aaccaagttt tatggcggtt gggacaatat gttgaggaat ctgattcaag  14160
gtgttgaaga ccctattctt atgggttggg attatcctaa gtgtgataga gcaatgccaa  14220
atttgctgcg tatagcagca tccttggtac ttgctcgcaa acacactaat tgttgtactt  14280
```

ggtctgaacg catttatagg ttgtataatg aatgcgctca ggttttatct gaaactgttt 14340
tagctacagg tggtgtttat gtaaaacctg gtggtactag cagtggtgat gctactactg 14400
cttatgcaaa cagcgttttc aacataatac aagccacatc tgctaatgtt gcgcgtcttt 14460
tgagtgttat aacgcgtgat attgtttatg atgacattaa gagcctgcag tatgagttgt 14520
accagcaggt ttataggcga gttaattttg acccagcctt tgtagaaaag ttttattctt 14580
acttatgtaa gaatttctct ttgatgatct tgtctgacga tggtgttgtt tgttacaaca 14640
acacattggc caaacagggt cttgttgcgg acatttctgg ctttagagaa attctctact 14700
accaaaataa tgtttatatg gctgattcta agtgttgggt tgaaccagac ttagaaaaag 14760
gcccacatga attttgttca cagcacacaa tgctagtgga ggtggatggt gagcctaagt 14820
atttgccata tccagatccc tcacgcattt tgggtgcatg tgtctttgta gatgaagtgg 14880
ataagacaga acctgtggct gttatggagc gttatatagc tcttgccata gacgcttacc 14940
cactagtaca tcacgaaaat gaggagtaca ggaaggtttt ctttgtgctt ctttcatata 15000
tcagaaaact ctatcaagag ctttctcaga atatgcttat ggactactct tttgtgatgg 15060
atatagacaa gggtagtaaa ttttgggaac aggagttcta tgagaatatg tatagagccc 15120
ctacaacttt acagtcttgt ggtgtttgtg tagtgtgcaa tagtcaaact atactacgct 15180
gtggtaattg tattcgaaaa ccatttttgt gttgtaaatg ttgttatgac catgtcatgc 15240
acacagacca taaaaatgtt ttgtctataa acccatacat ctgttcgcaa cccggttgcg 15300
gtgaagcaga tgttactaaa ttataccttg gaggtatgtc atacttctgt ggtaatcata 15360
aaccaaaatt gtcaataccg ttagtatcta atggtactgt ctttggtatt tacagggcta 15420
attgtgctgg tagtgaaaat gttgatgatt ttaatcaact agctactact aattgggcta 15480
ctgtagaacc ttatatttta gcaaatcgtt gtagtgactc attgagacgc tttgctgctg 15540
aaacagtaaa agccacagag gaattacata aacagcaatt tgctagtgct gaggtgagag 15600
aagtactctc agatcgtgaa ttgatcctat catgggagcc aggtaaaacc aggccaccat 15660
tgaatagaaa ttatgttttc acaggctatc actttacaag aactagtaag gtgcagcttg 15720
gtgattttac ctttgaaaaa ggtgaaggta aagatgttgt ctattataga gcaacgtcta 15780
ctgctaaatt gtctgttgga gacatttttg ttttaacctc acacaatgtt gtttctcttg 15840
tagcgccaac gttgtgtccg cagcaaacct tttctaggtt tgtgaattta agacctaatg 15900
taatggtacc ggaatgtttt gtaaataaca ttccacttta ccatttagta ggtaagcaga 15960
agcgtactac agtacaaggt cctcctggca gtggtaagtc acactttgct ataggccttg 16020
ctgcttactt tagtaacgcg cgtgttgtct ttactgcttg ttctcatgca gctgttgatg 16080
ctttatgtga aaaagctttt aagtttctta aagtcgatga ttgcactcgg atagtacctc 16140
aaaggactac tgtcgagtgc ttttctaagt ttaaagctaa cgacacaggc aaaaagtaca 16200
tttttagtac tataaatgcc ttgccagaag ttagttgtga cattcttttg gttgatgagg 16260
ttagtatgtt gaccaattac gaattgtctt ttattaatgg taagataaat taccaatatg 16320
ttgtgtatgt aggtgaccca gctcaattac cggcacctcg taccttactt aatggctcac 16380
tttcaccaaa ggattataat gttgtcacaa accttatggt ttgtgttaaa cctgatatat 16440
tccttgcgaa gtgttaccgt tgtcctaagg aaattgtaga cactgtgtct actctagtat 16500
atgatggaaa gtttattgca aataacccag aatcacgtca gtgtttcaag gttatagtta 16560
ataatggtaa ttctgatgta ggacatgaaa gtggttcagc ctacaacaca actcaattag 16620

-continued

```
aatttgtgaa agattttgtt tgtcgcaata aggaatggcg ggaagcaaca ttcatttcac  16680
cttacaatgc tatgaaccag agagcctacc gtatgcttgg acttaatgtt cagacagtag  16740
actcatctca aggttcggag tatgattatg ttattttctg tgtaactgca gattcgcagc  16800
atgcactgaa tattaacaga tttaatgtgg cgcttacaag agctaagcgt ggtatactag  16860
ttgtcatgcg tcagcgtgat gaattgtact ctgctcttaa gtttacagag ctaaatagtg  16920
aagcaagtct gcaaggtaca ggtttgttta aaatttgcaa caaagaattt agtggtgttc  16980
atcctgctta tgcagtcaca actaaggctc ttgctgcaac ttacaaagtt aatgatgaac  17040
ttgctgcact tgttaatgtg gaagccggtt cagaaataac atataaacat cttatttctc  17100
ttctaggatt taggatgagt gttaatgttg aaggttgcca taacatgttt ataacacgtg  17160
acgaggcaat tcgcaacgta agagggtggg taggattcga tgtagaagcc acacatgctt  17220
gtggtactaa cattggcact aacttacctt ttcaagtagg tttctcgact ggtgcagact  17280
ttgtagttac acctgaggga cttgtagata cttcgatagg caataatttt gagcctgtga  17340
attccaaagc acctccaggt gagcaattta atcacttgag agctttattt aagagtgcta  17400
aaccttggca cgttataaga ccaaggatag tgcaaatgtt agcagataat ctatgcaatg  17460
tctctgattg tgtagtgttt gttacttggt gtcatggcct agaactaact acgttgcgct  17520
attttgttaa aataggcaaa gaacaattgt gttcgtgtgg ttctagagct acgactttta  17580
attcacatac tcaagcttat gcttgttgga ggcattgttt gggttttgat tttgtctata  17640
acccactttt agtggatatt caacaatggg gttactcagg taatctacaa tttaaccatg  17700
gtttgcattg taatgtgcat ggacatgccc atgtggcttc tgcggacgcc attatgacgc  17760
gttgccttgc aattaacaat gcattttgtc aagatgtcaa ctgggatttg acatatcctc  17820
atattgcaaa tgaggatgaa gtcaactcta gttgtcggta tttacagcgc atgtatctta  17880
atgcatgtgt tgatgctctt aaagttaatg ttgtctatga tataggcaac cctaaaggta  17940
taaagtgtgt tagacgtgtg gatgtcaatt ttagattcta tgataagaat ccaattgtac  18000
ccaacgtcaa acagtttgag tatgactata atcagcacaa ggataagttt gctgatggtc  18060
tttgtatgtt ttggaattgc aatgtggatt gttatcctga caattcacta gtctgtagat  18120
acgacacacg aaatttgagt gtgtttaatc taccaggttg taatggtggt agtctgtatg  18180
tgaacaaaca tgcatttcac acacctaaat ttgaccgcat tagctttcgc aatttgaaag  18240
ctatgccatt tttcttctat gattcatcgc cttgtgaaac cattcaagtt gatggagttt  18300
cacaagacct tgtgtcatta gctactaagg attgtatcac aaaatgcaac attgggggtg  18360
ctgtttgtaa aaagcacgct cagatgtatg cagagtttgt gacttcttat aatgcagctg  18420
ttacagctgg ttttactttt tgggttacta ataattttaa cccttataat ttgtggaaaa  18480
gtttttcagc tctccagtct attgacaata ttgcttataa tatgtataag ggtggtcatt  18540
atgatgctat cgcaggagaa atgcccacag tcataactgg agataaagtt tttgttatag  18600
atcaaggtgt agaaaaggca gtttttgtta atcaaacaac actgcctacg tctgtggcgt  18660
ttgaattgta tgcgaagaga aatattcgca cactgccaaa caaccgtatt ttgaagggtc  18720
ttggtgtaga tgtaaccaat ggttttgtaa tttgggatta tgctaaccag acaccactat  18780
atcgtaatac tgtcaaggta tgtgcataca cagacattga gccaaatggc ctaatagttc  18840
tgtatgatga tagatatggt gattaccagt cttttcttgc tgctgacaat gctgttttaa  18900
tttctacaca gtgttataag cggtattcat atgtagaaat accatcagat ttgcttgttc  18960
agaatggtat gccactaaaa gatggagcga acctatatgt ttataagcgc gttaatggtg  19020
```

tgtttgttac actacccaac actttaaaca cacagggccg caattatgaa acttttgaac 19080
ctcgtagtga cgttgagcgt gattttctcg acatgtcaga ggaagatttt gtagaaaagt 19140
atggtaaaga cttaggtcta caacacatac tgtatggtga agttggtaaa ccacaattgg 19200
gtggtttaca cactgttata ggtatgtaca gacttttacg tgcgaataag ttgaatgcaa 19260
agtctgtcac taattcggat tctgatgtca tgcaaaatta ttttgtgttg gcagacaatg 19320
gttcttacaa gcaagtgtgc actgttgtgg atttactgct tgatgatttc ttagaacttc 19380
ttaggaacat actgaatgag tatggtacta ataagtcaaa agttgtaaca gtgtcaattg 19440
attaccatag cataaatttt atgacttggt ttgaagatgg cagtattaaa acatgttatc 19500
cacagcttca atcagcgtgg acatgtggtt ataatatgcc tgaactttat aaagtccaga 19560
attgcgttat ggaaccttgc aacattccta actatggtgt tggaataacg ttgccaagtg 19620
gtattatgat gaatgtagca aagtatacac aactttgtca atatctttcg aaaacaacaa 19680
tgtgtgtgcc gcataatatg cgagtaatgc attttggagc aggaagtgac aaaggagtgg 19740
ccccaggtag cgctgttctt aggcagtggc ttcccgaagg tacactcctt gtcgataatg 19800
atattgtaga ttatgtatct gatgcacatg tctctgtgct ttcagattgc aataaatgta 19860
aaacagagca caagtttgat cttgtgatat ctgatatgta tacagataat gattcaaaga 19920
gaaagcatga aggcgttgta gccaataacg gcaatgatga cgtcttcata tacctttcaa 19980
actttcttcg taacaattta gctctgggag gcagttttgc cgtaaaagta acagagacaa 20040
gttggcatga gagtttatat gacattgcac aggattgtgc atggtggaca atgttttgta 20100
cagcagtgaa tgcttcttcg tcagaagcat tcttgattgg tgttaattat ttgggtgcaa 20160
gtgaaaaggt tagagttagt ggtaaaaccc tgcacgcaaa ttatatattt tggaggaatt 20220
gtaattattt acaaacttca gcctatagta tatttgacgt tgctaagttt gatttgaaat 20280
taaaagcaac gccagttgtg aatttgaaaa ctgaacaaaa gacagactta gtctttaatt 20340
taattaagtg tggtaagtta ctggtaagag atgttggaca aaccgctttt actagtgact 20400
ctttggtatg cactatgtag tgctttgctc tatgataata atacttacgt ttactactac 20460
caaagtgcct ttaggcctgg tccaggttgg cacctatatg gggtgctta tgcagtagat 20520
agggttttta atgaaaccaa caatgcaggc agtgcatctg attgcactgc tggtactttt 20580
tatgaaagcc ataatatttc tgcttcttct gtagccatga cagtaccaca taatggtatg 20640
tcttggtcag cttcacaatt ttgtacagct cattgtaact tctcagactt tacagtgttc 20700
gttacgcatt gttttaaaaa tcaactcggt agttgtccct tgacaggtat gattcctcag 20760
aatcatattc gtatttctgc tatgagagat ggagttttgt tttataactt aacagttagc 20820
gtatctaaat accctagatt taaatcgctt caatgtgtta gcaattctac atctgtctat 20880
gtaaatggtg accttgtttt cacttctaat gaaacttctt acgttacggg tgcaggcgtt 20940
tattttaaaa gtggtgggcc tgtaacttat aaagttatga aagaagttaa agccctagcc 21000
tactttatta atggtaccgc acaagaggtt attttatgtg ataactcacc tagaggtttg 21060
cttgcatgtc agtataacac tggtaatttt tcagatggat tctacccttt tactaatcat 21120
tctttagtta aggataggtt tattgtatat cgagaaagta gcactaacac tactttaaag 21180
ttaactaatt tcagttttac taatgtaagt aatgcttctc ctaattcagg tggcgttgat 21240
actttccaat tatatcaaac aagtactgct caggatggtt attataattt taatttatca 21300
tttctgagta gttttgtgta taaaccatct gattttatgt atgggtcata ccacccacat 21360

```
tgtaagttta gaccagagaa tattaataat ggcttatggt ttaattcatt atctgtgtca  21420
cttacttacg gacccattca aggtggttgt aagcaatctg tttttagtaa tagagcaact  21480
tgttgctatg cttattctta tcaagggcct agtagatgta agggtgttta tagaggggag  21540
ctaacgcaat actttgaatg tggacttcta gtttacgtaa ctaagagtga tggctctcgt  21600
atacaaacta gaagtgaacc actggtgtta actcaatata attataacaa cattacttta  21660
aataagtgtg ttgagtataa tatatatggt agggttggtc aaggttttat tactaatgta  21720
actgaagcaa ctgctaatta tagttatcta gcagatggtg gtttagctat tttagatacc  21780
tcaggagcca tagacatatt tgttgttcaa ggtgcatatg gtcttaatta ttataaggtt  21840
aatccctgtg aagatgttaa ccaacagttt gtagtgtctg gtggcaactt agttggcatt  21900
cttacatctc ataatgaaac aggttctgaa tctattgaga accagtttta catcaaactc  21960
actaacggaa cacgtcgctc tagacgttct gttactggga atgttacaaa ttgcccttat  22020
gttagttatg gcaagttttg tataaaacca gatggttctt tatctataat agtaccacaa  22080
gaattagaac agtttgtggc gcctttattc aatgttactg agcatgtgct catacctgat  22140
agttttaatt taactgtcac agatgagtac atacaaactc gtatggataa ggttcaaatt  22200
atttgccttc agtatgtttg tggtaattct attgaatgca gaaagttgtt tcagcagtat  22260
ggacctgttt gtgataatat attgtctgtt gtaaatggtg taggtcaaag agaggatatg  22320
gaacttttaa gtttctattc ttctactaaa cctagtggtt acaatacacc aatttttaat  22380
aatgttagca ctggtgactt taatatttcg ctcctactaa caccacctaa tagtcctact  22440
gggcgctctt ttattgaaga tcttctcttt acaagtgtag aatctgttgg attaccaact  22500
gatgaagagt ataaaaagtg tacagcagga cctttaggtt ttgttaaaga ccttgtttgt  22560
gctagagagt ataatggttt gctcgttctg cctcctatta ttactgcgga aatgcaaacc  22620
atgtatacta gttctttagt agcctctatg gctttaggtg gcattactgc agctggtgct  22680
ataccttttg ctacacaact gcaggccaga attaaccatt tgggtattac taattctctt  22740
ttgttgaaaa accaagaaaa aattgctgct tcctttaata aggccatcgg tcatatgcag  22800
gaagggttta aaagtacttc tctagcatta caacagattc aagatgttgt taataaacag  22860
agttctattc ttacagagac tatgcaatca cttaataaaa attttggtgc tatttcctct  22920
gtaattcaag acatttacca gcaactagat gctattcagg cagatgctca ggttgatcgt  22980
cttattacag gtagactctc ttcactatct gttttagctt ctgctaaaca ggcagagtat  23040
catagagtgt cacaacagcg tgagttggcc actcagaaaa ttaatgagtg tgttaagtct  23100
cagtctaata ggtattcatt ttgtggtaat ggtagacatg ttctaaccat accacagaat  23160
gcacccaatg gcatagtgtt tatacacttt acatacactc cagagagttt tgttaatgtt  23220
acggcaatag tagggttttg cgtaaaccca gctaatgcta gtcattatgc aatagtgcct  23280
gttaatggca ggggtgtttt tatagaagtt aatggtagtt actatatcac tgctcgtgat  23340
atgtatatgc caagagatat tactgcagga gacatagtca ctttgacttc ttgtcaagca  23400
aactatgtta atgtaaataa aaccgtcatt aacacttttg tggaagatga cgattttgat  23460
ttttatgatg aattgtcaaa atggtggaat gatactaagc atgagctacc agattttgat  23520
gaattcaatt ataccgttcc agttttaaat attagtaatg aaattgacag aattcaacag  23580
gttattcagg gattaaatga ttccctaata gaccttgaaa cactctcaat tctcaaaact  23640
tatattaaat ggccttggta tgtgtggctt gccattgcat tccttaccat tatttttatt  23700
ctggtacttt gttggatatt tttcatgacc ggttgttgcg gttgttgttg tggatgcttt  23760
```

ggtatcatac cgttaatgag taagtgtggt aagaaatctt cttactacac gacttttgat 23820
aatgatgtgg taacttaaca atacagacct aaaaagtctg tttaatgatt aaaagtccca 23880
catcttttct aatattatta attcttcttt ggtgtaaact tgcattaagt tgttttaaag 23940
agtgtgttat aacactccag caactagtac aaattttact ccaaattatt aatagtaact 24000
tacaatctag acttctgctt tggcacagtc tagactaatg ttagattttg aagcaattat 24060
tgaaactggt cagcaaataa ctcaacaaat tagtttctat ttacagcata tttcaagggt 24120
gctaagtact gaattatttg accccttga agtttgtgtt tacagaggag gtaattgttg 24180
ggagttagag tcagctgacg agttttcagg tgatgacgaa tatattgagt agatcgctag 24240
aggagaacgg aagttttcta acagcggttt acgtgttttt aggattttta gcactttatc 24300
tactaggtag agcgcttcaa gcttttgtac aagcggctga cgcttgttgt ctttttggt 24360
atacatgggt agtagttcct ggagccaagg gcacagcctt tgtttataat catacatatg 24420
gtaaaaaact taacaaaccg gagttagaaa cggttattgt taacgaattt ccaaaaaacg 24480
gttggaaata tggataatac catcaattgt actcttggta ctgaacaagc agttcagctt 24540
tttaaggaat ataatctgtt tgtaactgca ttcctgttgt ttttaaccat actacttcag 24600
tatggatacg caactaggag caaggttatt tacatactga aatgatagt gttatggtgc 24660
ttttggcccc ttaacattgc agtaggtgta atctcatgta tatacccacc aaacacagga 24720
ggtcttgtcg cagcgataat tcttacagtg tttgcgtgtc tttcttttat aggttattgg 24780
atccagagta ttagactttt taagcggtgc aggtcatggt ggtcatttaa ccccgaatct 24840
aatgccgtag gttcaatact cctaactaat ggtcaacaat gtaattttgc tatagagagt 24900
gtgccgatgg tgctttctcc tattataaag aatggtgctc tttattgcga gggtcagtgg 24960
cttgctaaat gtgaaccaga ccacttgcct agagatatat ttgtatgcac accggataga 25020
cgtaatatct atcgtatggt gcaaaaatat actggtgacc aaagcggaag taagaaaagg 25080
tttgccacat ttgtctatgc aaagcagtca gtagatactg gcgagctaga aagtgtgtca 25140
gcagtaggag gtagtcttta cacataaatg tgtgtgtgta gagagtattt aaaattattc 25200
tttgacagtg cctccgtttt aagagcgcgg aagagtatta tttttgagga tattaatata 25260
aatcctcttt gtttcatact ctcctttcag gagttattat ttaaaaaaca gtttttccac 25320
tcttttgtgc caaaaacaat tgttgttaat ggtgtaacct ttcaggtaga caatggaaaa 25380
gtctactacg aaggaagacc aattttccaa aaaggttgtt gtagtttgtg gtccaattat 25440
aagaaagatt agaataatta aaccacctac aacacttatt tttacaaatg gcgttttagg 25500
ttacaaacgc ttaacaaata cggatgatga aatggctgac tagttttgga agagctttca 25560
tctcctgtta taaatcccta ttactaactc aattaagagt attagatagg ttaattttag 25620
atcacggacc caagcgcaca ttaacgtgtg ctaggcgagt gcttttagtt caattagatt 25680
tagtttatag gttggcttat acgcccaccc aatcgctggt atgaataata gtaaagataa 25740
tccttttcgc ggagcaatag caagaaaagc gcgaatttat ctgagaggag gattagattg 25800
tgtttacttt cttaacaaag caggacaagc agagccttgt cccgcgtgta cctccctagt 25860
attccaaggg aaaacttgtg aggaacacta ttataataac aatcttttgt catggcaagc 25920
ggtaaggcaa ctggaaagac agacgcccca gcgccagtca tcaaactagg aggaccaaag 25980
ccacctaaag ttggttcttc tggaaatgca tcatggtttc aaccgataaa ggccaagaag 26040
ctaaattcac ctgtgcctaa atttgacggt agtggtgttc ctgaaaatga aaatctcaag 26100

```
tcaagccagc aacatggata ctggagacgc caacacaggt ttaagcctgg caaaggtgga  26160

agaaaaccag tccctgatgc ttggtacttt tactacactg gaacaggacc ggccgccgac  26220

ctgaattggg gtgaaactca agatggtata gtgtgggttg ctgcaaaggg tgctgatact  26280

aaatctagat caaaccaggg tacaagggat cctgataagt ttgaccaata cccactacga  26340

ttctcagatg gaggaccgga tggtaatttc cgttgggact tcataccaat aaatcgtggt  26400

aggagtggga gatcaacagc agcttcatca gcagcatcta gtagagcacc atctcgtgag  26460

gggtcacgtg gacgtagaag cggagttgaa gatgatctta tagctcgcgc agcaaagatt  26520

atacaggacc agcaaaagaa gggtgcgcgc attaccaagg ctaaggctga tgaaatggct  26580

catcgccgct attgcaagcg cactatccca cctggttata aggttgagca agtatttggt  26640

ccccgtacta aaggtaagga aggaaatttt ggtgatgaca agatgaatga ggaaggtgtt  26700

aaggatgggc gtgttacggc aatgctcaac ctagtcccta gcagtcatgc ttgtcttttt  26760

ggaagtaggg tgacgcccaa actgcagcca gatggtcttc acctgagatt tgaatttact  26820

actgtggtgt cacgtgatga tccgcagttt gataattatg tgaaaatttg tgatcagtgt  26880

gtcgatggtg tagggacgcg tccaaaggac gatgaatcga gaccaaagtc acgcccaaat  26940

tcaagacctg caactagagg aaattctcca gcgccgagac aacagcgccc aaagaaggag  27000

aaaaagccca agaagcagga tgatgaagta gataaggcat tgacctcaga tgaggagagg  27060

aacaatgcac agctggaatt tgatgatgaa cccaaggtga ttaactgggg ggactctgca  27120

ctaggtgaaa atgaactttg attaacataa tggacttgct gcatttgctg tcacattttg  27180

ttaaatatta tttttgtgtt ttactatcaa ttattacagg tattgattgt gattatgttc  27240

aatacttaag cttcttctgg ttgctttttg cttgttgtat tgttgctgtg ctttttatta  27300

ttgtgattct cattagtttg ctttatcgta gaaattcaat agtaagagtt aaggaagata  27360

ggcatgtagc ttagcaccta catgtctatc gccagggaaa tgtctaatct gtctacttag  27420

tagcctggaa acgaacggta gacccttaga ttttaattta gtttaatttt tagtttagtt  27480

taagttagtt tagagtaggt ataaagatgc cagtgccggg gccacgcgta gtacgaccga  27540

gggtacagca ctaggacgcc cactagggga agagctaaat tttagtttaa gttaagttta  27600

attggctaaa tatagttaaa atttataggc tagtatagag ttagagcaaa aaaaaaaaa   27659
```

```
<210> SEQ ID NO 2
<211> LENGTH: 1155
<212> TYPE: PRT
<213> ORGANISM: Avian infectious bronchitis virus

<400> SEQUENCE: 2

Met Leu Asp Lys Pro Leu Leu Leu Val Thr Leu Trp Tyr Ala Leu Cys
1               5                   10                  15

Ser Ala Leu Leu Tyr Asp Asn Asn Thr Tyr Val Tyr Tyr Tyr Gln Ser
            20                  25                  30

Ala Phe Arg Pro Gly Pro Gly Trp His Leu Tyr Gly Gly Ala Tyr Ala
        35                  40                  45

Val Asp Arg Val Phe Asn Glu Thr Asn Asn Ala Gly Ser Ala Ser Asp
    50                  55                  60

Cys Thr Ala Gly Thr Phe Tyr Glu Ser His Asn Ile Ser Ala Ser Ser
65                  70                  75                  80

Val Ala Met Thr Val Pro His Asn Gly Met Ser Trp Ser Ala Ser Gln
                85                  90                  95

Phe Cys Thr Ala His Cys Asn Phe Ser Asp Phe Thr Val Phe Val Thr
```

```
            100                 105                 110

His Cys Phe Lys Asn Gln Leu Gly Ser Cys Pro Leu Thr Gly Met Ile
        115                 120                 125

Pro Gln Asn His Ile Arg Ile Ser Ala Met Arg Asp Gly Val Leu Phe
    130                 135                 140

Tyr Asn Leu Thr Val Ser Val Ser Lys Tyr Pro Arg Phe Lys Ser Leu
145                 150                 155                 160

Gln Cys Val Ser Asn Ser Thr Ser Val Tyr Val Asn Gly Asp Leu Val
                165                 170                 175

Phe Thr Ser Asn Glu Thr Ser Tyr Val Thr Gly Ala Gly Val Tyr Phe
            180                 185                 190

Lys Ser Gly Gly Pro Val Thr Tyr Lys Val Met Lys Glu Val Lys Ala
        195                 200                 205

Leu Ala Tyr Phe Ile Asn Gly Thr Ala Gln Glu Val Ile Leu Cys Asp
    210                 215                 220

Asn Ser Pro Arg Gly Leu Leu Ala Cys Gln Tyr Asn Thr Gly Asn Phe
225                 230                 235                 240

Ser Asp Gly Phe Tyr Pro Phe Thr Asn His Ser Leu Val Lys Asp Arg
                245                 250                 255

Phe Ile Val Tyr Arg Glu Ser Ser Thr Asn Thr Thr Leu Lys Leu Thr
            260                 265                 270

Asn Phe Ser Phe Thr Asn Val Ser Asn Ala Ser Pro Asn Ser Gly Gly
        275                 280                 285

Val Asp Thr Phe Gln Leu Tyr Gln Thr Ser Thr Ala Gln Asp Gly Tyr
    290                 295                 300

Tyr Asn Phe Asn Leu Ser Phe Leu Ser Ser Phe Val Tyr Lys Pro Ser
305                 310                 315                 320

Asp Phe Met Tyr Gly Ser Tyr His Pro His Cys Lys Phe Arg Pro Glu
                325                 330                 335

Asn Ile Asn Asn Gly Leu Trp Phe Asn Ser Leu Ser Val Ser Leu Thr
            340                 345                 350

Tyr Gly Pro Ile Gln Gly Gly Cys Lys Gln Ser Val Phe Ser Asn Arg
        355                 360                 365

Ala Thr Cys Cys Tyr Ala Tyr Ser Tyr Gln Gly Pro Ser Arg Cys Lys
    370                 375                 380

Gly Val Tyr Arg Gly Glu Leu Thr Gln Tyr Phe Glu Cys Gly Leu Leu
385                 390                 395                 400

Val Tyr Val Thr Lys Ser Asp Gly Ser Arg Ile Gln Thr Arg Ser Glu
                405                 410                 415

Pro Leu Val Leu Thr Gln Tyr Asn Tyr Asn Asn Ile Thr Leu Asn Lys
            420                 425                 430

Cys Val Glu Tyr Asn Ile Tyr Gly Arg Val Gly Gln Gly Phe Ile Thr
        435                 440                 445

Asn Val Thr Glu Ala Thr Ala Asn Tyr Ser Tyr Leu Ala Asp Gly Gly
    450                 455                 460

Leu Ala Ile Leu Asp Thr Ser Gly Ala Ile Asp Ile Phe Val Val Gln
465                 470                 475                 480

Gly Ala Tyr Gly Leu Asn Tyr Tyr Lys Val Asn Pro Cys Glu Asp Val
                485                 490                 495

Asn Gln Gln Phe Val Val Ser Gly Gly Asn Leu Val Gly Ile Leu Thr
            500                 505                 510

Ser His Asn Glu Thr Gly Ser Glu Ser Ile Glu Asn Gln Phe Tyr Ile
        515                 520                 525
```

```
Lys Leu Thr Asn Gly Thr Arg Arg Ser Arg Arg Ser Val Thr Gly Asn
    530                 535                 540

Val Thr Asn Cys Pro Tyr Val Ser Tyr Gly Lys Phe Cys Ile Lys Pro
545                 550                 555                 560

Asp Gly Ser Leu Ser Ile Ile Val Pro Gln Glu Leu Glu Gln Phe Val
                565                 570                 575

Ala Pro Leu Phe Asn Val Thr Glu His Val Leu Ile Pro Asp Ser Phe
            580                 585                 590

Asn Leu Thr Val Thr Asp Glu Tyr Ile Gln Thr Arg Met Asp Lys Val
        595                 600                 605

Gln Ile Ile Cys Leu Gln Tyr Val Cys Gly Asn Ser Ile Glu Cys Arg
    610                 615                 620

Lys Leu Phe Gln Gln Tyr Gly Pro Val Cys Asp Asn Ile Leu Ser Val
625                 630                 635                 640

Val Asn Gly Val Gly Gln Arg Glu Asp Met Glu Leu Leu Ser Phe Tyr
                645                 650                 655

Ser Ser Thr Lys Pro Ser Gly Tyr Asn Thr Pro Ile Phe Asn Asn Val
            660                 665                 670

Ser Thr Gly Asp Phe Asn Ile Ser Leu Leu Leu Thr Pro Pro Asn Ser
        675                 680                 685

Pro Thr Gly Arg Ser Phe Ile Glu Asp Leu Leu Phe Thr Ser Val Glu
    690                 695                 700

Ser Val Gly Leu Pro Thr Asp Glu Glu Tyr Lys Lys Cys Thr Ala Gly
705                 710                 715                 720

Pro Leu Gly Phe Val Lys Asp Leu Val Cys Ala Arg Glu Tyr Asn Gly
                725                 730                 735

Leu Leu Val Leu Pro Pro Ile Ile Thr Ala Glu Met Gln Thr Met Tyr
            740                 745                 750

Thr Ser Ser Leu Val Ala Ser Met Ala Leu Gly Gly Ile Thr Ala Ala
        755                 760                 765

Gly Ala Ile Pro Phe Ala Thr Gln Leu Gln Ala Arg Ile Asn His Leu
    770                 775                 780

Gly Ile Thr Asn Ser Leu Leu Leu Lys Asn Gln Glu Lys Ile Ala Ala
785                 790                 795                 800

Ser Phe Asn Lys Ala Ile Gly His Met Gln Glu Gly Phe Lys Ser Thr
                805                 810                 815

Ser Leu Ala Leu Gln Gln Ile Gln Asp Val Val Asn Lys Gln Ser Ser
            820                 825                 830

Ile Leu Thr Glu Thr Met Gln Ser Leu Asn Lys Asn Phe Gly Ala Ile
        835                 840                 845

Ser Ser Val Ile Gln Asp Ile Tyr Gln Gln Leu Asp Ala Ile Gln Ala
    850                 855                 860

Asp Ala Gln Val Asp Arg Leu Ile Thr Gly Arg Leu Ser Ser Leu Ser
865                 870                 875                 880

Val Leu Ala Ser Ala Lys Gln Ala Glu Tyr His Arg Val Ser Gln Gln
                885                 890                 895

Arg Glu Leu Ala Thr Gln Lys Ile Asn Glu Cys Val Lys Ser Gln Ser
            900                 905                 910

Asn Arg Tyr Ser Phe Cys Gly Asn Gly Arg His Val Leu Thr Ile Pro
        915                 920                 925

Gln Asn Ala Pro Asn Gly Ile Val Phe Ile His Phe Thr Tyr Thr Pro
    930                 935                 940
```

```
Glu Ser Phe Val Asn Val Thr Ala Ile Val Gly Phe Cys Val Asn Pro
945                 950                 955                 960

Ala Asn Ala Ser His Tyr Ala Ile Val Pro Val Asn Gly Arg Gly Val
                965                 970                 975

Phe Ile Glu Val Asn Gly Ser Tyr Tyr Ile Thr Ala Arg Asp Met Tyr
            980                 985                 990

Met Pro Arg Asp Ile Thr Ala Gly  Asp Ile Val Thr Leu  Thr Ser Cys
        995                 1000                 1005

Gln Ala  Asn Tyr Val Asn Val  Asn Lys Thr Val Ile  Asn Thr Phe
    1010                 1015                 1020

Val Glu  Asp Asp Asp Phe Asp  Phe Tyr Asp Glu Leu  Ser Lys Trp
    1025                 1030                 1035

Trp Asn  Asp Thr Lys His Glu  Leu Pro Asp Phe Asp  Glu Phe Asn
    1040                 1045                 1050

Tyr Thr  Val Pro Val Leu Asn  Ile Ser Asn Glu Ile  Asp Arg Ile
    1055                 1060                 1065

Gln Gln  Val Ile Gln Gly Leu  Asn Asp Ser Leu Ile  Asp Leu Glu
    1070                 1075                 1080

Thr Leu  Ser Ile Leu Lys Thr  Tyr Ile Lys Trp Pro  Trp Tyr Val
    1085                 1090                 1095

Trp Leu  Ala Ile Ala Phe Leu  Thr Ile Ile Phe Ile  Leu Val Leu
    1100                 1105                 1110

Cys Trp  Ile Phe Phe Met Thr  Gly Cys Cys Gly Cys  Cys Cys Gly
    1115                 1120                 1125

Cys Phe  Gly Ile Ile Pro Leu  Met Ser Lys Cys Gly  Lys Lys Ser
    1130                 1135                 1140

Ser Tyr  Tyr Thr Thr Phe Asp  Asn Asp Val Val Thr
    1145                 1150                 1155


<210> SEQ ID NO 3
<211> LENGTH: 409
<212> TYPE: PRT
<213> ORGANISM: Avian infectious bronchitis virus

<400> SEQUENCE: 3

Met Ala Ser Gly Lys Ala Thr Gly Lys Thr Asp Ala Pro Ala Pro Val
1               5                   10                  15

Ile Lys Leu Gly Gly Pro Lys Pro Pro Lys Val Gly Ser Ser Gly Asn
            20                  25                  30

Ala Ser Trp Phe Gln Pro Ile Lys Ala Lys Lys Leu Asn Ser Pro Val
        35                  40                  45

Pro Lys Phe Asp Gly Ser Gly Val Pro Glu Asn Glu Asn Leu Lys Ser
    50                  55                  60

Ser Gln Gln His Gly Tyr Trp Arg Arg Gln His Arg Phe Lys Pro Gly
65                  70                  75                  80

Lys Gly Gly Arg Lys Pro Val Pro Asp Ala Trp Tyr Phe Tyr Tyr Thr
                85                  90                  95

Gly Thr Gly Pro Ala Ala Asp Leu Asn Trp Gly Glu Thr Gln Asp Gly
            100                 105                 110

Ile Val Trp Val Ala Ala Lys Gly Ala Asp Thr Lys Ser Arg Ser Asn
        115                 120                 125

Gln Gly Thr Arg Asp Pro Asp Lys Phe Asp Gln Tyr Pro Leu Arg Phe
    130                 135                 140

Ser Asp Gly Gly Pro Asp Gly Asn Phe Arg Trp Asp Phe Ile Pro Ile
145                 150                 155                 160
```

```
Asn Arg Gly Arg Ser Gly Arg Ser Thr Ala Ala Ser Ser Ala Ala Ser
                165                 170                 175

Ser Arg Ala Pro Ser Arg Glu Gly Ser Arg Gly Arg Arg Ser Gly Val
            180                 185                 190

Glu Asp Asp Leu Ile Ala Arg Ala Ala Lys Ile Ile Gln Asp Gln Gln
        195                 200                 205

Lys Lys Gly Ala Arg Ile Thr Lys Ala Lys Ala Asp Glu Met Ala His
    210                 215                 220

Arg Arg Tyr Cys Lys Arg Thr Ile Pro Pro Gly Tyr Lys Val Glu Gln
225                 230                 235                 240

Val Phe Gly Pro Arg Thr Lys Gly Lys Glu Gly Asn Phe Gly Asp Asp
                245                 250                 255

Lys Met Asn Glu Glu Gly Val Lys Asp Gly Arg Val Thr Ala Met Leu
            260                 265                 270

Asn Leu Val Pro Ser Ser His Ala Cys Leu Phe Gly Ser Arg Val Thr
        275                 280                 285

Pro Lys Leu Gln Pro Asp Gly Leu His Leu Arg Phe Glu Phe Thr Thr
    290                 295                 300

Val Val Ser Arg Asp Asp Pro Gln Phe Asp Asn Tyr Val Lys Ile Cys
305                 310                 315                 320

Asp Gln Cys Val Asp Gly Val Gly Thr Arg Pro Lys Asp Asp Glu Ser
                325                 330                 335

Arg Pro Lys Ser Arg Pro Asn Ser Arg Pro Ala Thr Arg Gly Asn Ser
            340                 345                 350

Pro Ala Pro Arg Gln Gln Arg Pro Lys Lys Glu Lys Lys Pro Lys Lys
        355                 360                 365

Gln Asp Asp Glu Val Asp Lys Ala Leu Thr Ser Asp Glu Glu Arg Asn
    370                 375                 380

Asn Ala Gln Leu Glu Phe Asp Asp Glu Pro Lys Val Ile Asn Trp Gly
385                 390                 395                 400

Asp Ser Ala Leu Gly Glu Asn Glu Leu
                405
```

<210> SEQ ID NO 4
<211> LENGTH: 94
<212> TYPE: PRT
<213> ORGANISM: Avian infectious bronchitis virus

<400> SEQUENCE: 4

```
Met Thr Asn Ile Leu Ser Arg Ser Leu Glu Glu Asn Gly Ser Phe Leu
1               5                   10                  15

Thr Ala Val Tyr Val Phe Leu Gly Phe Leu Ala Leu Tyr Leu Leu Gly
            20                  25                  30

Arg Ala Leu Gln Ala Phe Val Gln Ala Ala Asp Ala Cys Cys Leu Phe
        35                  40                  45

Trp Tyr Thr Trp Val Val Val Pro Gly Ala Lys Gly Thr Ala Phe Val
    50                  55                  60

Tyr Asn His Thr Tyr Gly Lys Lys Leu Asn Lys Pro Glu Leu Glu Thr
65                  70                  75                  80

Val Ile Val Asn Glu Phe Pro Lys Asn Gly Trp Lys Tyr Gly
                85                  90
```

<210> SEQ ID NO 5
<211> LENGTH: 224
<212> TYPE: PRT

<213> ORGANISM: Avian infectious bronchitis virus

<400> SEQUENCE: 5

```
Met Asp Asn Thr Ile Asn Cys Thr Leu Gly Thr Glu Gln Ala Val Gln
1               5                   10                  15

Leu Phe Lys Glu Tyr Asn Leu Phe Val Thr Ala Phe Leu Leu Phe Leu
            20                  25                  30

Thr Ile Leu Leu Gln Tyr Gly Tyr Ala Thr Arg Ser Lys Val Ile Tyr
        35                  40                  45

Ile Leu Lys Met Ile Val Leu Trp Cys Phe Trp Pro Leu Asn Ile Ala
    50                  55                  60

Val Gly Val Ile Ser Cys Ile Tyr Pro Pro Asn Thr Gly Gly Leu Val
65                  70                  75                  80

Ala Ala Ile Ile Leu Thr Val Phe Ala Cys Leu Ser Phe Ile Gly Tyr
                85                  90                  95

Trp Ile Gln Ser Ile Arg Leu Phe Lys Arg Cys Arg Ser Trp Trp Ser
            100                 105                 110

Phe Asn Pro Glu Ser Asn Ala Val Gly Ser Ile Leu Leu Thr Asn Gly
        115                 120                 125

Gln Gln Cys Asn Phe Ala Ile Glu Ser Val Pro Met Val Leu Ser Pro
    130                 135                 140

Ile Ile Lys Asn Gly Ala Leu Tyr Cys Glu Gly Gln Trp Leu Ala Lys
145                 150                 155                 160

Cys Glu Pro Asp His Leu Pro Arg Asp Ile Phe Val Cys Thr Pro Asp
                165                 170                 175

Arg Arg Asn Ile Tyr Arg Met Val Gln Lys Tyr Thr Gly Asp Gln Ser
            180                 185                 190

Gly Ser Lys Lys Arg Phe Ala Thr Phe Val Tyr Ala Lys Gln Ser Val
        195                 200                 205

Asp Thr Gly Glu Leu Glu Ser Val Ser Ala Val Gly Gly Ser Leu Tyr
    210                 215                 220
```

<210> SEQ ID NO 6
<211> LENGTH: 1162
<212> TYPE: PRT
<213> ORGANISM: Avian infectious bronchitis virus

<400> SEQUENCE: 6

```
Met Leu Val Thr Pro Leu Leu Leu Val Thr Leu Leu Cys Ala Leu Cys
1               5                   10                  15

Ser Ala Ala Leu Tyr Asp Ser Ser Ser Tyr Val Tyr Tyr Tyr Gln Ser
            20                  25                  30

Ala Phe Arg Pro Pro Asp Gly Trp His Leu His Gly Gly Ala Tyr Ala
        35                  40                  45

Val Val Asn Ile Ser Ser Glu Ser Asn Asn Ala Gly Ser Ser Ser Gly
    50                  55                  60

Cys Thr Val Gly Ile Ile His Gly Gly Arg Val Val Asn Ala Ser Ser
65                  70                  75                  80

Ile Ala Met Thr Ala Pro Ser Ser Gly Met Ala Trp Ser Ser Ser Gln
                85                  90                  95

Phe Cys Thr Ala Tyr Cys Asn Phe Ser Asp Thr Thr Val Phe Val Thr
            100                 105                 110

His Cys Tyr Lys His Gly Gly Cys Pro Ile Thr Gly Met Leu Gln Gln
        115                 120                 125

His Ser Ile Arg Val Ser Ala Met Lys Asn Gly Gln Leu Phe Tyr Asn
```

-continued

```
    130                 135                 140

Leu Thr Val Ser Val Ala Lys Tyr Pro Thr Phe Lys Ser Phe Gln Cys
145                 150                 155                 160

Val Asn Asn Leu Thr Ser Val Tyr Leu Asn Gly Asp Leu Val Tyr Thr
                165                 170                 175

Ser Asn Glu Thr Thr Asp Val Thr Ser Ala Gly Val Tyr Phe Lys Ala
            180                 185                 190

Gly Gly Pro Ile Thr Tyr Lys Val Met Arg Glu Val Arg Ala Leu Ala
        195                 200                 205

Tyr Phe Val Asn Gly Thr Ala Gln Asp Val Ile Leu Cys Asp Gly Ser
    210                 215                 220

Pro Arg Gly Leu Leu Ala Cys Gln Tyr Asn Thr Gly Asn Phe Ser Asp
225                 230                 235                 240

Gly Phe Tyr Pro Phe Thr Asn Ser Ser Leu Val Lys Gln Lys Phe Ile
                245                 250                 255

Val Tyr Arg Glu Asn Ser Val Asn Thr Thr Phe Thr Leu His Asn Phe
            260                 265                 270

Thr Phe His Asn Glu Thr Gly Ala Asn Pro Asn Pro Ser Gly Val Gln
        275                 280                 285

Asn Ile Gln Thr Tyr Gln Thr Gln Thr Ala Gln Ser Gly Tyr Tyr Asn
    290                 295                 300

Phe Asn Phe Ser Phe Leu Ser Ser Phe Val Tyr Lys Glu Ser Asn Phe
305                 310                 315                 320

Met Tyr Gly Ser Tyr His Pro Ser Cys Asn Phe Arg Leu Glu Thr Ile
                325                 330                 335

Asn Asn Gly Leu Trp Phe Asn Ser Leu Ser Val Ser Ile Ala Tyr Gly
            340                 345                 350

Pro Leu Gln Gly Gly Cys Lys Gln Ser Val Phe Ser Gly Arg Ala Thr
        355                 360                 365

Cys Cys Tyr Ala Tyr Ser Tyr Gly Gly Pro Leu Leu Cys Lys Gly Val
    370                 375                 380

Tyr Ser Gly Glu Leu Asp His Asn Phe Glu Cys Gly Leu Leu Val Tyr
385                 390                 395                 400

Val Thr Lys Ser Gly Gly Ser Arg Ile Gln Thr Ala Thr Glu Pro Pro
                405                 410                 415

Val Ile Thr Gln His Asn Tyr Asn Asn Ile Thr Leu Asn Thr Cys Val
            420                 425                 430

Asp Tyr Asn Ile Tyr Gly Arg Thr Gly Gln Gly Phe Ile Thr Asn Val
        435                 440                 445

Thr Asp Ser Ala Val Ser Tyr Asn Tyr Leu Ala Asp Ala Gly Leu Ala
    450                 455                 460

Ile Leu Asp Thr Ser Gly Ser Ile Asp Ile Phe Val Val Gln Ser Glu
465                 470                 475                 480

Tyr Gly Leu Asn Tyr Tyr Lys Val Asn Pro Cys Glu Asp Val Asn Gln
                485                 490                 495

Gln Phe Val Val Ser Gly Gly Lys Leu Val Gly Ile Leu Thr Ser Arg
            500                 505                 510

Asn Glu Thr Gly Ser Gln Leu Leu Glu Asn Gln Phe Tyr Ile Lys Ile
        515                 520                 525

Thr Asn Gly Thr Arg Arg Phe Arg Arg Ser Ile Thr Glu Ser Val Glu
    530                 535                 540

Asn Cys Pro Tyr Val Ser Tyr Gly Lys Phe Cys Ile Lys Pro Asp Gly
545                 550                 555                 560
```

```
Ser Ile Ala Thr Ile Val Pro Lys Gln Leu Glu Gln Phe Val Ala Pro
                565                 570                 575

Leu Leu Asn Val Thr Glu Asn Val Leu Ile Pro Asn Ser Phe Asn Leu
            580                 585                 590

Thr Val Thr Asp Glu Tyr Ile Gln Thr Arg Met Asp Lys Val Gln Ile
        595                 600                 605

Asn Cys Leu Gln Tyr Ile Cys Gly Asn Ser Leu Glu Cys Arg Asn Leu
    610                 615                 620

Phe Gln Gln Tyr Gly Pro Val Cys Asp Asn Ile Leu Ser Val Val Asn
625                 630                 635                 640

Ser Val Gly Gln Lys Glu Asp Met Glu Leu Leu Asn Phe Tyr Ser Ser
                645                 650                 655

Thr Lys Pro Ala Gly Phe Asn Thr Pro Val Leu Ser Asn Val Ser Thr
            660                 665                 670

Gly Glu Phe Asn Ile Thr Leu Phe Leu Thr Thr Pro Ser Ser Pro Arg
        675                 680                 685

Arg Arg Ser Phe Ile Glu Asp Leu Leu Phe Thr Ser Val Glu Ser Val
    690                 695                 700

Gly Leu Pro Thr Asp Asp Ala Tyr Lys Asn Cys Thr Ala Gly Pro Leu
705                 710                 715                 720

Gly Phe Leu Lys Asp Leu Ala Cys Ala Arg Glu Tyr Asn Gly Leu Leu
                725                 730                 735

Val Leu Pro Pro Ile Ile Thr Ala Glu Met Gln Thr Leu Tyr Thr Ser
            740                 745                 750

Ser Leu Val Ala Ser Met Ala Phe Gly Gly Ile Thr Ala Ala Gly Ala
        755                 760                 765

Ile Pro Phe Ala Thr Gln Leu Gln Ala Arg Ile Asn His Leu Gly Ile
    770                 775                 780

Thr Gln Ser Leu Leu Leu Lys Asn Gln Glu Lys Ile Ala Ala Ser Phe
785                 790                 795                 800

Asn Lys Ala Ile Gly His Met Gln Glu Gly Phe Arg Ser Thr Ser Leu
                805                 810                 815

Ala Leu Gln Gln Ile Gln Asp Val Val Asn Lys Gln Ser Ala Ile Leu
            820                 825                 830

Thr Glu Thr Met Ala Ser Leu Asn Lys Asn Phe Gly Ala Ile Ser Ser
        835                 840                 845

Val Ile Gln Glu Ile Tyr Gln Gln Leu Asp Ala Ile Gln Ala Asn Ala
    850                 855                 860

Gln Val Asp Arg Leu Ile Thr Gly Arg Leu Ser Ser Leu Ser Val Leu
865                 870                 875                 880

Ala Ser Ala Lys Gln Ala Glu Tyr Ile Arg Val Ser Gln Gln Arg Glu
                885                 890                 895

Leu Ala Thr Gln Lys Ile Asn Glu Cys Val Lys Ser Gln Ser Ile Arg
            900                 905                 910

Tyr Ser Phe Cys Gly Asn Gly Arg His Val Leu Thr Ile Pro Gln Asn
        915                 920                 925

Ala Pro Asn Gly Ile Val Phe Ile His Phe Ser Tyr Thr Pro Asp Ser
    930                 935                 940

Phe Val Asn Val Thr Ala Ile Val Gly Phe Cys Val Lys Pro Ala Asn
945                 950                 955                 960

Ala Ser Gln Tyr Ala Ile Val Pro Ala Asn Gly Arg Gly Ile Phe Ile
                965                 970                 975
```

```
Gln Val Asn Gly Ser Tyr Tyr Ile Thr Ala Arg Asp Met Tyr Met Pro
            980                 985                 990

Arg Ala Ile Thr Ala Gly Asp Ile  Val Thr Leu Thr Ser  Cys Gln Ala
        995                 1000                1005

Asn Tyr  Val Ser Val Asn Lys  Thr Val Ile Thr Thr  Phe Val Asp
    1010                 1015                 1020

Asn Asp  Asp Phe Asp Phe Asn  Asp Glu Leu Ser Lys  Trp Trp Asn
    1025                 1030                 1035

Asp Thr  Lys His Glu Leu Pro  Asp Phe Asp Lys Phe  Asn Tyr Thr
    1040                 1045                 1050

Val Pro  Ile Leu Asp Ile Asp  Ser Glu Ile Asp Arg  Ile Gln Gly
    1055                 1060                 1065

Val Ile  Gln Gly Leu Asn Asp  Ser Leu Ile Asp Leu  Glu Lys Leu
    1070                 1075                 1080

Ser Ile  Leu Lys Thr Tyr Ile  Lys Trp Pro Trp Tyr  Val Trp Leu
    1085                 1090                 1095

Ala Ile  Ala Phe Ala Thr Ile  Ile Phe Ile Leu Ile  Leu Gly Trp
    1100                 1105                 1110

Val Phe  Phe Met Thr Gly Cys  Cys Gly Cys Cys Cys  Gly Cys Phe
    1115                 1120                 1125

Gly Ile  Met Pro Leu Met Ser  Lys Cys Gly Lys Lys  Ser Ser Tyr
    1130                 1135                 1140

Tyr Thr  Thr Phe Asp Asn Asp  Val Val Thr Glu Gln  Tyr Arg Pro
    1145                 1150                 1155

Lys Lys  Ser Val
    1160


<210> SEQ ID NO 7
<211> LENGTH: 1075
<212> TYPE: PRT
<213> ORGANISM: Avian infectious bronchitis virus

<400> SEQUENCE: 7

Ala Leu Tyr Asp Ser Ser Ser Tyr Val Tyr Tyr Tyr Gln Ser Ala Phe
1               5                   10                  15

Arg Pro Pro Asp Gly Trp His Leu His Gly Gly Ala Tyr Ala Val Val
            20                  25                  30

Asn Ile Ser Ser Glu Ser Asn Asn Ala Gly Ser Ser Ser Gly Cys Thr
        35                  40                  45

Val Gly Ile Ile His Gly Gly Arg Val Val Asn Ala Ser Ser Ile Ala
    50                  55                  60

Met Thr Ala Pro Ser Ser Gly Met Ala Trp Ser Ser Ser Gln Phe Cys
65                  70                  75                  80

Thr Ala Tyr Cys Asn Phe Ser Asp Thr Thr Val Phe Val Thr His Cys
                85                  90                  95

Tyr Lys His Gly Gly Cys Pro Ile Thr Gly Met Leu Gln Gln His Ser
            100                 105                 110

Ile Arg Val Ser Ala Met Lys Asn Gly Gln Leu Phe Tyr Asn Leu Thr
        115                 120                 125

Val Ser Val Ala Lys Tyr Pro Thr Phe Lys Ser Phe Gln Cys Val Asn
    130                 135                 140

Asn Leu Thr Ser Val Tyr Leu Asn Gly Asp Leu Val Tyr Thr Ser Asn
145                 150                 155                 160

Glu Thr Thr Asp Val Thr Ser Ala Gly Val Tyr Phe Lys Ala Gly Gly
                165                 170                 175
```

```
Pro Ile Thr Tyr Lys Val Met Arg Glu Val Arg Ala Leu Ala Tyr Phe
            180                 185                 190

Val Asn Gly Thr Ala Gln Asp Val Ile Leu Cys Asp Gly Ser Pro Arg
        195                 200                 205

Gly Leu Leu Ala Cys Gln Tyr Asn Thr Gly Asn Phe Ser Asp Gly Phe
    210                 215                 220

Tyr Pro Phe Thr Asn Ser Ser Leu Val Lys Gln Lys Phe Ile Val Tyr
225                 230                 235                 240

Arg Glu Asn Ser Val Asn Thr Thr Phe Thr Leu His Asn Phe Thr Phe
                245                 250                 255

His Asn Glu Thr Gly Ala Asn Pro Asn Pro Ser Gly Val Gln Asn Ile
            260                 265                 270

Gln Thr Tyr Gln Thr Gln Thr Ala Gln Ser Gly Tyr Tyr Asn Phe Asn
        275                 280                 285

Phe Ser Phe Leu Ser Ser Phe Val Tyr Lys Glu Ser Asn Phe Met Tyr
    290                 295                 300

Gly Ser Tyr His Pro Ser Cys Asn Phe Arg Leu Glu Thr Ile Asn Asn
305                 310                 315                 320

Gly Leu Trp Phe Asn Ser Leu Ser Val Ser Ile Ala Tyr Gly Pro Leu
                325                 330                 335

Gln Gly Gly Cys Lys Gln Ser Val Phe Ser Gly Arg Ala Thr Cys Cys
            340                 345                 350

Tyr Ala Tyr Ser Tyr Gly Gly Pro Leu Leu Cys Lys Gly Val Tyr Ser
        355                 360                 365

Gly Glu Leu Asp His Asn Phe Glu Cys Gly Leu Leu Val Tyr Val Thr
    370                 375                 380

Lys Ser Gly Gly Ser Arg Ile Gln Thr Ala Thr Glu Pro Pro Val Ile
385                 390                 395                 400

Thr Gln His Asn Tyr Asn Asn Ile Thr Leu Asn Thr Cys Val Asp Tyr
                405                 410                 415

Asn Ile Tyr Gly Arg Thr Gly Gln Gly Phe Ile Thr Asn Val Thr Asp
            420                 425                 430

Ser Ala Val Ser Tyr Asn Tyr Leu Ala Asp Ala Gly Leu Ala Ile Leu
        435                 440                 445

Asp Thr Ser Gly Ser Ile Asp Ile Phe Val Val Gln Ser Glu Tyr Gly
    450                 455                 460

Leu Asn Tyr Tyr Lys Val Asn Pro Cys Glu Asp Val Asn Gln Gln Phe
465                 470                 475                 480

Val Val Ser Gly Gly Lys Leu Val Gly Ile Leu Thr Ser Arg Asn Glu
                485                 490                 495

Thr Gly Ser Gln Leu Leu Glu Asn Gln Phe Tyr Ile Lys Ile Thr Asn
            500                 505                 510

Gly Thr Arg Arg Phe Arg Arg Ser Ile Thr Glu Ser Val Glu Asn Cys
        515                 520                 525

Pro Tyr Val Ser Tyr Gly Lys Phe Cys Ile Lys Pro Asp Gly Ser Ile
    530                 535                 540

Ala Thr Ile Val Pro Lys Gln Leu Glu Gln Phe Val Ala Pro Leu Leu
545                 550                 555                 560

Asn Val Thr Glu Asn Val Leu Ile Pro Asn Ser Phe Asn Leu Thr Val
                565                 570                 575

Thr Asp Glu Tyr Ile Gln Thr Arg Met Asp Lys Val Gln Ile Asn Cys
            580                 585                 590
```

```
Leu Gln Tyr Ile Cys Gly Asn Ser Leu Glu Cys Arg Asn Leu Phe Gln
        595                 600                 605

Gln Tyr Gly Pro Val Cys Asp Asn Ile Leu Ser Val Val Asn Ser Val
    610                 615                 620

Gly Gln Lys Glu Asp Met Glu Leu Leu Asn Phe Tyr Ser Ser Thr Lys
625                 630                 635                 640

Pro Ala Gly Phe Asn Thr Pro Val Leu Ser Asn Val Ser Thr Gly Glu
                645                 650                 655

Phe Asn Ile Thr Leu Phe Leu Thr Thr Pro Ser Ser Pro Arg Arg Arg
            660                 665                 670

Ser Phe Ile Glu Asp Leu Leu Phe Thr Ser Val Glu Ser Val Gly Leu
        675                 680                 685

Pro Thr Asp Asp Ala Tyr Lys Asn Cys Thr Ala Gly Pro Leu Gly Phe
    690                 695                 700

Leu Lys Asp Leu Ala Cys Ala Arg Glu Tyr Asn Gly Leu Leu Val Leu
705                 710                 715                 720

Pro Pro Ile Ile Thr Ala Glu Met Gln Thr Leu Tyr Thr Ser Ser Leu
                725                 730                 735

Val Ala Ser Met Ala Phe Gly Gly Ile Thr Ala Ala Gly Ala Ile Pro
            740                 745                 750

Phe Ala Thr Gln Leu Gln Ala Arg Ile Asn His Leu Gly Ile Thr Gln
        755                 760                 765

Ser Leu Leu Leu Lys Asn Gln Glu Lys Ile Ala Ala Ser Phe Asn Lys
    770                 775                 780

Ala Ile Gly His Met Gln Glu Gly Phe Arg Ser Thr Ser Leu Ala Leu
785                 790                 795                 800

Gln Gln Ile Gln Asp Val Val Asn Lys Gln Ser Ala Ile Leu Thr Glu
                805                 810                 815

Thr Met Ala Ser Leu Asn Lys Asn Phe Gly Ala Ile Ser Ser Val Ile
            820                 825                 830

Gln Glu Ile Tyr Gln Gln Leu Asp Ala Ile Gln Ala Asn Ala Gln Val
        835                 840                 845

Asp Arg Leu Ile Thr Gly Arg Leu Ser Ser Leu Ser Val Leu Ala Ser
    850                 855                 860

Ala Lys Gln Ala Glu Tyr Ile Arg Val Ser Gln Gln Arg Glu Leu Ala
865                 870                 875                 880

Thr Gln Lys Ile Asn Glu Cys Val Lys Ser Gln Ser Ile Arg Tyr Ser
                885                 890                 895

Phe Cys Gly Asn Gly Arg His Val Leu Thr Ile Pro Gln Asn Ala Pro
            900                 905                 910

Asn Gly Ile Val Phe Ile His Phe Ser Tyr Thr Pro Asp Ser Phe Val
        915                 920                 925

Asn Val Thr Ala Ile Val Gly Phe Cys Val Lys Pro Ala Asn Ala Ser
    930                 935                 940

Gln Tyr Ala Ile Val Pro Ala Asn Gly Arg Gly Ile Phe Ile Gln Val
945                 950                 955                 960

Asn Gly Ser Tyr Tyr Ile Thr Ala Arg Asp Met Tyr Met Pro Arg Ala
                965                 970                 975

Ile Thr Ala Gly Asp Ile Val Thr Leu Thr Ser Cys Gln Ala Asn Tyr
            980                 985                 990

Val Ser Val Asn Lys Thr Val Ile  Thr Thr Phe Val Asp  Asn Asp Asp
        995                 1000                1005

Phe Asp  Phe Asn Asp Glu Leu  Ser Lys Trp Trp Asn  Asp Thr Lys
```

```
    1010                1015                1020

His Glu  Leu Pro Asp Phe Asp  Lys Phe Asn Tyr Thr  Val Pro Ile
    1025                1030                1035

Leu Asp  Ile Asp Ser Glu Ile  Asp Arg Ile Gln Gly  Val Ile Gln
    1040                1045                1050

Gly Leu  Asn Asp Ser Leu Ile  Asp Leu Glu Lys Leu  Ser Ile Leu
    1055                1060                1065

Lys Thr  Tyr Ile Lys Trp Pro
    1070                1075


<210> SEQ ID NO 8
<211> LENGTH: 1156
<212> TYPE: PRT
<213> ORGANISM: Avian infectious bronchitis virus

<400> SEQUENCE: 8

Met Leu Val Lys Ser Leu Phe Leu Val Thr Ile Leu Cys Ala Leu Cys
1               5                   10                  15

Ser Ala Asn Leu Phe Asp Ser Asp Asn Asn Tyr Val Tyr Tyr Tyr Gln
            20                  25                  30

Ser Ala Phe Arg Pro Pro Asn Gly Trp His Leu Gln Gly Gly Ala Tyr
        35                  40                  45

Ala Val Val Ser Ser Thr Asn Tyr Thr Asn Asn Ala Gly Ser Ala His
    50                  55                  60

Gly Cys Thr Val Gly Val Ile Lys Asp Val Tyr Asn Gln Ser Val Ala
65                  70                  75                  80

Ser Ile Ala Met Thr Ala Pro Leu Gln Gly Met Ala Trp Ser Lys Ser
                85                  90                  95

Gln Phe Cys Ser Ala His Cys Asn Phe Ser Glu Ile Thr Val Phe Val
            100                 105                 110

Thr His Cys Tyr Ser Ser Gly Ser Gly Ser Cys Pro Ile Thr Gly Met
        115                 120                 125

Ile Pro Arg Asp His Ile Arg Ile Ser Ala Met Lys Asn Gly Ser Leu
    130                 135                 140

Phe Tyr Asn Leu Thr Val Ser Val Ser Lys Tyr Pro Asn Phe Lys Ser
145                 150                 155                 160

Phe Gln Cys Val Asn Asn Phe Thr Ser Val Tyr Leu Asn Gly Asp Leu
                165                 170                 175

Val Phe Thr Ser Asn Lys Thr Thr Asp Val Thr Ser Ala Gly Val Tyr
            180                 185                 190

Phe Lys Ala Gly Gly Pro Val Asn Tyr Ser Ile Met Lys Glu Phe Lys
        195                 200                 205

Val Leu Ala Tyr Phe Val Asn Gly Thr Ala Gln Asp Val Val Leu Cys
    210                 215                 220

Asp Asn Ser Pro Lys Gly Leu Leu Ala Cys Gln Tyr Asn Thr Gly Asn
225                 230                 235                 240

Phe Ser Asp Gly Phe Tyr Pro Phe Thr Asn Ser Thr Leu Val Arg Glu
                245                 250                 255

Lys Phe Ile Val Tyr Arg Glu Ser Ser Val Asn Thr Thr Leu Ala Leu
            260                 265                 270

Thr Asn Phe Thr Phe Ser Asn Val Ser Asn Ala Gln Pro Asn Ser Gly
        275                 280                 285

Gly Val Asn Thr Phe His Leu Tyr Gln Thr Gln Thr Ala Gln Ser Gly
    290                 295                 300
```

```
Tyr Tyr Asn Phe Asn Leu Ser Phe Leu Ser Gln Phe Val Tyr Lys Ala
305                 310                 315                 320

Ser Asp Phe Met Tyr Gly Ser Tyr His Pro Ser Cys Ser Phe Arg Pro
                325                 330                 335

Glu Thr Ile Asn Ser Gly Leu Trp Phe Asn Ser Leu Ser Val Ser Leu
            340                 345                 350

Thr Tyr Gly Pro Leu Gln Gly Gly Cys Lys Gln Ser Val Phe Ser Gly
        355                 360                 365

Lys Ala Thr Cys Cys Tyr Ala Tyr Ser Tyr Arg Gly Pro Met Ala Cys
    370                 375                 380

Lys Gly Val Tyr Ser Gly Glu Leu Ser Thr Asn Phe Glu Cys Gly Leu
385                 390                 395                 400

Leu Val Tyr Val Thr Lys Ser Asp Gly Ser Arg Ile Gln Thr Arg Thr
                405                 410                 415

Glu Pro Leu Val Leu Thr Gln Tyr Asn Tyr Asn Asn Ile Thr Leu Asp
            420                 425                 430

Lys Cys Val Ala Tyr Asn Ile Tyr Gly Arg Val Gly Gln Gly Phe Ile
        435                 440                 445

Thr Asn Val Thr Asp Ser Ala Ala Asn Phe Ser Tyr Leu Ala Asp Gly
    450                 455                 460

Gly Leu Ala Ile Leu Asp Thr Ser Gly Ala Ile Asp Val Phe Val Val
465                 470                 475                 480

Gln Gly Ile Tyr Gly Leu Asn Tyr Tyr Lys Val Asn Pro Cys Glu Asp
                485                 490                 495

Val Asn Gln Gln Phe Val Val Ser Gly Gly Asn Ile Val Gly Ile Leu
            500                 505                 510

Thr Ser Arg Asn Glu Thr Gly Ser Glu Gln Val Glu Asn Gln Phe Tyr
        515                 520                 525

Val Lys Leu Thr Asn Ser Ser His Arg Arg Lys Arg Ser Ile Gly Gln
    530                 535                 540

Asn Val Thr Ser Cys Pro Tyr Val Ser Tyr Gly Arg Phe Cys Ile Glu
545                 550                 555                 560

Pro Asp Gly Ser Leu Lys Met Ile Val Pro Glu Glu Leu Lys Gln Phe
                565                 570                 575

Val Ala Pro Leu Leu Asn Ile Thr Glu Ser Val Leu Ile Pro Asn Ser
            580                 585                 590

Phe Asn Leu Thr Val Thr Asp Glu Tyr Ile Gln Thr Arg Met Asp Lys
        595                 600                 605

Val Gln Ile Asn Cys Leu Gln Tyr Val Cys Gly Asn Ser Leu Glu Cys
    610                 615                 620

Arg Lys Leu Phe Gln Gln Tyr Gly Pro Val Cys Asp Asn Ile Leu Ser
625                 630                 635                 640

Val Val Asn Ser Val Ser Gln Lys Glu Asp Met Glu Leu Leu Ser Phe
                645                 650                 655

Tyr Ser Ser Thr Lys Pro Lys Gly Tyr Asp Thr Pro Val Leu Ser Asn
            660                 665                 670

Val Ser Thr Gly Glu Phe Asn Ile Ser Leu Leu Leu Lys Pro Pro Ser
        675                 680                 685

Ser Pro Ser Gly Arg Ser Phe Ile Glu Glu Leu Leu Phe Thr Ser Val
    690                 695                 700

Glu Thr Val Gly Leu Pro Thr Asp Ala Glu Tyr Lys Lys Cys Thr Ala
705                 710                 715                 720

Gly Pro Leu Gly Thr Leu Lys Asp Leu Ile Cys Ala Arg Glu Tyr Asn
```

```
                725                 730                 735

Gly Leu Leu Val Leu Pro Pro Ile Ile Thr Ala Asp Met Gln Thr Met
            740                 745                 750

Tyr Thr Ala Ser Leu Val Gly Ala Met Ala Phe Gly Gly Ile Thr Ser
        755                 760                 765

Ala Ala Ala Ile Pro Phe Ala Thr Gln Ile Gln Ala Arg Ile Asn His
    770                 775                 780

Leu Gly Ile Thr Gln Ser Leu Leu Met Lys Asn Gln Glu Lys Ile Ala
785                 790                 795                 800

Ala Ser Phe Asn Lys Ala Ile Gly His Met Gln Glu Gly Phe Arg Ser
                805                 810                 815

Thr Ser Leu Ala Leu Gln Gln Ile Gln Asp Val Val Asn Lys Gln Ser
            820                 825                 830

Ala Ile Leu Thr Glu Thr Met Asn Ser Leu Asn Lys Asn Phe Gly Ala
        835                 840                 845

Ile Thr Ser Val Ile Gln Asp Ile Tyr Ala Gln Leu Asp Ala Ile Gln
    850                 855                 860

Ala Asp Ala Gln Val Asp Arg Leu Ile Thr Gly Arg Leu Ser Ser Leu
865                 870                 875                 880

Ser Val Leu Ala Ser Ala Lys Gln Ser Glu Tyr Ile Arg Val Ser Gln
                885                 890                 895

Gln Arg Glu Leu Ala Thr Gln Lys Ile Asn Glu Cys Val Lys Ser Gln
            900                 905                 910

Ser Asn Arg Tyr Gly Phe Cys Gly Ser Gly Arg His Val Leu Ser Ile
        915                 920                 925

Pro Gln Asn Ala Pro Asn Gly Ile Val Phe Ile His Phe Thr Tyr Thr
    930                 935                 940

Pro Glu Ser Phe Val Asn Val Thr Ala Ile Val Gly Phe Cys Val Asn
945                 950                 955                 960

Pro Ala Asn Ala Ser Gln Tyr Ala Ile Val Pro Ala Asn Gly Arg Gly
                965                 970                 975

Ile Phe Ile Gln Val Asn Gly Thr Tyr Tyr Ile Thr Ala Arg Asp Met
            980                 985                 990

Tyr Met Pro Arg Asp Ile Thr Ala  Gly Asp Ile Val Thr  Leu Thr Ser
        995                 1000                1005

Cys Gln  Ala Asn Tyr Val Asn  Val Asn Lys Thr Val  Ile Thr Thr
    1010                1015                1020

Phe Val  Glu Asp Asp Asp Phe  Asp Phe Asp Asp Glu  Leu Ser Lys
    1025                1030                1035

Trp Trp  Asn Asp Thr Lys His  Gln Leu Pro Asp Phe  Asp Asp Phe
    1040                1045                1050

Asn Tyr  Thr Val Pro Ile Leu  Asn Ile Ser Gly Glu  Ile Asp Tyr
    1055                1060                1065

Ile Gln  Gly Val Ile Gln Gly  Leu Asn Asp Ser Leu  Ile Asp Leu
    1070                1075                1080

Glu Glu  Leu Ser Ile Ile Lys  Thr Tyr Ile Lys Trp  Pro Trp Tyr
    1085                1090                1095

Val Trp  Leu Ala Ile Phe Phe  Ala Ile Ile Ile Phe  Ile Leu Ile
    1100                1105                1110

Leu Gly  Trp Val Phe Phe Met  Thr Gly Cys Cys Gly  Cys Cys Cys
    1115                1120                1125

Gly Cys  Phe Gly Ile Ile Pro  Leu Met Ser Lys Cys  Gly Lys Lys
    1130                1135                1140
```

```
Ser Ser  Tyr Tyr Thr Thr Phe  Asp Asn Asp Val Val  Thr
    1145                 1150                 1155


<210> SEQ ID NO 9
<211> LENGTH: 1078
<212> TYPE: PRT
<213> ORGANISM: Avian infectious bronchitis virus

<400> SEQUENCE: 9

Asn Leu Phe Asp Ser Asp Asn Asn Tyr Val Tyr Tyr Tyr Gln Ser Ala
1               5                   10                  15

Phe Arg Pro Pro Asn Gly Trp His Leu Gln Gly Gly Ala Tyr Ala Val
            20                  25                  30

Val Ser Ser Thr Asn Tyr Thr Asn Asn Ala Gly Ser Ala His Gly Cys
        35                  40                  45

Thr Val Gly Val Ile Lys Asp Val Tyr Asn Gln Ser Val Ala Ser Ile
    50                  55                  60

Ala Met Thr Ala Pro Leu Gln Gly Met Ala Trp Ser Lys Ser Gln Phe
65                  70                  75                  80

Cys Ser Ala His Cys Asn Phe Ser Glu Ile Thr Val Phe Val Thr His
                85                  90                  95

Cys Tyr Ser Ser Gly Ser Gly Ser Cys Pro Ile Thr Gly Met Ile Pro
            100                 105                 110

Arg Asp His Ile Arg Ile Ser Ala Met Lys Asn Gly Ser Leu Phe Tyr
        115                 120                 125

Asn Leu Thr Val Ser Val Ser Lys Tyr Pro Asn Phe Lys Ser Phe Gln
    130                 135                 140

Cys Val Asn Asn Phe Thr Ser Val Tyr Leu Asn Gly Asp Leu Val Phe
145                 150                 155                 160

Thr Ser Asn Lys Thr Thr Asp Val Thr Ser Ala Gly Val Tyr Phe Lys
                165                 170                 175

Ala Gly Gly Pro Val Asn Tyr Ser Ile Met Lys Glu Phe Lys Val Leu
            180                 185                 190

Ala Tyr Phe Val Asn Gly Thr Ala Gln Asp Val Val Leu Cys Asp Asn
        195                 200                 205

Ser Pro Lys Gly Leu Leu Ala Cys Gln Tyr Asn Thr Gly Asn Phe Ser
    210                 215                 220

Asp Gly Phe Tyr Pro Phe Thr Asn Ser Thr Leu Val Arg Glu Lys Phe
225                 230                 235                 240

Ile Val Tyr Arg Glu Ser Ser Val Asn Thr Thr Leu Ala Leu Thr Asn
                245                 250                 255

Phe Thr Phe Ser Asn Val Ser Asn Ala Gln Pro Asn Ser Gly Gly Val
            260                 265                 270

Asn Thr Phe His Leu Tyr Gln Thr Gln Thr Ala Gln Ser Gly Tyr Tyr
        275                 280                 285

Asn Phe Asn Leu Ser Phe Leu Ser Gln Phe Val Tyr Lys Ala Ser Asp
    290                 295                 300

Phe Met Tyr Gly Ser Tyr His Pro Ser Cys Ser Phe Arg Pro Glu Thr
305                 310                 315                 320

Ile Asn Ser Gly Leu Trp Phe Asn Ser Leu Ser Val Ser Leu Thr Tyr
                325                 330                 335

Gly Pro Leu Gln Gly Gly Cys Lys Gln Ser Val Phe Ser Gly Lys Ala
            340                 345                 350

Thr Cys Cys Tyr Ala Tyr Ser Tyr Arg Gly Pro Met Ala Cys Lys Gly
```

```
        355                 360                 365

Val Tyr Ser Gly Glu Leu Ser Thr Asn Phe Glu Cys Gly Leu Leu Val
    370                 375                 380

Tyr Val Thr Lys Ser Asp Gly Ser Arg Ile Gln Thr Arg Thr Glu Pro
385                 390                 395                 400

Leu Val Leu Thr Gln Tyr Asn Tyr Asn Asn Ile Thr Leu Asp Lys Cys
                405                 410                 415

Val Ala Tyr Asn Ile Tyr Gly Arg Val Gly Gln Gly Phe Ile Thr Asn
            420                 425                 430

Val Thr Asp Ser Ala Ala Asn Phe Ser Tyr Leu Ala Asp Gly Gly Leu
        435                 440                 445

Ala Ile Leu Asp Thr Ser Gly Ala Ile Asp Val Phe Val Val Gln Gly
    450                 455                 460

Ile Tyr Gly Leu Asn Tyr Tyr Lys Val Asn Pro Cys Glu Asp Val Asn
465                 470                 475                 480

Gln Gln Phe Val Val Ser Gly Gly Asn Ile Val Gly Ile Leu Thr Ser
                485                 490                 495

Arg Asn Glu Thr Gly Ser Glu Gln Val Glu Asn Gln Phe Tyr Val Lys
            500                 505                 510

Leu Thr Asn Ser Ser His Arg Arg Lys Arg Ser Ile Gly Gln Asn Val
        515                 520                 525

Thr Ser Cys Pro Tyr Val Ser Tyr Gly Arg Phe Cys Ile Glu Pro Asp
    530                 535                 540

Gly Ser Leu Lys Met Ile Val Pro Glu Glu Leu Lys Gln Phe Val Ala
545                 550                 555                 560

Pro Leu Leu Asn Ile Thr Glu Ser Val Leu Ile Pro Asn Ser Phe Asn
                565                 570                 575

Leu Thr Val Thr Asp Glu Tyr Ile Gln Thr Arg Met Asp Lys Val Gln
            580                 585                 590

Ile Asn Cys Leu Gln Tyr Val Cys Gly Asn Ser Leu Glu Cys Arg Lys
        595                 600                 605

Leu Phe Gln Gln Tyr Gly Pro Val Cys Asp Asn Ile Leu Ser Val Val
    610                 615                 620

Asn Ser Val Ser Gln Lys Glu Asp Met Glu Leu Leu Ser Phe Tyr Ser
625                 630                 635                 640

Ser Thr Lys Pro Lys Gly Tyr Asp Thr Pro Val Leu Ser Asn Val Ser
                645                 650                 655

Thr Gly Glu Phe Asn Ile Ser Leu Leu Leu Lys Pro Pro Ser Ser Pro
            660                 665                 670

Ser Gly Arg Ser Phe Ile Glu Glu Leu Leu Phe Thr Ser Val Glu Thr
        675                 680                 685

Val Gly Leu Pro Thr Asp Ala Glu Tyr Lys Lys Cys Thr Ala Gly Pro
    690                 695                 700

Leu Gly Thr Leu Lys Asp Leu Ile Cys Ala Arg Glu Tyr Asn Gly Leu
705                 710                 715                 720

Leu Val Leu Pro Pro Ile Ile Thr Ala Asp Met Gln Thr Met Tyr Thr
                725                 730                 735

Ala Ser Leu Val Gly Ala Met Ala Phe Gly Gly Ile Thr Ser Ala Ala
            740                 745                 750

Ala Ile Pro Phe Ala Thr Gln Ile Gln Ala Arg Ile Asn His Leu Gly
        755                 760                 765

Ile Thr Gln Ser Leu Leu Met Lys Asn Gln Glu Lys Ile Ala Ala Ser
    770                 775                 780
```

```
Phe Asn Lys Ala Ile Gly His Met Gln Glu Gly Phe Arg Ser Thr Ser
785                 790                 795                 800

Leu Ala Leu Gln Gln Ile Gln Asp Val Val Asn Lys Gln Ser Ala Ile
                805                 810                 815

Leu Thr Glu Thr Met Asn Ser Leu Asn Lys Asn Phe Gly Ala Ile Thr
            820                 825                 830

Ser Val Ile Gln Asp Ile Tyr Ala Gln Leu Asp Ala Ile Gln Ala Asp
        835                 840                 845

Ala Gln Val Asp Arg Leu Ile Thr Gly Arg Leu Ser Ser Leu Ser Val
    850                 855                 860

Leu Ala Ser Ala Lys Gln Ser Glu Tyr Ile Arg Val Ser Gln Gln Arg
865                 870                 875                 880

Glu Leu Ala Thr Gln Lys Ile Asn Glu Cys Val Lys Ser Gln Ser Asn
                885                 890                 895

Arg Tyr Gly Phe Cys Gly Ser Gly Arg His Val Leu Ser Ile Pro Gln
            900                 905                 910

Asn Ala Pro Asn Gly Ile Val Phe Ile His Phe Thr Tyr Thr Pro Glu
        915                 920                 925

Ser Phe Val Asn Val Thr Ala Ile Val Gly Phe Cys Val Asn Pro Ala
    930                 935                 940

Asn Ala Ser Gln Tyr Ala Ile Val Pro Ala Asn Gly Arg Gly Ile Phe
945                 950                 955                 960

Ile Gln Val Asn Gly Thr Tyr Tyr Ile Thr Ala Arg Asp Met Tyr Met
                965                 970                 975

Pro Arg Asp Ile Thr Ala Gly Asp Ile Val Thr Leu Thr Ser Cys Gln
            980                 985                 990

Ala Asn Tyr Val Asn Val Asn Lys  Thr Val Ile Thr Thr  Phe Val Glu
        995                 1000                 1005

Asp Asp  Asp Phe Asp Phe Asp  Asp Glu Leu Ser Lys  Trp Trp Asn
    1010                 1015                 1020

Asp Thr  Lys His Gln Leu Pro  Asp Phe Asp Asp Phe  Asn Tyr Thr
    1025                 1030                 1035

Val Pro  Ile Leu Asn Ile Ser  Gly Glu Ile Asp Tyr  Ile Gln Gly
    1040                 1045                 1050

Val Ile  Gln Gly Leu Asn Asp  Ser Leu Ile Asp Leu  Glu Glu Leu
    1055                 1060                 1065

Ser Ile  Ile Lys Thr Tyr Ile  Lys Trp Pro
    1070                 1075
```

<210> SEQ ID NO 10
<211> LENGTH: 1166
<212> TYPE: PRT
<213> ORGANISM: Avian infectious bronchitis virus

<400> SEQUENCE: 10

```
Met Leu Gly Lys Ser Leu Phe Ile Val Thr Leu Leu Phe Ala Leu Cys
1               5                   10                  15

Ser Ala Ala Leu Phe Asp Asn Asn Glu Thr Val Tyr Tyr Tyr Gln Ser
            20                  25                  30

Ala Phe Arg Pro Ala Asp Gly Trp His Leu His Gly Gly Ala Tyr Ala
        35                  40                  45

Val Val Asn Val Ser Leu Glu Thr Asn Asn Ala Gly Thr Ala Ser Gln
    50                  55                  60

Cys Ile Ala Gly Ala Ile Ser Trp Ser Lys Asn Phe Ser Ala Ser Ala
```

-continued

```
65                  70                  75                  80

Val Ala Met Thr Ala Pro Glu Leu Gly Met Thr Trp Ser Thr Gly Gln
                85                  90                  95

Phe Cys Thr Ala His Cys Asn Phe Ser Asp Phe Thr Val Phe Val Thr
            100                 105                 110

His Cys Phe Lys His Gly Asn Gly Leu Cys Pro Leu Thr Gly Leu Ile
        115                 120                 125

Pro Ser Gly Phe Ile Arg Val Ser Ala Met Arg Lys Gly Ser Asn Ser
    130                 135                 140

Leu Phe Tyr Asn Leu Thr Val Ser Val Thr Lys Tyr Pro Arg Phe Lys
145                 150                 155                 160

Ser Leu Gln Cys Val Asn Asn Tyr Thr Ser Val Tyr Leu Asn Gly Asp
                165                 170                 175

Leu Val Phe Thr Ser Asn Glu Thr Lys Pro Val Ser Ala Ala Gly Val
            180                 185                 190

Ser Phe Lys Ala Gly Gly Pro Ile Thr Tyr Lys Thr Met Ser Glu Val
        195                 200                 205

Lys Val Leu Ala Tyr Phe Val Asn Gly Thr Ala Gln Thr Val Ile Pro
    210                 215                 220

Cys Asp Gly Ser Pro Arg Gly Leu Leu Ala Cys Gln Tyr Asn Thr Gly
225                 230                 235                 240

Asn Phe Ser Asp Gly Phe Tyr Pro Tyr Thr Asn Ser Ser Leu Val Lys
                245                 250                 255

Glu Arg Phe Ile Val Tyr Arg Glu Ser Ser Val Asn Thr Thr Leu Val
            260                 265                 270

Leu Thr Asn Phe Thr Phe Ser Asn Val Ser Asn Ala Pro Pro Asn Thr
        275                 280                 285

Gly Gly Val His Ser Ile Val Leu His Gln Thr Gln Thr Ala Gln Ser
    290                 295                 300

Gly Tyr Tyr Asn Phe Asn Phe Ser Phe Leu Ser Ser Phe Arg Tyr Val
305                 310                 315                 320

Glu Ser Asp Phe Met Tyr Gly Ser Tyr His Pro Lys Cys Ser Phe Arg
                325                 330                 335

Leu Glu Thr Ile Asn Asn Gly Leu Trp Phe Asn Ser Leu Ser Val Ser
            340                 345                 350

Leu Gly Tyr Gly Pro Leu Gln Gly Gly Cys Lys Gln Ser Val Phe Asn
        355                 360                 365

Asn Met Ala Thr Cys Cys Tyr Ala Tyr Ser Tyr Ser Gly Pro Thr Leu
    370                 375                 380

Cys Lys Gly Val Tyr Ser Gly Gln Leu Gln Lys Thr Phe Glu Cys Gly
385                 390                 395                 400

Leu Leu Val Phe Val Thr Lys Ser Asp Gly Ser Arg Ile Gln Thr Arg
                405                 410                 415

Asn Glu Pro Leu Val Leu Thr Gln His Asn Tyr Asn Asn Ile Thr Leu
            420                 425                 430

Asn Lys Cys Val Glu Tyr Asn Ile Tyr Gly Arg Val Gly Gln Gly Leu
        435                 440                 445

Ile Thr Asn Ile Thr Asp Ser Ala Ala Asn His Gly Tyr Leu Ala Asp
    450                 455                 460

Gly Gly Leu Ala Val Leu Asp Thr Ser Gly Ala Ile Asp Val Phe Val
465                 470                 475                 480

Val Gln Gly Val Tyr Gly Leu Thr Tyr Tyr Lys Val Asn Pro Cys Glu
                485                 490                 495
```

```
Asp Val Asn Gln Gln Phe Val Val Ser Gly Gly Gln Leu Val Gly Ile
            500                 505                 510

Leu Thr Ser Arg Asn Glu Thr Gly Ser Gln Pro Ile Glu Asn Arg Phe
        515                 520                 525

Tyr Val Lys Phe Pro Asn Ser Arg Arg Arg Thr Gly Arg Ser Thr Ile
    530                 535                 540

Ala Asn Val Thr Asn Cys Pro Tyr Val Ser Tyr Gly Lys Phe Cys Ile
545                 550                 555                 560

Lys Pro Asp Gly Ser Val Ser Glu Ile Val Pro Gln Glu Ile Glu His
                565                 570                 575

Phe Val Ala Pro Leu Leu Asn Val Thr Glu His Val Leu Ile Pro Asn
            580                 585                 590

Ser Phe Asn Leu Thr Val Thr Asp Glu Tyr Ile Gln Thr Arg Met Asp
        595                 600                 605

Lys Ile Gln Ile Asn Cys Arg Gln Tyr Val Cys Gly Asn Ser Ile Glu
    610                 615                 620

Cys Arg Lys Leu Phe Gln Gln Tyr Gly Pro Val Cys Asp Asn Ile Leu
625                 630                 635                 640

Ser Val Val Asn Thr Val Gly Gln Arg Glu Asp Met Glu Leu Leu Ser
                645                 650                 655

Phe Tyr Ser Ser Thr Lys Pro Lys Asp Tyr Asn Ile Pro Ile Phe Ser
            660                 665                 670

Asn Val Ser Thr Gly Asp Phe Asn Ile Ser Leu Leu Leu Thr Pro Pro
        675                 680                 685

Asn Ser Pro Thr Gly Arg Ser Phe Ile Glu Asp Ile Leu Phe Thr Ser
    690                 695                 700

Val Glu Ser Val Gly Leu Pro Thr Asp Glu Glu Tyr Lys Lys Cys Thr
705                 710                 715                 720

Ala Gly Pro Leu Gly Phe Val Lys Asp Leu Val Cys Ala Arg Glu Tyr
                725                 730                 735

Asn Gly Leu Leu Val Leu Pro Pro Ile Ile Thr Ala Asp Met Gln Thr
            740                 745                 750

Met Tyr Thr Ser Thr Leu Val Ala Ser Met Ala Leu Gly Gly Ile Thr
        755                 760                 765

Ala Ala Gly Ala Ile Pro Phe Ala Thr Gln Leu Gln Ala Arg Ile Asn
    770                 775                 780

His Leu Gly Ile Thr Gln Ser Leu Leu Leu Lys Asn Gln Glu Lys Ile
785                 790                 795                 800

Ala Ala Ser Phe Asn Lys Ala Ile Gly His Met Gln Glu Gly Phe Arg
                805                 810                 815

Ser Thr Ser Leu Ala Leu Gln Gln Ile Gln Asp Val Val Asn Lys Gln
            820                 825                 830

Ser Ser Ile Leu Thr Glu Thr Met Ala Ser Leu Asn Lys Asn Phe Gly
        835                 840                 845

Ala Ile Ser Ser Val Leu Gln Asp Ile Tyr Gln Gln Leu Asp Ala Ile
    850                 855                 860

Gln Ala Asp Ala Gln Val Asp Arg Ile Ile Thr Gly Arg Leu Ser Ser
865                 870                 875                 880

Leu Ser Val Leu Ala Ser Ala Lys Gln Ser Glu Tyr Tyr Arg Val Ser
                885                 890                 895

Gln Gln Arg Glu Leu Ala Thr Gln Lys Ile Asn Glu Cys Val Lys Ser
            900                 905                 910
```

```
Gln Ser Thr Arg Tyr Ser Phe Cys Gly Asn Gly Arg His Val Leu Thr
        915                 920                 925

Ile Pro Gln Asn Ala Pro Asn Gly Ile Val Phe Ile His Phe Thr Tyr
    930                 935                 940

Thr Pro Glu Ser Phe Val Asn Val Thr Ala Ile Val Gly Phe Cys Val
945                 950                 955                 960

Asn Pro Pro Asn Ala Ser Gln Tyr Ala Leu Val Pro Ala Asn Gly Arg
                965                 970                 975

Gly Ile Phe Ile Gln Val Asn Gly Ser Tyr Tyr Ile Thr Ala Arg Asp
            980                 985                 990

Met Tyr Met Pro Arg Asp Ile Thr  Ala Gly Asp Ile Val  Thr Leu Thr
        995                 1000                 1005

Ser Cys  Gln Ala Asn Tyr Val  Ser Val Asn Arg Thr  Val Ile Thr
    1010                 1015                 1020

Thr Phe  Val Asp Asn Asp Asp  Phe Asp Phe Asp Asp  Glu Leu Ser
    1025                 1030                 1035

Lys Trp  Trp Asn Asp Thr Lys  His Glu Leu Pro Asp  Phe Asp Glu
    1040                 1045                 1050

Phe Asn  Tyr Thr Ile Pro Val  Leu Asn Ile Ser Asn  Glu Ile Asp
    1055                 1060                 1065

Arg Ile  Gln Glu Val Ile Gln  Gly Leu Asn Asp Ser  Leu Ile Asp
    1070                 1075                 1080

Leu Glu  Ala Leu Ser Ile Leu  Lys Thr Tyr Ile Lys  Trp Pro Trp
    1085                 1090                 1095

Tyr Val  Trp Leu Ala Ile Ala  Phe Leu Thr Ile Ile  Phe Ile Leu
    1100                 1105                 1110

Val Leu  Cys Trp Ile Phe Phe  Met Thr Gly Cys Cys  Gly Cys Cys
    1115                 1120                 1125

Cys Gly  Cys Phe Gly Ile Met  Pro Leu Met Ser Lys  Cys Gly Lys
    1130                 1135                 1140

Lys Ser  Ser Tyr Tyr Thr Thr  Phe Asp Asn Asp Val  Val Thr Glu
    1145                 1150                 1155

Gln Tyr  Arg Pro Lys Lys Ser  Val
    1160                 1165


<210> SEQ ID NO 11
<211> LENGTH: 1079
<212> TYPE: PRT
<213> ORGANISM: Avian infectious bronchitis virus

<400> SEQUENCE: 11

Ala Leu Phe Asp Asn Asn Glu Thr Val Tyr Tyr Tyr Gln Ser Ala Phe
1               5                   10                  15

Arg Pro Ala Asp Gly Trp His Leu His Gly Gly Ala Tyr Ala Val Val
            20                  25                  30

Asn Val Ser Leu Glu Thr Asn Asn Ala Gly Thr Ala Ser Gln Cys Ile
        35                  40                  45

Ala Gly Ala Ile Ser Trp Ser Lys Asn Phe Ser Ala Ser Ala Val Ala
    50                  55                  60

Met Thr Ala Pro Glu Leu Gly Met Thr Trp Ser Thr Gly Gln Phe Cys
65                  70                  75                  80

Thr Ala His Cys Asn Phe Ser Asp Phe Thr Val Phe Val Thr His Cys
                85                  90                  95

Phe Lys His Gly Asn Gly Leu Cys Pro Leu Thr Gly Leu Ile Pro Ser
            100                 105                 110
```

```
Gly Phe Ile Arg Val Ser Ala Met Arg Lys Gly Ser Asn Ser Leu Phe
        115                 120                 125

Tyr Asn Leu Thr Val Ser Val Thr Lys Tyr Pro Arg Phe Lys Ser Leu
    130                 135                 140

Gln Cys Val Asn Asn Tyr Thr Ser Val Tyr Leu Asn Gly Asp Leu Val
145                 150                 155                 160

Phe Thr Ser Asn Glu Thr Lys Pro Val Ser Ala Ala Gly Val Ser Phe
                165                 170                 175

Lys Ala Gly Gly Pro Ile Thr Tyr Lys Thr Met Ser Glu Val Lys Val
            180                 185                 190

Leu Ala Tyr Phe Val Asn Gly Thr Ala Gln Thr Val Ile Pro Cys Asp
        195                 200                 205

Gly Ser Pro Arg Gly Leu Leu Ala Cys Gln Tyr Asn Thr Gly Asn Phe
    210                 215                 220

Ser Asp Gly Phe Tyr Pro Tyr Thr Asn Ser Ser Leu Val Lys Glu Arg
225                 230                 235                 240

Phe Ile Val Tyr Arg Glu Ser Ser Val Asn Thr Thr Leu Val Leu Thr
                245                 250                 255

Asn Phe Thr Phe Ser Asn Val Ser Asn Ala Pro Pro Asn Thr Gly Gly
            260                 265                 270

Val His Ser Ile Val Leu His Gln Thr Gln Thr Ala Gln Ser Gly Tyr
        275                 280                 285

Tyr Asn Phe Asn Phe Ser Phe Leu Ser Ser Phe Arg Tyr Val Glu Ser
    290                 295                 300

Asp Phe Met Tyr Gly Ser Tyr His Pro Lys Cys Ser Phe Arg Leu Glu
305                 310                 315                 320

Thr Ile Asn Asn Gly Leu Trp Phe Asn Ser Leu Ser Val Ser Leu Gly
                325                 330                 335

Tyr Gly Pro Leu Gln Gly Gly Cys Lys Gln Ser Val Phe Asn Asn Met
            340                 345                 350

Ala Thr Cys Cys Tyr Ala Tyr Ser Tyr Ser Gly Pro Thr Leu Cys Lys
        355                 360                 365

Gly Val Tyr Ser Gly Gln Leu Gln Lys Thr Phe Glu Cys Gly Leu Leu
    370                 375                 380

Val Phe Val Thr Lys Ser Asp Gly Ser Arg Ile Gln Thr Arg Asn Glu
385                 390                 395                 400

Pro Leu Val Leu Thr Gln His Asn Tyr Asn Asn Ile Thr Leu Asn Lys
                405                 410                 415

Cys Val Glu Tyr Asn Ile Tyr Gly Arg Val Gly Gln Gly Leu Ile Thr
            420                 425                 430

Asn Ile Thr Asp Ser Ala Ala Asn His Gly Tyr Leu Ala Asp Gly Gly
        435                 440                 445

Leu Ala Val Leu Asp Thr Ser Gly Ala Ile Asp Val Phe Val Val Gln
    450                 455                 460

Gly Val Tyr Gly Leu Thr Tyr Tyr Lys Val Asn Pro Cys Glu Asp Val
465                 470                 475                 480

Asn Gln Gln Phe Val Val Ser Gly Gly Gln Leu Val Gly Ile Leu Thr
                485                 490                 495

Ser Arg Asn Glu Thr Gly Ser Gln Pro Ile Glu Asn Arg Phe Tyr Val
            500                 505                 510

Lys Phe Pro Asn Ser Arg Arg Arg Thr Gly Arg Ser Thr Ile Ala Asn
        515                 520                 525
```

-continued

```
Val Thr Asn Cys Pro Tyr Val Ser Tyr Gly Lys Phe Cys Ile Lys Pro
    530                 535                 540

Asp Gly Ser Val Ser Glu Ile Val Pro Gln Glu Ile Glu His Phe Val
545                 550                 555                 560

Ala Pro Leu Leu Asn Val Thr Glu His Val Leu Ile Pro Asn Ser Phe
                565                 570                 575

Asn Leu Thr Val Thr Asp Glu Tyr Ile Gln Thr Arg Met Asp Lys Ile
            580                 585                 590

Gln Ile Asn Cys Arg Gln Tyr Val Cys Gly Asn Ser Ile Glu Cys Arg
        595                 600                 605

Lys Leu Phe Gln Gln Tyr Gly Pro Val Cys Asp Asn Ile Leu Ser Val
    610                 615                 620

Val Asn Thr Val Gly Gln Arg Glu Asp Met Glu Leu Leu Ser Phe Tyr
625                 630                 635                 640

Ser Ser Thr Lys Pro Lys Asp Tyr Asn Ile Pro Ile Phe Ser Asn Val
                645                 650                 655

Ser Thr Gly Asp Phe Asn Ile Ser Leu Leu Leu Thr Pro Pro Asn Ser
            660                 665                 670

Pro Thr Gly Arg Ser Phe Ile Glu Asp Ile Leu Phe Thr Ser Val Glu
        675                 680                 685

Ser Val Gly Leu Pro Thr Asp Glu Glu Tyr Lys Lys Cys Thr Ala Gly
    690                 695                 700

Pro Leu Gly Phe Val Lys Asp Leu Val Cys Ala Arg Glu Tyr Asn Gly
705                 710                 715                 720

Leu Leu Val Leu Pro Pro Ile Ile Thr Ala Asp Met Gln Thr Met Tyr
                725                 730                 735

Thr Ser Thr Leu Val Ala Ser Met Ala Leu Gly Gly Ile Thr Ala Ala
            740                 745                 750

Gly Ala Ile Pro Phe Ala Thr Gln Leu Gln Ala Arg Ile Asn His Leu
        755                 760                 765

Gly Ile Thr Gln Ser Leu Leu Leu Lys Asn Gln Glu Lys Ile Ala Ala
    770                 775                 780

Ser Phe Asn Lys Ala Ile Gly His Met Gln Glu Gly Phe Arg Ser Thr
785                 790                 795                 800

Ser Leu Ala Leu Gln Gln Ile Gln Asp Val Val Asn Lys Gln Ser Ser
                805                 810                 815

Ile Leu Thr Glu Thr Met Ala Ser Leu Asn Lys Asn Phe Gly Ala Ile
            820                 825                 830

Ser Ser Val Leu Gln Asp Ile Tyr Gln Gln Leu Asp Ala Ile Gln Ala
        835                 840                 845

Asp Ala Gln Val Asp Arg Ile Ile Thr Gly Arg Leu Ser Ser Leu Ser
    850                 855                 860

Val Leu Ala Ser Ala Lys Gln Ser Glu Tyr Tyr Arg Val Ser Gln Gln
865                 870                 875                 880

Arg Glu Leu Ala Thr Gln Lys Ile Asn Glu Cys Val Lys Ser Gln Ser
                885                 890                 895

Thr Arg Tyr Ser Phe Cys Gly Asn Gly Arg His Val Leu Thr Ile Pro
            900                 905                 910

Gln Asn Ala Pro Asn Gly Ile Val Phe Ile His Phe Thr Tyr Thr Pro
        915                 920                 925

Glu Ser Phe Val Asn Val Thr Ala Ile Val Gly Phe Cys Val Asn Pro
    930                 935                 940

Pro Asn Ala Ser Gln Tyr Ala Leu Val Pro Ala Asn Gly Arg Gly Ile
```

945 950 955 960

Phe Ile Gln Val Asn Gly Ser Tyr Tyr Ile Thr Ala Arg Asp Met Tyr
965 970 975

Met Pro Arg Asp Ile Thr Ala Gly Asp Ile Val Thr Leu Thr Ser Cys
980 985 990

Gln Ala Asn Tyr Val Ser Val Asn Arg Thr Val Ile Thr Thr Phe Val
995 1000 1005

Asp Asn Asp Asp Phe Asp Phe Asp Asp Glu Leu Ser Lys Trp Trp
1010 1015 1020

Asn Asp Thr Lys His Glu Leu Pro Asp Phe Asp Glu Phe Asn Tyr
1025 1030 1035

Thr Ile Pro Val Leu Asn Ile Ser Asn Glu Ile Asp Arg Ile Gln
1040 1045 1050

Glu Val Ile Gln Gly Leu Asn Asp Ser Leu Ile Asp Leu Glu Ala
1055 1060 1065

Leu Ser Ile Leu Lys Thr Tyr Ile Lys Trp Pro
1070 1075

<210> SEQ ID NO 12
<211> LENGTH: 1159
<212> TYPE: PRT
<213> ORGANISM: Avian infectious bronchitis virus

<400> SEQUENCE: 12

Met Leu Val Lys Ser Leu Phe Leu Val Thr Ile Leu Phe Ala Leu Cys
1 5 10 15

Ser Ala Asn Leu Tyr Asp Asn Glu Ser Phe Val Tyr Tyr Tyr Gln Ser
20 25 30

Ala Phe Arg Pro Gly His Gly Trp His Leu His Gly Gly Ala Tyr Ala
35 40 45

Val Val Asn Val Ser Ser Glu Asn Asn Asn Ala Gly Thr Ala Pro Ser
50 55 60

Cys Thr Ala Gly Ala Ile Gly Tyr Ser Lys Asn Phe Ser Ala Ala Ser
65 70 75 80

Val Ala Met Thr Ala Pro Leu Ser Gly Met Ser Trp Ser Ala Ser Ser
85 90 95

Phe Cys Thr Ala His Cys Asn Phe Thr Ser Tyr Ile Val Phe Val Thr
100 105 110

His Cys Phe Lys Ser Gly Ser Asn Ser Cys Pro Leu Thr Gly Leu Ile
115 120 125

Pro Ser Gly Tyr Ile Arg Ile Ala Ala Met Lys His Gly Ser Arg Thr
130 135 140

Pro Gly His Leu Phe Tyr Asn Leu Thr Val Ser Val Thr Lys Tyr Pro
145 150 155 160

Lys Phe Arg Ser Leu Gln Cys Val Asn Asn His Thr Ser Val Tyr Leu
165 170 175

Asn Gly Asp Leu Val Phe Thr Ser Gly Tyr Thr Glu Asp Val Val Ala
180 185 190

Ala Gly Val His Phe Lys Ser Gly Gly Pro Ile Thr Tyr Lys Val Met
195 200 205

Arg Glu Val Lys Ala Leu Ala Tyr Phe Val Asn Gly Thr Ala His Asp
210 215 220

Val Ile Leu Cys Asp Asp Thr Pro Arg Gly Leu Leu Ala Cys Gln Tyr
225 230 235 240

-continued

```
Asn Thr Gly Asn Phe Ser Asp Gly Phe Tyr Pro Phe Thr Asn Thr Ser
                245                 250                 255

Ile Val Lys Asp Lys Phe Ile Val Tyr Arg Glu Ser Ser Val Asn Thr
            260                 265                 270

Thr Leu Thr Leu Thr Asn Phe Thr Phe Ser Asn Glu Ser Gly Ala Pro
        275                 280                 285

Pro Asn Thr Gly Gly Val Asp Ser Phe Ile Leu Tyr Gln Thr Gln Thr
    290                 295                 300

Ala Gln Ser Gly Tyr Tyr Asn Phe Asn Phe Ser Phe Leu Ser Ser Phe
305                 310                 315                 320

Val Tyr Arg Glu Ser Asn Tyr Met Tyr Gly Ser Tyr His Pro Arg Cys
                325                 330                 335

Ser Phe Arg Pro Glu Thr Leu Asn Gly Leu Trp Phe Asn Ser Leu Ser
            340                 345                 350

Val Ser Leu Thr Tyr Gly Pro Ile Gln Gly Gly Cys Lys Gln Ser Val
        355                 360                 365

Phe Asn Gly Lys Ala Thr Cys Cys Tyr Ala Tyr Ser Tyr Gly Gly Pro
    370                 375                 380

Arg Ala Cys Lys Gly Val Tyr Arg Gly Glu Leu Thr Gln His Phe Glu
385                 390                 395                 400

Cys Gly Leu Leu Val Tyr Val Thr Lys Ser Asp Gly Ser Arg Ile Gln
                405                 410                 415

Thr Ala Thr Gln Pro Pro Val Leu Thr Gln Asn Phe Tyr Asn Asn Ile
            420                 425                 430

Thr Leu Gly Lys Cys Val Asp Tyr Asn Val Tyr Gly Arg Thr Gly Gln
        435                 440                 445

Gly Phe Ile Thr Asn Val Thr Asp Leu Ala Thr Ser His Asn Tyr Leu
    450                 455                 460

Ala Asp Gly Gly Leu Ala Ile Leu Asp Thr Ser Gly Ala Ile Asp Ile
465                 470                 475                 480

Phe Val Val Gln Gly Glu Tyr Gly Pro Asn Tyr Tyr Lys Val Asn Leu
                485                 490                 495

Cys Glu Asp Val Asn Gln Gln Phe Val Val Ser Gly Gly Lys Leu Val
            500                 505                 510

Gly Ile Leu Thr Ser Arg Asn Glu Thr Gly Ser Gln Pro Leu Glu Asn
        515                 520                 525

Gln Phe Tyr Ile Lys Ile Thr Asn Gly Thr His Arg Ser Arg Arg Ser
    530                 535                 540

Val Asn Glu Asn Val Thr Asn Cys Pro Tyr Val Ser Tyr Gly Lys Phe
545                 550                 555                 560

Cys Ile Lys Pro Asp Gly Ser Val Ser Pro Ile Val Pro Lys Glu Leu
                565                 570                 575

Glu Gln Phe Val Ala Pro Leu Leu Asn Val Thr Glu Asn Val Leu Ile
            580                 585                 590

Pro Asn Ser Phe Asn Leu Thr Val Thr Asp Glu Tyr Ile Gln Thr His
        595                 600                 605

Met Asp Lys Ile Gln Ile Asn Cys Leu Gln Tyr Val Cys Gly Asn Ser
    610                 615                 620

Leu Ala Cys Arg Lys Leu Phe Gln Gln Tyr Gly Pro Val Cys Asp Asn
625                 630                 635                 640

Ile Leu Ser Val Val Asn Ser Val Gly Gln Lys Glu Asp Met Glu Leu
                645                 650                 655

Leu Ser Phe Tyr Ser Ser Thr Lys Pro Ser Gly Phe Asn Thr Pro Val
```

```
            660                 665                 670

Phe Ser Asn Leu Ser Thr Gly Glu Phe Asn Ile Ser Leu Leu Leu Thr
        675                 680                 685

Thr Pro Ser Ser Pro Arg Gly Arg Ser Phe Ile Glu Asp Leu Leu Phe
    690                 695                 700

Thr Ser Val Glu Ser Val Gly Leu Pro Thr Asp Glu Ala Tyr Lys Lys
705                 710                 715                 720

Cys Thr Ala Gly Pro Leu Gly Phe Leu Lys Asp Leu Ala Cys Ala Arg
                725                 730                 735

Glu Tyr Asn Gly Leu Leu Val Leu Pro Pro Ile Ile Thr Ala Glu Met
            740                 745                 750

Gln Thr Leu Tyr Thr Ser Ser Leu Val Val Ser Met Ala Phe Gly Gly
        755                 760                 765

Ile Thr Ser Ala Gly Ala Ile Pro Phe Ala Thr Gln Leu Gln Ala Arg
    770                 775                 780

Ile Asn His Leu Gly Ile Thr Gln Ser Leu Leu Leu Lys Asn Gln Glu
785                 790                 795                 800

Lys Ile Ala Ala Ser Phe Asn Lys Ala Ile Gly His Met Gln Glu Gly
                805                 810                 815

Phe Arg Ser Thr Ser Leu Ala Leu Gln Gln Ile Gln Asp Val Val Asn
            820                 825                 830

Lys Gln Ser Ala Ile Leu Thr Glu Thr Met Ala Ser Leu Asn Lys Asn
        835                 840                 845

Phe Gly Ala Ile Ser Ser Val Ile Gln Glu Ile Tyr Gln Gln Leu Asp
    850                 855                 860

Ala Ile Gln Ala Asn Ala Gln Val Asp Arg Leu Ile Thr Gly Arg Leu
865                 870                 875                 880

Ser Ser Leu Ser Val Leu Ala Ser Ala Lys Gln Ala Glu Tyr Ile Arg
                885                 890                 895

Val Ser Gln Gln Arg Glu Leu Ala Thr Gln Lys Ile Asn Glu Cys Val
            900                 905                 910

Lys Ser Gln Ser Ile Arg Tyr Ser Phe Cys Gly Asn Gly Arg His Val
        915                 920                 925

Leu Thr Ile Pro Gln Asn Ala Pro Asn Gly Ile Val Phe Ile His Phe
    930                 935                 940

Ser Tyr Thr Pro Asp Ser Phe Val Asn Val Thr Ala Ile Val Gly Phe
945                 950                 955                 960

Cys Val Lys Pro Ala Asn Ala Ser Gln Tyr Ala Ile Val Pro Ala Asn
                965                 970                 975

Gly Arg Gly Ile Phe Ile Gln Val Asn Gly Ser Tyr Tyr Ile Thr Ala
            980                 985                 990

Arg Asp Met Tyr Met Pro Arg Ala  Ile Thr Ala Gly Asp  Ile Val Thr
        995                 1000                1005

Leu Thr  Ser Cys Gln Ala Asn  Tyr Val Ser Val Asn  Lys Thr Val
    1010                1015                1020

Ile Thr  Thr Phe Val Asp Asn  Asp Asp Phe Asp Phe  Asn Asp Glu
    1025                1030                1035

Leu Ser  Lys Trp Trp Asn Asp  Thr Lys His Glu Leu  Pro Asp Phe
    1040                1045                1050

Asp Lys  Phe Asn Tyr Thr Val  Pro Ile Leu Asp Ile  Asp Ser Glu
    1055                1060                1065

Ile Asp  Arg Ile Gln Gly Val  Ile Gln Gly Leu Asn  Asp Ser Leu
    1070                1075                1080
```

```
Ile Asp  Leu Glu Lys Leu Ser  Ile Leu Lys Thr Tyr  Ile Lys Trp
    1085                 1090                 1095

Pro Trp  Tyr Val Trp Leu Ala  Ile Ala Phe Ala Thr  Ile Ile Phe
    1100                 1105                 1110

Ile Leu  Ile Leu Gly Trp Val  Phe Phe Met Thr Gly  Cys Cys Gly
    1115                 1120                 1125

Cys Cys  Cys Gly Cys Phe Gly  Ile Met Pro Leu Met  Ser Lys Cys
    1130                 1135                 1140

Gly Lys  Lys Ser Ser Tyr Tyr  Thr Thr Phe Asp Asn  Asp Val Val
    1145                 1150                 1155

Thr


<210> SEQ ID NO 13
<211> LENGTH: 1081
<212> TYPE: PRT
<213> ORGANISM: Avian infectious bronchitis virus

<400> SEQUENCE: 13

Asn Leu Tyr Asp Asn Glu Ser Phe Val Tyr Tyr Tyr Gln Ser Ala Phe
1               5                   10                  15

Arg Pro Gly His Gly Trp His Leu His Gly Gly Ala Tyr Ala Val Val
            20                  25                  30

Asn Val Ser Ser Glu Asn Asn Asn Ala Gly Thr Ala Pro Ser Cys Thr
        35                  40                  45

Ala Gly Ala Ile Gly Tyr Ser Lys Asn Phe Ser Ala Ala Ser Val Ala
    50                  55                  60

Met Thr Ala Pro Leu Ser Gly Met Ser Trp Ser Ala Ser Ser Phe Cys
65                  70                  75                  80

Thr Ala His Cys Asn Phe Thr Ser Tyr Ile Val Phe Val Thr His Cys
                85                  90                  95

Phe Lys Ser Gly Ser Asn Ser Cys Pro Leu Thr Gly Leu Ile Pro Ser
            100                 105                 110

Gly Tyr Ile Arg Ile Ala Ala Met Lys His Gly Ser Arg Thr Pro Gly
        115                 120                 125

His Leu Phe Tyr Asn Leu Thr Val Ser Val Thr Lys Tyr Pro Lys Phe
    130                 135                 140

Arg Ser Leu Gln Cys Val Asn Asn His Thr Ser Val Tyr Leu Asn Gly
145                 150                 155                 160

Asp Leu Val Phe Thr Ser Gly Tyr Thr Glu Asp Val Val Ala Ala Gly
                165                 170                 175

Val His Phe Lys Ser Gly Gly Pro Ile Thr Tyr Lys Val Met Arg Glu
            180                 185                 190

Val Lys Ala Leu Ala Tyr Phe Val Asn Gly Thr Ala His Asp Val Ile
        195                 200                 205

Leu Cys Asp Asp Thr Pro Arg Gly Leu Leu Ala Cys Gln Tyr Asn Thr
    210                 215                 220

Gly Asn Phe Ser Asp Gly Phe Tyr Pro Phe Thr Asn Thr Ser Ile Val
225                 230                 235                 240

Lys Asp Lys Phe Ile Val Tyr Arg Glu Ser Ser Val Asn Thr Thr Leu
                245                 250                 255

Thr Leu Thr Asn Phe Thr Phe Ser Asn Glu Ser Gly Ala Pro Pro Asn
            260                 265                 270

Thr Gly Gly Val Asp Ser Phe Ile Leu Tyr Gln Thr Gln Thr Ala Gln
        275                 280                 285
```

```
Ser Gly Tyr Tyr Asn Phe Asn Phe Ser Phe Leu Ser Ser Phe Val Tyr
    290                 295                 300

Arg Glu Ser Asn Tyr Met Tyr Gly Ser Tyr His Pro Arg Cys Ser Phe
305                 310                 315                 320

Arg Pro Glu Thr Leu Asn Gly Leu Trp Phe Asn Ser Leu Ser Val Ser
                325                 330                 335

Leu Thr Tyr Gly Pro Ile Gln Gly Gly Cys Lys Gln Ser Val Phe Asn
            340                 345                 350

Gly Lys Ala Thr Cys Cys Tyr Ala Tyr Ser Tyr Gly Gly Pro Arg Ala
        355                 360                 365

Cys Lys Gly Val Tyr Arg Gly Glu Leu Thr Gln His Phe Glu Cys Gly
    370                 375                 380

Leu Leu Val Tyr Val Thr Lys Ser Asp Gly Ser Arg Ile Gln Thr Ala
385                 390                 395                 400

Thr Gln Pro Pro Val Leu Thr Gln Asn Phe Tyr Asn Asn Ile Thr Leu
                405                 410                 415

Gly Lys Cys Val Asp Tyr Asn Val Tyr Gly Arg Thr Gly Gln Gly Phe
            420                 425                 430

Ile Thr Asn Val Thr Asp Leu Ala Thr Ser His Asn Tyr Leu Ala Asp
        435                 440                 445

Gly Gly Leu Ala Ile Leu Asp Thr Ser Gly Ala Ile Asp Ile Phe Val
    450                 455                 460

Val Gln Gly Glu Tyr Gly Pro Asn Tyr Tyr Lys Val Asn Leu Cys Glu
465                 470                 475                 480

Asp Val Asn Gln Gln Phe Val Val Ser Gly Gly Lys Leu Val Gly Ile
                485                 490                 495

Leu Thr Ser Arg Asn Glu Thr Gly Ser Gln Pro Leu Glu Asn Gln Phe
            500                 505                 510

Tyr Ile Lys Ile Thr Asn Gly Thr His Arg Ser Arg Arg Ser Val Asn
        515                 520                 525

Glu Asn Val Thr Asn Cys Pro Tyr Val Ser Tyr Gly Lys Phe Cys Ile
    530                 535                 540

Lys Pro Asp Gly Ser Val Ser Pro Ile Val Pro Lys Glu Leu Glu Gln
545                 550                 555                 560

Phe Val Ala Pro Leu Leu Asn Val Thr Glu Asn Val Leu Ile Pro Asn
                565                 570                 575

Ser Phe Asn Leu Thr Val Thr Asp Glu Tyr Ile Gln Thr His Met Asp
            580                 585                 590

Lys Ile Gln Ile Asn Cys Leu Gln Tyr Val Cys Gly Asn Ser Leu Ala
        595                 600                 605

Cys Arg Lys Leu Phe Gln Gln Tyr Gly Pro Val Cys Asp Asn Ile Leu
    610                 615                 620

Ser Val Val Asn Ser Val Gly Gln Lys Glu Asp Met Glu Leu Leu Ser
625                 630                 635                 640

Phe Tyr Ser Ser Thr Lys Pro Ser Gly Phe Asn Thr Pro Val Phe Ser
                645                 650                 655

Asn Leu Ser Thr Gly Glu Phe Asn Ile Ser Leu Leu Leu Thr Thr Pro
            660                 665                 670

Ser Ser Pro Arg Gly Arg Ser Phe Ile Glu Asp Leu Leu Phe Thr Ser
        675                 680                 685

Val Glu Ser Val Gly Leu Pro Thr Asp Glu Ala Tyr Lys Lys Cys Thr
    690                 695                 700
```

```
Ala Gly Pro Leu Gly Phe Leu Lys Asp Leu Ala Cys Ala Arg Glu Tyr
705                 710                 715                 720

Asn Gly Leu Leu Val Leu Pro Pro Ile Ile Thr Ala Glu Met Gln Thr
                725                 730                 735

Leu Tyr Thr Ser Ser Leu Val Val Ser Met Ala Phe Gly Gly Ile Thr
            740                 745                 750

Ser Ala Gly Ala Ile Pro Phe Ala Thr Gln Leu Gln Ala Arg Ile Asn
        755                 760                 765

His Leu Gly Ile Thr Gln Ser Leu Leu Leu Lys Asn Gln Glu Lys Ile
    770                 775                 780

Ala Ala Ser Phe Asn Lys Ala Ile Gly His Met Gln Glu Gly Phe Arg
785                 790                 795                 800

Ser Thr Ser Leu Ala Leu Gln Gln Ile Gln Asp Val Val Asn Lys Gln
                805                 810                 815

Ser Ala Ile Leu Thr Glu Thr Met Ala Ser Leu Asn Lys Asn Phe Gly
            820                 825                 830

Ala Ile Ser Ser Val Ile Gln Glu Ile Tyr Gln Gln Leu Asp Ala Ile
        835                 840                 845

Gln Ala Asn Ala Gln Val Asp Arg Leu Ile Thr Gly Arg Leu Ser Ser
    850                 855                 860

Leu Ser Val Leu Ala Ser Ala Lys Gln Ala Glu Tyr Ile Arg Val Ser
865                 870                 875                 880

Gln Gln Arg Glu Leu Ala Thr Gln Lys Ile Asn Glu Cys Val Lys Ser
                885                 890                 895

Gln Ser Ile Arg Tyr Ser Phe Cys Gly Asn Gly Arg His Val Leu Thr
            900                 905                 910

Ile Pro Gln Asn Ala Pro Asn Gly Ile Val Phe Ile His Phe Ser Tyr
        915                 920                 925

Thr Pro Asp Ser Phe Val Asn Val Thr Ala Ile Val Gly Phe Cys Val
    930                 935                 940

Lys Pro Ala Asn Ala Ser Gln Tyr Ala Ile Val Pro Ala Asn Gly Arg
945                 950                 955                 960

Gly Ile Phe Ile Gln Val Asn Gly Ser Tyr Tyr Ile Thr Ala Arg Asp
                965                 970                 975

Met Tyr Met Pro Arg Ala Ile Thr Ala Gly Asp Ile Val Thr Leu Thr
            980                 985                 990

Ser Cys Gln Ala Asn Tyr Val Ser  Val Asn Lys Thr Val  Ile Thr Thr
        995                 1000                1005

Phe Val  Asp Asn Asp Asp Phe  Asp Phe Asn Asp Glu  Leu Ser Lys
    1010                1015                1020

Trp Trp  Asn Asp Thr Lys His  Glu Leu Pro Asp Phe  Asp Lys Phe
    1025                1030                1035

Asn Tyr  Thr Val Pro Ile Leu  Asp Ile Asp Ser Glu  Ile Asp Arg
    1040                1045                1050

Ile Gln  Gly Val Ile Gln Gly  Leu Asn Asp Ser Leu  Ile Asp Leu
    1055                1060                1065

Glu Lys  Leu Ser Ile Leu Lys  Thr Tyr Ile Lys Trp  Pro
    1070                1075                1080


<210> SEQ ID NO 14
<211> LENGTH: 1156
<212> TYPE: PRT
<213> ORGANISM: Avian infectious bronchitis virus

<400> SEQUENCE: 14
```

```
Met Leu Val Lys Ser Leu Phe Ile Val Thr Leu Leu Phe Ala Leu Cys
1               5                   10                  15

Ser Ala Ala Leu Phe Asp Asn Asn Gln Ala Val Tyr Tyr Tyr Gln Ser
            20                  25                  30

Ala Phe Arg Pro Ser Ser Gly Trp His Lys His Gly Gly Ala Tyr Ala
        35                  40                  45

Val Ala Asn Val Ser Leu Glu Tyr Ala Asn Ala Gly Ser Ser Thr His
    50                  55                  60

Cys Thr Ala Gly Ala Ile Tyr Trp Ser Lys Asn Phe Thr Ala Ser Ser
65                  70                  75                  80

Val Ala Met Thr Ala Pro Gly Thr Gly Met Ser Trp Ser Thr Ala Gln
                85                  90                  95

Phe Cys Thr Ala His Cys Asn Phe Ser Asp Phe Thr Val Phe Val Thr
            100                 105                 110

His Cys Tyr Lys Ser Gly Asp Val Cys Pro Leu Thr Gly Leu Ile Pro
        115                 120                 125

Ser Gly Tyr Ile Arg Ile Ser Ala Met Thr Lys Gly Thr Thr Ser Leu
    130                 135                 140

Phe Tyr Asn Leu Thr Val Pro Val Thr Lys Tyr Pro Lys Phe Lys Ser
145                 150                 155                 160

Leu Gln Cys Val Asp Asn Phe Thr Ser Val Tyr Leu Asn Gly Asp Leu
                165                 170                 175

Val Phe Thr Ser Asn Glu Thr Lys Asp Val Ser Ala Ala Gly Val His
            180                 185                 190

Phe Lys Ala Gly Gly Pro Ile Thr Tyr Lys Val Met Glu Lys Val Asp
        195                 200                 205

Val Leu Ala Tyr Phe Val Asn Gly Thr Ala Gln Asp Val Ile Leu Cys
    210                 215                 220

Asp Asn Ser Pro Arg Gly Leu Leu Ala Cys Gln Tyr Asn Thr Gly Asn
225                 230                 235                 240

Phe Ser Asp Gly Phe Tyr Pro Phe Thr Asn Ile Ser Leu Val Lys Glu
                245                 250                 255

Lys Phe Ile Val Tyr Arg Glu Thr Ser Val Asn Thr Thr Leu Val Leu
            260                 265                 270

Thr Asn Phe Thr Phe Thr Asn Val Ser Asn Ala Leu Pro Asn Thr Gly
        275                 280                 285

Gly Val Asn Thr Ile Asn Ile Tyr Gln Thr Gln Thr Ala Gln Ser Gly
    290                 295                 300

Cys Tyr Asn Phe Asn Phe Ser Phe Leu Ser Ser Phe Val Tyr Lys Gln
305                 310                 315                 320

Ser Asp Phe Met Tyr Gly Ser Tyr His Pro Lys Cys Asp Phe Arg Pro
                325                 330                 335

Glu Thr Ile Asn Asn Gly Leu Trp Phe Asn Ser Leu Ser Val Ser Leu
            340                 345                 350

Ala Tyr Gly Pro Leu Gln Gly Gly Cys Lys Gln Ser Val Phe Ser Asn
        355                 360                 365

Arg Ala Thr Cys Cys Tyr Ala Tyr Ser Tyr Asn Gly Pro Arg Leu Cys
    370                 375                 380

Lys Gly Val Tyr Ile Gly Glu Leu Gln Gln Tyr Phe Glu Cys Gly Leu
385                 390                 395                 400

Leu Val Tyr Val Thr Lys Ser Asp Gly Ser Arg Ile Gln Thr Arg Asn
                405                 410                 415
```

```
Glu Pro Leu Val Leu Thr His His Asn Tyr Asn Asn Ile Thr Leu Asp
            420                 425                 430

Arg Cys Val Glu Tyr Asn Ile Tyr Gly Arg Ser Gly Gln Gly Phe Ile
        435                 440                 445

Thr Asn Val Thr Ala Ala Ala Ala Asn Tyr Asn Tyr Leu Ala Asp Gly
    450                 455                 460

Gly Leu Ala Ile Leu Asp Thr Ser Gly Ala Ile Asp Ile Phe Val Val
465                 470                 475                 480

Gln Gly Glu Tyr Gly Pro Asn Tyr Tyr Lys Val Asn Pro Cys Glu Asp
                485                 490                 495

Val Asn Gln Gln Phe Val Val Ser Gly Gly Gly Ile Val Gly Val Leu
            500                 505                 510

Thr Ser His Asn Glu Thr Gly Ser Gln Gln Leu Glu Asn Leu Phe Tyr
        515                 520                 525

Val Lys Leu Thr Asn Ser Thr Arg Arg Thr Arg Arg Ser Thr Ile Ala
    530                 535                 540

Asn Val Thr Thr Cys Pro Tyr Val Ser Tyr Gly Arg Phe Cys Ile Lys
545                 550                 555                 560

Pro Asp Gly Leu Val Ser Glu Ile Val Pro Gln Glu Leu Asp Tyr Phe
                565                 570                 575

Val Ala Pro Leu Leu Asn Val Thr Glu His Val Leu Ile Pro Asn Ser
            580                 585                 590

Phe Asn Leu Thr Val Thr Asp Glu Tyr Ile Gln Thr Arg Met Glu Lys
        595                 600                 605

Val Gln Ile Asn Cys Leu Gln Tyr Val Cys Gly Asn Ser Ile Glu Cys
    610                 615                 620

Arg Asn Leu Phe Gln Gln Tyr Gly Pro Val Cys Asp Asn Ile Leu Ser
625                 630                 635                 640

Ile Val Asn Ser Val Gly Gln Arg Glu Asp Met Glu Ser Leu Thr Phe
                645                 650                 655

Tyr Ser Ser Thr Lys Pro Lys Gly Tyr Asn Thr Pro Ile Phe Ser Asn
            660                 665                 670

Ile Ser Thr Gly Asp Phe Asn Ile Ser Leu Met Leu Thr Pro Pro Ser
        675                 680                 685

Ser Pro Ser Gly Arg Ser Phe Ile Glu Asp Leu Leu Phe Thr Ser Val
    690                 695                 700

Glu Thr Val Gly Leu Pro Thr Asp Ala Glu Tyr Lys Lys Cys Thr Ala
705                 710                 715                 720

Gly Pro Leu Gly Thr Leu Lys Asp Leu Ile Cys Ala Arg Glu Tyr Asn
                725                 730                 735

Gly Leu Leu Val Leu Pro Pro Ile Ile Thr Ala Asp Met Gln Thr Met
            740                 745                 750

Tyr Thr Ala Ser Leu Val Gly Ala Met Ala Phe Gly Gly Ile Thr Ser
        755                 760                 765

Ala Ala Ala Ile Pro Phe Ala Thr Gln Ile Gln Ala Arg Ile Asn His
    770                 775                 780

Leu Gly Ile Thr Gln Ser Leu Leu Met Lys Asn Gln Glu Lys Ile Ala
785                 790                 795                 800

Ala Ser Phe Asn Lys Ala Ile Gly His Met Gln Glu Gly Phe Arg Ser
                805                 810                 815

Thr Ser Leu Ala Leu Gln Gln Ile Gln Asp Val Val Asn Lys Gln Ser
            820                 825                 830

Ala Ile Leu Thr Glu Thr Met Asn Ser Leu Asn Lys Asn Phe Gly Ala
```

```
        835                 840                 845

Ile Thr Ser Val Ile Gln Asp Ile Tyr Ala Gln Leu Asp Ala Ile Gln
    850                 855                 860

Ala Asp Ala Gln Val Asp Arg Leu Ile Thr Gly Arg Leu Ser Ser Leu
865                 870                 875                 880

Ser Val Leu Ala Ser Ala Lys Gln Ser Glu Tyr Ile Arg Val Ser Gln
                885                 890                 895

Gln Arg Glu Leu Ala Thr Gln Lys Ile Asn Glu Cys Val Lys Ser Gln
            900                 905                 910

Ser Asn Arg Tyr Gly Phe Cys Gly Ser Gly Arg His Val Leu Ser Ile
        915                 920                 925

Pro Gln Asn Ala Pro Asn Gly Ile Val Phe Ile His Phe Thr Tyr Thr
    930                 935                 940

Pro Glu Ser Phe Val Asn Val Thr Ala Ile Val Gly Phe Cys Val Ser
945                 950                 955                 960

Pro Ala Asn Ala Ser Gln Tyr Ala Ile Val Pro Ala Asn Gly Arg Gly
                965                 970                 975

Ile Phe Ile Gln Val Asn Gly Thr Tyr Tyr Ile Thr Ala Arg Asp Met
            980                 985                 990

Tyr Met Pro Arg Asp Ile Thr Ala  Gly Asp Ile Val Thr  Leu Thr Ser
        995                 1000                1005

Cys Gln  Ala Asn Tyr Val Asn  Val Asn Lys Thr Val  Ile Thr Thr
    1010                1015                1020

Phe Val  Glu Asp Asp Asp Phe  Asp Phe Asp Asp Glu  Leu Ser Lys
    1025                1030                1035

Trp Trp  Asn Glu Thr Lys His  Glu Ile Pro Asp Phe  Asp Glu Phe
    1040                1045                1050

Asn Tyr  Thr Val Pro Ile Leu  Asn Ile Ser Ser Glu  Ile Asp Arg
    1055                1060                1065

Ile Gln  Gly Val Ile Gln Gly  Leu Asn Asp Ser Leu  Ile Asn Leu
    1070                1075                1080

Glu Glu  Leu Ser Ile Ile Lys  Thr Tyr Ile Lys Trp  Pro Trp Tyr
    1085                1090                1095

Val Trp  Leu Ala Ile Gly Phe  Ala Ile Ile Ile Phe  Ile Leu Ile
    1100                1105                1110

Leu Gly  Trp Val Phe Phe Met  Thr Gly Cys Cys Gly  Cys Cys Cys
    1115                1120                1125

Gly Cys  Phe Gly Ile Ile Pro  Leu Met Ser Lys Cys  Gly Lys Lys
    1130                1135                1140

Ser Ser  Tyr Tyr Thr Thr Phe  Asp Asn Asp Val Val  Thr
    1145                1150                1155


<210> SEQ ID NO 15
<211> LENGTH: 1078
<212> TYPE: PRT
<213> ORGANISM: Avian infectious bronchitis virus

<400> SEQUENCE: 15

Ala Leu Phe Asp Asn Asn Gln Ala Val Tyr Tyr Tyr Gln Ser Ala Phe
1               5                   10                  15

Arg Pro Ser Ser Gly Trp His Lys His Gly Gly Ala Tyr Ala Val Ala
            20                  25                  30

Asn Val Ser Leu Glu Tyr Ala Asn Ala Gly Ser Ser Thr His Cys Thr
        35                  40                  45
```

-continued

```
Ala Gly Ala Ile Tyr Trp Ser Lys Asn Phe Thr Ala Ser Ser Val Ala
    50                  55                  60

Met Thr Ala Pro Gly Thr Gly Met Ser Trp Ser Thr Ala Gln Phe Cys
65                  70                  75                  80

Thr Ala His Cys Asn Phe Ser Asp Phe Thr Val Phe Val Thr His Cys
                85                  90                  95

Tyr Lys Ser Gly Asp Val Cys Pro Leu Thr Gly Leu Ile Pro Ser Gly
            100                 105                 110

Tyr Ile Arg Ile Ser Ala Met Thr Lys Gly Thr Thr Ser Leu Phe Tyr
        115                 120                 125

Asn Leu Thr Val Pro Val Thr Lys Tyr Pro Lys Phe Lys Ser Leu Gln
    130                 135                 140

Cys Val Asp Asn Phe Thr Ser Val Tyr Leu Asn Gly Asp Leu Val Phe
145                 150                 155                 160

Thr Ser Asn Glu Thr Lys Asp Val Ser Ala Ala Gly Val His Phe Lys
                165                 170                 175

Ala Gly Gly Pro Ile Thr Tyr Lys Val Met Glu Lys Val Asp Val Leu
            180                 185                 190

Ala Tyr Phe Val Asn Gly Thr Ala Gln Asp Val Ile Leu Cys Asp Asn
        195                 200                 205

Ser Pro Arg Gly Leu Leu Ala Cys Gln Tyr Asn Thr Gly Asn Phe Ser
    210                 215                 220

Asp Gly Phe Tyr Pro Phe Thr Asn Ile Ser Leu Val Lys Glu Lys Phe
225                 230                 235                 240

Ile Val Tyr Arg Glu Thr Ser Val Asn Thr Thr Leu Val Leu Thr Asn
                245                 250                 255

Phe Thr Phe Thr Asn Val Ser Asn Ala Leu Pro Asn Thr Gly Gly Val
            260                 265                 270

Asn Thr Ile Asn Ile Tyr Gln Thr Gln Thr Ala Gln Ser Gly Cys Tyr
        275                 280                 285

Asn Phe Asn Phe Ser Phe Leu Ser Ser Phe Val Tyr Lys Gln Ser Asp
    290                 295                 300

Phe Met Tyr Gly Ser Tyr His Pro Lys Cys Asp Phe Arg Pro Glu Thr
305                 310                 315                 320

Ile Asn Asn Gly Leu Trp Phe Asn Ser Leu Ser Val Ser Leu Ala Tyr
                325                 330                 335

Gly Pro Leu Gln Gly Gly Cys Lys Gln Ser Val Phe Ser Asn Arg Ala
            340                 345                 350

Thr Cys Cys Tyr Ala Tyr Ser Tyr Asn Gly Pro Arg Leu Cys Lys Gly
        355                 360                 365

Val Tyr Ile Gly Glu Leu Gln Gln Tyr Phe Glu Cys Gly Leu Leu Val
    370                 375                 380

Tyr Val Thr Lys Ser Asp Gly Ser Arg Ile Gln Thr Arg Asn Glu Pro
385                 390                 395                 400

Leu Val Leu Thr His His Asn Tyr Asn Asn Ile Thr Leu Asp Arg Cys
                405                 410                 415

Val Glu Tyr Asn Ile Tyr Gly Arg Ser Gly Gln Gly Phe Ile Thr Asn
            420                 425                 430

Val Thr Ala Ala Ala Ala Asn Tyr Asn Tyr Leu Ala Asp Gly Gly Leu
        435                 440                 445

Ala Ile Leu Asp Thr Ser Gly Ala Ile Asp Ile Phe Val Val Gln Gly
    450                 455                 460

Glu Tyr Gly Pro Asn Tyr Tyr Lys Val Asn Pro Cys Glu Asp Val Asn
```

```
465                 470                 475                 480

Gln Gln Phe Val Val Ser Gly Gly Gly Ile Val Gly Val Leu Thr Ser
                485                 490                 495

His Asn Glu Thr Gly Ser Gln Gln Leu Glu Asn Leu Phe Tyr Val Lys
            500                 505                 510

Leu Thr Asn Ser Thr Arg Arg Thr Arg Arg Ser Thr Ile Ala Asn Val
        515                 520                 525

Thr Thr Cys Pro Tyr Val Ser Tyr Gly Arg Phe Cys Ile Lys Pro Asp
    530                 535                 540

Gly Leu Val Ser Glu Ile Val Pro Gln Glu Leu Asp Tyr Phe Val Ala
545                 550                 555                 560

Pro Leu Leu Asn Val Thr Glu His Val Leu Ile Pro Asn Ser Phe Asn
                565                 570                 575

Leu Thr Val Thr Asp Glu Tyr Ile Gln Thr Arg Met Glu Lys Val Gln
            580                 585                 590

Ile Asn Cys Leu Gln Tyr Val Cys Gly Asn Ser Ile Glu Cys Arg Asn
        595                 600                 605

Leu Phe Gln Gln Tyr Gly Pro Val Cys Asp Asn Ile Leu Ser Ile Val
    610                 615                 620

Asn Ser Val Gly Gln Arg Glu Asp Met Glu Ser Leu Thr Phe Tyr Ser
625                 630                 635                 640

Ser Thr Lys Pro Lys Gly Tyr Asn Thr Pro Ile Phe Ser Asn Ile Ser
                645                 650                 655

Thr Gly Asp Phe Asn Ile Ser Leu Met Leu Thr Pro Pro Ser Ser Pro
            660                 665                 670

Ser Gly Arg Ser Phe Ile Glu Asp Leu Leu Phe Thr Ser Val Glu Thr
        675                 680                 685

Val Gly Leu Pro Thr Asp Ala Glu Tyr Lys Lys Cys Thr Ala Gly Pro
    690                 695                 700

Leu Gly Thr Leu Lys Asp Leu Ile Cys Ala Arg Glu Tyr Asn Gly Leu
705                 710                 715                 720

Leu Val Leu Pro Pro Ile Ile Thr Ala Asp Met Gln Thr Met Tyr Thr
                725                 730                 735

Ala Ser Leu Val Gly Ala Met Ala Phe Gly Gly Ile Thr Ser Ala Ala
            740                 745                 750

Ala Ile Pro Phe Ala Thr Gln Ile Gln Ala Arg Ile Asn His Leu Gly
        755                 760                 765

Ile Thr Gln Ser Leu Leu Met Lys Asn Gln Glu Lys Ile Ala Ala Ser
    770                 775                 780

Phe Asn Lys Ala Ile Gly His Met Gln Glu Gly Phe Arg Ser Thr Ser
785                 790                 795                 800

Leu Ala Leu Gln Gln Ile Gln Asp Val Val Asn Lys Gln Ser Ala Ile
                805                 810                 815

Leu Thr Glu Thr Met Asn Ser Leu Asn Lys Asn Phe Gly Ala Ile Thr
            820                 825                 830

Ser Val Ile Gln Asp Ile Tyr Ala Gln Leu Asp Ala Ile Gln Ala Asp
        835                 840                 845

Ala Gln Val Asp Arg Leu Ile Thr Gly Arg Leu Ser Ser Leu Ser Val
    850                 855                 860

Leu Ala Ser Ala Lys Gln Ser Glu Tyr Ile Arg Val Ser Gln Gln Arg
865                 870                 875                 880

Glu Leu Ala Thr Gln Lys Ile Asn Glu Cys Val Lys Ser Gln Ser Asn
                885                 890                 895
```

```
Arg Tyr Gly Phe Cys Gly Ser Gly Arg His Val Leu Ser Ile Pro Gln
            900                 905                 910

Asn Ala Pro Asn Gly Ile Val Phe Ile His Phe Thr Tyr Thr Pro Glu
        915                 920                 925

Ser Phe Val Asn Val Thr Ala Ile Val Gly Phe Cys Val Ser Pro Ala
    930                 935                 940

Asn Ala Ser Gln Tyr Ala Ile Val Pro Ala Asn Gly Arg Gly Ile Phe
945                 950                 955                 960

Ile Gln Val Asn Gly Thr Tyr Tyr Ile Thr Ala Arg Asp Met Tyr Met
                965                 970                 975

Pro Arg Asp Ile Thr Ala Gly Asp Ile Val Thr Leu Thr Ser Cys Gln
            980                 985                 990

Ala Asn Tyr Val Asn Val Asn Lys  Thr Val Ile Thr Thr  Phe Val Glu
        995                 1000                 1005

Asp Asp  Asp Phe Asp Phe Asp  Asp Glu Leu Ser Lys  Trp Trp Asn
    1010                 1015                 1020

Glu Thr  Lys His Glu Ile Pro  Asp Phe Asp Glu Phe  Asn Tyr Thr
    1025                 1030                 1035

Val Pro  Ile Leu Asn Ile Ser  Ser Glu Ile Asp Arg  Ile Gln Gly
    1040                 1045                 1050

Val Ile  Gln Gly Leu Asn Asp  Ser Leu Ile Asn Leu  Glu Glu Leu
    1055                 1060                 1065

Ser Ile  Ile Lys Thr Tyr Ile  Lys Trp Pro
    1070                 1075


<210> SEQ ID NO 16
<211> LENGTH: 1169
<212> TYPE: PRT
<213> ORGANISM: Avian infectious bronchitis virus

<400> SEQUENCE: 16

Met Leu Val Gln Pro Leu Leu Leu Val Thr Leu Leu Cys Ala Leu Cys
1               5                   10                  15

Ser Ala Ser Leu Tyr Asn Asn Asp Ser Tyr Val Tyr Tyr Tyr Gln Ser
            20                  25                  30

Ala Phe Arg Pro Phe Asn Gly Trp His Leu His Gly Gly Ala Tyr Ala
        35                  40                  45

Val Val Asn Val Ser Gln Glu Thr Ala Asn Ala Gly Ser Ser Pro Ser
    50                  55                  60

Cys Thr Ala Gly Ala Ile Tyr Trp Ser Lys Asn Phe Thr Ala Ser Ser
65                  70                  75                  80

Val Ala Met Thr Ala Pro Leu Gln Gly Met Gln Trp Ser Thr Ile Gln
                85                  90                  95

Phe Cys Thr Ala His Cys Asn Phe Thr Asn Ile Val Val Phe Val Thr
            100                 105                 110

His Cys Tyr Lys Ser Gly Ser Thr Val Cys Pro Leu Thr Gly Leu Ile
        115                 120                 125

Pro Gln Asn His Ile Arg Ile Ser Ala Met Lys Gln Gly Asn Asn Gly
    130                 135                 140

Pro Ser Gly Leu Phe Tyr Asn Leu Thr Val Pro Val Thr Lys Tyr Ser
145                 150                 155                 160

Lys Phe Lys Ser Leu Gln Cys Val Asn Asn Gln Thr Ser Val Tyr Leu
                165                 170                 175

Asn Gly Asp Leu Val Phe Thr Ser Asn Glu Thr Lys Asp Val Ser Gly
```

```
            180                 185                 190

Ala Gly Val Tyr Phe Lys Ala Gly Gly Pro Ile Thr Tyr Lys Val Met
        195                 200                 205

Arg Glu Val Lys Ala Leu Ala Tyr Phe Val Asn Gly Thr Ala His Asp
    210                 215                 220

Val Ile Leu Cys Asp Gly Ser Pro Arg Gly Leu Leu Ala Cys Gln Tyr
225                 230                 235                 240

Asn Thr Gly Lys Phe Ser Asp Gly Phe Tyr Pro Phe Thr Asn Asp Thr
                245                 250                 255

Leu Val Lys Glu Lys Phe Ile Val Tyr Arg Glu Asn Ser Val Asn Thr
            260                 265                 270

Thr Leu Thr Leu Thr Asn Phe Thr Phe Tyr Asn Glu Ser Asn Ala Leu
        275                 280                 285

Pro Asn Asn Gly Gly Val Asp Thr Ile Gln Leu Tyr Gln Thr His Thr
    290                 295                 300

Ala Gln Ser Gly Tyr Tyr Asn Phe Asn Phe Ser Phe Leu Ser Ser Phe
305                 310                 315                 320

Gln Tyr Val Glu Ser Asn Phe Met Tyr Gly Ser Tyr His Pro Lys Cys
                325                 330                 335

Gly Phe Arg Pro Glu Ser Ile Asn Asn Gly Leu Trp Phe Asn Ser Leu
            340                 345                 350

Ser Val Ser Leu Ala Tyr Gly Pro Leu Gln Gly Gly Cys Lys Gln Ser
        355                 360                 365

Val Phe His Gly Arg Ala Thr Cys Cys Tyr Ala Tyr Ser Tyr Asn Gly
    370                 375                 380

Pro Thr Leu Cys Lys Gly Val Tyr Ser Gly Glu Leu Thr Arg Ser Tyr
385                 390                 395                 400

Gln Cys Gly Leu Leu Val Phe Val Thr Lys Ser Asp Gly Ser Arg Ile
                405                 410                 415

Gln Thr Ser Thr Lys Pro Ile Val Leu Thr Gln His Asn Tyr Asn Asn
            420                 425                 430

Ile Thr Leu Asp Arg Cys Val Glu Tyr Asn Ile Tyr Gly Arg Val Gly
        435                 440                 445

Gln Gly Phe Ile Thr Asn Val Thr Glu Ser Ala Ala Ala Phe Asn Tyr
    450                 455                 460

Leu Glu Asp Gly Gly Leu Ala Ile Leu Asp Thr Ser Gly Ala Ile Asp
465                 470                 475                 480

Ile Phe Val Val Gln Gly Glu Tyr Gly Phe Asn Tyr Tyr Lys Val Asn
                485                 490                 495

Pro Cys Glu Asp Val Asn Gln Gln Phe Val Val Ser Gly Gly Asn Leu
            500                 505                 510

Val Gly Ile Leu Thr Ser Ile Asn Gln Thr Gly Ser Gln Ser Ile Glu
        515                 520                 525

Asn Gln Phe Tyr Val Lys Leu Thr Asn Gly Ser Arg Arg Ser Arg Arg
    530                 535                 540

Ser Val Ser Glu Asn Val Thr Ser Cys Pro Tyr Val Ser Tyr Gly Lys
545                 550                 555                 560

Phe Cys Ile Lys Pro Asp Gly Ser Leu Ser Thr Ile Val Pro Lys Glu
                565                 570                 575

Leu Glu Gln Phe Val Ala Pro Leu Leu Asn Val Thr Glu His Val Leu
            580                 585                 590

Ile Pro Asp Ser Phe Asn Leu Thr Val Thr Asp Glu Tyr Ile Gln Thr
        595                 600                 605
```

```
Arg Met Asp Lys Val Gln Ile Asn Cys Leu Gln Tyr Val Cys Gly Asn
    610                 615                 620

Ser Phe Glu Cys Arg Lys Leu Phe Gln Gln Tyr Gly Pro Val Cys Asp
625                 630                 635                 640

Asn Ile Leu Ser Val Val Asn Ser Val Gly Gln Lys Glu Asp Met Glu
                645                 650                 655

Leu Leu Ser Phe Tyr Ser Ser Thr Lys Pro Ser Gly Ile Ser Gln Pro
            660                 665                 670

Leu Phe Asn Asn Phe Ser Thr Gly Asp Phe Asn Ile Ser Leu Leu Leu
        675                 680                 685

Thr Ser Pro Ser Ser Pro Ser Gly Arg Ser Phe Ile Glu Asp Leu Leu
    690                 695                 700

Phe Thr Ser Val Glu Ser Val Gly Leu Pro Thr Asp Glu Ala Tyr Lys
705                 710                 715                 720

Lys Cys Thr Ser Gly Pro Leu Gly Phe Val Lys Asp Leu Val Cys Ala
                725                 730                 735

Arg Glu Tyr Asn Gly Leu Leu Val Leu Pro Pro Ile Ile Thr Ala Glu
            740                 745                 750

Met Gln Thr Met Tyr Thr Ser Ser Leu Val Ala Ser Met Ala Leu Gly
        755                 760                 765

Gly Ile Thr Ala Ala Gly Ala Ile Pro Phe Ala Thr Gln Leu Gln Ala
    770                 775                 780

Arg Ile Asn His Leu Gly Ile Thr Gln Ser Leu Leu Met Lys Asn Gln
785                 790                 795                 800

Glu Lys Ile Ala Ala Ser Phe Asn Arg Ala Ile Gly His Met Gln Glu
                805                 810                 815

Gly Phe Lys Ser Thr Ser Leu Ala Leu Gln Gln Ile Gln Asp Val Val
            820                 825                 830

Asn Lys Gln Ser Ala Ile Leu Thr Glu Thr Met Ala Ser Leu Asn Lys
        835                 840                 845

Asn Phe Gly Ala Ile Ser Ser Val Leu Gln Asp Ile Tyr Gln Gln Leu
    850                 855                 860

Asp Val Ile Gln Ala Asp Ala Gln Val Asp Arg Ile Ile Thr Gly Arg
865                 870                 875                 880

Leu Ser Ser Leu Ser Val Leu Ala Ser Ala Lys Gln Ser Glu Tyr Ile
                885                 890                 895

Ala Val Ser Gln Gln Arg Ala Leu Ala Thr Gln Lys Ile Asn Glu Cys
            900                 905                 910

Val Lys Ser Gln Ser Thr Arg Tyr Ser Phe Cys Gly Asn Gly Arg His
        915                 920                 925

Val Leu Thr Ile Pro Gln Asn Ala Pro Asn Gly Ile Val Phe Ile His
    930                 935                 940

Phe Thr Tyr Thr Pro Glu Ser Phe Val Asn Val Thr Ala Ile Val Gly
945                 950                 955                 960

Phe Cys Val Lys Pro Pro Asn Ala Ser His Tyr Ala Ile Val Pro Val
                965                 970                 975

Asn Gly Arg Gly Ile Phe Ile Gln Val Asn Gly Thr Tyr Tyr Ile Thr
            980                 985                 990

Ser Arg Asp Met Tyr Met Pro Arg  Asn Ile Thr Ala Gly  Asp Ile Val
        995                 1000                1005

Thr Leu  Thr Ser Cys Gln Ala  Asn Tyr Val Ser Val  Asn Lys Thr
    1010                1015                1020
```

```
Val Ile  Ser Thr Phe Val Glu  Asp Asp Asp Phe Asp  Phe Asp Asp
    1025                 1030                 1035

Glu Leu  Ser Lys Trp Trp Asn  Asp Thr Lys His Glu  Leu Pro Asp
    1040                 1045                 1050

Phe Asp  Glu Phe Asn Tyr Thr  Ile Pro Val Leu Asn  Ile Ser Asn
    1055                 1060                 1065

Glu Ile  Asp Arg Ile Gln Gly  Val Ile Gln Gly Leu  Asn Asp Ser
    1070                 1075                 1080

Leu Ile  Asp Leu Glu Thr Leu  Ser Ile Leu Lys Thr  Tyr Ile Lys
    1085                 1090                 1095

Trp Pro  Trp Tyr Val Trp Leu  Ala Ile Phe Phe Ala  Ile Val Ile
    1100                 1105                 1110

Phe Ile  Leu Ile Ile Gly Trp  Val Phe Phe Met Thr  Gly Cys Cys
    1115                 1120                 1125

Gly Cys  Cys Cys Gly Cys Phe  Gly Ile Ile Pro Leu  Met Asn Lys
    1130                 1135                 1140

Cys Gly  Lys Lys Ser Ser Tyr  Tyr Thr Thr Phe Asp  Asn Asp Val
    1145                 1150                 1155

Val Thr  Glu Gln Tyr Arg Pro  Lys Lys Ser Val
    1160                 1165


<210> SEQ ID NO 17
<211> LENGTH: 1082
<212> TYPE: PRT
<213> ORGANISM: Avian infectious bronchitis virus

<400> SEQUENCE: 17

Ser Leu Tyr Asn Asn Asp Ser Tyr Val Tyr Tyr Tyr Gln Ser Ala Phe
1               5                   10                  15

Arg Pro Phe Asn Gly Trp His Leu His Gly Gly Ala Tyr Ala Val Val
            20                  25                  30

Asn Val Ser Gln Glu Thr Ala Asn Ala Gly Ser Ser Pro Ser Cys Thr
        35                  40                  45

Ala Gly Ala Ile Tyr Trp Ser Lys Asn Phe Thr Ala Ser Ser Val Ala
    50                  55                  60

Met Thr Ala Pro Leu Gln Gly Met Gln Trp Ser Thr Ile Gln Phe Cys
65                  70                  75                  80

Thr Ala His Cys Asn Phe Thr Asn Ile Val Val Phe Val Thr His Cys
                85                  90                  95

Tyr Lys Ser Gly Ser Thr Val Cys Pro Leu Thr Gly Leu Ile Pro Gln
            100                 105                 110

Asn His Ile Arg Ile Ser Ala Met Lys Gln Gly Asn Asn Gly Pro Ser
        115                 120                 125

Gly Leu Phe Tyr Asn Leu Thr Val Pro Val Thr Lys Tyr Ser Lys Phe
    130                 135                 140

Lys Ser Leu Gln Cys Val Asn Asn Gln Thr Ser Val Tyr Leu Asn Gly
145                 150                 155                 160

Asp Leu Val Phe Thr Ser Asn Glu Thr Lys Asp Val Ser Gly Ala Gly
                165                 170                 175

Val Tyr Phe Lys Ala Gly Gly Pro Ile Thr Tyr Lys Val Met Arg Glu
            180                 185                 190

Val Lys Ala Leu Ala Tyr Phe Val Asn Gly Thr Ala His Asp Val Ile
        195                 200                 205

Leu Cys Asp Gly Ser Pro Arg Gly Leu Leu Ala Cys Gln Tyr Asn Thr
    210                 215                 220
```

```
Gly Lys Phe Ser Asp Gly Phe Tyr Pro Phe Thr Asn Asp Thr Leu Val
225                 230                 235                 240

Lys Glu Lys Phe Ile Val Tyr Arg Glu Asn Ser Val Asn Thr Thr Leu
                245                 250                 255

Thr Leu Thr Asn Phe Thr Phe Tyr Asn Glu Ser Asn Ala Leu Pro Asn
            260                 265                 270

Asn Gly Gly Val Asp Thr Ile Gln Leu Tyr Gln Thr His Thr Ala Gln
        275                 280                 285

Ser Gly Tyr Tyr Asn Phe Asn Phe Ser Phe Leu Ser Ser Phe Gln Tyr
    290                 295                 300

Val Glu Ser Asn Phe Met Tyr Gly Ser Tyr His Pro Lys Cys Gly Phe
305                 310                 315                 320

Arg Pro Glu Ser Ile Asn Asn Gly Leu Trp Phe Asn Ser Leu Ser Val
                325                 330                 335

Ser Leu Ala Tyr Gly Pro Leu Gln Gly Gly Cys Lys Gln Ser Val Phe
            340                 345                 350

His Gly Arg Ala Thr Cys Cys Tyr Ala Tyr Ser Tyr Asn Gly Pro Thr
        355                 360                 365

Leu Cys Lys Gly Val Tyr Ser Gly Glu Leu Thr Arg Ser Tyr Gln Cys
    370                 375                 380

Gly Leu Leu Val Phe Val Thr Lys Ser Asp Gly Ser Arg Ile Gln Thr
385                 390                 395                 400

Ser Thr Lys Pro Ile Val Leu Thr Gln His Asn Tyr Asn Asn Ile Thr
                405                 410                 415

Leu Asp Arg Cys Val Glu Tyr Asn Ile Tyr Gly Arg Val Gly Gln Gly
            420                 425                 430

Phe Ile Thr Asn Val Thr Glu Ser Ala Ala Ala Phe Asn Tyr Leu Glu
        435                 440                 445

Asp Gly Gly Leu Ala Ile Leu Asp Thr Ser Gly Ala Ile Asp Ile Phe
    450                 455                 460

Val Val Gln Gly Glu Tyr Gly Phe Asn Tyr Tyr Lys Val Asn Pro Cys
465                 470                 475                 480

Glu Asp Val Asn Gln Gln Phe Val Val Ser Gly Gly Asn Leu Val Gly
                485                 490                 495

Ile Leu Thr Ser Ile Asn Gln Thr Gly Ser Gln Ser Ile Glu Asn Gln
            500                 505                 510

Phe Tyr Val Lys Leu Thr Asn Gly Ser Arg Arg Ser Arg Arg Ser Val
        515                 520                 525

Ser Glu Asn Val Thr Ser Cys Pro Tyr Val Ser Tyr Gly Lys Phe Cys
    530                 535                 540

Ile Lys Pro Asp Gly Ser Leu Ser Thr Ile Val Pro Lys Glu Leu Glu
545                 550                 555                 560

Gln Phe Val Ala Pro Leu Leu Asn Val Thr Glu His Val Leu Ile Pro
                565                 570                 575

Asp Ser Phe Asn Leu Thr Val Thr Asp Glu Tyr Ile Gln Thr Arg Met
            580                 585                 590

Asp Lys Val Gln Ile Asn Cys Leu Gln Tyr Val Cys Gly Asn Ser Phe
        595                 600                 605

Glu Cys Arg Lys Leu Phe Gln Gln Tyr Gly Pro Val Cys Asp Asn Ile
    610                 615                 620

Leu Ser Val Val Asn Ser Val Gly Gln Lys Glu Asp Met Glu Leu Leu
625                 630                 635                 640
```

```
Ser Phe Tyr Ser Ser Thr Lys Pro Ser Gly Ile Ser Gln Pro Leu Phe
            645                 650                 655

Asn Asn Phe Ser Thr Gly Asp Phe Asn Ile Ser Leu Leu Leu Thr Ser
            660                 665                 670

Pro Ser Ser Pro Ser Gly Arg Ser Phe Ile Glu Asp Leu Leu Phe Thr
        675                 680                 685

Ser Val Glu Ser Val Gly Leu Pro Thr Asp Glu Ala Tyr Lys Lys Cys
    690                 695                 700

Thr Ser Gly Pro Leu Gly Phe Val Lys Asp Leu Val Cys Ala Arg Glu
705                 710                 715                 720

Tyr Asn Gly Leu Leu Val Leu Pro Pro Ile Ile Thr Ala Glu Met Gln
            725                 730                 735

Thr Met Tyr Thr Ser Ser Leu Val Ala Ser Met Ala Leu Gly Gly Ile
            740                 745                 750

Thr Ala Ala Gly Ala Ile Pro Phe Ala Thr Gln Leu Gln Ala Arg Ile
        755                 760                 765

Asn His Leu Gly Ile Thr Gln Ser Leu Leu Met Lys Asn Gln Glu Lys
    770                 775                 780

Ile Ala Ala Ser Phe Asn Arg Ala Ile Gly His Met Gln Glu Gly Phe
785                 790                 795                 800

Lys Ser Thr Ser Leu Ala Leu Gln Gln Ile Gln Asp Val Val Asn Lys
            805                 810                 815

Gln Ser Ala Ile Leu Thr Glu Thr Met Ala Ser Leu Asn Lys Asn Phe
            820                 825                 830

Gly Ala Ile Ser Ser Val Leu Gln Asp Ile Tyr Gln Gln Leu Asp Val
        835                 840                 845

Ile Gln Ala Asp Ala Gln Val Asp Arg Ile Ile Thr Gly Arg Leu Ser
    850                 855                 860

Ser Leu Ser Val Leu Ala Ser Ala Lys Gln Ser Glu Tyr Ile Ala Val
865                 870                 875                 880

Ser Gln Gln Arg Ala Leu Ala Thr Gln Lys Ile Asn Glu Cys Val Lys
            885                 890                 895

Ser Gln Ser Thr Arg Tyr Ser Phe Cys Gly Asn Gly Arg His Val Leu
            900                 905                 910

Thr Ile Pro Gln Asn Ala Pro Asn Gly Ile Val Phe Ile His Phe Thr
        915                 920                 925

Tyr Thr Pro Glu Ser Phe Val Asn Val Thr Ala Ile Val Gly Phe Cys
    930                 935                 940

Val Lys Pro Pro Asn Ala Ser His Tyr Ala Ile Val Pro Val Asn Gly
945                 950                 955                 960

Arg Gly Ile Phe Ile Gln Val Asn Gly Thr Tyr Tyr Ile Thr Ser Arg
            965                 970                 975

Asp Met Tyr Met Pro Arg Asn Ile Thr Ala Gly Asp Ile Val Thr Leu
            980                 985                 990

Thr Ser Cys Gln Ala Asn Tyr Val  Ser Val Asn Lys Thr  Val Ile Ser
        995                 1000                1005

Thr Phe  Val Glu Asp Asp Asp  Phe Asp Phe Asp Asp  Glu Leu Ser
    1010                1015                1020

Lys Trp  Trp Asn Asp Thr Lys  His Glu Leu Pro Asp  Phe Asp Glu
    1025                1030                1035

Phe Asn  Tyr Thr Ile Pro Val  Leu Asn Ile Ser Asn  Glu Ile Asp
    1040                1045                1050

Arg Ile  Gln Gly Val Ile Gln  Gly Leu Asn Asp Ser  Leu Ile Asp
```

```
    1055                1060                1065

Leu Glu  Thr Leu Ser Ile Leu  Lys Thr Tyr Ile Lys  Trp Pro
    1070                1075                1080


<210> SEQ ID NO 18
<211> LENGTH: 11860
<212> TYPE: DNA
<213> ORGANISM: Artificial Sequence
<220> FEATURE:
<223> OTHER INFORMATION: Plasmit with IBV

<400> SEQUENCE: 18

tcgcgcgttt cggtgatgac ggtgaaaacc tctgacacat gcagctcccg gagacggtca     60

cagcttgtct gtaagcggat gccgggagca gacaagcccg tcagggcgcg tcagcgggtg    120

ttggcgggtg tcggggctgg cttaactatg cggcatcaga gcagattgta ctgagagtgc    180

accatatgcg gtgtgaaata ccgcacagat gcgtaaggag aaaataccgc atcaggcgcc    240

attcgccatt caggctgcgc aactgttggg aagggcgatc ggtgcgggcc tcttcgctat    300

tacgccagct ggcgaaaggg ggatgtgctg caaggcgatt aagttgggta acgccagggt    360

tttcccagtc acgacgttgt aaaacgacgg ccagtgaatt ggagatcggt acttcgcgaa    420

tgcgtcgaga tgagctctaa tacgactcac tatagggact taagtgtgat ataaatatat    480

atcatacata ctagccttgt gctagatttc caacttaaca aaacggactt aaatacctac    540

agttggtccc tataggtgtt ccattgcagt gcactttagt gccctggatg gcacctggcc    600

acctgtcagg tttttgttat taaaataata ttgttgctgg tatcactgct tgttttgccg    660

tgtctcactt tatacatccg ttgcttgggc tacctagtat ccagcgtcct actggcgttg    720

tggtcggttc gagtgcgaag aacctctggt tcatctagcg gtacgcgggt gtgtggaagt    780

agcgcttcag acgtaccggt tctgttgcgt gaaatacggg gtcacctccc cccacatacc    840

tctaagggct tttgagccta gcgttgggct acgttctcgc acaaggtcgg ctatacggcg    900

tttgtagggg gtagtgccaa acaacccctg aggtgacagg ttctggtggt gtttcgaaaa    960

caacaatgtg tgtgccgcat aatatgcgag taatgcattt tggagcagga agtgacaaag   1020

gagtggcccc aggtagcgct gttcttaggc agtggcttcc cgaaggtaca ctccttgtcg   1080

ataatgatat tgtagattat gtatctgatg cacatgtctc tgtgctttca gattgcaata   1140

aatgtaaaac agagcacaag tttgatcttg tgatatctga tatgtataca gataatgatt   1200

caaagagaaa gcatgaaggc gttgtagcca ataacggcaa tgatgacgtc ttcatatacc   1260

tttcaaactt tcttcgtaac aatttagctc tgggaggcag ttttgccgta aaagtaacag   1320

agacaagttg gcatgagagt ttatatgaca ttgcacagga ttgtgcatgg tggacaatgt   1380

tttgtacagc agtgaatgct tcttcgtcag aagcattctt gattggtgtt aattatttgg   1440

gtgcaagtga aaaggttaga gttagtggta aaaccctgca cgcaaattat atattttgga   1500

ggaattgtaa ttatttacaa acttcagcct atagtatatt tgacgttgct aagtttgatt   1560

tgaaattaaa agcaacgcca gttgtgaatt tgaaaactga acaaaagaca gacttagtct   1620

ttaatttaat taagtgtggt aagttactgg taagagatgt tggacaaacc gcttttacta   1680

gtgactcttt ggtatgcact atgtagtgct ttgctctatg ataataatta tattggtgat   1740

tttagatgta tccagcttgt gaactcaaac ggtgctaatg ttagtgctcc aagcattagc   1800

actgagaccg ttgaagtttc acaaggcctg ggacatattt atgtgttaga tcgagtttat   1860

ttaaatgcca cattattgct tactggttac tacccggtcg atggttctaa gtttagaaac   1920
```

```
ctcgctctta cgggaactaa ctcagttagc ttgtcgtggt ttcaaccacc ctatttaagt   1980
cagtttaatg atggcatatt tgcgaaggtg cagaacctta agacaagtac gccatcaggt   2040
gcaactgcat attttcctac tatagttata ggtagtttgt ttggctatac ttcctatacc   2100
gttgtaatag agccatataa tggtgttata atggcctcag tgtgccagta taccatttgt   2160
cagttacctt acactgattg taagcctaac actaatggta ataagcttat agggttttgg   2220
cacacggatg taaaaccccc aatttgtgtg ttaaagcgaa atttcacgct taatgttaat   2280
gctgatgcat tttattttca tttttaccaa catggtggta ctttttatgc gtactatgcg   2340
gataaaccct ccgctactac gtttttgttt agtgtatata ttggcgatat tttaacacag   2400
tattatgtgt tacctttcat ctgcaaccca acagctggta gcacttttgc tccgcgctat   2460
tgggttacac ctttggttaa gcgccaatat ttgtttaatt tcaaccagaa gggtgtcatt   2520
actagtgctg ttgattgtgc tagtagttat accagtgaaa taaaatgtaa gacccagagc   2580
atgttaccta gcactggtgt ctatgagtta tccggttata cggtccaacc agttggagtt   2640
gtataccggc gtgttgctaa cctcccagct tgtaatatag aggagtggct tactgctagg   2700
tcagtcccct cccctctcaa ctgggagcgt aagacttttc agaattgtaa ttttaattta   2760
agcagcctgt tacgttatgt tcaggctgag agtttgtttt gtaataatat cgatgcttcc   2820
aaagtgtatg gcaggtgctt tggtagtatt tcagttgata agtttgctgt accccgaagt   2880
aggcaagttg atttacagct tggtaactct ggatttctgc agactgctaa ttataagatt   2940
gatacagctg ccacttcgtg tcagctgcat tacaccttgc ctaagaataa tgtcaccata   3000
aacaaccata accccctcgtc ttggaatagg aggtatggct ttaatgatgc tggcgtcttt   3060
ggcaaaaacc aacatgacgt tgtttacgct cagcaatgtt ttactgtaag atctagttat   3120
tgcccgtgtg ctcaaccgga catagttagc ccttgcacta ctcagactaa gcctaagtct   3180
gcttttgtta atgtgggtga ccattgtgaa ggcttaggtg ttttagaaga taattgtggc   3240
aatgctgatc cacataaggg ttgtatctgt gccaacaatt catttattgg atggtcacat   3300
gatacctgcc ttgttaatga tcgctgccaa atttttgcta atatattgtt aaatggcatt   3360
aatagtggta ccacatgttc cacagatttg cagttgccta atactgaagt ggttactggc   3420
atttgtgtca aatatgacct ctacggtatt actggacaag gtgtttttaa agaggttaag   3480
gctgactatt ataatagctg gcaaaccctt ctgtatgatg ttaatggtaa tttgaatggt   3540
tttcgtgatc ttaccactaa caagacttat acgataagga gctgttatag tggccgtgtt   3600
tctgctgcat ttcataaaga tgcacccgaa ccggctctgc tctatcgtaa tataaattgt   3660
agctatgttt ttagcaataa tatttcccgt gaggagaacc cacttaatta ctttgatagt   3720
tatttgggtt gtgttgttaa tgctgataac cgcacggatg aggcgcttcc taattgtgat   3780
ctccgtatgg gtgctggctt atgcgttgat tattcaaaat cacgcagggc tcaccgatca   3840
gtttctactg gctatcggtt aactacattt gagccataca ctccgatgtt agttaatgat   3900
agtgtccaat ccgttgatgg attatatgag atgcaaatac caaccaattt tactattggg   3960
caccatgagg agttcattca aactagatct ccaaaggtga ctatagattg tgctgcattt   4020
gtctgtggtg ataacactgc atgcaggcag cagttggttg agtatggctc tttctgtgtt   4080
aatgttaatg ccattcttaa tgaggttaat aacctcttgg ataatatgca actacaagtt   4140
gctagtgcat taatgcaggg tgttactata agttcgagac tgccagacgg catctcaggc   4200
cctatagatg acattaattt tagtcctcta cttggatgca taggttcaac atgtgctgaa   4260
gacggcaatg gacctagtgc aatccgaggg cgttctgcta tagaggattt gttatttgac   4320
```

```
aaggtcaaat tatctgatgt tggctttgtc gaggcttata ataattgcac cggtggtcaa   4380
gaagttcgtg acctcctttg tgtacaatct tttaatggca tcaaagtatt acctcctgtg   4440
ttgtcagaga gtcagatctc tggctacaca accggtgcta ctgcggcagc tatgttccca   4500
ccgtggtcag cagctgccgg tgtgccattt agtttaagtg ttcaatatag aattaatggt   4560
ttaggtgtca ctatgaatgt gcttagtgag aaccaaaaga tgattgctag tgcttttaac   4620
aatgcgctgg gtgctatcca ggatgggttt gatgcaacca attctgcttt aggtaagatc   4680
cagtccgttg ttaatgcaaa tgctgaagca ctcaataact tactaaatca actttctaac   4740
aggtttggtg ctattagtgc ttctttacaa gaaattctaa ctcggcttga ggctgtagaa   4800
gcaaaagccc agatagatcg tcttattaat ggcaggttaa ctgcacttaa tgcgtatata   4860
tccaagcaac ttagtgatag tacgcttatt aaagttagtg ctgctcaggc catagaaaag   4920
gtcaatgagt gcgttaagag ccaaaccacg cgtattaatt tctgtggcaa tggtaatcat   4980
atattatctc ttgtccagaa tgcgccttat ggcttatatt tttatacactt cagctatgtg   5040
ccaatatcct ttacaaccgc aaatgtgagt cctggacttt gcatttctgg tgatagagga   5100
ttagcaccta aagctggata ttttgttcaa gatgatggag aatggaagtt cacaggcagt   5160
tcatattact accctgaacc cattacagat aaaaacagtg tcattatgag tagttgcgca   5220
gtaaactaca caaaggcacc tgaagttttc ttgaacactt caatacctaa tccacccgac   5280
tttaaggagg agttagataa atggtttaag aatcagacgt ctattgcgcc tgatttatct   5340
ctcgatttcg agaagttaaa tgttactttg ctggacctga cgtatgagat gaacaggatt   5400
caggatgcaa ttaagaagtt aaatgagagc tacatcaacc tcaaggaagt tggcacatat   5460
gaaatgtatg tgaaatggcc ttggtatgtg tggcttgcca ttgcattcct taccattatt   5520
tttattctgg tactttgttg gatatttttc atgaccggtt gttgcggttg ttgttgtgga   5580
tgctttggta tcataccgtt aatgagtaag tgtggtaaga aatcttctta ctacacgact   5640
tttgataatg atgtggtaac ttaacaatac agacctaaaa agtctgttta atgattaaaa   5700
gtcccacatc ttttctaata ttattaattc ttctttggtg taaacttgca ttaagttgtt   5760
ttaaagagtg tgttataaca ctccagcaac tagtacaaat tttactccaa attattaata   5820
gtaacttaca atctagactt ctgctttggc acagtctaga ctaatgttag attttgaagc   5880
aattattgaa actggtcagc aaataactca acaaattagt ttctatttac agcatatttc   5940
aagggtgcta agtactgaat tatttgaccc ctttgaagtt tgtgtttaca gaggaggtaa   6000
ttgttgggag ttagagtcag ctgacgagtt ttcaggtgat gacgaatata ttgagtagat   6060
cgctcgagga gaacggaagt tttctaacag cggtttacgt gtttttagga tttttagcac   6120
tttatctact aggtagagcg cttcaagctt ttgtacaagc ggctgacgct tgttgtcttt   6180
tttggtatac atgggtagta gttcctggag ccaagggcac agcctttgtt tataatcata   6240
catatggtaa aaaacttaac aaaccggagt tagaaacggt tattgttaac gaatttccaa   6300
aaaacggttg gaaatatgga taataccatc aattgtactc ttggtactga acaagcagtt   6360
cagcttttta aggaatataa tctgtttgta actgcattcc tgttgttttt aaccatacta   6420
cttcagtatg gatacgcaac taggagcaag gttatttaca tactgaaaat gatagtgtta   6480
tggtgctttt ggcccettaa cattgcagta ggtgtaatct catgtatata cccaccaaac   6540
acaggaggtc ttgtcgcagc gataattctt acagtgtttg cgtgtctttc ttttataggt   6600
tattggatcc agagtattag actttttaag cggtgcaggt catggtggtc atttaacccc   6660
```

```
gaatctaatg ccgtaggttc aatactccta actaatggtc aacaatgtaa ttttgctata   6720

gagagtgtgc cgatggtgct ttctcctatt ataaagaatg gtgctcttta ttgcgagggt   6780

cagtggcttg ctaaatgtga accagaccac ttgcctagag atatatttgt atgcacaccg   6840

gatagacgta atatctatcg tatggtgcaa aaatatactg gtgaccaaag cggaagtaag   6900

aaaaggtttg ccacatttgt ctatgcaaag cagtcagtag atactggcga gctagaaagt   6960

gtgtcagcag taggaggtag tctttacaca taaatgtgtg tgtgtagaga gtatttaaaa   7020

ttattctttg acagtgcctc cgttttaaga gcgcggaaga gtattatttt tgaggatatt   7080

aatataaatc ctctttgttt catactctcc tttcaggagt tattatttaa aaaacagttt   7140

ttccactctt ttgtgccaaa aacaattgtt gttaatggtg taacctttca ggtagacaat   7200

ggaaaagtct actacgaagg aagaccaatt ttccaaaaag gttgttgtag tttgtggtcc   7260

aattataaga aagattagaa taattaaacc acctacaaca cttattttta caaatggcgt   7320

tttaggttac aaacgcttaa caaatacgga tgatgaaatg gctgactagt tttggaagag   7380

ctttcatctc ctgttataaa tccctattac taactcaatt aagagtatta gataggttaa   7440

ttttagatca cggacccaag cgcacattaa cgtgtgctag gcgagtgctt ttagttcaat   7500

tagatttagt ttataggttg gcttatacgc ccacccaatc gctggtatga ataatagtaa   7560

agataatcct tttcgcggag caatagcaag aaaagcgcga atttatctga gaggaggatt   7620

agattgtgtt tactttctta acaaagcagg acaagcagag ccttgtcccg cgtgtacctc   7680

cctagtattc caagggaaaa cttgtgagga acactattat aataacaatc ttttgtcatg   7740

gcaagcggta aggcaactgg aaagacagac gccccagcgc cagtcatcaa actaggagga   7800

ccaaagccac ctaaagttgg ttcttctgga aatgcatcat ggtttcaacc gataaaggcc   7860

aagaagctaa attcacctgt gcctaaattt gacggtagtg gtgttcctga aaatgaaaat   7920

ctcaagtcaa gccagcaaca tggatactgg agacgccaac acaggtttaa gcctggcaaa   7980

ggtggaagaa aaccagtccc tgatgcttgg tacttttact acactggaac aggaccggcc   8040

gccgacctga attggggtga aactcaagat ggtatagtgt gggttgctgc aaagggtgct   8100

gatactaaat ctagatcaaa ccagggtaca agggatcctg ataagtttga ccaataccca   8160

ctacgattct cagatggagg accggatggt aatttccgtt gggacttcat accaataaat   8220

cgtggtagga gtgggagatc aacagcagct tcatcagcag catctagtag agcaccatct   8280

cgtgaggggt cacgtggacg tagaagcgga gttgaagatg atcttatagc tcgcgcagca   8340

aagattatac aggaccagca aaagaagggt gcgcgcatta ccaaggctaa ggctgatgaa   8400

atggctcatc gccgctattg caagcgcact atcccacctg gttataaggt tgagcaagta   8460

tttggtcccc gtactaaagg taaggaagga aattttggtg atgacaagat gaatgaggaa   8520

ggtgttaagg atgggcgtgt tacggcaatg ctcaacctag tccctagcag tcatgcttgt   8580

ctttttggaa gtagggtgac gcccaaactg cagccagatg gtcttcacct gagatttgaa   8640

tttactactg tggtgtcacg tgatgatccg cagtttgata attatgtgaa aatttgtgat   8700

cagtgtgtcg atggtgtagg gacgcgtcca aaggacgatg aatcgagacc aaagtcacgc   8760

ccaaattcaa gacctgcaac tagaggaaat tctccagcgc cgagacaaca gcgcccaaag   8820

aaggagaaaa agcccaagaa gcaggatgat gaagtagata aggcattgac ctcagatgag   8880

gagaggaaca atgcacagct ggaatttgat gatgaaccca aggtgattaa ctggggggac   8940

tctgcactag gtgaaaatga actttgatta acataatgga cttgctgcat ttgctgtcac   9000

attttgttaa atattatttt tgtgttttac tatcaattat tacaggtatt gattgtgatt   9060
```

```
atgttcaata cttaagcttc ttctggttgc tttttgcttg ttgtattgtt gctgtgcttt   9120
ttattattgt gattctcatt agtttgcttt atcgtagaaa ttcaatagta agagttaagg   9180
aagataggca tgtagcttag cacctacatg tctatcgcca gggaaatgtc taatctgtct   9240
acttagtagc ctggaaacga acggtagacc cttagatttt aatttagttt aatttttagt   9300
ttagtttaag ttagtttaga gtaggtataa agatgccagt gccggggcca cgcgtagtac   9360
gaccgagggt acagcactag gacgcccact aggggaagag ctaaatttta gtttaagtta   9420
agtttaattg gctaaatata gttaaaattt ataggctagt atagagttag agcaaaaaaa   9480
aaaaaaaaaa aaaaaaaaaa aaaaaaaaaa aaaaaaaaaa aaaaaaaaaa aaaaaaaaaa   9540
aaaaaaaaaa aaaaaaaaaa aaaaaaaaaa aaagcggccg catcggatgc cgggaccgac   9600
gagtgcagag gcgtgcaagc gagcttggcg taatcatggt catagctgtt tcctgtgtga   9660
aattgttatc cgctcacaat tccacacaac atacgagccg gaagcataaa gtgtaaagcc   9720
tggggtgcct aatgagtgag ctaactcaca ttaattgcgt tgcgctcact gcccgctttc   9780
cagtcgggaa acctgtcgtg ccagctgcat taatgaatcg gccaacgcgc ggggagaggc   9840
ggtttgcgta ttgggcgctc ttccgcttcc tcgctcactg actcgctgcg ctcggtcgtt   9900
cggctgcggc gagcggtatc agctcactca aaggcggtaa tacggttatc cacagaatca   9960
ggggataacg caggaaagaa catgtgagca aaaggccagc aaaaggccag gaaccgtaaa  10020
aaggccgcgt tgctggcgtt tttccatagg ctccgccccc ctgacgagca tcacaaaaat  10080
cgacgctcaa gtcagaggtg gcgaaacccg acaggactat aaagatacca ggcgtttccc  10140
cctggaagct ccctcgtgcg ctctcctgtt ccgaccctgc cgcttaccgg atacctgtcc  10200
gcctttctcc cttcgggaag cgtggcgctt tctcatagct cacgctgtag gtatctcagt  10260
tcggtgtagg tcgttcgctc caagctgggc tgtgtgcacg aaccccccgt tcagcccgac  10320
cgctgcgcct tatccggtaa ctatcgtctt gagtccaacc cggtaagaca cgacttatcg  10380
ccactggcag cagccactgg taacaggatt agcagagcga ggtatgtagg cggtgctaca  10440
gagttcttga agtggtggcc taactacggc tacactagaa gaacagtatt tggtatctgc  10500
gctctgctga agccagttac cttcggaaaa agagttggta gctcttgatc cggcaaacaa  10560
accaccgctg gtagcggtgg tttttttgtt tgcaagcagc agattacgcg cagaaaaaaa  10620
ggatctcaag aagatccttt gatcttttct acggggtctg acgctcagtg gaacgaaaac  10680
tcacgttaag ggattttggt catgagatta tcaaaaagga tcttcaccta gatcctttta  10740
aattaaaaat gaagttttaa atcaatctaa agtatatatg agtaaacttg gtctgacagt  10800
taccaatgct taatcagtga ggcacctatc tcagcgatct gtctatttcg ttcatccata  10860
gttgcctgac tccccgtcgt gtagataact acgatacggg agggcttacc atctggcccc  10920
agtgctgcaa tgataccgcg agacccacgc tcaccggctc cagatttatc agcaataaac  10980
cagccagccg gaagggccga gcgcagaagt ggtcctgcaa ctttatccgc ctccatccag  11040
tctattaatt gttgccggga agctagagta agtagttcgc cagttaatag tttgcgcaac  11100
gttgttgcca ttgctacagg catcgtggtg tcacgctcgt cgtttggtat ggcttcattc  11160
agctccggtt cccaacgatc aaggcgagtt acatgatccc ccatgttgtg caaaaaagcg  11220
gttagctcct tcggtcctcc gatcgttgtc agaagtaagt tggccgcagt gttatcactc  11280
atggttatgg cagcactgca taattctctt actgtcatgc catccgtaag atgcttttct  11340
gtgactggtg agtactcaac caagtcattc tgagaatagt gtatgcggcg accgagttgc  11400
```

```
tcttgcccgg cgtcaatacg ggataatacc gcgccacata gcagaacttt aaaagtgctc  11460
atcattggaa aacgttcttc ggggcgaaaa ctctcaagga tcttaccgct gttgagatcc  11520
agttcgatgt aacccactcg tgcacccaac tgatcttcag catcttttac tttcaccagc  11580
gtttctgggt gagcaaaaac aggaaggcaa aatgccgcaa aaaagggaat aagggcgaca  11640
cggaaatgtt gaatactcat actcttcctt tttcaatatt attgaagcat ttatcagggt  11700
tattgtctca tgagcggata catatttgaa tgtatttaga aaaataaaca aataggggtt  11760
ccgcgcacat ttccccgaaa agtgccacct gacgtctaag aaaccattat tatcatgaca  11820
ttaacctata aaaataggcg tatcacgagg ccctttcgtc                        11860
```

```
<210> SEQ ID NO 19
<211> LENGTH: 3489
<212> TYPE: DNA
<213> ORGANISM: Avian infectious bronchitis virus

<400> SEQUENCE: 19

atgttggtaa cacctctttt actagtgact cttttgtgtg cactatgtag tgctgctttg     60
tatgactcga gttcttacgt gtactactac caaagtgcct tcagaccacc tgatggttgg    120
catttacatg gggtgcgta tgcggttgtt aatatttcta gtgaatctaa taatgcaggc     180
tcttcatctg ggtgtactgt tggtattatt catggtggtc gtgttgttaa tgcttcttct    240
atagctatga cggcaccgtc atcaggtatg gcttggtcta gcagtcagtt ttgtactgca    300
tactgtaact tttcagatac tacagtgttt gttacacatt gttataaaca tggtgggtgt    360
cctataactg gcatgcttca acagcattct atacgtgttt ctgctatgaa aaatggccag    420
cttttctata atttaacagt tagtgtagct aagtacccta cttttaaatc atttcagtgt    480
gttaataatt taacatccgt atatttaaat ggtgatcttg tttacacctc taatgagacc    540
acagatgtta catctgcagg tgtttatttt aaagctggtg gacctataac ttataaagtt    600
atgagagaag ttagagccct ggcttatttt gttaatggta ctgcacaaga tgttattttg    660
tgtgatgggt cacctagagg cttgttagca tgccagtata atactggcaa tttttcagat    720
ggcttttatc cttttactaa tagtagttta gttaagcaga agtttattgt ctatcgtgaa    780
aatagtgtta atactacttt tacgttacac aatttcactt ttcataatga gactggcgcc    840
aacccaaatc ctagtggtgt ccagaatatt caaacttacc aaacacaaac agctcagagt    900
ggttattata attttaattt ttcctttctg agtagttttg tttataagga gtctaatttt    960
atgtatggat cttatcaccc aagttgtaat tttagactag aaactattaa taatggtttg   1020
tggtttaatt cactttcagt tagtattgct tacggtcctc ttcaaggtgg ttgcaagcaa   1080
tctgtcttta gtggtagagc aacctgttgt tatgcttact catatggagg tcctttgctg   1140
tgtaaaggtg tttattcagg tgagttagat cataattttg aatgtggact gttagtttat   1200
gttactaaga gcggtggctc tcgtatacaa acagccactg aaccgccagt tataactcaa   1260
cacaattata ataatattac tttaaatact tgtgttgatt ataatatata tggcagaact   1320
ggccagggtt ttattactaa tgtaaccgac tcagctgtta gttataatta tctagcagac   1380
gcaggtttgg ctattttaga tacatctggt tccatagaca tctttgtcgt acaaagtgaa   1440
tatggtctta attattataa ggttaaccct tgcgaagatg tcaaccagca gtttgtagtt   1500
tctggtggta aattagtagg tattcttact tcacgtaatg agactggttc ccagcttctt   1560
gagaatcagt tttacatcaa aatcactaat ggaacacgtc gttttagacg ttctattact   1620
gaaagtgttg aaaattgccc ttatgttagt tatggtaagt tttgtataaa acctgatggc   1680
```

```
agtattgcca caatagtacc aaaacagtta gaacagtttg tggcaccttt acttaatgtt   1740

actgaaaatg tgctcatacc taacagtttt aatttaactg ttacagatga gtacatacaa   1800

actcggatgg ataaggtcca aattaattgc ctgcagtata tttgtggcaa ttctctggag   1860

tgcagaaatt tgtttcaaca atatggtcct gtttgcgaca acatattgtc tgtagtaaat   1920

agtgttggtc aaaaagaaga tatggaactt ttgaatttct attcttctac taagccggct   1980

ggttttaata caccagttct tagtaatgtt agcactggtg agtttaatat tactcttttt   2040

ttaacaacgc ctagtagtcc tagaaggcgt tcttttattg aagaccttct atttacaagt   2100

gttgaatctg ttggattacc aacagatgac gcatacaaaa attgcactgc aggtccttta   2160

ggctttctga aagaccttgc atgtgctcgt gaatataatg gtttgcttgt gttgcctcct   2220

attataacag cagaaatgca aactttgtat acaagctctc tagtagcttc tatggctttt   2280

ggtggtatta ctgcagctgg tgctatacct tttgccacac aactgcaggc tagaattaat   2340

cacttgggta ttacccagtc acttcttttg aagaatcaag aaaaaattgc tgcttccttt   2400

aataaggcca tcggtcatat gcaggaaggt tttagaagta catctttagc attacaacaa   2460

attcaagatg ttgttaataa gcagagtgct attcttactg agactatggc atcacttaat   2520

aaaaattttg gtgccatttc ttctgtgatt caagaaatct accagcaact tgacgccata   2580

caagcaaatg ctcaagtgga tcgtcttata actggtagat tgtcatcact ttctgtttta   2640

gcatctgcta agcaggcgga gtatattaga gtgtcacaac agcgtgagtt agctactcag   2700

aagattaatg agtgtgttaa gtcacagtcc attaggtact ccttttgtgg taatggacga   2760

catgttttaa ccataccgca aaatgcacct aatggtatag tgtttataca cttttcttac   2820

actccagata gttttgttaa tgttactgca atagtgggtt tttgtgtaaa gccagctaat   2880

gctagtcagt atgcaatagt acccgctaat ggtaggggta tttttataca agttaatggt   2940

agttactaca tcactgcacg agatatgtat atgccaagag ctattactgc aggagatata   3000

gttacgctta cttcttgtca agcaaattat gtaagtgtaa ataagaccgt cattactaca   3060

ttcgtagaca atgatgattt tgattttaat gacgaattgt caaaatggtg gaatgatact   3120

aagcatgagc taccagactt tgacaaattc aattacacag tacctatact tgacattgat   3180

agtgaaattg atcgtattca aggcgttata cagggtctta atgactctct aatagacctt   3240

gaaaaacttt caatactcaa aacttatatt aagtggcctt ggtatgtgtg gctagccata   3300

gcttttgcca ctattatctt catcttaata ttaggatggg ttttcttcat gactgggtgt   3360

tgtggttgtt gttgtggatg ctttggcatt atgcctctaa tgagtaagtg tggtaagaaa   3420

tcttcttatt acacgacttt tgataacgat gtggtaactg aacaatacag acctaaaaag   3480

tctgtttaa                                                           3489
```

<210> SEQ ID NO 20
<211> LENGTH: 3495
<212> TYPE: DNA
<213> ORGANISM: Avian infectious bronchitis virus

<400> SEQUENCE: 20

```
atgttggaca aaccgctttt actagtgact ctttggtatg cactatgtag tgctttgctc     60

tatgataata atacttacgt ttactactac caaagtgcct ttaggcctgg tccaggttgg    120

cacctatatg gggtgctta tgcagtagat agggttttta atgaaaccaa caatgcaggc    180

agtgcatctg attgcactgc tggtactttt tatgaaagcc ataatatttc tgcttcttct    240
```

-continued

```
gtagccatga cagtaccaca taatggtatg tcttggtcag cttcacaatt ttgtacagct    300
cattgtaact tctcagactt tacagtgttc gttacgcatt gttttaaaaa tcaactcggt    360
agttgtccct tgacaggtat gattcctcag aatcatattc gtatttctgc tatgagagat    420
ggagttttgt tttataactt aacagttagc gtatctaaat accctagatt taaatcgctt    480
caatgtgtta gcaattctac atctgtctat gtaaatggtg accttgtttt cacttctaat    540
gaaacttctt acgttacggg tgcaggcgtt tattttaaaa gtggtgggcc tgtaacttat    600
aaagttatga aagaagttaa agccctagcc tactttatta atggtaccgc acaagaggtt    660
attttatgtg ataactcacc tagaggtttg cttgcatgtc agtataacac tggtaatttt    720
tcagatggat tctacccttt tactaatcat tctttagtta aggataggtt tattgtatat    780
cgagaaagta gcactaacac tactttaaag ttaactaatt tcagttttac taatgtaagt    840
aatgcttctc ctaattcagg tggcgttgat actttccaat tatatcaaac aagtactgct    900
caggatggtt attataattt taatttatca tttctgagta gttttgtgta taaaccatct    960
gattttatgt atgggtcata ccacccacat tgtaagttta gaccagagaa tattaataat   1020
ggcttatggt ttaattcatt atctgtgtca cttacttacg gacccattca aggtggttgt   1080
aagcaatctg tttttagtaa tagagcaact tgttgctatg cttattctta tcaagggcct   1140
agtagatgta agggtgttta tagaggggag ctaacgcaat actttgaatg tggacttcta   1200
gtttacgtaa ctaagagtga tggctctcgt atacaaacta gaagtgaacc actggtgtta   1260
actcaatata attataacaa cattacttta aataagtgtg ttgagtataa tatatatggt   1320
agggttggtc aaggttttat tactaatgta actgaagcaa ctgctaatta tagttatcta   1380
gcagatggtg gtttagctat tttagatacc tcaggagcca tagacatatt tgttgttcaa   1440
ggtgcatatg gtcttaatta ttataaggtt aatccctgtg aagatgttaa ccaacagttt   1500
gtagtgtctg gtggcaactt agttggcatt cttacatctc ataatgaaac aggttctgaa   1560
tctattgaga accagtttta catcaaactc actaacggaa cacgtcgctc tagacgttct   1620
gttactggga atgttacaaa ttgcccttat gttagttatg gcaagttttg tataaaacca   1680
gatggttctt tatctataat agtaccacaa gaattagaac agtttgtggc gcctttattc   1740
aatgttactg agcatgtgct catacctgat agttttaatt taactgtcac agatgagtac   1800
atacaaactc gtatggataa ggttcaaatt atttgccttc agtatgtttg tggtaattct   1860
attgaatgca gaaagttgtt tcagcagtat ggacctgttt gtgataatat attgtctgtt   1920
gtaaatggtg taggtcaaag agaggatatg gaacttttaa gtttctattc ttctactaaa   1980
cctagtggtt acaatacacc aatttttaat aatgttagca ctggtgactt taatatttcg   2040
ctcctactaa caccacctaa tagtcctact gggcgctctt ttattgaaga tcttctcttt   2100
acaagtgtag aatctgttgg attaccaact gatgaagagt ataaaaagtg tacagcagga   2160
cctttaggtt ttgttaaaga ccttgtttgt gctagagagt ataatggttt gctcgttctg   2220
cctcctatta ttactgcgga aatgcaaacc atgtatacta gttctttagt agcctctatg   2280
gctttaggtg gcattactgc agctggtgct ataccttttg ctacacaact gcaggccaga   2340
attaaccatt tgggtattac taattctctt ttgttgaaaa accaagaaaa aattgctgct   2400
tcctttaata aggccatcgg tcatatgcag gaagggttta aaagtacttc tctagcatta   2460
caacagattc aagatgttgt taataaacag agttctattc ttacagagac tatgcaatca   2520
cttaataaaa attttggtgc tatttcctct gtaattcaag acatttacca gcaactagat   2580
gctattcagg cagatgctca ggttgatcgt cttattacag gtagactctc ttcactatct   2640
```

```
gttttagctt ctgctaaaca ggcagagtat catagagtgt cacaacagcg tgagttggcc   2700

actcagaaaa ttaatgagtg tgttaagtct cagtctaata ggtattcatt ttgtggtaat   2760

ggtagacatg ttctaaccat accacagaat gcacccaatg gcatagtgtt tatacacttt   2820

acatacactc cagagagttt tgttaatgtt acggcaatag tagggttttg cgtaaaccca   2880

gctaatgcta gtcattatgc aatagtgcct gttaatggca ggggtgtttt tatagaagtt   2940

aatggtagtt actatatcac tgctcgtgat atgtatatgc caagagatat tactgcagga   3000

gacatagtca ctttgacttc ttgtcaagca aactatgtta atgtaaataa aaccgtcatt   3060

aacacttttg tggaagatga cgattttgat ttttatgatg aattgtcaaa atggtggaat   3120

gatactaagc atgagctacc agattttgat gaattcaatt ataccgttcc agttttaaat   3180

attagtaatg aaattgacag aattcaacag gttattcagg gattaaatga ttccctaata   3240

gaccttgaaa cactctcaat tctcaaaact tatattaaat ggccttggta tgtgtggctt   3300

gccattgcat tccttaccat tatttttatt ctggtacttt gttggatatt tttcatgacc   3360

ggttgttgcg gttgttgttg tggatgcttt ggtatcatac cgttaatgag taagtgtggt   3420

aagaaatctt cttactacac gacttttgat aatgatgtgg taacttaaca atacagacct   3480

aaaaagtctg tttaa                                                    3495
```

```
<210> SEQ ID NO 21
<211> LENGTH: 11320
<212> TYPE: DNA
<213> ORGANISM: Artificial Sequence
<220> FEATURE:
<223> OTHER INFORMATION: Plasmid with IBV

<400> SEQUENCE: 21

tcgcgcgttt cggtgatgac ggtgaaaacc tctgacacat gcagctcccg gagacggtca     60

cagcttgtct gtaagcggat gccgggagca gacaagcccg tcagggcgcg tcagcgggtg    120

ttggcgggtg tcggggctgg cttaactatg cggcatcaga gcagattgta ctgagagtgc    180

accatatgcg gtgtgaaata ccgcacagat gcgtaaggag aaaataccgc atcaggcgcc    240

attcgccatt caggctgcgc aactgttggg aagggcgatc ggtgcgggcc tcttcgctat    300

tacgccagct ggcgaaaggg ggatgtgctg caaggcgatt aagttgggta acgccagggt    360

tttcccagtc acgacgttgt aaaacgacgg ccagtgaatt ggagatcggt acttcgcgaa    420

tgcgtcgaga tgagctctaa tacgactcac tatagggact taagtgtgat ataaatatat    480

atcatacata ctagccttgt gctagatttc caacttaaca aaacggactt aaatacctac    540

agttggtccc tataggtgtt ccattgcagt gcactttagt gccctggatg gcacctggcc    600

acctgtcagg tttttgttat taaaataata ttgttgctgg tatcactgct tgttttgccg    660

tgtctcactt tatacatccg ttgcttgggc tacctagtat ccagcgtcct actggcgttg    720

tggtcggttc gagtgcgaag aacctctggt tcatctagcg gtacgcgggt gtgtggaagt    780

agcgcttcag acgtaccggt tctgttgcgt gaaatacggg gtcacctccc cccacatacc    840

tctaagggct tttgagccta gcgttgggct acgttctcgc acaaggtcgg ctatacggcg    900

tttgtagggg gtagtgccaa acaacccctg aggtgacagg ttctggtggt gtttcgaaaa    960

caacaatgtg tgtgccgcat aatatgcgag taatgcattt tggagcagga agtgacaaag   1020

gagtggcccc aggtagcgct gttcttaggc agtggcttcc cgaaggtaca ctccttgtcg   1080

ataatgatat tgtagattat gtatctgatg cacatgtctc tgtgctttca gattgcaata   1140
```

```
aatgtaaaac agagcacaag tttgatcttg tgatatctga tatgtataca gataatgatt   1200
caaagagaaa gcatgaaggc gttgtagcca ataacggcaa tgatgacgtc ttcatatacc   1260
tttcaaactt tcttcgtaac aatttagctc tgggaggcag ttttgccgta aaagtaacag   1320
agacaagttg gcatgagagt ttatatgaca ttgcacagga ttgtgcatgg tggacaatgt   1380
tttgtacagc agtgaatgct tcttcgtcag aagcattctt gattggtgtt aattatttgg   1440
gtgcaagtga aaaggttaga gttagtggta aaaccctgca cgcaaattat atattttgga   1500
ggaattgtaa ttatttacaa acttcagcct atagtatatt tgacgttgct aagtttgatt   1560
tgaaattaaa agcaacgcca gttgtgaatt tgaaaactga acaaaagaca gacttagtct   1620
ttaatttaat taagtgtggt aagttactgg taagagatgt tggacaaacc gcttttacta   1680
gtgactcttt ggtatgcact atgtagtgct ttgctctatg ataataatac ttacgtttac   1740
tactaccaaa gtgcctttag gcctggtcca ggttggcacc tatatggggg tgcttatgca   1800
gtagataggg tttttaatga aaccaacaat gcaggcagtg catctgattg cactgctggt   1860
actttttatg aaagccataa tatttctgct tcttctgtag ccatgacagt accacataat   1920
ggtatgtctt ggtcagcttc acaattttgt acagctcatt gtaacttctc agactttaca   1980
gtgttcgtta cgcattgttt taaaaatcaa ctcggtagtt gtcccttgac aggtatgatt   2040
cctcagaatc atattcgtat ttctgctatg agagatggag ttttgtttta taacttaaca   2100
gttagcgtat ctaaataccc tagatttaaa tcgcttcaat gtgttagcaa ttctacatct   2160
gtctatgtaa atggtgacct tgttttcact tctaatgaaa cttcttacgt tacgggtgca   2220
ggcgtttatt ttaaaagtgg tgggcctgta acttataaag ttatgaaaga agttaaagcc   2280
ctagcctact ttattaatgg taccgcacaa gaggttattt tatgtgataa ctcacctaga   2340
ggtttgcttg catgtcagta taacactggt aatttttcag atggattcta cccttttact   2400
aatcattctt tagttaagga taggtttatt gtatatcgag aaagtagcac taacactact   2460
ttaaagttaa ctaatttcag ttttactaat gtaagtaatg cttctcctaa ttcaggtggc   2520
gttgatactt tccaattata tcaaacaagt actgctcagg atggttatta taattttaat   2580
ttatcatttc tgagtagttt tgtgtataaa ccatctgatt ttatgtatgg gtcataccac   2640
ccacattgta agtttagacc agagaatatt aataatggct tatggtttaa ttcattatct   2700
gtgtcactta cttacggacc cattcaaggt ggttgtaagc aatctgtttt tagtaataga   2760
gcaacttgtt gctatgctta ttcttatcaa gggcctagta gatgtaaggg tgtttataga   2820
ggggagctaa cgcaatactt tgaatgtgga cttctagttt acgtaactaa gagtgatggc   2880
tctcgtatac aaactagaag tgaaccactg gtgttaactc aatataatta taacaacatt   2940
actttaaata agtgtgttga gtataatata tatggtaggg ttggtcaagg ttttattact   3000
aatgtaactg aagcaactgc taattatagt tatctagcag atggtggttt agctatttta   3060
gatacctcag gagccataga catatttgtt gttcaaggtg catatggtct taattattat   3120
aaggttaatc cctgtgaaga tgttaaccaa cagtttgtag tgtctggtgg caacttagtt   3180
ggcattctta catctcataa tgaaacaggt tctgaatcta ttgagaacca gttttacatc   3240
aaactcacta acggaacacg tcgctctaga cgttctgtta ctgggaatgt tacaaattgc   3300
ccttatgtta gttatggcaa gttttgtata aaaccagatg gttctttatc tataatagta   3360
ccacaagaat tagaacagtt tgtggcgcct ttattcaatg ttactgagca tgtgctcata   3420
cctgatagtt ttaatttaac tgtcacagat gagtacatac aaactcgtat ggataaggtt   3480
caaattattt gccttcagta tgtttgtggt aattctattg aatgcagaaa gttgtttcag   3540
```

-continued

```
cagtatggac ctgtttgtga taatatattg tctgttgtaa atggtgtagg tcaaagagag   3600
gatatggaac ttttaagttt ctattcttct actaaaccta gtggttacaa tacaccaatt   3660
tttaataatg ttagcactgg tgactttaat atttcgctcc tactaacacc acctaatagt   3720
cctactgggc gctcttttat tgaagatctt ctctttacaa gtgtagaatc tgttggatta   3780
ccaactgatg aagagtataa aaagtgtaca gcaggacctt taggttttgt taaagacctt   3840
gtttgtgcta gagagtataa tggtttgctc gttctgcctc ctattattac tgcggaaatg   3900
caaaccatgt atactagttc tttagtagcc tctatggctt taggtggcat tactgcagct   3960
ggtgctatac cttttgctac acaactgcag gccagaatta accatttggg tattactaat   4020
tctcttttgt tgaaaaacca agaaaaaatt gctgcttcct ttaataaggc catcggtcat   4080
atgcaggaag ggtttaaaag tacttctcta gcattacaac agattcaaga tgttgttaat   4140
aaacagagtt ctattcttac agagactatg caatcactta ataaaaattt tggtgctatt   4200
tcctctgtaa ttcaagacat ttaccagcaa ctagatgcta ttcaggcaga tgctcaggtt   4260
gatcgtctta ttacaggtag actctcttca ctatctgttt tagcttctgc taaacaggca   4320
gagtatcata gagtgtcaca acagcgtgag ttggccactc agaaaattaa tgagtgtgtt   4380
aagtctcagt ctaataggta ttcattttgt ggtaatggta gacatgttct aaccatacca   4440
cagaatgcac ccaatggcat agtgtttata cactttacat acactccaga gagttttgtt   4500
aatgttacgg caatagtagg gttttgcgta aacccagcta atgctagtca ttatgcaata   4560
gtgcctgtta atggcagggg tgtttttata gaagttaatg gtagttacta tatcactgct   4620
cgtgatatgt atatgccaag agatattact gcaggagaca tagtcacttt gacttcttgt   4680
caagcaaact atgttaatgt aaataaaacc gtcattaaca cttttgtgga agatgacgat   4740
tttgattttt atgatgaatt gtcaaaatgg tggaatgata ctaagcatga gctaccagat   4800
tttgatgaat tcaattatac cgttccagtt ttaaatatta gtaatgaaat tgacagaatt   4860
caacaggtta ttcagggatt aaatgattcc ctaatagacc ttgaaacact ctcaattctc   4920
aaaacttata ttaaatggcc ttggtatgtg tggcttgcca ttgcattcct taccattatt   4980
tttattctgg tactttgttg gatatttttc atgaccggtt gttgcggttg ttgttgtgga   5040
tgctttggta tcataccgtt aatgagtaag tgtggtaaga aatcttctta ctacacgact   5100
tttgataatg atgtggtaac ttaacaatac agacctaaaa agtctgttta atgattaaaa   5160
gtcccacatc ttttctaata ttattaattc ttctttggtg taaacttgca ttaagttgtt   5220
ttaaagagtg tgttataaca ctccagcaac tagtacaaat tttactccaa attattaata   5280
gtaacttaca atctagactt ctgctttggc acagtctaga ctaatgttag attttgaagc   5340
aattattgaa actggtcagc aaataactca acaaattagt ttctatttac agcatatttc   5400
aagggtgcta agtactgaat tatttgaccc ctttgaagtt tgtgtttaca gaggaggtaa   5460
ttgttgggag ttagagtcag ctgacgagtt ttcaggtgat gacgaatata ttgagtagat   5520
cgctcgagga gaacggaagt tttctaacag cggtttacgt gtttttagga tttttagcac   5580
tttatctact aggtagagcg cttcaagctt ttgtacaagc ggctgacgct tgttgtcttt   5640
tttggtatac atgggtagta gttcctggag ccaagggcac agcctttgtt tataatcata   5700
catatggtaa aaaacttaac aaaccggagt tagaaacggt tattgttaac gaatttccaa   5760
aaaacggttg gaaatatgga taataccatc aattgtactc ttggtactga acaagcagtt   5820
cagcttttta aggaatataa tctgtttgta actgcattcc tgttgttttt aaccatacta   5880
```

```
cttcagtatg gatacgcaac taggagcaag gttatttaca tactgaaaat gatagtgtta   5940
tggtgctttt ggccccttaa cattgcagta ggtgtaatct catgtatata cccaccaaac   6000
acaggaggtc ttgtcgcagc gataattctt acagtgtttg cgtgtctttc ttttataggt   6060
tattggatcc agagtattag actttttaag cggtgcaggt catggtggtc atttaacccc   6120
gaatctaatg ccgtaggttc aatactccta actaatggtc aacaatgtaa ttttgctata   6180
gagagtgtgc cgatggtgct ttctcctatt ataaagaatg gtgctcttta ttgcgagggt   6240
cagtggcttg ctaaatgtga accagaccac ttgcctagag atatatttgt atgcacaccg   6300
gatagacgta atatctatcg tatggtgcaa aaatatactg gtgaccaaag cggaagtaag   6360
aaaaggtttg ccacatttgt ctatgcaaag cagtcagtag atactggcga gctagaaagt   6420
gtgtcagcag taggaggtag tctttacaca taaatgtgtg tgtgtagaga gtatttaaaa   6480
ttattctttg acagtgcctc cgttttaaga gcgcggaaga gtattatttt tgaggatatt   6540
aatataaatc ctctttgttt catactctcc tttcaggagt tattatttaa aaaacagttt   6600
ttccactctt ttgtgccaaa aacaattgtt gttaatggtg taacctttca ggtagacaat   6660
ggaaaagtct actacgaagg aagaccaatt ttccaaaaag gttgttgtag tttgtggtcc   6720
aattataaga aagattagaa taattaaacc acctacaaca cttattttta caaatggcgt   6780
tttaggttac aaacgcttaa caaatacgga tgatgaaatg gctgactagt tttggaagag   6840
ctttcatctc ctgttataaa tccctattac taactcaatt aagagtatta gataggttaa   6900
ttttagatca cggacccaag cgcacattaa cgtgtgctag gcgagtgctt ttagttcaat   6960
tagatttagt ttataggttg gcttatacgc ccacccaatc gctggtatga ataatagtaa   7020
agataatcct tttcgcggag caatagcaag aaaagcgcga atttatctga gaggaggatt   7080
agattgtgtt tactttctta acaaagcagg acaagcagag ccttgtcccg cgtgtacctc   7140
cctagtattc caagggaaaa cttgtgagga acactattat aataacaatc ttttgtcatg   7200
gcaagcggta aggcaactgg aaagacagac gccccagcgc cagtcatcaa actaggagga   7260
ccaaagccac ctaaagttgg ttcttctgga aatgcatcat ggtttcaacc gataaaggcc   7320
aagaagctaa attcacctgt gcctaaattt gacggtagtg gtgttcctga aaatgaaaat   7380
ctcaagtcaa gccagcaaca tggatactgg agacgccaac acaggtttaa gcctggcaaa   7440
ggtggaagaa aaccagtccc tgatgcttgg tacttttact acactggaac aggaccggcc   7500
gccgacctga attggggtga aactcaagat ggtatagtgt gggttgctgc aaagggtgct   7560
gatactaaat ctagatcaaa ccagggtaca agggatcctg ataagtttga ccaataccca   7620
ctacgattct cagatggagg accggatggt aatttccgtt gggacttcat accaataaat   7680
cgtggtagga gtgggagatc aacagcagct tcatcagcag catctagtag agcaccatct   7740
cgtgaggggt cacgtggacg tagaagcgga gttgaagatg atcttatagc tcgcgcagca   7800
aagattatac aggaccagca aaagaagggt gcgcgcatta ccaaggctaa ggctgatgaa   7860
atggctcatc gccgctattg caagcgcact atcccacctg gttataaggt tgagcaagta   7920
tttggtcccc gtactaaagg taaggaagga aattttggtg atgacaagat gaatgaggaa   7980
ggtgttaagg atgggcgtgt tacggcaatg ctcaacctag tccctagcag tcatgcttgt   8040
ctttttggaa gtagggtgac gcccaaactg cagccagatg gtcttcacct gagatttgaa   8100
tttactactg tggtgtcacg tgatgatccg cagtttgata attatgtgaa aatttgtgat   8160
cagtgtgtcg atggtgtagg gacgcgtcca aaggacgatg aatcgagacc aaagtcacgc   8220
ccaaattcaa gacctgcaac tagaggaaat tctccagcgc cgagacaaca gcgcccaaag   8280
```

```
aaggagaaaa agcccaagaa gcaggatgat gaagtagata aggcattgac ctcagatgag   8340

gagaggaaca atgcacagct ggaatttgat gatgaaccca aggtgattaa ctggggggac   8400

tctgcactag gtgaaaatga actttgatta acataatgga cttgctgcat ttgctgtcac   8460

attttgttaa atattatttt tgtgttttac tatcaattat tacaggtatt gattgtgatt   8520

atgttcaata cttaagcttc ttctggttgc tttttgcttg ttgtattgtt gctgtgcttt   8580

ttattattgt gattctcatt agtttgcttt atcgtagaaa ttcaatagta agagttaagg   8640

aagataggca tgtagcttag cacctacatg tctatcgcca gggaaatgtc taatctgtct   8700

acttagtagc ctggaaacga acggtagacc cttagatttt aatttagttt aatttttagt   8760

ttagtttaag ttagtttaga gtaggtataa agatgccagt gccggggcca cgcgtagtac   8820

gaccgagggt acagcactag gacgcccact aggggaagag ctaaatttta gtttaagtta   8880

agtttaattg gctaaatata gttaaaattt ataggctagt atagagttag agcaaaaaaa   8940

aaaaaaaaaa aaaaaaaaaa aaaaaaaaaa aaaaaaaaaa aaaaaaaaaa aaaaaaaaaa   9000

aaaaaaaaaa aaaaaaaaaa aaaaaaaaaa aaagcggccg catcggatgc cgggaccgac   9060

gagtgcagag gcgtgcaagc gagcttggcg taatcatggt catagctgtt tcctgtgtga   9120

aattgttatc cgctcacaat tccacacaac atacgagccg gaagcataaa gtgtaaagcc   9180

tggggtgcct aatgagtgag ctaactcaca ttaattgcgt tgcgctcact gcccgctttc   9240

cagtcgggaa acctgtcgtg ccagctgcat taatgaatcg gccaacgcgc ggggagaggc   9300

ggtttgcgta ttgggcgctc ttccgcttcc tcgctcactg actcgctgcg ctcggtcgtt   9360

cggctgcggc gagcggtatc agctcactca aaggcggtaa tacggttatc cacagaatca   9420

ggggataacg caggaaagaa catgtgagca aaaggccagc aaaaggccag gaaccgtaaa   9480

aaggccgcgt tgctggcgtt tttccatagg ctccgccccc ctgacgagca tcacaaaaat   9540

cgacgctcaa gtcagaggtg gcgaaacccg acaggactat aaagatacca ggcgtttccc   9600

cctggaagct ccctcgtgcg ctctcctgtt ccgaccctgc cgcttaccgg atacctgtcc   9660

gcctttctcc cttcgggaag cgtggcgctt tctcatagct cacgctgtag gtatctcagt   9720

tcggtgtagg tcgttcgctc caagctgggc tgtgtgcacg aaccccccgt tcagcccgac   9780

cgctgcgcct tatccggtaa ctatcgtctt gagtccaacc cggtaagaca cgacttatcg   9840

ccactggcag cagccactgg taacaggatt agcagagcga ggtatgtagg cggtgctaca   9900

gagttcttga agtggtggcc taactacggc tacactagaa gaacagtatt tggtatctgc   9960

gctctgctga agccagttac cttcggaaaa agagttggta gctcttgatc cggcaaacaa  10020

accaccgctg gtagcggtgg tttttttgtt tgcaagcagc agattacgcg cagaaaaaaa  10080

ggatctcaag aagatccttt gatcttttct acggggtctg acgctcagtg gaacgaaaac  10140

tcacgttaag ggattttggt catgagatta tcaaaaagga tcttcaccta gatcctttta  10200

aattaaaaat gaagttttaa atcaatctaa agtatatatg agtaaacttg gtctgacagt  10260

taccaatgct taatcagtga ggcacctatc tcagcgatct gtctatttcg ttcatccata  10320

gttgcctgac tccccgtcgt gtagataact acgatacggg agggcttacc atctggcccc  10380

agtgctgcaa tgataccgcg agacccacgc tcaccggctc cagatttatc agcaataaac  10440

cagccagccg gaagggccga gcgcagaagt ggtcctgcaa ctttatccgc ctccatccag  10500

tctattaatt gttgccggga agctagagta agtagttcgc cagttaatag tttgcgcaac  10560

gttgttgcca ttgctacagg catcgtggtg tcacgctcgt cgtttggtat ggcttcattc  10620
```

```
agctccggtt cccaacgatc aaggcgagtt acatgatccc ccatgttgtg caaaaaagcg  10680

gttagctcct tcggtcctcc gatcgttgtc agaagtaagt tggccgcagt gttatcactc  10740

atggttatgg cagcactgca taattctctt actgtcatgc catccgtaag atgcttttct  10800

gtgactggtg agtactcaac caagtcattc tgagaatagt gtatgcggcg accgagttgc  10860

tcttgcccgg cgtcaatacg ggataatacc gcgccacata gcagaacttt aaaagtgctc  10920

atcattggaa aacgttcttc ggggcgaaaa ctctcaagga tcttaccgct gttgagatcc  10980

agttcgatgt aacccactcg tgcacccaac tgatcttcag catcttttac tttcaccagc  11040

gtttctgggt gagcaaaaac aggaaggcaa aatgccgcaa aaaagggaat aagggcgaca  11100

cggaaatgtt gaatactcat actcttcctt tttcaatatt attgaagcat ttatcagggt  11160

tattgtctca tgagcggata catatttgaa tgtatttaga aaaataaaca aataggggtt  11220

ccgcgcacat ttccccgaaa agtgccacct gacgtctaag aaaccattat tatcatgaca  11280

ttaacctata aaaataggcg tatcacgagg ccctttcgtc                        11320
```

<210> SEQ ID NO 22
<211> LENGTH: 11314
<212> TYPE: DNA
<213> ORGANISM: Artificial Sequence
<220> FEATURE:
<223> OTHER INFORMATION: Plasmid with IBV

<400> SEQUENCE: 22

```
tcgcgcgttt cggtgatgac ggtgaaaacc tctgacacat gcagctcccg gagacggtca     60

cagcttgtct gtaagcggat gccgggagca gacaagcccg tcagggcgcg tcagcgggtg    120

ttggcgggtg tcggggctgg cttaactatg cggcatcaga gcagattgta ctgagagtgc    180

accatatgcg gtgtgaaata ccgcacagat gcgtaaggag aaaataccgc atcaggcgcc    240

attcgccatt caggctgcgc aactgttggg aagggcgatc ggtgcgggcc tcttcgctat    300

tacgccagct ggcgaaaggg ggatgtgctg caaggcgatt aagttgggta acgccagggt    360

tttcccagtc acgacgttgt aaaacgacgg ccagtgaatt ggagatcggt acttcgcgaa    420

tgcgtcgaga tgagctctaa tacgactcac tatagggact taagtgtgat ataaatatat    480

atcatacata ctagccttgt gctagatttc caacttaaca aaacggactt aaatacctac    540

agttggtccc tataggtgtt ccattgcagt gcactttagt gccctggatg gcacctggcc    600

acctgtcagg tttttgttat taaaataata ttgttgctgg tatcactgct tgttttgccg    660

tgtctcactt tatacatccg ttgcttgggc tacctagtat ccagcgtcct actggcgttg    720

tggtcggttc gagtgcgaag aacctctggt tcatctagcg gtacgcgggt gtgtggaagt    780

agcgcttcag acgtaccggt tctgttgcgt gaaatacggg gtcacctccc cccacatacc    840

tctaagggct tttgagccta gcgttgggct acgttctcgc acaaggtcgg ctatacggcg    900

tttgtagggg gtagtgccaa acaacccctg aggtgacagg ttctggtggt gtttcgaaaa    960

caacaatgtg tgtgccgcat aatatgcgag taatgcattt tggagcagga agtgacaaag   1020

gagtggcccc aggtagcgct gttcttaggc agtggcttcc cgaaggtaca ctccttgtcg   1080

ataatgatat tgtagattat gtatctgatg cacatgtctc tgtgctttca gattgcaata   1140

aatgtaaaac agagcacaag tttgatcttg tgatatctga tatgtataca gataatgatt   1200

caaagagaaa gcatgaaggc gttgtagcca ataacggcaa tgatgacgtc ttcatatacc   1260

tttcaaactt tcttcgtaac aatttagctc tgggaggcag ttttgccgta aaagtaacag   1320

agacaagttg gcatgagagt ttatatgaca ttgcacagga ttgtgcatgg tggacaatgt   1380
```

```
tttgtacagc agtgaatgct tcttcgtcag aagcattctt gattggtgtt aattatttgg   1440
gtgcaagtga aaaggttaga gttagtggta aaaccctgca cgcaaattat atattttgga   1500
ggaattgtaa ttatttacaa acttcagcct atagtatatt tgacgttgct aagtttgatt   1560
tgaaattaaa agcaacgcca gttgtgaatt tgaaaactga acaaaagaca gacttagtct   1620
ttaatttaat taagtgtggt aagttactgg taagagatgt tggtaacacc tcttttacta   1680
gtgactcttt tgtgtgcact atgtagtgct gctttgtatg actcgagttc ttacgtgtac   1740
tactaccaaa gtgccttcag accacctgat ggttggcatt tacatggggg tgcgtatgcg   1800
gttgttaata tttctagtga atctaataat gcaggctctt catctgggtg tactgttggt   1860
attattcatg gtggtcgtgt tgttaatgct tcttctatag ctatgacggc accgtcatca   1920
ggtatggctt ggtctagcag tcagttttgt actgcatact gtaacttttc agatactaca   1980
gtgtttgtta cacattgtta taaacatggt gggtgtccta taactggcat gcttcaacag   2040
cattctatac gtgtttctgc tatgaaaaat ggccagcttt tctataattt aacagttagt   2100
gtagctaagt accctacttt taaatcattt cagtgtgtta ataatttaac atccgtatat   2160
ttaaatggtg atcttgttta cacctctaat gagaccacag atgttacatc tgcaggtgtt   2220
tattttaaag ctggtggacc tataacttat aaagttatga gagaagttag agccctggct   2280
tattttgtta atggtactgc acaagatgtt attttgtgtg atgggtcacc tagaggcttg   2340
ttagcatgcc agtataatac tggcaatttt tcagatggct tttatccttt tactaatagt   2400
agtttagtta agcagaagtt tattgtctat cgtgaaaata gtgttaatac tacttttacg   2460
ttacacaatt tcacttttca taatgagact ggcgccaacc caaatcctag tggtgtccag   2520
aatattcaaa cttaccaaac acaaacagct cagagtggtt attataattt taatttttcc   2580
tttctgagta gttttgttta taaggagtct aattttatgt atggatctta tcacccaagt   2640
tgtaatttta gactagaaac tattaataat ggtttgtggt ttaattcact ttcagttagt   2700
attgcttacg gtcctcttca aggtggttgc aagcaatctg tctttagtgg tagagcaacc   2760
tgttgttatg cttactcata tggaggtcct ttgctgtgta aaggtgttta ttcaggtgag   2820
ttagatcata attttgaatg tggactgtta gtttatgtta ctaagagcgg tggctctcgt   2880
atacaaacag ccactgaacc gccagttata actcaacaca attataataa tattacttta   2940
aatacttgtg ttgattataa tatatatggc agaactggcc agggttttat tactaatgta   3000
accgactcag ctgttagtta taattatcta gcagacgcag gtttggctat tttagataca   3060
tctggttcca tagacatctt tgtcgtacaa agtgaatatg gtcttaatta ttataaggtt   3120
aacccttgcg aagatgtcaa ccagcagttt gtagtttctg gtggtaaatt agtaggtatt   3180
cttacttcac gtaatgagac tggttcccag cttcttgaga atcagtttta catcaaaatc   3240
actaatggaa cacgtcgttt tagacgttct attactgaaa gtgttgaaaa ttgcccttat   3300
gttagttatg gtaagttttg tataaaacct gatggcagta ttgccacaat agtaccaaaa   3360
cagttagaac agtttgtggc acctttactt aatgttactg aaaatgtgct catacctaac   3420
agttttaatt taactgttac agatgagtac atacaaactc ggatggataa ggtccaaatt   3480
aattgcctgc agtatatttg tggcaattct ctggagtgca gaaatttgtt tcaacaatat   3540
ggtcctgttt gcgacaacat attgtctgta gtaaatagtg ttggtcaaaa agaagatatg   3600
gaacttttga atttctattc ttctactaag ccggctggtt ttaatacacc agttcttagt   3660
aatgttagca ctggtgagtt taatattact ctttttttaa caacgcctag tagtcctaga   3720
```

```
aggcgttctt ttattgaaga ccttctattt acaagtgttg aatctgttgg attaccaaca   3780
gatgacgcat acaaaaattg cactgcaggt cctttaggct ttctgaaaga ccttgcatgt   3840
gctcgtgaat ataatggttt gcttgtgttg cctcctatta taacagcaga aatgcaaact   3900
ttgtatacaa gctctctagt agcttctatg gcttttggtg gtattactgc agctggtgct   3960
atacctttg ccacacaact gcaggctaga attaatcact tgggtattac ccagtcactt   4020
cttttgaaga atcaagaaaa aattgctgct tcctttaata aggccatcgg tcatatgcag   4080
gaaggtttta gaagtacatc tttagcatta caacaaattc aagatgttgt taataagcag   4140
agtgctattc ttactgagac tatggcatca cttaataaaa attttggtgc catttcttct   4200
gtgattcaag aaatctacca gcaacttgac gccatacaag caaatgctca agtggatcgt   4260
cttataactg gtagattgtc atcactttct gttttagcat ctgctaagca ggcggagtat   4320
attagagtgt cacaacagcg tgagttagct actcagaaga ttaatgagtg tgttaagtca   4380
cagtccatta ggtactcctt ttgtggtaat ggacgacatg ttttaaccat accgcaaaat   4440
gcacctaatg gtatagtgtt tatacacttt tcttacactc cagatagttt tgttaatgtt   4500
actgcaatag tgggtttttg tgtaaagcca gctaatgcta gtcagtatgc aatagtaccc   4560
gctaatggta ggggtatttt tatacaagtt aatggtagtt actacatcac tgcacgagat   4620
atgtatatgc caagagctat tactgcagga gatatagtta cgcttacttc ttgtcaagca   4680
aattatgtaa gtgtaaataa gaccgtcatt actacattcg tagacaatga tgattttgat   4740
tttaatgacg aattgtcaaa atggtggaat gatactaagc atgagctacc agactttgac   4800
aaattcaatt acacagtacc tatacttgac attgatagtg aaattgatcg tattcaaggc   4860
gttatacagg gtcttaatga ctctctaata gaccttgaaa aactttcaat actcaaaact   4920
tatattaagt ggccttggta tgtgtggcta gccatagctt ttgccactat tatcttcatc   4980
ttaatattag gatgggtttt cttcatgact gggtgttgtg gttgttgttg tggatgcttt   5040
ggcattatgc ctctaatgag taagtgtggt aagaaatctt cttattacac gacttttgat   5100
aacgatgtgg taactgaaca atacagacct aaaaagtctg tttaatgatt aaaagtccca   5160
catcttttct aatattatta attcttcttt ggtgtaaact tgcattaagt tgttttaaag   5220
agtgtgttat aacactccag caactagtac aaattttact ccaaattatt aatagtaact   5280
tacaatctag acttctgctt tggcacagtc tagactaatg ttagattttg aagcaattat   5340
tgaaactggt cagcaaataa ctcaacaaat tagtttctat ttacagcata tttcaagggt   5400
gctaagtact gaattatttg accccttga agtttgtgtt tacagaggag gtaattgttg   5460
ggagttagag tcagctgacg agttttcagg tgatgacgaa tatattgagt agatcgctcg   5520
aggagaacgg aagttttcta acagcggttt acgtgttttt aggattttta gcactttatc   5580
tactaggtag agcgcttcaa gcttttgtac aagcggctga cgcttgttgt ctttttggt   5640
atacatgggt agtagttcct ggagccaagg gcacagcctt tgtttataat catacatatg   5700
gtaaaaaact taacaaaccg gagttagaaa cggttattgt taacgaattt ccaaaaaacg   5760
gttggaaata tggataatac catcaattgt actcttggta ctgaacaagc agttcagctt   5820
tttaaggaat ataatctgtt tgtaactgca ttcctgttgt ttttaaccat actacttcag   5880
tatggatacg caactaggag caaggttatt tacatactga aaatgatagt gttatggtgc   5940
ttttggcccc ttaacattgc agtaggtgta atctcatgta tatacccacc aaacacagga   6000
ggtcttgtcg cagcgataat tcttacagtg tttgcgtgtc tttcttttat aggttattgg   6060
atccagagta ttagactttt taagcggtgc aggtcatggt ggtcatttaa ccccgaatct   6120
```

```
aatgccgtag gttcaatact cctaactaat ggtcaacaat gtaattttgc tatagagagt   6180
gtgccgatgg tgctttctcc tattataaag aatggtgctc tttattgcga gggtcagtgg   6240
cttgctaaat gtgaaccaga ccacttgcct agagatatat ttgtatgcac accggataga   6300
cgtaatatct atcgtatggt gcaaaaatat actggtgacc aaagcggaag taagaaaagg   6360
tttgccacat ttgtctatgc aaagcagtca gtagatactg gcgagctaga aagtgtgtca   6420
gcagtaggag gtagtcttta cacataaatg tgtgtgtgta gagagtattt aaaattattc   6480
tttgacagtg cctccgtttt aagagcgcgg aagagtatta tttttgagga tattaatata   6540
aatcctcttt gtttcatact ctcctttcag gagttattat ttaaaaaaca gtttttccac   6600
tcttttgtgc caaaaacaat tgttgttaat ggtgtaacct ttcaggtaga caatggaaaa   6660
gtctactacg aaggaagacc aattttccaa aaaggttgtt gtagtttgtg gtccaattat   6720
aagaaagatt agaataatta aaccacctac aacacttatt tttacaaatg gcgttttagg   6780
ttacaaacgc ttaacaaata cggatgatga aatggctgac tagttttgga agagctttca   6840
tctcctgtta taaatcccta ttactaactc aattaagagt attagatagg ttaattttag   6900
atcacggacc caagcgcaca ttaacgtgtg ctaggcgagt gcttttagtt caattagatt   6960
tagtttatag gttggcttat acgcccaccc aatcgctggt atgaataata gtaaagataa   7020
tccttttcgc ggagcaatag caagaaaagc gcgaatttat ctgagaggag gattagattg   7080
tgtttacttt cttaacaaag caggacaagc agagccttgt cccgcgtgta cctccctagt   7140
attccaaggg aaaacttgtg aggaacacta ttataataac aatcttttgt catggcaagc   7200
ggtaaggcaa ctggaaagac agacgcccca gcgccagtca tcaaactagg aggaccaaag   7260
ccacctaaag ttggttcttc tggaaatgca tcatggtttc aaccgataaa ggccaagaag   7320
ctaaattcac ctgtgcctaa atttgacggt agtggtgttc ctgaaaatga aaatctcaag   7380
tcaagccagc aacatggata ctggagacgc caacacaggt ttaagcctgg caaaggtgga   7440
agaaaaccag tccctgatgc ttggtacttt tactacactg gaacaggacc ggccgccgac   7500
ctgaattggg gtgaaactca agatggtata gtgtgggttg ctgcaaaggg tgctgatact   7560
aaatctagat caaaccaggg tacaagggat cctgataagt ttgaccaata cccactacga   7620
ttctcagatg gaggaccgga tggtaatttc cgttgggact tcataccaat aaatcgtggt   7680
aggagtggga gatcaacagc agcttcatca gcagcatcta gtagagcacc atctcgtgag   7740
gggtcacgtg gacgtagaag cggagttgaa gatgatctta tagctcgcgc agcaaagatt   7800
atacaggacc agcaaaagaa gggtgcgcgc attaccaagg ctaaggctga tgaaatggct   7860
catcgccgct attgcaagcg cactatccca cctggttata aggttgagca agtatttggt   7920
ccccgtacta aaggtaagga aggaaatttt ggtgatgaca agatgaatga ggaaggtgtt   7980
aaggatgggc gtgttacggc aatgctcaac ctagtcccta gcagtcatgc ttgtcttttt   8040
ggaagtaggg tgacgcccaa actgcagcca gatggtcttc acctgagatt tgaatttact   8100
actgtggtgt cacgtgatga tccgcagttt gataattatg tgaaaatttg tgatcagtgt   8160
gtcgatggtg tagggacgcg tccaaaggac gatgaatcga gaccaaagtc acgcccaaat   8220
tcaagacctg caactagagg aaattctcca gcgccgagac aacagcgccc aaagaaggag   8280
aaaaagccca agaagcagga tgatgaagta gataaggcat tgacctcaga tgaggagagg   8340
aacaatgcac agctggaatt tgatgatgaa cccaaggtga ttaactgggg ggactctgca   8400
ctaggtgaaa atgaactttg attaacataa tggacttgct gcatttgctg tcacattttg   8460
```

```
ttaaatatta tttttgtgtt ttactatcaa ttattacagg tattgattgt gattatgttc   8520
aatacttaag cttcttctgg ttgctttttg cttgttgtat tgttgctgtg ctttttatta   8580
ttgtgattct cattagtttg ctttatcgta gaaattcaat agtaagagtt aaggaagata   8640
ggcatgtagc ttagcaccta catgtctatc gccagggaaa tgtctaatct gtctacttag   8700
tagcctggaa acgaacggta gacccttaga ttttaattta gtttaatttt tagtttagtt   8760
taagttagtt tagagtaggt ataaagatgc cagtgccggg gccacgcgta gtacgaccga   8820
gggtacagca ctaggacgcc cactagggga agagctaaat tttagtttaa gttaagttta   8880
attggctaaa tatagttaaa atttataggc tagtatagag ttagagcaaa aaaaaaaaaa   8940
aaaaaaaaaa aaaaaaaaaa aaaaaaaaaa aaaaaaaaaa aaaaaaaaaa aaaaaaaaaa   9000
aaaaaaaaaa aaaaaaaaaa aaaaaaagcg gccgcatcgg atgccgggac cgacgagtgc   9060
agaggcgtgc aagcgagctt ggcgtaatca tggtcatagc tgtttcctgt gtgaaattgt   9120
tatccgctca caattccaca caacatacga gccggaagca taaagtgtaa agcctggggt   9180
gcctaatgag tgagctaact cacattaatt gcgttgcgct cactgcccgc tttccagtcg   9240
ggaaacctgt cgtgccagct gcattaatga atcggccaac gcgcggggag aggcggtttg   9300
cgtattgggc gctcttccgc ttcctcgctc actgactcgc tgcgctcggt cgttcggctg   9360
cggcgagcgg tatcagctca ctcaaaggcg gtaatacggt tatccacaga atcaggggat   9420
aacgcaggaa agaacatgtg agcaaaaggc cagcaaaagg ccaggaaccg taaaaaggcc   9480
gcgttgctgg cgtttttcca taggctccgc ccccctgacg agcatcacaa aaatcgacgc   9540
tcaagtcaga ggtggcgaaa cccgacagga ctataaagat accaggcgtt tccccctgga   9600
agctccctcg tgcgctctcc tgttccgacc ctgccgctta ccggatacct gtccgccttt   9660
ctcccttcgg gaagcgtggc gctttctcat agctcacgct gtaggtatct cagttcggtg   9720
taggtcgttc gctccaagct gggctgtgtg cacgaacccc ccgttcagcc cgaccgctgc   9780
gccttatccg gtaactatcg tcttgagtcc aacccggtaa gacacgactt atcgccactg   9840
gcagcagcca ctggtaacag gattagcaga gcgaggtatg taggcggtgc tacagagttc   9900
ttgaagtggt ggcctaacta cggctacact agaagaacag tatttggtat ctgcgctctg   9960
ctgaagccag ttaccttcgg aaaaagagtt ggtagctctt gatccggcaa acaaaccacc  10020
gctggtagcg gtggtttttt tgtttgcaag cagcagatta cgcgcagaaa aaaaggatct  10080
caagaagatc ctttgatctt ttctacgggg tctgacgctc agtggaacga aaactcacgt  10140
taagggattt tggtcatgag attatcaaaa aggatcttca cctagatcct tttaaattaa  10200
aaatgaagtt ttaaatcaat ctaaagtata tatgagtaaa cttggtctga cagttaccaa  10260
tgcttaatca gtgaggcacc tatctcagcg atctgtctat ttcgttcatc catagttgcc  10320
tgactccccg tcgtgtagat aactacgata cgggagggct taccatctgg ccccagtgct  10380
gcaatgatac cgcgagaccc acgctcaccg gctccagatt tatcagcaat aaaccagcca  10440
gccggaaggg ccgagcgcag aagtggtcct gcaactttat ccgcctccat ccagtctatt  10500
aattgttgcc gggaagctag agtaagtagt tcgccagtta atagtttgcg caacgttgtt  10560
gccattgcta caggcatcgt ggtgtcacgc tcgtcgtttg gtatggcttc attcagctcc  10620
ggttcccaac gatcaaggcg agttacatga tcccccatgt tgtgcaaaaa agcggttagc  10680
tccttcggtc ctccgatcgt tgtcagaagt aagttggccg cagtgttatc actcatggtt  10740
atggcagcac tgcataattc tcttactgtc atgccatccg taagatgctt ttctgtgact  10800
ggtgagtact caaccaagtc attctgagaa tagtgtatgc ggcgaccgag ttgctcttgc  10860
```

ccggcgtcaa tacgggataa taccgcgcca catagcagaa ctttaaaagt gctcatcatt 10920
ggaaaacgtt cttcggggcg aaaactctca aggatcttac cgctgttgag atccagttcg 10980
atgtaaccca ctcgtgcacc caactgatct tcagcatctt ttactttcac cagcgtttct 11040
gggtgagcaa aaacaggaag gcaaaatgcc gcaaaaaagg gaataagggc gacacggaaa 11100
tgttgaatac tcatactctt cctttttcaa tattattgaa gcatttatca gggttattgt 11160
ctcatgagcg gatacatatt tgaatgtatt tagaaaaata aacaaatagg ggttccgcgc 11220
acatttcccc gaaaagtgcc acctgacgtc taagaaacca ttattatcat gacattaacc 11280
tataaaaata ggcgtatcac gaggcccttt cgtc 11314

<210> SEQ ID NO 23
<211> LENGTH: 47
<212> TYPE: DNA
<213> ORGANISM: Artificial Sequence
<220> FEATURE:
<223> OTHER INFORMATION: Primer

<400> SEQUENCE: 23
tgattaaaag tcccacatct tttctaatat tattaattct tctttgg 47

<210> SEQ ID NO 24
<211> LENGTH: 46
<212> TYPE: DNA
<213> ORGANISM: Artificial Sequence
<220> FEATURE:
<223> OTHER INFORMATION: Primer

<400> SEQUENCE: 24
ctcttaccag taacttacca cacttaatta aattaaagac taagtc 46

<210> SEQ ID NO 25
<211> LENGTH: 47
<212> TYPE: DNA
<213> ORGANISM: Artificial Sequence
<220> FEATURE:
<223> OTHER INFORMATION: Primer

<400> SEQUENCE: 25
aagtgtggta agttactggt aagagatgtt ggtaacacct cttttac 47

<210> SEQ ID NO 26
<211> LENGTH: 47
<212> TYPE: DNA
<213> ORGANISM: Artificial Sequence
<220> FEATURE:
<223> OTHER INFORMATION: Primer

<400> SEQUENCE: 26
agaaaagatg tgggactttt aatcattaaa cagacttttt aggtctg 47

<210> SEQ ID NO 27
<211> LENGTH: 20
<212> TYPE: DNA
<213> ORGANISM: Artificial Sequence
<220> FEATURE:
<223> OTHER INFORMATION: Primer

<400> SEQUENCE: 27
caggattgtg catggtggac 20

<210> SEQ ID NO 28

<211> LENGTH: 20
<212> TYPE: DNA
<213> ORGANISM: Artificial Sequence
<220> FEATURE:
<223> OTHER INFORMATION: Primer

<400> SEQUENCE: 28
agaaaaccta aaggtcctgc 20

<210> SEQ ID NO 29
<211> LENGTH: 18
<212> TYPE: DNA
<213> ORGANISM: Artificial Sequence
<220> FEATURE:
<223> OTHER INFORMATION: Primer

<400> SEQUENCE: 29
taaatggtga tcttgttt 18

<210> SEQ ID NO 30
<211> LENGTH: 20
<212> TYPE: DNA
<213> ORGANISM: Artificial Sequence
<220> FEATURE:
<223> OTHER INFORMATION: Primer

<400> SEQUENCE: 30
tttgtatacg agagccatca 20

<210> SEQ ID NO 31
<211> LENGTH: 20
<212> TYPE: DNA
<213> ORGANISM: Artificial Sequence
<220> FEATURE:
<223> OTHER INFORMATION: Primer

<400> SEQUENCE: 31
ttgccttcag tatgtttgtg 20

<210> SEQ ID NO 32
<211> LENGTH: 18
<212> TYPE: DNA
<213> ORGANISM: Artificial Sequence
<220> FEATURE:
<223> OTHER INFORMATION: Primer

<400> SEQUENCE: 32
ctgcgacaag acctcctg 18

<210> SEQ ID NO 33
<211> LENGTH: 19
<212> TYPE: DNA
<213> ORGANISM: Artificial Sequence
<220> FEATURE:
<223> OTHER INFORMATION: Primer

<400> SEQUENCE: 33
tgctgcttcc tttaataag 19

<210> SEQ ID NO 34
<211> LENGTH: 20
<212> TYPE: DNA
<213> ORGANISM: Artificial Sequence
<220> FEATURE:
<223> OTHER INFORMATION: Primer

<400> SEQUENCE: 34
cgctgttgtg acactctatg 20

<210> SEQ ID NO 35
<211> LENGTH: 18
<212> TYPE: DNA
<213> ORGANISM: Artificial Sequence
<220> FEATURE:
<223> OTHER INFORMATION: Primer

<400> SEQUENCE: 35
tggccttggt atgtgtgg 18

<210> SEQ ID NO 36
<211> LENGTH: 19
<212> TYPE: DNA
<213> ORGANISM: Artificial Sequence
<220> FEATURE:
<223> OTHER INFORMATION: Primer

<400> SEQUENCE: 36
agcactacat agtgcatac 19

<210> SEQ ID NO 37
<211> LENGTH: 45
<212> TYPE: DNA
<213> ORGANISM: Artificial Sequence
<220> FEATURE:
<223> OTHER INFORMATION: Primer

<400> SEQUENCE: 37
tctttggtat gcactatgta gtgctgcttt gtatgactcg agttc 45

<210> SEQ ID NO 38
<211> LENGTH: 58
<212> TYPE: DNA
<213> ORGANISM: Artificial Sequence
<220> FEATURE:
<223> OTHER INFORMATION: Primer

<400> SEQUENCE: 38
tggcaagcca cacataccaa ggccacttaa tataagtttt gagtattgaa agtttttc 58

<210> SEQ ID NO 39
<211> LENGTH: 43
<212> TYPE: DNA
<213> ORGANISM: Artificial Sequence
<220> FEATURE:
<223> OTHER INFORMATION: Primer

<400> SEQUENCE: 39
aagtgtggta agttactggt aagagatgtt ggtgaagtca ctg 43

<210> SEQ ID NO 40
<211> LENGTH: 53
<212> TYPE: DNA
<213> ORGANISM: Artificial Sequence
<220> FEATURE:
<223> OTHER INFORMATION: Primer

<400> SEQUENCE: 40
tctttggtat gcactatgta gtgctaattt gtttgattct gataataatt atg 53

<210> SEQ ID NO 41
<211> LENGTH: 58
<212> TYPE: DNA

<213> ORGANISM: Artificial Sequence
<220> FEATURE:
<223> OTHER INFORMATION: Primer

<400> SEQUENCE: 41
tggcaagcca cacataccaa ggccacttaa tataagtttt aattattgaa agttcttc 58

<210> SEQ ID NO 42
<211> LENGTH: 43
<212> TYPE: DNA
<213> ORGANISM: Artificial Sequence
<220> FEATURE:
<223> OTHER INFORMATION: Primer

<400> SEQUENCE: 42
aagtgtggta agttactggt aagagatgtt ggggaagtca ctg 43

<210> SEQ ID NO 43
<211> LENGTH: 48
<212> TYPE: DNA
<213> ORGANISM: Artificial Sequence
<220> FEATURE:
<223> OTHER INFORMATION: Primer

<400> SEQUENCE: 43
tctttggtat gcactatgta gtgctgcttt gtttgataat aatgaaac 48

<210> SEQ ID NO 44
<211> LENGTH: 52
<212> TYPE: DNA
<213> ORGANISM: Artificial Sequence
<220> FEATURE:
<223> OTHER INFORMATION: Primer

<400> SEQUENCE: 44
tggcaagcca cacataccaa ggccatttaa tataagtctt gagtattgaa ag 52

<210> SEQ ID NO 45
<211> LENGTH: 31
<212> TYPE: DNA
<213> ORGANISM: Artificial Sequence
<220> FEATURE:
<223> OTHER INFORMATION: Primer

<400> SEQUENCE: 45
gtctgtattg ttaagttacc acatcgttat c 31

<210> SEQ ID NO 46
<211> LENGTH: 50
<212> TYPE: DNA
<213> ORGANISM: Artificial Sequence
<220> FEATURE:
<223> OTHER INFORMATION: Primer

<400> SEQUENCE: 46
tctttggtat gcactatgta gtgctaattt atatgacaac gaatcttttg 50

<210> SEQ ID NO 47
<211> LENGTH: 52
<212> TYPE: DNA
<213> ORGANISM: Artificial Sequence
<220> FEATURE:
<223> OTHER INFORMATION: Primer

<400> SEQUENCE: 47
tggcaagcca cacataccaa ggccacttaa tataagtttt gagtattgaa ag 52

<210> SEQ ID NO 48
<211> LENGTH: 36
<212> TYPE: DNA
<213> ORGANISM: Artificial Sequence
<220> FEATURE:
<223> OTHER INFORMATION: Primer

<400> SEQUENCE: 48
gtctgtattg ttaagttacc acatcattat caaaag 36

<210> SEQ ID NO 49
<211> LENGTH: 46
<212> TYPE: DNA
<213> ORGANISM: Artificial Sequence
<220> FEATURE:
<223> OTHER INFORMATION: Primer

<400> SEQUENCE: 49
tctttggtat gcactatgta gtgctgctct gtttgataat aatcag 46

<210> SEQ ID NO 50
<211> LENGTH: 47
<212> TYPE: DNA
<213> ORGANISM: Artificial Sequence
<220> FEATURE:
<223> OTHER INFORMATION: Primer

<400> SEQUENCE: 50
aagtgtggta agttactggt aagagatgtt ggttcaacct cttttac 47

<210> SEQ ID NO 51
<211> LENGTH: 50
<212> TYPE: DNA
<213> ORGANISM: Artificial Sequence
<220> FEATURE:
<223> OTHER INFORMATION: Primer

<400> SEQUENCE: 51
tctttggtat gcactatgta gtgcttcttt gtacaataat gatagctatg 50

<210> SEQ ID NO 52
<211> LENGTH: 58
<212> TYPE: DNA
<213> ORGANISM: Artificial Sequence
<220> FEATURE:
<223> OTHER INFORMATION: Primer

<400> SEQUENCE: 52
tggcaagcca cacataccaa ggccatttaa tataagtttt taaaatagaa agtgtttc 58

<210> SEQ ID NO 53
<211> LENGTH: 27618
<212> TYPE: DNA
<213> ORGANISM: Avian infectious bronchitis virus

<400> SEQUENCE: 53
acttaagtgt gatataaata tatatcatac atactagcct tgcgctagat ttccaactta 60
acaaaacgga cttaaatacc tacagctggt ccccataggt gttccattgc agtgcacttt 120
agtgccctgg atggcacctg gccacctgtc aggtttttgt tgttaaaata tcattgttgc 180
tggtatcact gcttgttttg ccgtgtctca ctttatacat ccgttgcttg ggctacctag 240
tgtccagcgt cctacgggcg ccgtggctgg tccgagtgcg aagaacctct ggttcatcta 300

```
gcggtacgcg ggtgtgtgga agtagcgctt cagacgtatc ggttctgttg cgtgaaatac    360
ggggtcacct ccccccacat acctctaagg gcttttgagc ctagcgttgg gctacgttct    420
cgcacaaggt cggttatacg acgtttgtag gggtagtgc cgaacaaccc ctgaggtgac    480
aggttctggt ggtgtttagt gagcagacat acaatagaca gtgacaacat ggcttcaagc    540
ctaaaacagg gagtatctcc caaaccaagg gatgtcattc ttgttgccaa agacattccc    600
gaacaattat gtgacgcttt gtttttctat acgtcacatg accccaagga ttacgctgat    660
gcttttgcca ttaggcagaa gtttgaccgt aaccttcaga ctgggaagca gtttaaactt    720
gaaactgtgt gtggtctctt cctcttgaag ggagttgaca aaataacacc tggtgtccca    780
gcaaaagtct taaaagccac ctctaagctg gctgatttgg aagacatctt tggtgtctct    840
cctcttgcac gtaaatatcg tgatttgttg aagacagcat gccagtggtc tctcactgtg    900
gaaacactgg atgctcgtgc gcaaactctt gatgaaatct ttgacccaac tgaaatactt    960
tggcttcagg tagcttcaaa gatccaggtt tcagctatgg caatgcgcag acttgttgga   1020
gaagtaactg caagagtcat ggaatctcta ggttcaaatt tgagcgttct ttttcaagtt   1080
gttaaagaac aaatagtcag aatctttgaa aaggcactgg ctatttttga gagtgtgaat   1140
gatttaccac agcgtattgc agcactaaaa atggcttttg ccaagtgtgc gaaatcaatt   1200
acagttgtgg ttgttggaaa gactcttctt gttaaagagt ttgctggaac ttgtcttgca   1260
agcattaatg gtgctattgc aaaggttttt gaagaactgc caactggctt tatgggtgcc   1320
aaaattttca caacacttgc cttctttaaa gaagcagctg tgaaaattgt ggaaaatata   1380
ccaaatgcac caagaggtac tagaggtttt gaagtcgttg gtaacgccaa gggaacgcaa   1440
gttgttgtgc gtggcatgcg aaatgattta actctgctcg accaaaaagc tgacattcct   1500
gttgagaaag aaggttggtc tgcaattctt gaaggacatc tgtgttatgt ctttaagagt   1560
ggtgatcgtt tttatgcggc acctctttct gggaattttg cattgcatga tgtgcattgt   1620
tgtgagcgtg ttgtctgtct gtctgatggt gtaacaccag agataaatga tggactcatt   1680
ctagcagcaa tctattcatc ttttagtgtc tcagaactcg tggcagcact taaaaagggt   1740
gaaccattca agttcttggg tcataaattt gtgtatgcga aggatgcagc agtctctttc   1800
actcttgcaa aagcagccac tattgcagat gtactgaagc tgtttcaatc agctcgtgtg   1860
caaatagaag atgtgtggtc tgcatttact gaaaagtctt ttaatttctg gaaattcgca   1920
tatggaaaag tgcgtaatct tgaagaagtt gtgaagactc atttttgtaa agctcaaatg   1980
tcaattatta ttctagcagc agtgcttggc gaaggcattt ggcatcttgt ttcacaggtc   2040
atctataaag taggtggtct ttttactaga gtcgttgact tttgtgaaaa acactggaag   2100
ggtttctgtg cacaacttaa aaaggctaag ctcgttgtca cagaaacttt ttgtgttctt   2160
aagggagtgg cacagcattg ttttcaacta ttgctggatg caatacattc tttgtatatg   2220
agttttaaga agtgtgcact tggtagaatt catggagact tactcttctg gaaagggggt   2280
gtacacaaaa ttgttcaaga tggcgatgaa gtttggtttg acgccattga tagtattgat   2340
gttgaagatc tgggtgttgt ccaagaaaaa cccatagatt ttgaggtttg tgaagacgta   2400
acacttccag aaaatcaacc tggtcatatg gttcaaatcg aggatgacgg aaagaactat   2460
atgttcttcc gcttcaaaag ggatgagaac atctactata caccaatgtc tcaacttggt   2520
gcaattaatg tagtttgcaa agcaggcggt aaaaccgtta cctttggaga caccattgtg   2580
aaagaaatac cgccacctga tgttgtgcct attaaggtta gcatagagtg ttgtggtgaa   2640
ccatggaata caatcttcaa gaaagcttat aaagagccca ttgaagttga aactgacctc   2700
```

```
acagtagaac aattgctctc tgtgatctat gagaaaatgt gcgacgacct caaattgttt   2760
ccagaggcac cagagccacc gccatttgag aatgtcgcac ttgttgataa aaacggtaaa   2820
gacttggatt gcataaaatc atgccatctt atctaccgtg attatgagag tgatgatgac   2880
atcgaggaag aagatgctga ggagtgtgat actgatttag aatgtgaaga agaggatgag   2940
gatactaaag tgttggctct tatacaagac cctgcaagta ataaataccc tcttcctctt   3000
gatgatgatt atagcgtctt taatggatgt attgtacata aggacgctct tgacgtcgta   3060
aatctaccat ctggtgaaga aacctttgtt gtcaacaact gctttgaggg agctgtaaaa   3120
ccactgcctc agaaagttgt tgatgttcta ggtgactggg gtgaggctgt tgatgcgcaa   3180
gagcaaattg cacaaactac ttcagaggaa acccctatca gtagtttgga ggcaactatt   3240
gagcaagttg ttgttgagga acagaaaata atttctgttg ttgaagaaga acagcaggtg   3300
gcggtctaca cacctgcaga cctacaagtt gttgaagaaa cactagatga gtttattctt   3360
attgctgatg tttccacaga agaaattgtg cctcatgaag agaaggagtc acagattgaa   3420
caggagccta ttcaagttgt taaatcacaa cgtgaaaaga aggctaaaaa gttcaaggtt   3480
aaatctacta catgtgagaa acccaaattt ttggagtaca caacatgtgt gggtggccta   3540
acggtagtga ttgccaaagc attggatgag tttaaagagt tctgcattgt aaatgctgct   3600
aatgagcata tgtctcacgg tggcggcgtt gctaaggcaa ttgcggactt ttgtggacct   3660
gattttgtgg agtattgtga ggactatgtt aagaaacatg ggcctcaaca aagacttgtc   3720
acaccttcat ttgtcaaagg cattcaatgt gtgaacaatg ttgtaggacc tcgccatgga   3780
gacagtaact tgcatgataa gcttgttgct gcttacaaga atgttcttgt agatggtgtt   3840
gtcaattatg ttgtgccagt cctctcatca ggaatttttg gtgttgattt taagatgtct   3900
atagacgcta tgcgcaaggc ttttgaaggt tgcgacatac gcgttcttct tttctccttg   3960
tctcaagaac acatcgatta tttcgatgtt acttgtaaac agaagacaat ttatcttaca   4020
gaggacggtg ttaaataccg ctctgctact gtgaaaccag gtgactcttt gagtcaattt   4080
ggaccggttt ttgctagaaa caagacagtc tttacagcag acgatgttga ggacaaagaa   4140
attctcttca ttcctactac tgacaagact gtcctcgaat attatggttt ggatgcgcaa   4200
aagtatgtaa tatacttgca aactcttgca cagaagtgga atgtccaata tagggacaat   4260
tttgttatac ttgagtggcg tgatggaaat tgctggatta atgcagcagt agtgctcctt   4320
caagctgcta agattaggtt taaaggtttt cttgcagaag catgggcaca acttttgggt   4380
ggagacccaa ctgattttgt agcctggtgc tatgcaagtt gcaatgctaa tgttggtgag   4440
ttttcagatg ctaattggct tcttgctaat ttggcagaat actttgatgc tgattacacg   4500
aatgcattcc ttaagaggcg tgtgtcatgt aactgtgggg ttaagaattg tgaagttaga   4560
ggccttgaag cttgtattca accagtaaag gcacccaatc ttcttcattt taagactcag   4620
tacacaaatt gtacagtgtg tgatgcaaat agtgtggatg aggtggtaga agcctcacta   4680
ccatatctgt tgctccttgc tactgatggt cctactacag tggattgtga tgaaaatgct   4740
gtagggaatg ttgttttcat tggctctact aacagtggcc attgttatac acaagccatt   4800
ggtaaggctt ttgacaatct tgctaaagat agaaaatttg gaaagaagtc tccttacatt   4860
actgcaatgt atacacactt ctctcttaag ggtgaaaatc ctttacctgt tgttaaacag   4920
agtaaaggaa aaactaaagt tgtaaaagag gatgtttcta atcttgccac tagttctaaa   4980
gtcagttttg ataatcttac tgattttgaa cagtggtatg atagtaacat ctacgagtgt   5040
```

-continued

```
cttagagtac aggaaatgcc tgataatttt gatgaatatg tgtcatttac aacaaaggaa   5100
gattctaagt tgccattgac gcttaaagtt agaggtatta gatcagttgt tgattttaaa   5160
tcaaaggatg gttttactta caagttaaca cctgatactg atgaaaattc aaaggcacca   5220
gtatactacc ctgtcttaga tgctattagt cttaaggcaa tatgggttga aggtactgca   5280
aattttcttg ttggtcatcc aaactactat agtaaatctc ttcgcattcc cactttttgg   5340
gaaaatgcag agagctttgt taaaatagga gaaaaagttg atggtgtgac tactggtctt   5400
tggcgtgcag aacaccttaa taaacctaac ttggagagaa ttttcaacat tgctaagaaa   5460
gcaattgttg ggaccagtgt tgttactaca caatgtggta aattacttag taaagcagct   5520
acattcattg ctgataaact aggtgggggt gtagttcgca atattacaga tagagttaag   5580
ggtctttgtg gattcacacg tgggcatttt gaaagaaaat tgtctccaca attcataaaa   5640
acacttatat tcttcttctt ttattttgta aaggctagtg ctaagagtgt cgccactagt   5700
tataagcgtg tgttatgtaa ggtggtcttt actacgctat ttatattatg gtttatgtac   5760
acaagtaaac cagtaatttt tactggaata cgtatattag actttttatt tgaaggttct   5820
gtctgtggtc cttataatga ctatggtaaa gatacttttg atgtactacg ctattgtgaa   5880
gatgatttta cttgtcgtgt gtgtttacat gacagggatt cactacactt atataagcat   5940
gcttatagcg tagaacaatt ttataaaagt gcagtttctg gcattagttt taattggaat   6000
tggctttatt tggtctttct aattttattt gttaagccag tagcgggttt tgttattatt   6060
tgctattgtg ttaagtattt ggtactgagt tcaactgtat tacaaactgg tgtaggtttt   6120
ctagattggt ttgttcagac agttttcact cactttaatt tcatgggtgc agggttttat   6180
ttctggctct tttataagat atacatacag gttcatcata tactgtattg taaggatata   6240
acatgtgaag tgtgcaagaa ggttgtacgc agcaataggc aagaggttag cgttgtagtt   6300
ggtggacgca agcaaatagt gcatgtctac actaactcag gctataattt ttgtaagaga   6360
cataactggt attgtagaaa ttgtgatgag tatggtcatc aaaacacatt tatgtctccc   6420
gaagttgctg gcgagctctc cgataagctt aagcgtcatg ttaaacctac agcatatgct   6480
taccacgttg tggatgatgc gtgcgtagtt gatggttttg ttaatttaaa atacaaagct   6540
gcaattcctg gcaaggatag tgcatctcct gccgttaagt gttttagtgt tacagatttc   6600
ttgaagaaag ctgtttttct taaggaagca ttgaaatgtg aacaaatatc caatgatagt   6660
tttatagtgt gtaatacaca gagtgcgcat gcattagagg aagcaaaaaa tgctgccatc   6720
tattatgcgc aatgtctgtg taagccaata cttatacttg accaggcact ttatgagcaa   6780
ttagtagtgg aacctgtgtc taagtgtgtt gtagacaagg tgtgtagcat tttgtccaat   6840
ataaatatctg tagatactgc agccttaaat tataaagcgg gcacacttcg tgattgtctg   6900
ctttctgtta ctaaagacga agaagctgta gatatggcta tcttctgtca taaccatgat   6960
gttgaataca ctactgatgg ttttactaat gtgataccat cttatggtgt agacactgat   7020
aggttgacac ctcgtgatag aggattttta ataaatgcgg atgcttctgt tgctaattta   7080
cgagttaaaa attctccacc agtagtatgg aagttttctg atcttattaa gttgtctgac   7140
agttgcctta aatatttaat ttcagctact gtcaagtcag gggtcgttt ctttataaca   7200
aagtctggtg ctaagcaagt tttttcttgc cacacccaga aattgttggt agagaaaaag   7260
gcaggtggtg tcactagtga tacttttaaa tggttgaaaa gctgttttaa gtggctattt   7320
atcttttaca tactttttac agcatgttgt ttgagttact actatgtgga gatgaataga   7380
agttttgttc accccatgta tgatgtaaac tctacactgc atgttgaagg ttttaaagtt   7440
```

```
atagataaag gtgttattag ggaaattgtg tctgaagata catgtttctc taataaatac   7500
gttaattttg atgccttctg ggtaaacca tatgaaaata atagaaactg tccaattgtc    7560
actgctgtta tagatggtga tgggacagta gctgctggtg ttcctggttt tgtatcatgg   7620
gttttggatg gtgctatgtt tgtacatatg acacagactg agagaaaacc gtggtacatt   7680
cctacttggt ttaatagaga aattgtaggt tacactcagg attcaattat tactgagggt   7740
agtttttata catctatagc tttattttca gctagatgtt tgtacctgac agccagcaat   7800
acacctcaat tgtattgctt taatggtgat aatgatgcac ctggagcctt atcattcggt   7860
agtattattc ctcatagggt ttacttccaa ccaaatggtg ttaggcttat agttcctcaa   7920
caaatatttc acacaccata catagtaaag tttgtatcag acagctattg tagaggtagt   7980
gtatgtgaat atactaaacc aggttactgt gtatcattaa actcccaatg ggttttgttt   8040
aatgatgaat acacaagtaa gccaggcgtg ttttgtggtt ctactgttag agaacttatg   8100
tttaatatgg ttagtacatt tttcacaggt gtcaacccta atatttatat gcagctagca   8160
attatgtttt tgatactagt tgttgttgta ttaatttttg caatggtcat aaagtttcaa   8220
ggtgttttta aagcttatgc aaccgttgtg tttacaataa tgttagtttg ggttattaat   8280
gcatttgttt tgtgtgtaca tagttataat agtgttttag ctgttgtatt actagtactt   8340
tattgttatg cctcattggt aacaagccgc aatacttcta ttataatgca ttgctggctt   8400
gtcttcactt ttggtttaat agtacccacg tggctggctt gtgtttattt agggtttatt   8460
ctctatatgt atacaccact atttttctgg tgttatggta ctactaaaaa tactcgtaaa   8520
ctgtatgatg gcaacgagtt tgttggtagt tatgatcttg ctgcgaagag cacttttgtt   8580
attcgtggtt ctgaatttgt taagcttacg aatgagatag gtgataaatt tgaagcttac   8640
cttgcagcgt atgctagact taaatattac tcaggcactg gcagtgagca agactacttg   8700
caagcctgtc gtgcatggtt agcttatgct ttggaccaat atagaaatag tggtgtggaa   8760
attgtgtata caccaccacg ttactctatt ggtgttagta gattacaggc tggttttaag   8820
aaactagttt ctcctagtag tgctgttgaa aggtgcattg ttagtgtctc ttatagaggt   8880
aataatctta atggactatg gctaggtgac actacttatt gtcctcgcca tgtgttaggt   8940
aagttttcag gtgaccaatg gaatgatgta cttaaccttg ctaataatca cgagtttgaa   9000
attacaactc aaaatggtgt tgctttgaat gttgtcagta ggcggctaag aggtgcagtt   9060
ttgattttac aaactgctgt cgctaatgct gaaactccaa agtataagtt tattaaagca   9120
aattgtggtg atagttttac catagcttgc tcttatggtg gtacggtagt aggactttac   9180
cctgttacaa tgcgttctaa tggtactatt agagcctcat ttcttgcagg agcttgtggc   9240
tctgttggtt ttaatataga aaagggtgta gttaatttct tctatatgca ccatcttgag   9300
ttgcctaatg cattacacac aggaactgac ctaacgggag agttctatgg tggttatgtg   9360
gatgaagagg ttgcacaaag ggtgccacca gataatttag ttactaacaa tattgtagca   9420
tggctttatg ccgcaattat tagtgttaaa gagagtagtt tctcattgcc taaatggttg   9480
gagagtacta cagttactgt tgatgattat aataagtggg ctggtgataa tggttttaca   9540
ccgtttgcta ctagtactgc cattactaaa ttaagtgcta ttacgggagt ggatgtttgt   9600
aaactccttc gcactattat ggcaaaaagt tgtcaatggg gtagtaaccc catttttaggc  9660
caatataatt ttgaagatga attgacacct gagtctgttt ttaaccagat aggcggtgtt   9720
agattacagt cttcgtttgt aagaaaagct acatcttggt tttggagtag atgtatttta   9780
```

```
gcttgtttct tatttgtgtt gtgtgctatt gtcttattta cggcagtgcc acttaggtat   9840

tatgtacatg cagctgttat tttgttagca gctgtattct ttatttcttt tactgttaag   9900

catgttatgg cttatatgga cactttccta ttgccgacat tgcttacagt cattattgga   9960

gtttgtgctg aagtaccttt catctacaat actctaatta gtaggatagt tgtctttgtt  10020

agtcaatggt atgatcctgt agtctttgat actatggtac catggatgtt cttgccacta  10080

gtgttgtaca cagcatttaa gtgtgtgcag ggttgctata gtgtgaattc tttcaatact  10140

tctttgctag tactgtacca gttcttgaag ttaggctttg ttatttatgc ctcttctagc  10200

acgctggcag catacacaga aggtaattgg gatttatttt ttgaattagt tcacactact  10260

gtgttggcta atgttagtag taattcctta ataggtttgt ttgtgttcaa gttagctaag  10320

tggatgttgt attattgtaa tgctacatac tttaataatt atgtgctaat ggctgtcatt  10380

attaatggct ttggttggct cttcacttgt tactttggag tttattggtg gattaataag  10440

gtttttggtt taaccttagg taaatatgaa ttcaaagttt cagtagacca atataggtat  10500

atgtgtcttc ataagataaa tccgcctaaa actgtgtggg aagttttttc gacaaatata  10560

cttatacaag gaattggtgg tgatcgtgtg ttgcctattg ctacagttca atctaaattg  10620

agtgatataa agtgtacaac tgttgtttta atgcagcttt tgactaagct taatgttgaa  10680

gcaaattcaa aaatgcatgc ttatcttgtt gatttacaca ataaaattct tgcatctgat  10740

gatgttggag agtgcatgga taatttgttg ggtatgctta ttacactatt ttgtatagat  10800

tctactattg atttgagtga gtattgtgat gatatactta agaggtcaac tgttttacag  10860

tcagttactc aagagttctc acacataccc tcttatgctg aatatgaaag agctaagaat  10920

ctttatgaaa aggttttagc tgattctaaa aatggtggtg taacacagca agagcttgct  10980

gtatatcgta aagctgccaa tattgcaaag tcagtttttg atagagactt ggctgttcaa  11040

aagaagttag acagcatggc agaacgtgct atgacaacaa tgtataaaga ggcgcgtgta  11100

actgatagac gagcaaaatt agtttcatca ctacatgcgt tactgttttc aatgctcaag  11160

aaaatagatt ctgaaaagct taatgtatta tttgatcagg ctagtagtgg tgttgtacct  11220

ctagctactg ttccaattgt ttgtagtaat aagcttaccc ttgtaatacc agatccagaa  11280

acttgggtca agtgtgtgga aggtatgcat gttacttact caacagttgt ctggaatata  11340

gacactgtta ttgatgctga tggcacagaa ttacatccta cttctacagg tagtggattg  11400

acatactgtg taagtggtga caatatagcg tggcctttaa aggttagctt aactagaaat  11460

gggcataata gagttgacgt tgcgttgcag aacaacgagc ttatgcctca tggtgtaaag  11520

acaaaggctt gcgtggcggg tgtagatcaa gcacactgta gcgttgagtc taaatgttat  11580

tatacaaata ttagtggtaa ttcagttgta gctgctatta cttcttcaag tccaaatctg  11640

aaagttgcat ccttcttgaa cgaggcaggc aaccagattt atgtagactt agacccacct  11700

tgtaagtttg gtatgaaagt gggtgataag gttgaggttg tttacctgta ttttataaaa  11760

aatacaaggt ctattgttag ggtatggta cttggtgcta tatccaatgt tgttgtttta  11820

cagtctaaag ggcacgagac agaggaagta gatgctgttg gtattctttc actttgttca  11880

tttgcagtag atcctgcaga aacgtattgt aaatatgtgg ctgcaggtaa tcaaccttta  11940

ggtaactgtg ttaaaatgtt gacagttcat aatggtagtg gttttgctat aacatcaaag  12000

ccaagtccaa ctcctgatca agattcttat ggaggagctt ctgtgtgtct cttttgtaga  12060

gcacatatag cacacccagg aggtgcagga aatttagatg gacgttgtca atttaaaggt  12120

tcctttgtgc aaatacctac tacggagaaa gatcctgttg gtttttgtct acgtaataag  12180
```

```
gtttgcactg tttgtcagtg ttggattggt tatggctgtc agtgtgattc acttagacaa  12240
ctaaaaccct ttgtacaatc aactgctggt gcaattgatt ttgataagaa ttatttaaac  12300
gggtacgggg tagcagtgag gctcggctga taccccttgc taatggatgt gatcctgatg  12360
ttgtaaagcg agcctttgat gtttgtaata aggaatcatg tggtatgttt caaaatttga  12420
agcgtaactg tgcaagattc caagaagtgc gtgatactga agacggaaat cttgagtatt  12480
gtgactctta ttttgtggtt aaacaaacca cccctagtaa ttatgaacat gagaaagctt  12540
gttacgaaga cttgaagtca gaagtaacag ctgctcatga ttttttgtg ttcaataaga  12600
acatttataa tattagtagg caacggctta ctaagtatac tatgatggac ttttgctacg  12660
ccttgaggca ttttgaccca aaggactgcg aagttcttaa agaaatactt gtcacttatg  12720
gttgtataga agattatcac cctaagtggt ttgaagataa taaggattgg tacgacccaa  12780
tagaaaaccc aaaatattat gccatgttgg ctaaaatggg gcctattgta cgtcgtgctt  12840
tattgaatgc tattgagttc ggaaacctta tggttgaaaa aggttatgtt ggtgttgtta  12900
cactagataa ccaagatctt aatggtaaat tttatgactt tggtgatttt cagaaaacgg  12960
cacctggtgc tggtgttcct gtttttgata catattattc ttacatgatg cccatcatag  13020
ccatgacgga tgctttggca cctgaaaggt attttgaata tgatgtgcat aagggttata  13080
agtcttatga tctcctcaag tatgattata ctgaggagaa acaagagttg tttcagaagt  13140
actttaagta ttgggatcag gagtaccatc ctaactgccg tgactgtagt gatgacaggt  13200
gtttgataca ttgtgcaaac ttcaacatct tgttttctac attgataccg cagacctctt  13260
ttggtaattt gtgtagaaaa gtgtttgttg atggtgtacc ttttatagct acttgtggct  13320
atcattctaa agaacttggt gttattatga atcaagataa caccatgtcg ttctcaaaaa  13380
tgggtttaag tcaactcatg cagtttgttg gagatcctgc cttgttagtg ggaacatcca  13440
ataatttagt tgatcttaga acgtcttgtt ttagtgtttg tgcattagcg tctggtatta  13500
ctcatcaaac agtaaaacca ggtcacttta acaaggattt ctatgatttt gcagagaagg  13560
ctggtatgtt taaagagggt tcttctatac cacttaaaca tttcttctac ccacaaactg  13620
gtaatgctgc tataaacgat tatgattact atcgttataa caggcctacc atgtttgata  13680
tacgtcaact tctattttgt ttagaagtga cttctaaata ctttgaatgt tatgaaggcg  13740
gctgtatacc agcaagccaa gttgtagtta acaatttaga taagagcgca ggctatccgt  13800
tcaataagtt tggaaaagct cgtctctatt atgaaatgag tctagatgaa caggaccaac  13860
tctttgagat tacaaagaag aatgtcctac ccaccataac tcaaatgaat ttaaaatatg  13920
ccatatccgc gaaaaataga gcgcgtactg tggcaggtgt ttctatcctt tctactatga  13980
ctaataggca atttcatcag aaagttctta agtctatagt caatactaga aacgctcctg  14040
tagttattgg aacaaccaaa ttttatggtg gttgggacaa catgttgaga aatttgattc  14100
aaggtgttga agacccgatt ctcatgggtt gggattatcc aaagtgtgat agagcaatgc  14160
ctaatttgtt gcgtatagct gcatctttgg ttcttgcccg taaacatact aattgttgta  14220
cttggtctga ccgcgtttat aggttgtata atgaatgcgc tcaggtttta tcggaaactg  14280
tcttagctac aggtggtatt tatgtgaaac ctggtggcac tagcagtggt gatgcaacta  14340
ctgcttatgc aaatagtgtt tttaacataa tacaagcgac atctgctaat gtcgcgcgtc  14400
ttttgagtgt cataacgcat gatattgtct atgatgacat taagagcctg cagtatgaat  14460
tgtatcagca ggtttatagg cgagtcaatt ttgacccatc ctttgttgag aagttttatt  14520
```

```
cttacttatg taagaacttt tcattgatga tcctgtctga tgatggtgtt gtttgttata  14580
acaacacact agccaggcaa ggtcttgttg cagatatttc tggttttaga gaaattctct  14640
actaccaaaa taatgtttat atggctgatt ctaagtgttg ggttgagcct gacttagaaa  14700
aaggcccaca tgaattttgt tcacaacaca ccatgctagt ggaggttgat ggtgagctta  14760
aatacttgcc atacccagac ccttcacgca tcttaggtgc atgtgtattt gtagatgacg  14820
cggataagac agaacctgtg gctgttatgg agcgttatat cgctcttgcc atagatgctt  14880
acccgctagt acatcatgaa aatgaagagt acaaaaaggt gttctttgtg ctccttgcgt  14940
atatcagaaa actctatcaa gagctttctc aaaatatgct tatggactac tcttttgtaa  15000
tggatataga caagggtagt aaattttggg agcaggagtt ctatgaaaat atgtatagag  15060
cccctacaac tttacagtct tgtggcgttt gtgtagtgtg caatagtcaa actatactgc  15120
gctgtggtaa ttgtattcgc aaaccatttt tgtgttgtaa atgttgctat gaccacgtca  15180
tgcatacaga ccacaaaaat gttttgtcta taaacccata catttgctca cagcctggtt  15240
gcggcgaagc agatgttact aaattgtacc tcggaggcat gtcgtacttc tgtggtaatc  15300
ataaaccaaa gttatcaata ccgttagtat ctaatggtac agtttttgga atttacaggg  15360
ctaattgtgc tggtagcgaa aatgttgatg attttaatca actagctact accaattggt  15420
ctactgtgga accctatata ttagcaaatc gctgtagtga ttcattgaga cgctttgctg  15480
cagagacggt aaaagctaca gaggaattgc ataagcagca atttgctagt gcagaggtga  15540
gagaagttct ctcagaccgc gaattgattc tatcctggga gccaggtaaa actaggcctc  15600
cactgaatag aaactatgtc ttcacaggct accactttac aagaactagt aaagtgcagc  15660
ttggtgactt tatttttgaa aaaggtgagg gtaaggatgt tgtctattac agggcaacgt  15720
ctactgctaa attgtctgtt ggggacattt ttgttttaac ttcacacaat gttgtttctc  15780
ttgtagcgcc aacattgtgt ccacaacaaa ctttttctag gtttgtaaat ttaagaccta  15840
atgtaatggt accagaatgt tttgtgaata acattcctct ttaccattta gtaggtaagc  15900
acaagcgtac tacagtacaa ggcccacctg gcagtggtaa atcccacttt gctataggcc  15960
ttgcagctta ctttagtaat gctcgtgttg tttttactgc gtgctcccat gcagctgtag  16020
atgctttatg tgaaaaagct tttaagtttc tcaaagttga tgattgcact cgtatagtac  16080
ctcaaaggac tactatcgat tgtttctcaa agtttaaagc taatgacaca ggcaaaaagt  16140
acatttttag tactataaat gccttgcctg aagttagttg tgacattctt ttggtcgatg  16200
aggtcagtat gttgaccaat tatgaattgt ctttcattaa tggtaagata aactaccaat  16260
atgttgtgta tgtaggtgat cctgctcaat taccagcacc tcgcactttg cttaatggtt  16320
cgctttcacc aaaggattat aatgttgtca caaaccttat ggtttgtgtt aaacccgaca  16380
ttttccttgc aaagtgttac cgctgtccta aagagattgt agacactgtg tctactcttg  16440
tctatgatgg aaagtttatt gcaaataacc cagaatcacg tcagtgcttc aaggttatag  16500
ttaataatgg taattctgat gtaggacacg aaagtggttc agcctacaac acaacccaat  16560
tagaatttgt gaaagatttt gtttgtcgca ataaagaatg gcgggaagca acattcattt  16620
caccttataa tgctatgaac cagagggcct accgtatgct tggacttaat gttcaaacag  16680
tagattcctc tcaaggttct gagtatgatt atgttatctt ttgtgttact gcggattcgc  16740
agcatgcgct gaatattaac aggtttaatg tggcgcttac aagagctaag cgtggtatat  16800
tggttgtcat gcgtcagcgt gatgaattgt attctgctct taagtttata gagttagata  16860
gtgaaacaag tctgcagggt acaggtttgt ttaaaatttg caacaaagaa tttagtggtg  16920
```

```
ttcaccctgc ttatgcggtc acaactaaag ctcttgctgc aacctacaaa gttaatgaag  16980
aacttgcagc ccttgttaat gtggaagctg gttcagaaat aacatataaa catctcattt  17040
ctcttcttgg gtttaagatg agtgttagtg ttgaaggttg tcacaacatg tttattacac  17100
gtgatgaggc aattcgcaat gtaagaggtt gggtaggttt cgatgtggaa gctacacatg  17160
cctgtggtac taacattggt actaacctcc cttttcaagt gggcttctcg acaggtgcag  17220
attttgtagt cacacctgag ggacttgtag acacttcaat aggcaataat tttgagcctg  17280
tgaattctaa agcacctcca ggtgaacaat ttaatcactt gagagcttta tttaagagtg  17340
ctaaaccttg gcatgttata agaccaagga tagtgcaaat gttagcagat aacctatgca  17400
atgtttcaga ttgtgtagtg tttgtcacgt ggtgtcatgg tctagaacta actaccctgc  17460
gctattttgt taaaataggc aaggaacaaa tttgttcatg tggttctaga gctacgacct  17520
ttaattctcg cactcaaact tatgcttgtt ggaggcattg tttgggtttt gattttgtct  17580
ataacccact cttagtggat atccaacaat ggggttactc aggtaatctg cagtttaatc  17640
atgacttgca ctgtaatgtg catggacacg cgcatgtggc atctgcagat gctattatga  17700
cgcgttgtct tgcagttaac aatgcatttt gtcaagatgt taactgggat ttaacatacc  17760
ctcatattgc aaatgaggat gaagttaatt ctagttgtag atatttacag cgcatgtatc  17820
tcaatgcatg tgttgatgct cttaaagtta atgttgtcta tgacataggc aaccctaaag  17880
gcattaaatg tgttaggcgt ggggatgtca ctttcagatt ctatgataag aatccaatag  17940
tacccaacgt caagcagttt gagtatgact ataatcagca caaagataag tttgctgatg  18000
gtctttgtat gttttggaat tgtaatgtgg gttgttatcc tgataattct ttggtttgta  18060
ggtatgacac acgaaatttg agtgtgttta acctaccagg ttgtaatggt ggtagccttt  18120
atgtcaacaa acatgcattc cacacaccta aatttgagcg caatagcttc cgtaatttga  18180
aagctatgcc attctttttc tatgactcgt caccgtgtga caccattcaa atagatggtg  18240
ttgcacagga tcttgtgtca ctagctacaa aagactgtat cacaaaatgc aacataggcg  18300
gcgccgtttg taaaaagcac gcgcaaatgt atgcagagtt cgtgacatct tataatgcag  18360
ctgttacggc tggctttact ttttgggtta ctaataattt taacccatac aatttgtgga  18420
aaagtttctc agctctccag tccattgaca acattgctta taatatgtat aagggtggcc  18480
attatgatgc tattgcagga gaaatgccca ctatagtaac tggagataaa gtttttgtta  18540
ttgatcaagg tgtagaaaag gcagttttcg ttaatcaaac aactctgcct acatctgtgg  18600
catttgaatt gtatgcgaag agaaatattc gcacactgcc aaacaatcgt attttgaaag  18660
gccttggtgt agatgtgacc catggttttg taatttggga ttatgcaaac caagtaccat  18720
tgtatcgtaa tactgttaaa gtgtgtgtat acacagatat cgagccaaat ggcctaacgg  18780
ttctgtatga tgatagatat ggtgattacc agtcttttct tgctgctgat aatgctgttc  18840
tagtttctac acagtgttat aagcggtact catatgtaga aataccatca gatcttcttg  18900
tccagaatgg tatgtcatta aaagatgggg cgaatctgta tgtttataag cgtgttaatg  18960
gtgcgtttgt tacgctacct aacacgctaa atacacaggg tcgcagttat gaaacttttg  19020
aaactcgtag tgacgttgag cgggattttc tcgccatgtc agaagaagac tttgtagaaa  19080
agtatggtaa agacctaggt ctacaacaca tactatatgg tgaagttgat aatcctcaat  19140
taggcggttt acacactgtt ataggtatgt atagactttt acgtgcgaat aaattgaacg  19200
caaagtctgt cactaattca gattctgatg tcatgcaaaa ttattttgta ttggcagaaa  19260
```

```
atggttccta taagcaggtc tgcaccgtag tggacttgtt gcttgatgac ttcttagaac  19320

ttcttagaaa catactcaag gagtatggtg ctaacaagtc taaagttgta acagtgtcaa  19380

ttgattacca tagcataaat tttatgacgt ggtttgataa tggcagtatt aaaacgtgtt  19440

atccgcagct tcaatctgca tggacgtgtg gttataatat gcctgagctc tataaagttc  19500

agaattgtgt tatggaacct tgcaatattc caaactatgg tgttggaata acgttgccaa  19560

gtggtattat gatgaatgtt gcaaagtaca cacaactttg ccaatatctt tctaaaacaa  19620

caatgtgtgt accgcataat atgcgagtta tgcattttgg agtaggtagt gacaaaggag  19680

tagcgccagg tagtactgtt cttaaacagt ggcttcctga aggaacactc ctcgttgaca  19740

atgatattgt agattatgtg tctgatgcac atgtttctgt gctttcagat tgcaataaat  19800

ataagacaga tcacaagttt gatcttgtga tatctgatat gtatacagat aatgattcta  19860

agagaaagca tgaaggcatg gtagccaata atggtaatga tgacgtcttc atataccttt  19920

ccaacttcct tcgtaacaat ttggctctgg gtggcagttt tgctgtgaaa ttaacagaga  19980

caagttggca cgagaattta tatgacattg cacaggactg tgcatggtgg acaatgtttt  20040

gtacagcggt taatgcttct tcctcggagg catttctgat tggtgttaat tacttgggtg  20100

caagtaaaaa ggttaaagtt agtggaaaaa cactgcacgc aaattatata ttttggagga  20160

attgtaatta tttacaaacc tctgcttata gtgtatttga cgttgcaaag tttgaattaa  20220

aactaaaagc aacgccagtt gttaatttga aaactgaaca aaagacagac ttagtcttta  20280

atttaattaa gtgtggtaag ttactggtaa gagatgttgg gcaaaccgct tttactagtg  20340

actctttggt atgcactatg tagtgctttg ctttatgata aaaatactta cgtttactac  20400

taccaaagtg cctttaggcc tggtcaaggt tggcatctac atgggggtgc ttatgcagta  20460

gataaggttt ttaatggaac caacaatgca gtcagtgtat ctgattgcac tgctggtact  20520

ttttatgaaa gctataatat ttctgctgct tctgtagcca tgacagtacc acctgctggt  20580

atgtcttggt cagttgcaca gttttgtaca gctcattgta acttctcaga ctttacagtg  20640

tttgttacgc attgttttaa aagtcaacaa ggtagttgtc cattgacagg tatgattcct  20700

cagaatcata ttcgtatttc tgctatgaga tctggatttt tgttttataa tttaacagtt  20760

agcgtatcta aataccctaa atttaaatcg cttcaatgtg ttggcaattc tacatctgtc  20820

tatttaaatg gtgatcttgt tttcactcct aatgaaacaa ctcacgttac gggtgcaggc  20880

gtttatttta aaagtggtgg gcctgtaact tataaagtta tgaaagaagt taaagcccta  20940

gcctacttta ttaatggtac cgcacaagag gttattttat gtgataactc acctagaggt  21000

ttgcttgcat gtcagtataa cactggtaat tttttcagatg gattctaccc ttttactaat  21060

tcttctttag ttaaggatag gtttattgta tatcgagaaa gtagcactaa cactacttta  21120

gagttaacta atttcacttt tactaatgta agtaatgctt ctcctaattc aggtggcgtt  21180

gatactttcc aattatatca aacacatact gctcaggatg gttattataa ttttaattta  21240

tcatttctga gtagttttgt gtataaacca tctgatttta tgtatgggtc ataccaccca  21300

aattgtaatt ttagaccaga gaatattaat aatggcttat ggtttaattc attatctgtg  21360

tcacttactt acggacccat tcaaggtggt tgtaagcaat ctgtttttag taataaagca  21420

acttgttgct atgcttattc ttaccgaggt cctactagat gtaagggtgt ttatagaggg  21480

gagctaacgc aatactttga atgtggactt ctagtttatg taactaagag tgatggctct  21540

cgtatacaaa ctagaagtga accactggtg ttaactcaat ataattataa caacattact  21600

ttaaataagt gtgttgagta taatatatat ggtagagttg gtcaaggttt tattactaat  21660
```

gtaactgaag caactgctaa ttatagttat ctagcagatg gtggtttagc tattttagat 21720
acttcaggag ccatagacat atttgttgtt cgaggtgcat atggtcttaa ttattataag 21780
gttaatccct gtgaagatgt taaccaacag tttgtagtgt ctggtggcaa tttagttggc 21840
attcttacat ctcataatga aacagattct gaatttattg agaaccagtt ttacatcaaa 21900
ctcactaacg gaacacgtcg ctctagacgt tctgttactg ggaatgttac aaattgccct 21960
tatgttagtt atggcaagtt ttgtataaaa ccagatggtt ctttatttat aatagtacca 22020
caagagttag aacagtttgt ggcgccttta ctcaatgtta ctgagcatgt gctcatacct 22080
gatagtttta atttaactgt cacagatgag tacatacaaa ctcgtatgga taaggttcaa 22140
attaattgcc ttcagtatgt ttgtggtaat tctattgaat gcagaaagtt gtttcagcag 22200
tatggacctg tttgtgataa tatattgtct gttgtaaatg gtgtaggtca aagagaggat 22260
atggaacttt taagtttcta ttcgtctact aaacctagtg gttacaatac accaattttt 22320
aataatgtta gcactggtga ctttaatatt tctctcttac taacaccacc taatagtcct 22380
actgggcgct cttttattga agatcttctt tttacaagtg tagaatctgt tggattacca 22440
actgatgaag agtataaaaa gtgtacagca ggacctttag gttttgttaa ggaccttgtt 22500
tgtgctagag agtataatgg cttgcttgtg ttgcctccta ttattactgc agacatgcaa 22560
actatgtata ctagctcttt agtagcctct atggctttag gtggcattac tgcagctggt 22620
gctatacctt ttgctacaca actgcaggcc agaattaacc atttgggtat tactaattct 22680
cttttgttga aaaatcaaga aaaaattgct gcttccttta ataaggccat cggtcatatg 22740
caggaagggt ttaaaagtac ttctctagca ttacaacaga ttcaagatgt tgttaataaa 22800
cagagttcta ttcttacaga gactatgcaa tcacttaata aaaattttgg tgctatttcc 22860
tccgtacttc aagacattta ccagcaactt gatgctattc aggcagatgc tcaggttgat 22920
cgtcttatta caggtagact ttcttcacta tctgttttag cttctgctaa acaggcagag 22980
tatcatagag tgtcacaaca gcgtgagttg gccactcaga aaattaatga gtgtgttaag 23040
tctcagtcta ataggtattc attttgtggt aatggaagac atgttttaac cataccacaa 23100
aatgcaccta atggtatagt gtttatacac tttacttata ctccagagag ttttgttaat 23160
gttactgcaa tagtgggttt ttgtgtaaat ccagctaatg ccagtcagta tgcaatagtg 23220
cccgttaata acagaggtat ttttattcaa gttaatggta gttactacat cactgcacgt 23280
gatatgtata tgccaagaga cattacagca ggagacatag ttatgcttac ttcttgtcaa 23340
gcaaattatg taagtgtaaa taagactgtc attactacat ttgtagataa tgatgacttt 23400
gattttgatg acgaattgtc aaaatggtgg aatgatacta agcatgagct accagatttc 23460
gacgaattca attatacagt accagtatta aatattagta atgaaattga cagaattcaa 23520
gaagttattc agggattaaa tgactcccta atagatcttg aaacactctc aattcttaaa 23580
acttatatta agtggccttg gtatgtgtgg cttgccatag cttttgccat tattatcttc 23640
atcctaatct taggatgggt tttcttcatg actggttgtt gtggttgttg ttgtgggtgc 23700
ttcggcatta ttcctttaat gagtaagtgt ggtaaaaaat cttcttacta cacgactttt 23760
gataatgatg tggtaactga acaatacaga cctaaaaagt ctgtttaatg attcaaagtc 23820
ccacatcttt tctaatagta ttaattcttc tttggtgtaa acttgcatta agctgtttta 23880
aagagtgtgt tataacactc cagcaactaa tacaagtttt actccaaatt attaatagta 23940
acttacagtc tagacttctg ctttggcaca gtctagacta atgttagatt ttgaagcaat 24000

```
tattgaaact ggtcagcaaa taattcaaca aatcagtttc aatttacagc acatttcaag  24060
tgtgttaagt tctgaattat ttgacccctt tgaagtttgt ttttacagag gaggtaatta  24120
ttgggaggta gattcagctg aagaattttc aggtgatgat gaacctactg aataagtcgt  24180
tagaggaaaa tggaagtttt ctaacagcgg tttacgtgtt ttgtgcattt gtagcacttt  24240
acctattagg tagagcgctc caagctttcg tacaagctgc tgatgcttgt tgtctttttt  24300
ggtacacatg ggtagttgtt cctggagcca agggtacatc ctttgtgtac aaacacacat  24360
atgggaaaaa acttaacaat ccggaattag aaagcgttat tgttaacgag tttcctaaga  24420
acggttggaa taataaaaac ccagcaaatt tccaaaatgg aaaattgcac acttgacgct  24480
gaacaggcag ttcagctatt taaagattat aatctattta taactgcatt cctgttgttt  24540
ctaaccatac tacttcagta cggctatgca actaggagtc ggattattta catactgaaa  24600
atgatagtgt tatggtgctt ctggcccctt aacattgcag taggtgtaat ttcatgtata  24660
tacccaccaa acacaggagg tcttgtcgca gcgataatac ttactgtgtt tgcgtgtctt  24720
tctttttag gttattggat ccagagcatt aggctcttta agcggtgcag atcatggtgg  24780
tcatttaacc cagaatctaa cgccgtaggt tcaatactcc taactaatgg tcaacaatgt  24840
aattttgcta tagagagtgt gccgatggtg ctttctccta ttataaagaa tggtgctctt  24900
tattgtgagg gtcagtggct tgctaagtgt gaaccagacc acttgcctaa agacattttt  24960
gtttgcacac cagatagacg taatatctat cgtatggtgc agaaatacac tggtgaccaa  25020
agcggaaata agaaaaggtt tgctacattt gtctatgcga agcagtcagt agatactggc  25080
gagctagaaa gtgtagcaac agtaggaagt agtctttaca cataaatgtg tgtgtgtaaa  25140
gaatatttaa aattattctt tgacagtgcc tctatcttaa gagcgtggaa gagtattatt  25200
tttgaggata ttaatataaa ccctctttgc ttcatactct cttttcagga gttattattt  25260
aaaaaacagt ttttccactc ttttgtgcca aaaacagttt gtgttaatgg ggtgtccttc  25320
caagtagaca atggaaaagt ctattacgaa ggaaaaccaa ttttccaaaa aggttgttgt  25380
aggttgtggt ctagttataa gaaagattag aataattaaa ccaccaacaa cacttacttt  25440
taaaaagggc gttttatgtt ataagcgctt aacaaacacg gacgatgaaa tggcttacta  25500
gttttggaag agcattcatc tcctgttata aatccctatt actaactcaa cttagagtat  25560
tagataggtt aaatttagag cacggaccaa accgcgtttt aacgtgtagt aggcgagtgc  25620
ttttagttca attagattta gtttataggt tggcttgtac gcccacccaa tcgctggtat  25680
gaataatagt aaagataatc cttttcgcgg agcaatagca agaaaagcgc gaatttatct  25740
gagagaagga ttagattgtg tttactttct taacaaagca ggacaagcag agccttgtcc  25800
cgcgtgcacc tctctagtat tccacgggaa aacttgtgag gcgcacataa ataataataa  25860
tcttttatca tggcaagcgg taaggcagct ggaaaaacag acgccccagc gccagtcatc  25920
aaactaggcg gaccaaaacc accaaaagtt ggttcttcag gaaatgcatc ttggttccag  25980
gcaataaagg ccaagaaact taattcaccc cagcctaagt ttgaaggtag tggtgttcct  26040
gaaaatgaaa acttaaaatc aagccagcag cacggatact ggagacgcca acaccggtat  26100
aaaccaggta aaggcggaag aaaaccagtt ccagatgctt ggtactttta ttacactgga  26160
acaggaccag ccgctgacct gaattggggt gataaccaag atggtatagt gtgggttgct  26220
gctaaaggtg ctgatactaa atctagatct aaccagggta caagagatcc tgataagttt  26280
gaccaatacc cactgcgatt ctcagacggg ggaccggatg gtaacttccg ttgggatttc  26340
attcctataa atcgtggtag gagtggaaga tcaacagcag cttcatctgc tgcttctagt  26400
```

```
agagcaccat ctcgtgaagg gtcacgtgga cgtagaagtg gagctgaaga tgatcttata  26460

gctcgtgcag caaagattat tcaggaccaa caaaagaagg gttctcgcat taccaaggca  26520

aaggctgatg aaatggctca tcgccggtat tgcaagcgca ctgttccacc cggttataag  26580

gttgatcaag tatttggtcc ccgtactaaa ggtaaggagg gaaattttgg tgatgacaag  26640

atgaatgagg aaggtattaa ggatgggcgt gttacagcaa tgctcaacct agtccctagc  26700

agccatgctt gtctttttgg aagtagagtg acgcctaaac ttcaaccaga tgggctccac  26760

ttgagatttg agtttactac tgtggttcca cgtgatgacc cgcagtttga taattatgtg  26820

aaaatttgtg atcagtgtgt cgatggtgta ggaacgcgtc caaaagacga tgaaccgaga  26880

ccaaagtcac gcccaaattc aagacctgca acaagaggaa attctcctgc gccaagacaa  26940

cagcgccaaa agaaggagaa aaagccaaag aagcaggaag atgatgtaga taaggcattg  27000

acctcagatg aagagaggaa caatgcacag ctcgagtttg atgatgaacc caaagtgatt  27060

aattggggag attcagctct tggggaaaat gaattgtaag taacataatg gacttgctgc  27120

atttgctgtc acattttgtt aaatactatt ttgttgcttt cctatcaatt attacaggca  27180

ttgattgtga ttatgtgcaa tatttaagct actttttggtt gctttttgct tgttgtattg  27240

ttgctgtgct ttttattatt gtgattctca ttagtttgct ttatcgtaga agtgcaatag  27300

taagagttaa ggaagatagg catgtagctt gattacctac atgtctatcg ccagggaaat  27360

gtctaatctg tctacttagt agcctggaaa cgaacggtag acccttagat tttaatttag  27420

tttaattttt agtttagttt aagttagttt agagtaggta taaagaagcc agtgccgggg  27480

ccacgcggag tacgatcgag ggtacagcac taggacgccc actaggggaa gagctaaatt  27540

ttagtttaag ttaagtttaa ttggctaagt atagttaaaa tttataggct agtatagagt  27600

tagagcaaaa aaaaaaaa                                               27618
```

<210> SEQ ID NO 54
<211> LENGTH: 1164
<212> TYPE: PRT
<213> ORGANISM: Avian infectious bronchitis virus

<400> SEQUENCE: 54

```
Met Leu Gly Lys Pro Leu Leu Leu Val Thr Leu Trp Tyr Ala Leu Cys
1               5                   10                  15

Ser Ala Leu Leu Tyr Asp Lys Asn Thr Tyr Val Tyr Tyr Tyr Gln Ser
            20                  25                  30

Ala Phe Arg Pro Gly Gln Gly Trp His Leu His Gly Gly Ala Tyr Ala
        35                  40                  45

Val Asp Lys Val Phe Asn Gly Thr Asn Asn Ala Val Ser Val Ser Asp
    50                  55                  60

Cys Thr Ala Gly Thr Phe Tyr Glu Ser Tyr Asn Ile Ser Ala Ala Ser
65                  70                  75                  80

Val Ala Met Thr Val Pro Pro Ala Gly Met Ser Trp Ser Val Ala Gln
                85                  90                  95

Phe Cys Thr Ala His Cys Asn Phe Ser Asp Phe Thr Val Phe Val Thr
            100                 105                 110

His Cys Phe Lys Ser Gln Gln Gly Ser Cys Pro Leu Thr Gly Met Ile
        115                 120                 125

Pro Gln Asn His Ile Arg Ile Ser Ala Met Arg Ser Gly Phe Leu Phe
    130                 135                 140

Tyr Asn Leu Thr Val Ser Val Ser Lys Tyr Pro Lys Phe Lys Ser Leu
```

-continued

```
145                 150                 155                 160

Gln Cys Val Gly Asn Ser Thr Ser Val Tyr Leu Asn Gly Asp Leu Val
                165                 170                 175

Phe Thr Pro Asn Glu Thr Thr His Val Thr Gly Ala Gly Val Tyr Phe
            180                 185                 190

Lys Ser Gly Gly Pro Val Thr Tyr Lys Val Met Lys Glu Val Lys Ala
        195                 200                 205

Leu Ala Tyr Phe Ile Asn Gly Thr Ala Gln Glu Val Ile Leu Cys Asp
    210                 215                 220

Asn Ser Pro Arg Gly Leu Leu Ala Cys Gln Tyr Asn Thr Gly Asn Phe
225                 230                 235                 240

Ser Asp Gly Phe Tyr Pro Phe Thr Asn Ser Ser Leu Val Lys Asp Arg
                245                 250                 255

Phe Ile Val Tyr Arg Glu Ser Ser Thr Asn Thr Thr Leu Glu Leu Thr
            260                 265                 270

Asn Phe Thr Phe Thr Asn Val Ser Asn Ala Ser Pro Asn Ser Gly Gly
        275                 280                 285

Val Asp Thr Phe Gln Leu Tyr Gln Thr His Thr Ala Gln Asp Gly Tyr
    290                 295                 300

Tyr Asn Phe Asn Leu Ser Phe Leu Ser Ser Phe Val Tyr Lys Pro Ser
305                 310                 315                 320

Asp Phe Met Tyr Gly Ser Tyr His Pro Asn Cys Asn Phe Arg Pro Glu
                325                 330                 335

Asn Ile Asn Asn Gly Leu Trp Phe Asn Ser Leu Ser Val Ser Leu Thr
            340                 345                 350

Tyr Gly Pro Ile Gln Gly Gly Cys Lys Gln Ser Val Phe Ser Asn Lys
        355                 360                 365

Ala Thr Cys Cys Tyr Ala Tyr Ser Tyr Arg Gly Pro Thr Arg Cys Lys
    370                 375                 380

Gly Val Tyr Arg Gly Glu Leu Thr Gln Tyr Phe Glu Cys Gly Leu Leu
385                 390                 395                 400

Val Tyr Val Thr Lys Ser Asp Gly Ser Arg Ile Gln Thr Arg Ser Glu
                405                 410                 415

Pro Leu Val Leu Thr Gln Tyr Asn Tyr Asn Asn Ile Thr Leu Asn Lys
            420                 425                 430

Cys Val Glu Tyr Asn Ile Tyr Gly Arg Val Gly Gln Gly Phe Ile Thr
        435                 440                 445

Asn Val Thr Glu Ala Thr Ala Asn Tyr Ser Tyr Leu Ala Asp Gly Gly
    450                 455                 460

Leu Ala Ile Leu Asp Thr Ser Gly Ala Ile Asp Ile Phe Val Val Arg
465                 470                 475                 480

Gly Ala Tyr Gly Leu Asn Tyr Tyr Lys Val Asn Pro Cys Glu Asp Val
                485                 490                 495

Asn Gln Gln Phe Val Val Ser Gly Gly Asn Leu Val Gly Ile Leu Thr
            500                 505                 510

Ser His Asn Glu Thr Asp Ser Glu Phe Ile Glu Asn Gln Phe Tyr Ile
        515                 520                 525

Lys Leu Thr Asn Gly Thr Arg Arg Ser Arg Arg Ser Val Thr Gly Asn
    530                 535                 540

Val Thr Asn Cys Pro Tyr Val Ser Tyr Gly Lys Phe Cys Ile Lys Pro
545                 550                 555                 560

Asp Gly Ser Leu Phe Ile Ile Val Pro Gln Glu Leu Glu Gln Phe Val
                565                 570                 575
```

```
Ala Pro Leu Leu Asn Val Thr Glu His Val Leu Ile Pro Asp Ser Phe
            580                 585                 590

Asn Leu Thr Val Thr Asp Glu Tyr Ile Gln Thr Arg Met Asp Lys Val
        595                 600                 605

Gln Ile Asn Cys Leu Gln Tyr Val Cys Gly Asn Ser Ile Glu Cys Arg
    610                 615                 620

Lys Leu Phe Gln Gln Tyr Gly Pro Val Cys Asp Asn Ile Leu Ser Val
625                 630                 635                 640

Val Asn Gly Val Gly Gln Arg Glu Asp Met Glu Leu Leu Ser Phe Tyr
                645                 650                 655

Ser Ser Thr Lys Pro Ser Gly Tyr Asn Thr Pro Ile Phe Asn Asn Val
            660                 665                 670

Ser Thr Gly Asp Phe Asn Ile Ser Leu Leu Leu Thr Pro Pro Asn Ser
        675                 680                 685

Pro Thr Gly Arg Ser Phe Ile Glu Asp Leu Leu Phe Thr Ser Val Glu
    690                 695                 700

Ser Val Gly Leu Pro Thr Asp Glu Glu Tyr Lys Lys Cys Thr Ala Gly
705                 710                 715                 720

Pro Leu Gly Phe Val Lys Asp Leu Val Cys Ala Arg Glu Tyr Asn Gly
                725                 730                 735

Leu Leu Val Leu Pro Pro Ile Ile Thr Ala Asp Met Gln Thr Met Tyr
            740                 745                 750

Thr Ser Ser Leu Val Ala Ser Met Ala Leu Gly Gly Ile Thr Ala Ala
        755                 760                 765

Gly Ala Ile Pro Phe Ala Thr Gln Leu Gln Ala Arg Ile Asn His Leu
    770                 775                 780

Gly Ile Thr Asn Ser Leu Leu Leu Lys Asn Gln Glu Lys Ile Ala Ala
785                 790                 795                 800

Ser Phe Asn Lys Ala Ile Gly His Met Gln Glu Gly Phe Lys Ser Thr
                805                 810                 815

Ser Leu Ala Leu Gln Gln Ile Gln Asp Val Val Asn Lys Gln Ser Ser
            820                 825                 830

Ile Leu Thr Glu Thr Met Gln Ser Leu Asn Lys Asn Phe Gly Ala Ile
        835                 840                 845

Ser Ser Val Leu Gln Asp Ile Tyr Gln Gln Leu Asp Ala Ile Gln Ala
    850                 855                 860

Asp Ala Gln Val Asp Arg Leu Ile Thr Gly Arg Leu Ser Ser Leu Ser
865                 870                 875                 880

Val Leu Ala Ser Ala Lys Gln Ala Glu Tyr His Arg Val Ser Gln Gln
                885                 890                 895

Arg Glu Leu Ala Thr Gln Lys Ile Asn Glu Cys Val Lys Ser Gln Ser
            900                 905                 910

Asn Arg Tyr Ser Phe Cys Gly Asn Gly Arg His Val Leu Thr Ile Pro
        915                 920                 925

Gln Asn Ala Pro Asn Gly Ile Val Phe Ile His Phe Thr Tyr Thr Pro
    930                 935                 940

Glu Ser Phe Val Asn Val Thr Ala Ile Val Gly Phe Cys Val Asn Pro
945                 950                 955                 960

Ala Asn Ala Ser Gln Tyr Ala Ile Val Pro Val Asn Asn Arg Gly Ile
                965                 970                 975

Phe Ile Gln Val Asn Gly Ser Tyr Tyr Ile Thr Ala Arg Asp Met Tyr
            980                 985                 990
```

```
Met Pro Arg Asp Ile Thr Ala Gly  Asp Ile Val Met Leu  Thr Ser Cys
        995                 1000                 1005

Gln Ala  Asn Tyr Val Ser Val  Asn Lys Thr Val Ile  Thr Thr Phe
    1010                 1015                 1020

Val Asp  Asn Asp Asp Phe Asp  Phe Asp Asp Glu Leu  Ser Lys Trp
    1025                 1030                 1035

Trp Asn  Asp Thr Lys His Glu  Leu Pro Asp Phe Asp  Glu Phe Asn
    1040                 1045                 1050

Tyr Thr  Val Pro Val Leu Asn  Ile Ser Asn Glu Ile  Asp Arg Ile
    1055                 1060                 1065

Gln Glu  Val Ile Gln Gly Leu  Asn Asp Ser Leu Ile  Asp Leu Glu
    1070                 1075                 1080

Thr Leu  Ser Ile Leu Lys Thr  Tyr Ile Lys Trp Pro  Trp Tyr Val
    1085                 1090                 1095

Trp Leu  Ala Ile Ala Phe Ala  Ile Ile Ile Phe Ile  Leu Ile Leu
    1100                 1105                 1110

Gly Trp  Val Phe Phe Met Thr  Gly Cys Cys Gly Cys  Cys Cys Gly
    1115                 1120                 1125

Cys Phe  Gly Ile Ile Pro Leu  Met Ser Lys Cys Gly  Lys Lys Ser
    1130                 1135                 1140

Ser Tyr  Tyr Thr Thr Phe Asp  Asn Asp Val Val Thr  Glu Gln Tyr
    1145                 1150                 1155

Arg Pro  Lys Lys Ser Val
    1160
```

<210> SEQ ID NO 55
<211> LENGTH: 588
<212> TYPE: PRT
<213> ORGANISM: Avian infectious bronchitis virus

<400> SEQUENCE: 55

```
Met Leu Val Lys Pro Leu Leu Leu Val Thr Leu Leu Phe Ala Leu Cys
1               5                   10                  15

Ser Ala Leu Leu Tyr Asp Glu Gly His Asn Tyr Val Tyr Tyr Tyr Gln
            20                  25                  30

Ser Ala Phe Arg Pro Gly Val Gly Trp His Leu His Gly Gly Ala Tyr
        35                  40                  45

Ala Val Asp Ser Val Phe Asn Val Thr Asn Ala Gly Ser Ala His Cys
    50                  55                  60

Thr Ala Gly Thr Phe Tyr Glu Ser Leu Asn Ile Ser Ala Ala Ser Val
65                  70                  75                  80

Ala Met Thr Ala Pro Asp Thr Gly Met Ser Trp Ser Val Val Gln Phe
                85                  90                  95

Cys Thr Ala His Cys Asn Phe Ser Asp Val Thr Val Phe Val Thr His
            100                 105                 110

Cys Tyr Ile Asn Gln Gln Gly Ser Cys Ser Leu Thr Gly Met Ile Pro
        115                 120                 125

Lys Asn His Ile Arg Ile Ala Ala Met Lys Asn Arg Gln Leu Phe Phe
    130                 135                 140

Asn Ser Thr Val Ser Val Ser Lys Tyr Pro Arg Phe Lys Ser Leu Gln
145                 150                 155                 160

Cys Val Ser Asn Phe Thr Ser Val Tyr Leu Asn Gly Asp Leu Val Phe
                165                 170                 175

Ser Ser Asn Glu Thr Ser Pro Val Thr Gly Ala Gly Val Tyr Phe Gly
            180                 185                 190
```

```
Arg Gly Gly Pro Val Thr Tyr Lys Val Met Lys Glu Val Lys Ala Leu
        195                 200                 205

Ala Tyr Phe Val Asn Gly Thr Ala Gln Glu Val Ile Leu Cys Asp Asn
    210                 215                 220

Ser Pro Arg Gly Leu Leu Ala Cys Gln Tyr Asn Thr Gly Asn Phe Ser
225                 230                 235                 240

Asp Gly Phe Tyr Pro Phe Thr Asn Ser Ser Leu Val Lys Asp Arg Phe
                245                 250                 255

Ile Val Tyr Arg Glu Ser Ser Thr Asn Thr Thr Leu Glu Leu Thr Asn
            260                 265                 270

Phe Thr Phe Thr Asn Val Ser Asn Ala Ser Pro Asn Ser Gly Gly Val
        275                 280                 285

Asp Thr Phe Gln Leu Tyr Gln Thr His Thr Ala Gln Asp Gly Tyr Tyr
    290                 295                 300

Asn Phe Asn Leu Ser Phe Leu Ser Ser Phe Val Tyr Ile Pro Ser Asp
305                 310                 315                 320

Phe Met Tyr Gly Ser Tyr His Pro Glu Cys Thr Phe Arg Pro Glu Thr
                325                 330                 335

Ile Asn Asn Gly Leu Trp Phe Asn Ser Leu Ser Val Ser Leu Thr Tyr
            340                 345                 350

Gly Pro Ile Gln Gly Gly Cys Lys Gln Ser Val Phe Asn Lys Arg Ala
        355                 360                 365

Thr Cys Cys Tyr Ala Tyr Ser Tyr Gln Gly Pro Asn Arg Cys Lys Gly
    370                 375                 380

Val Tyr Arg Gly Glu Leu Lys Gln Glu Phe Glu Cys Gly Leu Leu Val
385                 390                 395                 400

Tyr Val Thr Lys Ser Gly Gly Ser Arg Ile Gln Thr Arg Ser Glu Pro
                405                 410                 415

Leu Val Leu Thr Gln Tyr Asn Tyr Asn Asn Ile Thr Leu Asn Lys Cys
            420                 425                 430

Val Asp Tyr Asn Ile Tyr Gly Arg Val Gly Gln Gly Phe Ile Thr Asn
        435                 440                 445

Val Thr Glu Ala Thr Ala Asn Tyr Ser Tyr Leu Ala Asp Gly Gly Leu
    450                 455                 460

Ala Ile Leu Asp Thr Ser Gly Ala Ile Asp Ile Phe Val Val Gln Gly
465                 470                 475                 480

Ala Tyr Gly Leu Asn Tyr Tyr Lys Val Asn Pro Cys Glu Asp Val Asn
                485                 490                 495

Gln Gln Phe Val Val Ser Gly Gly Asn Leu Val Gly Ile Leu Thr Ser
            500                 505                 510

Tyr Asn Glu Thr Gly Ser Glu Ser Ile Glu Asn Gln Phe Tyr Ile Lys
        515                 520                 525

Leu Thr Ile Gly Thr Arg Arg Ser Arg Arg Ser Ile Thr Gly Asn Val
    530                 535                 540

Thr Asn Cys Pro Tyr Val Ser Tyr Gly Lys Phe Cys Ile Lys Pro Asp
545                 550                 555                 560

Gly Ser Leu Ser Thr Ile Val Pro Gln Glu Leu Glu His Phe Val Ala
                565                 570                 575

Pro Leu Leu Asn Val Thr Glu His Val Leu Ile Pro
            580                 585
```

<210> SEQ ID NO 56
<211> LENGTH: 539

```
<212> TYPE: PRT
<213> ORGANISM: Avian infectious bronchitis virus

<400> SEQUENCE: 56

Met Leu Asp Lys Pro Leu Leu Leu Val Thr Leu Trp Tyr Ala Leu Cys
1               5                   10                  15

Ser Ala Leu Leu Tyr Asp Asn Asn Thr Tyr Val Tyr Tyr Tyr Gln Ser
            20                  25                  30

Ala Phe Arg Pro Gly Pro Gly Trp His Leu Tyr Gly Gly Ala Tyr Ala
        35                  40                  45

Val Asp Arg Val Phe Asn Glu Thr Asn Asn Ala Gly Ser Ala Ser Asp
    50                  55                  60

Cys Thr Ala Gly Thr Phe Tyr Glu Ser His Asn Ile Ser Ala Ser Ser
65                  70                  75                  80

Val Ala Met Thr Val Pro His Asn Gly Met Ser Trp Ser Ala Ser Gln
                85                  90                  95

Phe Cys Thr Ala His Cys Asn Phe Ser Asp Phe Thr Val Phe Val Thr
            100                 105                 110

His Cys Phe Lys Asn Gln Leu Gly Ser Cys Pro Leu Thr Gly Met Ile
        115                 120                 125

Pro Gln Asn His Ile Arg Ile Ser Ala Met Arg Asp Gly Val Leu Phe
    130                 135                 140

Tyr Asn Leu Thr Val Ser Val Ser Lys Tyr Pro Arg Phe Lys Ser Leu
145                 150                 155                 160

Gln Cys Val Ser Asn Ser Thr Ser Val Tyr Val Asn Gly Asp Leu Val
                165                 170                 175

Phe Thr Ser Asn Glu Thr Ser Tyr Val Thr Gly Ala Gly Val Tyr Phe
            180                 185                 190

Lys Ser Gly Gly Pro Val Thr Tyr Lys Val Met Lys Glu Val Lys Ala
        195                 200                 205

Leu Ala Tyr Phe Ile Asn Gly Thr Ala Gln Glu Val Ile Leu Cys Asp
    210                 215                 220

Asn Ser Pro Arg Gly Leu Leu Ala Cys Gln Tyr Asn Thr Gly Asn Phe
225                 230                 235                 240

Ser Asp Gly Phe Tyr Pro Phe Thr Asn His Ser Leu Val Lys Asp Arg
                245                 250                 255

Phe Ile Val Tyr Arg Glu Ser Ser Thr Asn Thr Thr Leu Lys Leu Thr
            260                 265                 270

Asn Phe Ser Phe Thr Asn Val Ser Asn Ala Ser Pro Asn Ser Gly Gly
        275                 280                 285

Val Asp Thr Phe Gln Leu Tyr Gln Thr Ser Thr Ala Gln Asp Gly Tyr
    290                 295                 300

Tyr Asn Phe Asn Leu Ser Phe Leu Ser Ser Phe Val Tyr Lys Pro Ser
305                 310                 315                 320

Asp Phe Met Tyr Gly Ser Tyr His Pro His Cys Lys Phe Arg Pro Glu
                325                 330                 335

Asn Ile Asn Asn Gly Leu Trp Phe Asn Ser Leu Ser Val Ser Leu Thr
            340                 345                 350

Tyr Gly Pro Ile Gln Gly Gly Cys Lys Gln Ser Val Phe Ser Asn Arg
        355                 360                 365

Ala Thr Cys Cys Tyr Ala Tyr Ser Tyr Gln Gly Pro Ser Arg Cys Lys
    370                 375                 380

Gly Val Tyr Arg Gly Glu Leu Thr Gln Tyr Phe Glu Cys Gly Leu Leu
385                 390                 395                 400
```

```
Val Tyr Val Thr Lys Ser Asp Gly Ser Arg Ile Gln Thr Arg Ser Glu
                405                 410                 415

Pro Leu Val Leu Thr Gln Tyr Asn Tyr Asn Asn Ile Thr Leu Asn Lys
            420                 425                 430

Cys Val Glu Tyr Asn Ile Tyr Gly Arg Val Gly Gln Gly Phe Ile Thr
        435                 440                 445

Asn Val Thr Glu Ala Thr Ala Asn Tyr Ser Tyr Leu Ala Asp Gly Gly
    450                 455                 460

Leu Ala Ile Leu Asp Thr Ser Gly Ala Ile Asp Ile Phe Val Val Gln
465                 470                 475                 480

Gly Ala Tyr Gly Leu Asn Tyr Tyr Lys Val Asn Pro Cys Glu Asp Val
                485                 490                 495

Asn Gln Gln Phe Val Val Ser Gly Gly Asn Leu Val Gly Ile Leu Thr
            500                 505                 510

Ser His Asn Glu Thr Gly Ser Glu Ser Ile Glu Asn Gln Phe Tyr Ile
        515                 520                 525

Lys Leu Thr Asn Gly Thr Arg Arg Ser Arg Arg
    530                 535


<210> SEQ ID NO 57
<211> LENGTH: 409
<212> TYPE: PRT
<213> ORGANISM: Avian infectious bronchitis virus

<400> SEQUENCE: 57

Met Ala Ser Gly Lys Ala Ala Gly Lys Thr Asp Ala Pro Ala Pro Val
1               5                   10                  15

Ile Lys Leu Gly Gly Pro Lys Pro Pro Lys Val Gly Ser Ser Gly Asn
            20                  25                  30

Ala Ser Trp Phe Gln Ala Ile Lys Ala Lys Lys Leu Asn Ser Pro Gln
        35                  40                  45

Pro Lys Phe Glu Gly Ser Gly Val Pro Glu Asn Glu Asn Leu Lys Ser
    50                  55                  60

Ser Gln Gln His Gly Tyr Trp Arg Arg Gln His Arg Tyr Lys Pro Gly
65                  70                  75                  80

Lys Gly Gly Arg Lys Pro Val Pro Asp Ala Trp Tyr Phe Tyr Tyr Thr
                85                  90                  95

Gly Thr Gly Pro Ala Ala Asp Leu Asn Trp Gly Asp Asn Gln Asp Gly
            100                 105                 110

Ile Val Trp Val Ala Ala Lys Gly Ala Asp Thr Lys Ser Arg Ser Asn
        115                 120                 125

Gln Gly Thr Arg Asp Pro Asp Lys Phe Asp Gln Tyr Pro Leu Arg Phe
    130                 135                 140

Ser Asp Gly Gly Pro Asp Gly Asn Phe Arg Trp Asp Phe Ile Pro Ile
145                 150                 155                 160

Asn Arg Gly Arg Ser Gly Arg Ser Thr Ala Ala Ser Ser Ala Ala Ser
                165                 170                 175

Ser Arg Ala Pro Ser Arg Glu Gly Ser Arg Gly Arg Arg Ser Gly Ala
            180                 185                 190

Glu Asp Asp Leu Ile Ala Arg Ala Ala Lys Ile Ile Gln Asp Gln Gln
        195                 200                 205

Lys Lys Gly Ser Arg Ile Thr Lys Ala Lys Ala Asp Glu Met Ala His
    210                 215                 220

Arg Arg Tyr Cys Lys Arg Thr Val Pro Pro Gly Tyr Lys Val Asp Gln
```

225 230 235 240

Val Phe Gly Pro Arg Thr Lys Gly Lys Glu Gly Asn Phe Gly Asp Asp
245 250 255

Lys Met Asn Glu Glu Gly Ile Lys Asp Gly Arg Val Thr Ala Met Leu
260 265 270

Asn Leu Val Pro Ser Ser His Ala Cys Leu Phe Gly Ser Arg Val Thr
275 280 285

Pro Lys Leu Gln Pro Asp Gly Leu His Leu Arg Phe Glu Phe Thr Thr
290 295 300

Val Val Pro Arg Asp Asp Pro Gln Phe Asp Asn Tyr Val Lys Ile Cys
305 310 315 320

Asp Gln Cys Val Asp Gly Val Gly Thr Arg Pro Lys Asp Asp Glu Pro
325 330 335

Arg Pro Lys Ser Arg Pro Asn Ser Arg Pro Ala Thr Arg Gly Asn Ser
340 345 350

Pro Ala Pro Arg Gln Gln Arg Gln Lys Lys Glu Lys Lys Pro Lys Lys
355 360 365

Gln Glu Asp Asp Val Asp Lys Ala Leu Thr Ser Asp Glu Glu Arg Asn
370 375 380

Asn Ala Gln Leu Glu Phe Asp Asp Glu Pro Lys Val Ile Asn Trp Gly
385 390 395 400

Asp Ser Ala Leu Gly Glu Asn Glu Leu
405

<210> SEQ ID NO 58
<211> LENGTH: 106
<212> TYPE: PRT
<213> ORGANISM: Avian infectious bronchitis virus

<400> SEQUENCE: 58

Met Met Asn Leu Leu Asn Lys Ser Leu Glu Glu Asn Gly Ser Phe Leu
1 5 10 15

Thr Ala Val Tyr Val Phe Cys Ala Phe Val Ala Leu Tyr Leu Leu Gly
20 25 30

Arg Ala Leu Gln Ala Phe Val Gln Ala Ala Asp Ala Cys Cys Leu Phe
35 40 45

Trp Tyr Thr Trp Val Val Val Pro Gly Ala Lys Gly Thr Ser Phe Val
50 55 60

Tyr Lys His Thr Tyr Gly Lys Lys Leu Asn Asn Pro Glu Leu Glu Ser
65 70 75 80

Val Ile Val Asn Glu Phe Pro Lys Asn Gly Trp Asn Asn Lys Asn Pro
85 90 95

Ala Asn Phe Gln Asn Gly Lys Leu His Thr
100 105

<210> SEQ ID NO 59
<211> LENGTH: 222
<212> TYPE: PRT
<213> ORGANISM: Avian infectious bronchitis virus

<400> SEQUENCE: 59

Met Glu Asn Cys Thr Leu Asp Ala Glu Gln Ala Val Gln Leu Phe Lys
1 5 10 15

Asp Tyr Asn Leu Phe Ile Thr Ala Phe Leu Leu Phe Leu Thr Ile Leu
20 25 30

Leu Gln Tyr Gly Tyr Ala Thr Arg Ser Arg Ile Ile Tyr Ile Leu Lys

```
        35                  40                  45

Met Ile Val Leu Trp Cys Phe Trp Pro Leu Asn Ile Ala Val Gly Val
    50                  55                  60

Ile Ser Cys Ile Tyr Pro Pro Asn Thr Gly Gly Leu Val Ala Ala Ile
65                  70                  75                  80

Ile Leu Thr Val Phe Ala Cys Leu Ser Phe Leu Gly Tyr Trp Ile Gln
                85                  90                  95

Ser Ile Arg Leu Phe Lys Arg Cys Arg Ser Trp Trp Ser Phe Asn Pro
            100                 105                 110

Glu Ser Asn Ala Val Gly Ser Ile Leu Leu Thr Asn Gly Gln Gln Cys
        115                 120                 125

Asn Phe Ala Ile Glu Ser Val Pro Met Val Leu Ser Pro Ile Ile Lys
    130                 135                 140

Asn Gly Ala Leu Tyr Cys Glu Gly Gln Trp Leu Ala Lys Cys Glu Pro
145                 150                 155                 160

Asp His Leu Pro Lys Asp Ile Phe Val Cys Thr Pro Asp Arg Arg Asn
                165                 170                 175

Ile Tyr Arg Met Val Gln Lys Tyr Thr Gly Asp Gln Ser Gly Asn Lys
            180                 185                 190

Lys Arg Phe Ala Thr Phe Val Tyr Ala Lys Gln Ser Val Asp Thr Gly
        195                 200                 205

Glu Leu Glu Ser Val Ala Thr Val Gly Ser Ser Leu Tyr Thr
    210                 215                 220


<210> SEQ ID NO 60
<211> LENGTH: 539
<212> TYPE: PRT
<213> ORGANISM: Avian infectious bronchitis virus

<400> SEQUENCE: 60

Met Leu Gly Lys Pro Leu Leu Leu Val Thr Leu Trp Tyr Ala Leu Cys
1               5                   10                  15

Ser Ala Leu Leu Tyr Asp Lys Asn Thr Tyr Val Tyr Tyr Tyr Gln Ser
            20                  25                  30

Ala Phe Arg Pro Gly Gln Gly Trp His Leu His Gly Gly Ala Tyr Ala
        35                  40                  45

Val Asp Lys Val Phe Asn Gly Thr Asn Asn Ala Val Ser Val Ser Asp
    50                  55                  60

Cys Thr Ala Gly Thr Phe Tyr Glu Ser Tyr Asn Ile Ser Ala Ala Ser
65                  70                  75                  80

Val Ala Met Thr Val Pro Pro Ala Gly Met Ser Trp Ser Val Ala Gln
                85                  90                  95

Phe Cys Thr Ala His Cys Asn Phe Ser Asp Phe Thr Val Phe Val Thr
            100                 105                 110

His Cys Phe Lys Ser Gln Gln Gly Ser Cys Pro Leu Thr Gly Met Ile
        115                 120                 125

Pro Gln Asn His Ile Arg Ile Ser Ala Met Arg Ser Gly Phe Leu Phe
    130                 135                 140

Tyr Asn Leu Thr Val Ser Val Ser Lys Tyr Pro Lys Phe Lys Ser Leu
145                 150                 155                 160

Gln Cys Val Gly Asn Ser Thr Ser Val Tyr Leu Asn Gly Asp Leu Val
                165                 170                 175

Phe Thr Ser Asn Glu Thr Thr His Val Thr Gly Ala Gly Val Tyr Phe
            180                 185                 190
```

```
Lys Ser Gly Gly Pro Val Thr Tyr Lys Val Met Lys Glu Val Lys Ala
        195                 200                 205

Leu Ala Tyr Phe Ile Asn Gly Thr Ala Gln Glu Val Ile Leu Cys Asp
    210                 215                 220

Asn Ser Pro Arg Gly Leu Leu Ala Cys Gln Tyr Asn Thr Gly Asn Phe
225                 230                 235                 240

Ser Asp Gly Phe Tyr Pro Phe Thr Asn Ser Ser Leu Val Lys Asp Arg
                245                 250                 255

Phe Ile Val Tyr Arg Glu Ser Ser Thr Asn Thr Thr Leu Glu Leu Thr
            260                 265                 270

Asn Phe Thr Phe Thr Asn Val Ser Asn Ala Ser Pro Asn Ser Gly Gly
        275                 280                 285

Val Asp Thr Phe Gln Leu Tyr Gln Thr His Thr Ala Gln Asp Gly Tyr
    290                 295                 300

Tyr Asn Phe Asn Leu Ser Phe Leu Ser Ser Phe Val Tyr Lys Pro Ser
305                 310                 315                 320

Asp Phe Met Tyr Gly Ser Tyr His Pro Asn Cys Asn Phe Arg Pro Glu
                325                 330                 335

Asn Ile Asn Asn Gly Leu Trp Phe Asn Ser Leu Ser Val Ser Leu Thr
            340                 345                 350

Tyr Gly Pro Ile Gln Gly Gly Cys Lys Gln Ser Val Phe Ser Asn Lys
        355                 360                 365

Ala Thr Cys Cys Tyr Ala Tyr Ser Tyr Arg Gly Pro Thr Arg Cys Lys
    370                 375                 380

Gly Val Tyr Arg Gly Glu Leu Thr Gln Tyr Phe Glu Cys Gly Leu Leu
385                 390                 395                 400

Val Tyr Val Thr Lys Ser Asp Gly Ser Arg Ile Gln Thr Arg Ser Glu
                405                 410                 415

Pro Leu Val Leu Thr Gln Tyr Asn Tyr Asn Asn Ile Thr Leu Asn Lys
            420                 425                 430

Cys Val Glu Tyr Asn Ile Tyr Gly Arg Val Gly Gln Gly Phe Ile Thr
        435                 440                 445

Asn Val Thr Glu Ala Thr Ala Asn Tyr Ser Tyr Leu Ala Asp Gly Gly
    450                 455                 460

Leu Ala Ile Leu Asp Thr Ser Gly Ala Ile Asp Ile Phe Val Val Arg
465                 470                 475                 480

Gly Ala Tyr Gly Leu Asn Tyr Tyr Lys Val Asn Pro Cys Glu Asp Val
                485                 490                 495

Asn Gln Gln Phe Val Val Ser Gly Gly Asn Leu Ile Gly Ile Leu Thr
            500                 505                 510

Ser His Asn Glu Thr Asp Ser Glu Phe Ile Glu Asn Gln Phe Tyr Ile
        515                 520                 525

Lys Pro Thr Asn Gly Thr Arg Arg Ser Arg Arg
    530                 535
```

<210> SEQ ID NO 61
<211> LENGTH: 32
<212> TYPE: DNA
<213> ORGANISM: Artificial Sequence
<220> FEATURE:
<223> OTHER INFORMATION: Primer

<400> SEQUENCE: 61

```
ggtaacttaa caatacagac ctaaaaagtc tg                                32
```

4/91 IBV VACCINE WITH HETEROLOGOUS SPIKE PROTEIN

CROSS-REFERENCE TO OTHER APPLICATIONS

This application claims the benefit of E.P. Patent Application No. 18203626.9, filed Oct. 31, 2018, the entire contents of which are hereby incorporated by reference herein.

SEQUENCE LISTING

This application contains a sequence listing in accordance with 37 C.F.R. 1.821-1.825. The sequence listing accompanying this application is hereby incorporated by reference in its entirety.

BACKGROUND OF THE INVENTION

Avian coronavirus infectious bronchitis virus (IBV) is the prototype gammacoronavirus of the family Coronaviridae, order Nidovirales. Infectious bronchitis virus principally infects the upper respiratory epithelium of chickens, causing a respiratory disease, commonly complicated by secondary bacterial pathogens (Cook et al. 2012. Avian Pathol. 41:239-250). Some IBV strains additionally affect the renal tubuli, oviduct and parts of the gastrointestinal tract, leading to pathological lesions and clinical symptoms in these organ systems. The virus has a worldwide presence in both commercial and backyard chicken. Due to its high genomic variability IBV is discriminated in a wide variety of geno-, sero- and protectotypes. IBV is currently regarded as one of the economically most relevant viral pathogens in the poultry industry.

Infectious bronchitis virus is an enveloped virus with a positive sense single-stranded RNA genome of 27.6 kb (Cavanagh 2007. Vet. Res. 38:281-297). The first two-thirds of the viral genome comprise a large coding region (also designated as gene 1), divided into two open reading frames 1a and 1b, which encode for 15 nonstructural proteins involved in RNA replication, editing, and transcription. The last one-third of the viral genome codes for structural proteins: the spike protein (S, encoded by gene 2), the envelope protein (E, encoded by gene 3c), the membrane protein (M, encoded by gene 4), and the nucleocapsid protein (N, encoded by gene 6). Proteins S, E and M are part of the viral envelope while protein N forms the ribonucleoprotein core along with the viral RNA. The coronavirus spike protein determines the host species tropism (Kuo et al. 2000. J. Virol. 74:1393-1406). It is a dimeric or trimeric transmembrane protein, which is proteolytically cleaved into two subunits, S1 and S2. The heavily glycosylated S1 domain forms the 'head' of the spike protein and contains the receptor binding domain that interacts with 2,3-linked sialic acids on the host cell surface (Promkuntod et al. 2014. Virology. 448:26-32). The S2 domain contains the remaining part of the ectodomain (the 'stalk'), the transmembrane domain and the endodomain located in the cytoplasm.

The to date most widely used live-attenuated IBV vaccine strains were developed in the 1960s in the Netherlands, by serial passaging of a Massachusetts-like IBV strain (Bijlenga et al. 2004; Avian Pathol. 33:550-557). However, since the 1970s new IBV serotypes emerged for which the traditional Massachusetts-like vaccines did not protect sufficiently (Cook et al. 2012. Avian Pathol. 41:239-250). Therefore, there is a need for new and highly efficacious IBV vaccines against other IBV serotypes.

IBV Beaudette (Geilhausen et al. 1973. Arch Gesamte Virusforsch.: 40 (3) (1973), pp. 285-290) and H120 (G. Bijlenga et al. 2004. Avian Pathol.: 33 (6); pp. 550-557) are attenuated IBVs. However, attenuation may result in a loss of immunogenicity.

Further, recombinant IBVs have been generated. Zhou et al. 2016 (Arch Virol.; 161:3179-3187) disclose a H120 (Massachusetts genotype) IBV with Beaudette (Massachusetts genotype) spike protein. Hodgson et al. 2004 (J Virol 78: 13804-13811) disclose a Beaudette (Massachusetts genotype) IBV with M41 (Massachusetts genotype) Spike protein. Furthermore, Armesto et al. 2011 (PLoS One: 6(8):e24352) disclose IBV Beaudette (Massachusetts genotype) with a heterologous spike protein from 4/91 (4/91 genotype).

However, the recombinant IBVs disclosed in Zhou et al. 2016 and Hodgson et al. 2004 cannot be regarded as IBVs with a heterologous Spike protein as both, the IBV and the inserted spike is from the same genotype/serotype (Massachusetts). Further, all mentioned vaccines are based on a Beaudette based backbone or have a spike protein from Beaudette.

Further, no Beaudette based vaccines and no such recombinant vaccines (with heterologous spike proteins) are commercially available although Beaudette was already described many decades ago and recombinant approaches using Beaudette are known for more than one decade, respectively. Recombinant IBVs based on Beaudette are not suitable as vaccines. Wei et al 2014 (Apl Microbiol Biotechnol 98) discloses a Beaudette IBV having the S1 subunit of H120.

Ellis et al 2018 (J. Virol. 92(23)), Hodgson et al (J. Virol. 78(24)) and Armesto et al. 2011 (PLoS One: 6(8):e24352) all disclose Beaudette IBV with a M41 or 4/91 spike protein. However, Ellis et al 2018 (J. Virol. 92(23)) describe that recombinant Beaudette with chimeric spikes with heterologous S1 subunits from M41 or QX in combination with Beaudette spike S2 subunit do not confer sufficient protection against S1 homologous challenges ("A single vaccination of specific-pathogen-free chickens with rIBV expressing 1 of virulent strains M41 or QX, BeauR-M41(S1) and BeauR-QX (S1), gave incomplete protection against homologous challenge, based on ciliary activity and clinical signs"; abstract). Further, Ellis et al 2018 (J. Virol. 92(23)) describe that the full length S gene (S1 and S2 from M41) only gave partial protection against challenge with an IBV of the homologous serotype (page 12), suggesting that the IBV Beaudette strain is not suitable as a backbone for recombinant IBV vaccines. Hodgson et al (J. Virol. 78(24)) further discloses that the Baudette strain "is also considered to be poorly immunogenic" and consequently, "it has never been used as a vaccinal strain" (page 13802, left column, second paragraph). Therefore, there is a need for generating novel and highly efficacious IBV vaccines and recombinant IBV vaccines, respectively. Further, there is a need for highly efficacious IBV vaccine vectors.

DETAILED DESCRIPTION OF THE INVENTION

Before the aspects of the present invention are described, it must be noted that as used herein and in the appended claims, the singular forms "a", "an", and "the" include plural reference unless the context clearly dictates otherwise. Thus, for example, reference to "an antigen" includes a plurality of antigens, reference to the "virus" is a reference to one or more viruses and equivalents thereof known to those skilled in the art, and so forth. Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications mentioned herein are incorporated herein by reference for the purpose of describing and disclosing the cell lines, vectors, and methodologies as reported in the publications which might be used in connection with the invention. Nothing herein is to be construed as an admission that the invention is not entitled to antedate such disclosure by virtue of prior invention.

Composition of Matter

The present invention solves the problems inherent in the prior art and provides a distinct advance in the state of the art.

Generally, the present invention provides an 4/91 IBV (infectious bronchitis virus) encoding for a heterologous IBV S (spike) protein or fragment thereof.

The term "4/91 IBV" is well known to the person skilled in the art. The term "IBV" refers to an infectious bronchitis virus. The term "4/91" is interchangeably used with the term "793B" and defines the specific IBV serotype or genotype. The 4/91 serotype or genotype is well known to the person skilled in the art and comprises strains such as UK/4/91, UK/793B/91 and CR88. IBV strains are typically differentiated by the coding sequence of the S1 subunit of the spike protein (Valastro et al. 2016. Infect Genet Evol. 39:349-364) but can also be differentiated by their complete nucleotide sequence or the sequences of specific proteins such as the spike protein, nucleocapsid protein, envelope (E) protein or membrane (M) glycoprotein. Because the spike protein determines host tropism and antigenicity of IBV, the IBV genotypes are classified by the coding sequence of the subunit 1 of the spike proteins. Alternatively, IBV strains can be differentiated by their serotype. Serotype classification involves treatment of the virus with neutralizing antibodies.

It is in the general knowledge of a person skilled in the art where to obtain 4/91IBVs. 4/91 IBV strains can be commercially purchased such as exemplary NOBILIS® IB 4-91 (MSD Animal Health), CEVAC IBird® (CEVA; strain 1/96), or Gallivac IB88 (Boehringer Ingelheim; strain CR88121). Furthermore, 4/91 IBV specific vaccine strains are used for decades (Jones 2010 Rev. Bras. Cienc. Avic. vol. 12 no. 2) and, therefore, can be isolated from the field. The methods to isolate 4/91 IBV strains and to characterize the 4/91 IBV strains are well known to the person skilled in the art. Exemplary, 4/91 IBV strains can be characterized as described in SHIMAZAKI et al. 2008 (J. Vet. Med. Sci. 71(5): 583-588), Martin et al. 2014 (Avian Pathology Vol. 43, No. 3, 264-268), Zanaty et al. 2016 (World J Virol; 5(3): 125-134) or Stenzel et al. 2017 (Polish Journal of Veterinary Sciences Vol. 20, No. 3, 599-601). Further, 4/91 IBVs have been sequenced and the genomic sequences are available such as KF377577. Thus, the virus genome can be generated by synthesizing its sequence and generated upon the application of reverse genetic systems.

The term "spike" refers to a specific protein of the IBV that is well known by the person skilled in the art. The spike protein is the major inducer of antibodies and protective immune response. Further, the spike (S) protein facilitates cell entry of IBV by binding cellular receptors of the host cell and also by mediating virus-cell membrane fusion with the host cell. In addition, it determines the tissue and cell tropism of the virus strain.

The term "heterologous S (spike)" means that the spike protein or fragment thereof that has been introduced into the 4/91 IBV is from a different genotype or serotype than the 4/91 IBV. Thus, the heterologous spike is of a non-4/91 genotype or serotype.

The term "protein", "amino acid" and "polypeptide" are used interchangeably. The term "protein" refers to a sequence of amino acids composed of the naturally occurring amino acids as well as derivatives thereof. The naturally occurring amino acids are well known in the art and are described in standard text books of biochemistry. Within the amino acid sequence the amino acids are connected by peptide bonds. Further, the two ends of the amino acid sequence are referred to as the carboxyl terminus (C-terminus) and the amino terminus (N-terminus). The term "protein" encompasses essentially purified proteins or protein preparations comprising other proteins in addition. Further, the term also relates to protein fragments. Moreover, it includes chemically modified proteins. Such modifications may be artificial modifications or naturally occurring modifications such as phosphorylation, glycosylation, myristylation and the like.

Further, the present invention also provides an immunogenic composition comprising a 4/91 IBV (infectious bronchitis virus) encoding for a heterologous S (spike) protein or fragment thereof.

Furthermore, the present invention also provides an immunogenic composition comprising an IBV (infectious bronchitis virus) as described herein. Thus, provided is an immunogenic composition comprising a 4/91 IBV (infectious bronchitis virus) encoding for a heterologous IBV S (spike) protein or fragment thereof.

The term "immunogenic composition" refers to a composition that comprises at least one antigen, which elicits an immunological response in the host to which the immunogenic composition is administered. Such immunological response may be a cellular and/or antibody-mediated immune response to the immunogenic composition of the invention. Preferably, the immunogenic composition induces an immune response and, more preferably, confers protective immunity against one or more of the clinical signs of a IBV infection. The host is also described as "subject". Preferably, any of the hosts or subjects described or mentioned herein is an avian or poultry.

Usually, an "immunological response" includes but is not limited to one or more of the following effects: the production or activation of antibodies, B cells, helper T cells, suppressor T cells, and/or cytotoxic T cells and/or gamma-delta T cells, directed specifically to an antigen or antigens included in the immunogenic composition of the invention. Preferably, the host will display either a protective immunological response or a therapeutically response.

A "protective immunological response" or "protective immunity" will be demonstrated by either a reduction or lack of clinical signs normally displayed by an infected host, a quicker recovery time and/or a lowered duration of infectivity or lowered pathogen titer in the tissues or body fluids or excretions of the infected host.

In case where the host displays a protective immunological response such that resistance to new infection will be enhanced and/or the clinical severity of the disease reduced, the immunogenic composition is described as a "vaccine".

4/91—IBV Definition by Protein Encoding Sequences

In another specific aspect of the IBV or the immunogenic composition according to the present invention the 4/91 IBV has a nucleotide sequence as shown for KF377577 (SEQ ID NO 53) or a sequence having at least 90%, 91%, 92%, 93%, 94%, 95%, 96%, 97%, 98%, 99%, 99.2%, 99.5%, 99.6%, 99.7%, 99.8%, 99.9%, 99.95%, 99.98% or 99.99% sequence identity thereto.

In another specific aspect of the IBV or the immunogenic composition according to the present invention the 4/91 IBV has a nucleotide sequence as shown for SEQ ID NO 1 or a sequence having at least 90%, 91%, 92%, 93%, 94%, 95%, 96%, 97%, 98%, 99%, 99.2%, 99.5%, 99.6%, 99.7%, 99.8%, 99.9%, 99.95%, 99.98% or 99.99% sequence identity thereto.

The term "nucleic acid" or "nucleic acid sequence" or "nucleotide sequence" refers to polynucleotides including DNA molecules, RNA molecules, cDNA molecules or derivatives. The term encompasses single as well as double stranded polynucleotides. The nucleic acid of the present invention encompasses isolated polynucleotides (i.e. isolated from its natural context) and genetically modified forms. Moreover, comprised are also chemically modified polynucleotides including naturally occurring modified polynucleotides such as glycosylated or methylated polynucleotides or artificially modified ones such as biotinylated polynucleotides. Further, the terms "nucleic acid" and "polynucleotide" are interchangeable and refer to any nucleic acid. The terms "nucleic acid" and "polynucleotide" also specifically include nucleic acids composed of bases other than the five biologically occurring bases (adenine, guanine, thymine, cytosine and uracil).

The term "RNA" refers to any ribonucleic acid. The term encompasses single as well as double stranded RNA's. The RNA of the present invention encompasses isolated RNA (i.e. isolated from its natural context) and genetically modified forms. Moreover, comprised are also chemically modified RNAs including naturally occurring modified RNA such as methylated RNA or artificially modified ones such as biotinylated RNA. The terms "RNA" also specifically include RNA composed of bases other than the four biologically occurring nucleotides/bases (adenine, guanine, cytosine and uracil).

In another specific aspect of the IBV or the immunogenic composition according to the present invention the 4/91 IBV strain has a spike (S) protein having an amino acid sequence as shown for AGY56140 (SEQ ID NO 54) or a sequence having at least 90%, 91%, 92%, 93%, 94%, 95%, 96%, 97%, 98%, 99%, 99.2%, 99.5%, 99.6%, 99.7%, 99.8%, 99.9%, 99.95%, 99.98% or 99.99% sequence identity thereto.

In another specific aspect of the IBV or the immunogenic composition according to the present invention the 4/91 IBV strain has a spike (S1) protein having an amino acid sequence as shown for AF093793 (SEQ ID NO 60) or a sequence having at least 90%, 91%, 92%, 93%, 94%, 95%, 96%, 97%, 98%, 99%, 99.2%, 99.5%, 99.6%, 99.7%, 99.8%, 99.9%, 99.95%, 99.98% or 99.99% sequence identity thereto.

In another specific aspect of the IBV or the immunogenic composition according to the present invention the 4/91 IBV strain has a spike (S1) protein having an amino acid sequence as shown for EU914938 (SEQ ID NO 55) or a sequence having at least 90%, 91%, 92%, 93%, 94%, 95%, 96%, 97%, 98%, 99%, 99.2%, 99.5%, 99.6%, 99.7%, 99.8%, 99.9%, 99.95%, 99.98% or 99.99% sequence identity thereto.

In another specific aspect of the IBV or the immunogenic composition according to the present invention the 4/91 IBV strain has a spike (S1) protein having an amino acid sequence as shown for KM067900 (SEQ ID NO 56) or a sequence having at least 90%, 91%, 92%, 93%, 94% 95%, 96%, 97%, 98%, 99%, 99.2%, 99.5%, 99.6%, 99.7%, 99.8%, 99.9%, 99.95%, 99.98% or 99.99% sequence identity thereto.

It has to be understood that the spike protein sequence or nucleic acid can be used to determine whether any IBV strain is of 4/91 origin. However, because the 4/91 IBV is used as a backbone and the 4/91 spike protein or nucleic acid sequence is replaced by a heterologous spike protein or fragment thereof, the final IBV with the heterologous spike protein does not comprise any or only remaining parts of the 4/91 spike protein anymore.

In another specific aspect of the IBV or the immunogenic composition according to the present invention the 4/91 IBV strain has a spike (S) protein having an amino acid sequence as shown in SEQ ID NO:2 or a sequence having at least 90%, 91%, 92%, 93%, 94%, 95%, 96%, 97%, 98%, 99%, 99.2%, 99.5%, 99.6%, 99.7%, 99.8%, 99.9%, 99.95%, 99.98% or 99.99% sequence identity thereto.

In another specific aspect of the IBV or the immunogenic composition according to the present invention the 4/91 IBV has a nucleocapsid (N) protein having an amino acid sequence as shown for EU780081 (SEQ ID NO 57) or a sequence having at least 95%, 96%, 97%, 98%, 99%, 99.2%, 99.5%, 99.6%, 99.7%, 99.8%, 99.9%, 99.95%, 99.98% or 99.99% sequence identity to at least one of the above mentioned sequences.

In another specific aspect of the IBV or the immunogenic composition according to the present invention the 4/91 IBV has a nucleocapsid (N) protein having an amino acid sequence as shown in SEQ ID NO:3 or a sequence having at least 95%, 96%, 97%, 98%, 99%, 99.2%, 99.5%, 99.6%, 99.7%, 99.8%, 99.9%, 99.95%, 99.98% or 99.99% sequence identity thereto.

In another specific aspect of the IBV or the immunogenic composition according to the present invention the 4/91 IBV has an envelope (E) protein having an amino acid sequence as shown for AGY56143 (SEQ ID NO 58) or a sequence having at least least 85%, 88%, 90%, 91%, 92%, 93%, 94%, 95%, 96%, 97%, 98%, 99%, 99.2%, 99.5%, 99.6%, 99.7%, 99.8%, 99.9%, 99.95%, 99.98% or 99.99% sequence identity thereto.

In another specific aspect of the IBV or the immunogenic composition according to the present invention the 4/91 IBV has an envelope (E) protein having an amino acid sequence as shown in SEQ ID NO:4 or a sequence having at least 95%, 96%, 97%, 98%, 99%, 99.2%, 99.5%, 99.6%, 99.7%, 99.8%, 99.9%, 99.95%, 99.98% or 99.99% sequence identity thereto.

In another specific aspect of the IBV or the immunogenic composition according to the present invention the 4/91 IBV has a membrane glycoprotein (M) protein having an amino acid sequence as shown for AGY56144 (SEQ ID NO 59) or a sequence having at least 95%, 96%, 97%, 98%, 99%, 99.2%, 99.5%, 99.6%, 99.7%, 99.8%, 99.9%, 99.95%, 99.98% or 99.99% sequence identity thereto.

In another specific aspect of the IBV or the immunogenic composition according to the present invention the 4/91 IBV has a membrane glycoprotein (M) protein having an amino acid sequence as shown in SEQ ID NO:5 or a sequence having at least 95%, 96%, 97%, 98%, 99%, 99.2%, 99.5%, 99.6%, 99.7%, 99.8%, 99.9%, 99.95%, 99.98% or 99.99% sequence identity thereto.

The term "identity" or "sequence identity" is known in the art and refers to a relationship between two or more polypeptide sequences or two or more polynucleotide sequences, namely a reference sequence and a given sequence to be compared with the reference sequence. Sequence identity is determined by comparing the given sequence to the reference sequence after the sequences have been optimally aligned to produce the highest degree of sequence similarity, as determined by the match between strings of such sequences. Upon such alignment, sequence identity is ascertained on a position-by-position basis, e.g., the sequences are "identical" at a particular position if at that position, the nucleotides or amino acid residues are identical. The total number of such position identities is then divided by the total number of nucleotides or residues in the reference sequence to give % sequence identity. Sequence identity can be readily calculated by known methods, including but not limited to, those described in Computational Molecular Biology, Lesk, A. N., ed., Oxford University Press, New York (1988), Biocomputing: Informatics and Genome Projects, Smith, D. W., ed., Academic Press, New York (1993); Computer Analysis of Sequence Data, Part I, Griffin, A. M., and Griffin, H. G., eds., Humana Press, New Jersey (1994); Sequence Analysis in Molecular Biology, von Heinge, G., Academic Press (1987); Sequence Analysis Primer, Gribskov, M. and Devereux, J., eds., M. Stockton Press, New York (1991); and Carillo, H., and Lipman, D., SIAM J. Applied Math., 48: 1073 (1988), the teachings of which are incorporated herein by reference. Preferred methods to determine the sequence identity are designed to give the largest match between the sequences tested. Methods to determine sequence identity are codified in publicly available computer programs which determine sequence identity between given sequences. Examples of such programs include, but are not limited to, the GCG program package (Devereux, J., et al., Nucleic Acids Research, 12(1):387 (1984)), BLASTP, BLASTN and FASTA (Altschul, S. F. et al., J. Molec. Biol., 215:403-410 (1990). The BLASTX program is publicly available from NCBI and other sources (BLAST Manual, Altschul, S. et al., NCVI NLM NIH Bethesda, Md. 20894, Altschul, S. F. et al., J. Molec. Biol., 215:403-410 (1990), the teachings of which are incorporated herein by reference). These programs optimally align sequences using default gap weights in order to produce the highest level of sequence identity between the given and reference sequences. As an illustration, by a polynucleotide having a nucleotide sequence having at least, for example, 85%, preferably 90%, even more preferably 95% "sequence identity" to a reference nucleotide sequence, it is intended that the nucleotide sequence of the given polynucleotide is identical to the reference sequence except that the given polynucleotide sequence may include up to 15, preferably up to 10, even more preferably up to 5 point mutations per each 100 nucleotides of the reference nucleotide sequence. In other words, in a polynucleotide having a nucleotide sequence having at least 85%, preferably 90%, even more preferably 95% identity relative to the reference nucleotide sequence, up to 15%, preferably 10%, even more preferably 5% of the nucleotides in the reference sequence may be deleted or substituted with another nucleotide, or a number of nucleotides up to 15%, preferably 10%, even more preferably 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence. Analogously, by a polypeptide having a given amino acid sequence having at least, for example, 85%, preferably 90%, even more preferably 95% sequence identity to a reference amino acid sequence, it is intended that the given amino acid sequence of the polypeptide is identical to the reference sequence except that the given polypeptide sequence may include up to 15, preferably up to 10, even more preferably up to 5 amino acid alterations per each 100 amino acids of the reference amino acid sequence. In other words, to obtain a given polypeptide sequence having at least 85%, preferably 90%, even more preferably 95% sequence identity with a reference amino acid sequence, up to 15%, preferably up to 10%, even more preferably up to 5% of the amino acid residues in the reference sequence may be deleted or substituted with another amino acid, or a number of amino acids up to 15%, preferably up to 10%, even more preferably up to 5% of the total number of amino acid residues in the reference sequence may be inserted into the reference sequence. These alterations of the reference sequence may occur at the amino or the carboxy terminal positions of the reference amino acid sequence or anywhere between those terminal positions, interspersed either individually among residues in the reference sequence or in the one or more contiguous groups within the reference sequence. Preferably, residue positions which are not identical differ by conservative amino acid substitutions. However, conservative substitutions are not included as a match when determining sequence identity.

The terms "identity", "sequence identity" and "percent identity" are used interchangeably herein. For the purpose of this invention, it is defined here that in order to determine the percent identity of two amino acid sequences or two nucleic acid sequences, the sequences are aligned for optimal comparison purposes (e.g., gaps can be introduced in the sequence of a first amino acid or nucleic acid for optimal alignment with a second amino or nucleic acid sequence). The amino acid or nucleotide residues at corresponding amino acid or nucleotide positions are then compared. When a position in the first sequence is occupied by the same amino acid or nucleotide residue as the corresponding position in the second sequence, then the molecules are identical at that position. The percent identity between the two sequences is a function of the number of identical positions shared by the sequences (i.e., % identity=number of identical positions/total number of positions (i.e. overlapping positions)×100). Preferably, the two sequences are of the same length.

A sequence comparison may be carried out over the entire lengths of the two sequences being compared or over fragments of the two sequences. Typically, the comparison will be carried out over the full length of the two sequences being compared. However, sequence identity may be carried out over a region of, for example, twenty, fifty, one hundred or more contiguous amino acid residues.

The skilled person will be aware of the fact that different computer programs are available to determine the homology between two sequences. For instance, a comparison of sequences and determination of percent identity between two sequences can be accomplished using a mathematical algorithm. In a preferred embodiment, the percent identity between two amino acid or nucleic acid sequences is determined using the Needleman and Wunsch (J. Mol. Biol. (48): 444-453 (1970)) algorithm which has been incorporated into the GAP program in the Accelrys GCG software package, using either a Blosum 62 matrix or a PAM250 matrix, and a gap weight of 16, 14, 12, 10, 8, 6, or 4 and a length weight of 1, 2, 3, 4, 5, or 6. The skilled person will appreciate that all these different parameters will yield slightly different results but that the overall percentage identity of two sequences is not significantly altered when using different algorithms.

The protein sequences or nucleic acid sequences of the present invention can further be used as a "query sequence" to perform a search against public databases to, for example, to identify other family members or related sequences. Such searches can be performed using the BLASTN and BLASTP programs (version 2.0) of Altschul, et al. (1990) J. Mol. Biol. 215:403-10. BLAST protein searches can be performed with the BLASTP program, score=50, wordlength=3 to obtain amino acid sequences homologous to protein molecules of the invention. To obtain gapped alignments for comparison purposes, Gapped BLAST can be utilized as described in Altschul et al. (1997) Nucleic Acids Res. 25(17): 3389-3402. When utilizing BLAST and Gapped BLAST programs, the default parameters of the respective programs (e.g., BLASTP and BLASTN) can be used. See the internet homepage of the National Center for Biotechnology Information.

As used herein, it is in particular understood that the term "identical to the sequence of SEQ ID NO: X" is equivalent to the term "identical to the sequence of SEQ ID NO: X over the length of SEQ ID NO: X" or to the term "identical to the sequence of SEQ ID NO: X over the whole length of SEQ ID NO: X", respectively. In this context, "X" is any integer selected from 1 to 61 so that "SEQ ID NO: X" represents any of the SEQ ID NOs mentioned herein.

In another specific aspect of the IBV or the immunogenic composition according to the present invention the 4/91 IBV is selected from a list of strains consisting of Spain/98/328, Spain/92/35, IR-3654-VM, FR-CR88061-88, FR-85131-85, UK-1233-95, UK/3/91, Spain/00/336, UK/4/91, UK/7/91, UK/793B/91, 4/91-pathogenic, 4/91 attenuated, IB4-91 and CR88.

Heterologous S Protein

IBV Strains

IBV strains can be classified by serotype and genotype. Serotype classification involves treatment of the virus with neutralizing antibodies, whereas genotype classification generally involves examining the sequence of the S1 (spike) protein. However, the different IBV strains are well known to the person skilled in the art. Infectious bronchitis virus was first discovered in the United States in the 1930s.

The first IBV serotype identified was Massachusetts and remained the only serotype until the discovery of a different IBV serotype in 1956. Nowadays, several additional serotypes, including Arkansas and Delaware have been identified in the United States of America in addition to the originally identified Massachusetts type. Today, IBV Mass viruses can be identified in many countries of the world.

The IBV strain Beaudette is of Massachusetts type and was derived following at least 150 passages in chick embryos. The IBV strain Beaudette was originally isolated by Beaudette and Hudson (J. Am. Vet. Med. A. 90, 51-60, 1937) and passaged in chicken embryos. Other Massachusetts type IBV strains besides Beaudette are H120, H52, and M41. The H120 strain was passaged 120 times.

IBV QX is described as virulent field isolate of IBV which was originally isolated in China. However, the virus has spread towards Europe and has been identified in parts of Western Europe, predominantly in the Netherlands, but also in Germany, France, Belgium, Denmark and in the UK. In addition, the QX genotype or serotype has been described in several countries in Asia and Africa.

The strains designated "Italien-02" or "Italy-02" was isolated in the late 1990's in Italy. The sequence analysis of one of these isolates was published in 2002 (NCBI-BLAST, number AJ457137). However, studies have shown that this Italian-02 strain is widespread in Europe and that, apart from IBV variant strain 4/91 it has become one of the most predominant genotypes in the UK, Spain, France and The Netherlands.

Since 1996 a new Infectious Bronchitis virus (IBV) genotype, referred to as Q1, has circulated in China and was reported for the first time in Italy in 2011. Q1 is associated with an increase of mortality, kidney lesions and proventriculitis.

Furthermore, strains D274, B1648/D8880, D1466, V1397 and Arkansas have been identified in Europe as well.

It is in the general knowledge of a person skilled in the art where to obtain any IBV strains. IBV strains can be be commercially purchased, obtained from scientific Institutes or the genomes can be synthetical synthesized as complementary DNA as IBV strains have been sequenced and the sequences have been published and are, thus, available. Furthermore, IBV strains can be isolated from the field. The methods to isolate IBV strains and to characterize the IBV strains are well known to the person skilled in the art. Valter Leonardo de Quadros 2011 (Dissertation, Das Infektiose Bronchitis Virus (IBV): Molekularbiologische Untersuchungen zur Diagnostik and zum Vorkommen sowie zur Pathogenitat des Genotyps IBV QX in spezifisch pathogenfreien (SPF) Broilern, Freie Universitat Berlin), Worthington et al. 2009 (Avian Pathology 37(3), 247-257), Liu et al. 2009 (Virus Genes 38: 56-65), Dolz et al. 2006 (Avian Pathology 35 (2): 77-85), Farsang et al. 2002 (Avian Pathology 31: 229-236) and Feng et al. 2014 (Virus Genes 49: 292-303) describe how to isolate and differentiate different IBV strains.

In another specific aspect of the IBV or the immunogenic composition according to the present invention the heterologous spike is of a non-4/91 genotype or serotype.

In another specific aspect of the IBV or the immunogenic composition according to the present invention the heterologous S protein or fragment thereof is from an IBV with a genotype or serotype selected from a list consisting of: Arkansas (such as Arkansas 99), Brazil (such as BR-1, BR-2, 23/2013, IBV/Brasil/351/1984), California (such as California 1734/04, California 99), Connecticut, Delaware (such as Delaware 98), Dutch (such as D207, D212, D274, D3128, D3896, D8880, D1466), Florida, Georgia (such as Georgia GA-07, GA-08, GA-12, GA-13), Gray, Holte, Iowa (such as Iowa 97 and Iowa 69), Italy (such as Italy 02), JMK, LDT3, Maine (such as Maine 209), Massachusetts (M41, H52, H120), Pennsylvania (such as Pennsylvania 1220/98, Pennsylvania Wolg/98), PL84084, Qu (such as Qu-mv), QX (such as GB341/96), Q1, SE 17 and Variant 2 (such as IS/1494/06, IBV/Ck/EG/CU/4/2014, gammaCoV/Ck/Poland/G052/2016).

In another specific aspect of the IBV or the immunogenic composition according to the present invention the heterologous S protein or fragment thereof is from an IBV selected from a list of genotypes or serotypes consisting of Massachusetts, QX, Q1, Italy 02, Arkansas, Conneticut, Georgia, LDT3, PL84084, Variant 2 or Brazil.

In another specific aspect of the IBV or the immunogenic composition according to the present invention the heterologous S protein or fragment thereof is from an IBV selected from a list of genotypes or serotypes consisting of Massachusetts, QX, Q1, Arkansas, Variant 2 and Brazil.

In another specific aspect of the IBV or the immunogenic composition according to the present invention the Massachusetts strain is selected from a list consisting of: H120, H52, Spain/98/308, IBMA5-1, SD/97/01, Spain/96/334, M41-M21883.

In another specific aspect of the IBV or the immunogenic composition according to the present invention the QX strain is selected from a list consisting of: FR-L1450T-05, FR-L1450L-05, NL-L1449T-04, NL-L1449K-04, IBV/Ck/SP/170/09, IBV/Ck/SP/79/08, IBV/Ck/SP/248/09, HBN, IBVQX, LX4, BJQ, CK/CH/LGD/03 and GB341/96.

In another specific aspect of the IBV or the immunogenic composition according to the present invention the Q1 strain is selected from a list consisting of: CK/CH/LDL/98I, CK/CH/LSD/08-10, J2, Q1, AR08ER22, AR08BA21 and Chile-295-10.

In another specific aspect of the IBV or the immunogenic composition according to the present invention the Arkansas strain is selected from a list consisting of: Ark99, ArkGA, ArkDPI, AL/5364/00, ARKDPI11, AL/0803/01, AL/7149/00, ArkDPI101, AL/1221/01, AL/1793/01 and AL/4614/98.

In another specific aspect of the IBV or the immunogenic composition according to the present invention the Variant 2 strain is selected from a list consisting of: IS/1494/06, IBV/Ck/EG/CU/4/2014, gammaCoV/Ck/Poland/G052/2016, Eg/CLEVB-2/IBV/012, D1344/2/4/10_EG, TR8 and IB VAR2-06.

In another specific aspect of the IBV or the immunogenic composition according to the present invention the Brazil strain is selected from a list consisting of: BR-1, BR-2, 23/2013 and IBV/Brasil/351/1984.

In another specific aspect of the IBV or the immunogenic composition according to the present invention the heterologous S protein or fragment thereof is from Massachusetts genotype or serotype.

In another specific aspect of the IBV or the immunogenic composition according to the present invention the heterologous S protein or fragment thereof is from genotype or serotype Massachusetts having at least 90%, 91%, 92%, 93%, 94%, 95%, 96%, 97%, 98%, 99%, 99.2%, 99.5%, 99.6%, 99.7%, 99.8%, 99.9%, 99.95%, 99.98% or 99.99% sequence identity to SEQ ID NO: 6 or 7.

In another specific aspect of the IBV or the immunogenic composition according to the present invention the heterologous S protein or fragment thereof is from genotype or serotype QX having at least 90%, 91%, 92%, 93%, 94%, 95%, 96%, 97%, 98%, 99%, 99.2%, 99.5%, 99.6%, 99.7%, 99.8%, 99.9%, 99.95%, 99.98% or 99.99% sequence identity to SEQ ID NO: 8 or 9.

In another specific aspect of the IBV or the immunogenic composition according to the present invention the heterologous S protein or fragment thereof is from genotype or serotype Q1 having at least 90%, 91%, 92%, 93%, 94%, 95%, 96%, 97%, 98%, 99%, 99.2%, 99.5%, 99.6%, 99.7%, 99.8%, 99.9%, 99.95%, 99.98% or 99.99% sequence identity to SEQ ID NO: 10 or 11.

In another specific aspect of the IBV or the immunogenic composition according to the present invention the heterologous S protein or fragment thereof is from genotype or serotype Arkansas having at least 90%, 91%, 92%, 93%, 94%, 95%, 96%, 97%, 98%, 99%, 99.2%, 99.5%, 99.6%, 99.7%, 99.8%, 99.9%, 99.95%, 99.98% or 99.99% sequence identity to SEQ ID NO: 12 or 13.

In another specific aspect of the IBV or the immunogenic composition according to the present invention the heterologous S protein or fragment thereof is from genotype or serotype Variant 2 having at least 90%, 91%, 92%, 93%, 94%, 95%, 96%, 97%, 98%, 99%, 99.2%, 99.5%, 99.6%, 99.7%, 99.8%, 99.9%, 99.95%, 99.98% or 99.99% sequence identity to SEQ ID NO: 14 or 15.

In another specific aspect of the IBV or the immunogenic composition according to the present invention the heterologous S protein or fragment thereof is from genotype or serotype Brazil having at least 90%, 91%, 92%, 93%, 94%, 95%, 96%, 97%, 98%, 99%, 99.2%, 99.5%, 99.6%, 99.7%, 99.8%, 99.9%, 99.95%, 99.98% or 99.99% sequence identity to SEQ ID NO:16 or 17.

In another specific aspect of the IBV or the immunogenic composition according to the present invention the heterologous S protein or fragment thereof is selected from a list consisting of SEQ ID NO: 6, 7, 8, 9, 10, 11, 12, 13, 14, 15, 16 or 17.

In another specific aspect of the IBV or the immunogenic composition according to the present invention the heterologous S protein is the full length spike protein.

The present experimental data show that full length spike protein sequences can be used. However, it is well known that fragments of the spike protein sequence can be used as well such as the ectodomain of the spike protein.

In another specific aspect of the IBV or the immunogenic composition according to the present invention the fragment of the heterologous S (spike) protein has a length of at least 500, 750, 1000 or 1075 amino acids.

In another specific aspect of the IBV or the immunogenic composition according to the present invention the fragment of the heterologous S (spike) protein has a length of at least 500, 750, 1000 or 1075 amino acids from the N-Terminus.

The term "N-terminus" is well known to the person skilled in the art. The N-terminus is also termed amino-terminus, NH2-terminus, N-terminal end or amine-terminus. When the protein is translated from messenger RNA, it is created from N-terminus to C-terminus. Thus, the N-terminus is the start of an amino acid chain (protein or polypeptide) comprising said amine group (—NH2).

In another specific aspect of the IBV or the immunogenic composition according to the present invention the fragment of the heterologous S (spike) protein has a length of at least 1000 amino acids.

In another specific aspect of the IBV or the immunogenic composition according to the present invention the fragment of the heterologous S (spike) protein is the ectodomain of the spike protein.

The term "ectodomain" is well known to a person skilled in the art. The spike protein comprises different functional parts, the signal sequence, the ectodomain, the transmembrane domain and the endodomain (from N-terminus to C-terminus). Thus, after cleavage of the signal sequence, the N-terminus of the spike protein starts with the ectodoamin. The IBV spike ectodoamins has a length of about 1075 amino acids and differs by a a few amino acids in length dependent on the IBV strain.

In another specific aspect of the IBV or the immunogenic composition according to the present invention the heterologous S (spike) protein or fragment thereof replaces the homologous S protein or fragment thereof.

In another specific aspect of the IBV or the immunogenic composition according to the present invention the heterologous S (spike) protein or fragment thereof replaces the natural occurring S protein or fragment thereof.

In another specific aspect of the IBV or the immunogenic composition according to the present invention the heterologous S (spike) protein or fragment thereof replaces the S protein or fragment thereof in 4/91 IBV.

In another specific aspect of the IBV or the immunogenic composition according to the present invention the IBV is attenuated.

The term "attenuated" refers to a pathogen having a reduced virulence in comparison to the wildtype isolate. In the present invention, an attenuated IBV is one in which the virulence has been reduced so that it does not cause clinical signs of an IBV infection but is capable of inducing an immune response in the target animal, but may also mean that the clinical signs are reduced in incidence or severity in animals infected with the attenuated IBV in comparison with a "control group" of animals infected with non-attenuated IBV and not receiving the attenuated virus. In this context, the term "reduce/reduced" means a reduction of at least 10%, preferably 25%, even more preferably 50%, still more preferably 60%, even more preferably 70%, still more preferably 80%, still more preferably 90%, even more preferably 95% and most preferably of 100% as compared to the control group infected with non-attenuated IBV as defined above. Thus, an attenuated, IBV strain is one that is suitable for incorporation into an immunogenic composition comprising a modified live IBV.

In another specific aspect of the IBV or the immunogenic composition according to the present invention the IBV is inactivated.

Any conventional inactivation method can be used for purposes of the present invention. Thus, inactivation can be performed by chemical and/or physical treatments which are known to the person skilled in the art. Preferred inactivation methods include the addition of cyclized binary ethylenimine (BEI) including the addition of a solution of 2-bromoethyleneamine hydrobromide (BEA), which has been cyclized to binary ethylenimine (BEI). Preferred further chemical inactivation agents comprise but are not limited to Triton X-100, Sodium deoxycholate, Cetyltrimethylammonium bromide, 0-Propiolactone, Thimerosal, Phenol and Formaldehyde (Formalin). However, the inactivation may also comprise a neutralization step. Preferred neutralization agents include but are not limited to sodium thiosulfate, sodium bisulfate and the alike.

Preferred formalin inactivation conditions include formalin concentration between from about 0.02% (v/v) 2.0% (v/v), more preferably from about 0.1% (v/v) 1.0% (v/v), still more preferably from about 0.15% (v/v) 0.8% (v/v), even more preferably from about 0.16% (v/v) 0.6% (v/v), and most preferably about 0.2% (v/v) 0.4% (v/v). Incubation time depends on the resistance of the IBV. In general, the inaction process is performed until no growth of the IBV can be detected in a suitable cultivation system.

Preferably, the inactivated IBV of the present invention is formalin inactivated, preferably using the concentrations as described hereinabove.

The inactivated IBV of the invention may be incorporated into liposomes using known technology such as that described in Nature, 1974, 252, 252-254 or Journal of Immunology, 1978, 120, 1109-13. In another embodiment of the invention, the inactivated IBV of the invention may be conjugated to suitable biological compounds such as polysaccharides, peptides, proteins, or the like, or a combination thereof.

In another specific aspect of the IBV or the immunogenic composition according to the present invention the IBV is genetically engineered.

The term "genetically engineered" refers to an IBV which has been mutated by using "reverse genetics" approaches. Preferably, the IBV according to the present invention has been genetically engineered. The reverse genetics technique involves the preparation of synthetic recombinant viral RNAs. However, "reverse genetics" techniques are well known to the person skilled in the art.

In another specific aspect of the IBV or the immunogenic composition according to the present invention the IBV is a recombinant IBV.

The term "recombinant" as used herein relates to a RNA genome (or RNA sequence, cDNA sequence or protein) having any modifications that do not naturally occur to the corresponding RNA genome (or RNA sequence, cDNA sequence or protein). For instance, a RNA genome (or RNA sequence, cDNA sequence or protein) is considered "recombinant" if it contains an insertion, deletion, inversion, relocation or a point mutation introduced artificially, e.g., by human intervention. Therefore, the RNA genomic sequence (or RNA sequence, cDNA sequence or protein) is not associated with all or a portion of the sequences (or RNA sequence, cDNA sequence or protein) with which it is associated in nature. The term "recombinant" as used with respect to a virus, means a virus produced by artificial manipulation of the viral genome. The term "recombinant virus" encompasses genetically modified viruses.

In another specific aspect of the IBV or the immunogenic composition according to the present invention the IBV is chimeric.

The term "chimeric" refers to an IBV comprising one or more nucleotide sequences from another coronavirus, preferably from another IBV strain. Exemplary, an IBV 4/91 encoding for a heterologous S (spike) protein or fragment thereof is a chimeric IBV.

In another specific aspect of the immunogenic composition according to the present invention the immunogenic composition is a vaccine. The term "vaccine" already has been described elsewhere herein. However, in case where the host displays a protective immunological response such that resistance to new infection will be enhanced and/or the clinical severity of the disease reduced, the immunogenic composition is described as a "vaccine.

In another specific aspect of the immunogenic composition according to the present invention the immunogenic composition comprises a pharmaceutically acceptable carrier.

The term "pharmaceutical-acceptable carrier" includes any and all solvents, dispersion media, coatings, stabilizing agents, diluents, preservatives, antibacterial and antifungal agents, isotonic agents, adsorption delaying agents, adjuvants, immune stimulants, and combinations thereof.

"Diluents" can include water, saline, dextrose, ethanol, glycerol, and the like. Isotonic agents can include sodium chloride, dextrose, mannitol, sorbitol, and lactose, among others. Stabilizers include albumin and alkali salts of ethylendiamintetracetic acid, among others.

In another specific aspect of the immunogenic composition according to the present invention the pharmaceutically acceptable carrier is phosphate buffered saline.

Preferably, the immunogenic composition further comprises sucrose gelatin stabilizer.

Preferably, the pharmaceutically acceptable carrier is chitosan.

Chitosan is a natural deacetylated polysaccharide from chitin in crustaceans (e.g., shrimp, crab), insects, and other invertebrates. Recently, Rauw et al. 2009 (Vet Immunol Immunop 134:249-258) demonstrated that chitosan enhanced the cellular immune response of live Newcastle disease vaccine and promoted its protective effect. Further, Wang et al., 2012 (Arch Virol (2012) 157:1451-1461) have shown results revealing the potential of chitosan as an adjuvant for use in a live attenuated influenza vaccine.

Preferably, the immunogenic composition can further include one or more other immunomodulatory agents such as, e.g. interleukins, interferons, or other cytokines. The amounts and concentrations of adjuvants and additives useful in the context of the present invention can readily be determined by the skilled artisan.

In some aspects, the immunogenic composition of the present invention contains an adjuvant. "Adjuvants" as used herein, can include aluminum hydroxide and aluminum phosphate, saponins e.g., Quil A, QS-21 (Cambridge Biotech Inc., Cambridge Mass.), GPI-0100 (Galenica Pharmaceuticals, Inc., Birmingham, Ala.), water-in-oil emulsion, oil-in-water emulsion, water-in-oil-in-water emulsion. The emulsion can be based in particular on light liquid paraffin oil (European Pharmacopea type); isoprenoid oil such as squalane or squalene; oil resulting from the oligomerization of alkenes, in particular of isobutene or decene; esters of acids or of alcohols containing a linear alkyl group, more particularly plant oils, ethyl oleate, propylene glycol di-(caprylate/caprate), glyceryl tri-(caprylate/caprate) or propylene glycol dioleate; esters of branched fatty acids or alcohols, in particular isostearic acid esters. The oil is used in combination with emulsifiers to form the emulsion. The emulsifiers are preferably nonionic surfactants, in particular esters of sorbitan, of mannide (e.g. anhydromannitol oleate), of glycol, of polyglycerol, of propylene glycol and of oleic, isostearic, ricinoleic or hydroxystearic acid, which are optionally ethoxylated, and polyoxypropylene-polyoxyethylene copolymer blocks, in particular the Pluronic products, especially L121. See Hunter et al., The Theory and Practical Application of Adjuvants (Ed.Stewart-Tull, D. E. S.), JohnWiley and Sons, N.Y., pp 51-94 (1995) and Todd et al., Vaccine 15:564-570 (1997). Exemplary adjuvants are the SPT emulsion described on page 147 of "Vaccine Design, The Subunit and Adjuvant Approach" edited by M. Powell and M. Newman, Plenum Press, 1995, and the emulsion MF59 described on page 183 of this same book.

A further instance of an adjuvant is a compound chosen from the polymers of acrylic or methacrylic acid and the copolymers of maleic anhydride and alkenyl derivative. Advantageous adjuvant compounds are the polymers of acrylic or methacrylic acid which are cross-linked, especially with polyalkenyl ethers of sugars or polyalcohols. These compounds are known by the term carbomer (Phameuropa Vol. 8, No. 2, June 1996). Persons skilled in the art can also refer to U.S. Pat. No. 2,909,462 which describes such acrylic polymers cross-linked with a polyhydroxylated compound having at least 3 hydroxyl groups, preferably not more than 8, the hydrogen atoms of at least three hydroxyls being replaced by unsaturated aliphatic radicals having at least 2 carbon atoms. The preferred radicals are those containing from 2 to 4 carbon atoms, e.g. vinyls, allyls and other ethylenically unsaturated groups. The unsaturated radicals may themselves contain other substituents, such as methyl. The products sold under the name Carbopol; (BF Goodrich, Ohio, USA) are particularly appropriate. They are cross-linked with an allyl sucrose or with allyl pentaerythritol. Among then, there may be mentioned Carbopol 974P, 934P and 971P. Most preferred is the use of Carbopol 971P. Among the copolymers of maleic anhydride and alkenyl derivative, are the copolymers EMA (Monsanto), which are copolymers of maleic anhydride and ethylene. The dissolution of these polymers in water leads to an acid solution that will be neutralized, preferably to physiological pH, in order to give the adjuvant solution into which the immunogenic, immunological or vaccine composition itself will be incorporated.

Further suitable adjuvants include, but are not limited to, the RIBI adjuvant system (Ribi Inc.), Block co-polymer (CytRx, Atlanta Ga.), SAF-M (Chiron, Emeryville Calif.), monophosphoryl lipid A, Avridine lipid-amine adjuvant, heat-labile enterotoxin from *E. coli* (recombinant or otherwise), cholera toxin, IMS 1314 or muramyl dipeptide, or naturally occurring or recombinant cytokines or analogs thereof or stimulants of endogenous cytokine release, among many others.

It is expected that an adjuvant can be added in an amount of about 100 μg to about 10 mg per dose, preferably in an amount of about 100 μg to about 10 mg per dose, more preferably in an amount of about 500 μg to about 5 mg per dose, even more preferably in an amount of about 750 μg to about 2.5 mg per dose, and most preferably in an amount of about 1 mg per dose. Alternatively, the adjuvant may be at a concentration of about 0.01 to 50%, preferably at a concentration of about 2% to 30%, more preferably at a concentration of about 5% to 25%, still more preferably at a concentration of about 7% to 22%, and most preferably at a concentration of 10% to 20% by volume of the final product.

In another specific aspect of the immunogenic composition according to the present invention the immunogenic composition is effective in the treatment and/or prophylaxis of clinical signs caused by IBV in a subject of need. The terms "treatment and/or prophylaxis", "clinical signs" and "of need" have been defined elsewhere.

In another specific aspect of the immunogenic composition according to the present invention the immunogenic composition protects against a challenge with an IBV strain of the genotype or serotype of the heterologous spike protein.

In another specific aspect of the immunogenic composition according to the present invention the immunogenic composition protects against a challenge with strains of Massachusetts, QX, Q1, Arkansas, Variant 2 or Brazil genotype.

In another specific aspect of the immunogenic composition according to the present invention the immunogenic composition protects against a challenge with strains of Massachusetts genotype.

In another specific aspect of the immunogenic composition according to the present invention said immunogenic composition is formulated for a single-dose administration.

The volume for a single-dose has been defined elsewhere herein.

It has furthermore been shown that one dose of the immunogenic composition of the present invention is effective after the administration of such single dose of such immunogenic composition.

In another specific aspect of the immunogenic composition according to the present invention the immunogenic composition is administered subcutaneously, intramuscularly, oral, in ovo, via spray, via drinking water or by eye drop.

In another specific aspect of the immunogenic composition according to the present invention the immunogenic composition comprises 1 to 10 $\log_{10}$ EID50 per dose of the IBV.

In another specific aspect of the immunogenic composition according to the present invention the immunogenic composition comprises 2 to 5 $\log_{10}$ EID50 per dose of the IBV.

In another specific aspect of the immunogenic composition according to the present invention the immunogenic composition comprises 2 to 4 $\log_{10}$ EID50 per dose of the IBV.

Kits

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration preferably for administration to subjects, especially poultry. Associated with such container(s) can be a notice in the form prescribed by a governmental agency regulating the manufacture, use or sale of pharmaceuticals or biological products, which notice reflects approval by the agency of manufacture, use or sale for human administration.

Thus, the present invention provides a kit comprising the IBV or the immunogenic composition as described herein.

In one specific aspect of the kit according to the present invention the kit further comprises an instruction letter for the treatment and/or prophylaxis of diseases of avians.

In one specific aspect of the kit according to the present invention the kit further comprises an instruction letter for the treatment and/or prophylaxis of diseases of poultry.

In one specific aspect of the kit according to the present invention the kit further comprises an instruction letter for the treatment and/or prophylaxis of IB (infectious bronchitis).

Method of Treatments

Further, the present invention provides a method for immunizing a subject comprising administering to such subject an immunogenic composition as described herein.

The term "immunizing" relates to an active immunization by the administration of an immunogenic composition to a subject to be immunized, thereby causing an immunological response against the antigen included in such immunogenic composition.

Preferably, immunization results in lessening of the incidence of the particular IBV infection in a flock or in the reduction in the severity of clinical signs caused by or associated with the particular IBV infection.

Further, the immunization of a subject in need with the immunogenic compositions as provided herewith, results in preventing infection of a subject by IBV infection. Even more preferably, immunization results in an effective, long-lasting, immunological-response against IBV infection. It will be understood that the said period of time will last more than 1 month, preferably more than 2 months, preferably more than 3 months, more preferably more than 4 months, more preferably more than 5 months, more preferably more than 6 months. It is to be understood that immunization may not be effective in all subjects immunized. However, the term requires that a significant portion of subjects of a flock are effectively immunized.

Preferably, a flock of subjects is envisaged in this context which normally, i.e. without immunization, would develop clinical signs normally caused by or associated with a IBV infection. Whether the subjects of a flock are effectively immunized can be determined without further ado by the person skilled in the art. Preferably, the immunization shall be effective if clinical signs in at least 33%, at least 50%, at least 60%, at least 70%, at least 80%, at least 90%, still more preferably in at least 95% and most preferably in 100% of the subjects of a given flock are lessened in incidence or severity by at least 10%, more preferably by at least 20%, still more preferably by at least 30%, even more preferably by at least 40%, still more preferably by at least 50%, even more preferably by at least 60%, still more preferably by at least 70%, even more preferably by at least 80%, still more preferably by at least 90%, still more preferably by at least 95% and most preferably by 100% in comparison to subjects that are either not immunized or immunized with an immunogenic composition that was available prior to the present invention but subsequently infected by the particular IBV.

Further, the present invention provides a method of treating or preventing clinical signs caused by IBV in a subject of need, the method comprising administering to the subject a therapeutically effective amount of an immunogenic composition as described herein.

The term "treating or preventing" refers to the lessening of the incidence of the particular IBV infection in a flock or the reduction in the severity of clinical signs caused by or associated with the particular IBV infection. Thus, the term "treating or preventing" also refers to the reduction of the number of subjects in a flock that become infected with the particular IBV (=lessening of the incidence of the particular IBV infection) or to the reduction of the severity of clinical signs normally associated with or caused by a IBV infection or the reduction of virus shedding after infection with the particular IBV or preventing or lessening egg drop in laying hens after infection with the particular IBV in a group of subjects which subjects have received an effective amount of the immunogenic composition as provided herein in comparison to a group of subjects which subjects have not received such immunogenic composition.

The "treating or preventing" generally involves the administration of an effective amount of the immunogenic composition of the present invention to a subject or flock of subjects in need of or that could benefit from such a treatment/prophylaxis. The term "treatment" refers to the administration of the effective amount of the immunogenic composition once the subject or at least some subjects of the flock is/are already infected with such IBV and wherein such subjects already show some clinical signs caused by or associated with such IBV infection. The term "prophylaxis" refers to the administration of a subject prior to any infection of such subject with IBV or at least where such subject or none of the subjects in a group of subjects do not show any clinical signs caused by or associated with the infection by such IBV. The terms "prophylaxis" and "preventing" are used interchangeable in this application.

The term "an effective amount" as used herein means, but is not limited to an amount of antigen, that elicits or is able to elicit an immune response in a subject. Such effective amount is able to lessen the incidence of the particular IBV infection in a flock or to reduce the severity of clinical signs of the particular IBV infection.

Preferably, clinical signs are lessened in incidence or severity by at least 10%, more preferably by at least 20%, still more preferably by at least 30%, even more preferably by at least 40%, still more preferably by at least 50%, even more preferably by at least 60%, still more preferably by at least 70%, even more preferably by at least 80%, still more preferably by at least 90%, still more preferably by at least 95% and most preferably by 100% in comparison to subjects that are either not treated or treated with an immunogenic composition that was available prior to the present invention but subsequently infected by the particular IBV.

The term "clinical signs" as used herein refers to signs of infection of a subject from IBV. The clinical signs of infection depend on the pathogen selected. Examples for such clinical signs include but are not limited to respiratory distress, nephritis, salphingitis, abnormal egg production, ruffled feathers, depression, reduced growth rates and reduced appetite. Signs of respiratory distress encompass respiratory signs including gasping, coughing, sneezing, tracheal rales, nasal and ocular discharge, tracheal lesions and ciliostasis in the trachea. Signs of nephritis encompass kidney lesions and watery diarrhea. Signs of abnormal egg production encompass egg drop, eggs of smaller size, inferior shell, reduced internal egg quality, eggs with thin albumen and ciliostasis in the oviduct. However, the clinical signs also include but are not limited to clinical signs that are directly observable from a live animal. Examples for clinical signs that are directly observable from a live animal include nasal and ocular discharge, coughing, gasping, sneezing, tracheal rales, ruffled feathers, conjunctivitis, weight loss, reduced growth rates, reduced appetite, dehydration, watery diarrhea, lameness, lethargy, wasting and unthriftiness and the like.

Preferably, the clinical signs lessened in incidence or severity in a treated subject compared to subjects that are either not treated or treated with an immunogenic composition that was available prior to the present invention but subsequently infected by the particular IBV refer to a reduction of ciliostasis, a reduction of rales, a reduction of egg drop, a reduction of kidney lesions, a reduction of watery diarrhea, a reduction in weight loss, a lower virus load, a reduced viral shedding, or combinations thereof.

The term "in need" or "of need", as used herein means that the administration/treatment is associated with the boosting or improvement in health or clinical signs or any other positive medicinal effect on health of the subjects which receive the immunogenic composition in accordance with the present invention.

The term "reducing" or or "reduced" or "reduction" or lower" are used interchangeable in this application. The term "reduction" means, that the clinical sign is reduced by at least 10%, more preferably by at least 20%, still more preferably by at least 30%, even more preferably by at least 40%, still more preferably by at least 50%, even more preferably by at least 60%, still more preferably by at least 70%, even more preferably by at least 80%, even more preferably by at least 90%, still more preferably by at least 95% most preferably by 100% in comparison to subjects that are not treated (not immunized) but subsequently infected by the particular IBV.

Further, the present invention provides a method of reducing the ciliostasis in a subject of need, in comparison to a subject of a non-immunized control group of the same species, the method comprising administering to the subject a therapeutically effective amount of an immunogenic composition as described herein.

As shown in the Examples, the immunogenic composition as provided herein has been proven to be efficacious in reducing ciliostasis.

The term "ciliostasis" refers to a reduced movement of the cilia in the trachea. Thus, ciliostasis may be determined by examining the inner lining of the tracheal rings for the movement of the cilia. It is in the general knowledge of a person skilled in the art how to determine the movement of the cilia in the trachea.

Preferably, the movement of the cilia is not reduced from day 10 after challenge or infection, more preferably from day 5 after challenge or infection, more preferably from day 4 after challenge or infection, more preferably from day 3 after challenge or infection and most preferably from day 1 or 2 after challenge or infection with the IBV as compared to a subject of a non-immunized control group of the same species.

The term "reduction of ciliostasis" means, that the ciliostasis is reduced by at least 10%, preferably by at least 20%, more preferably by at least 30%, even more preferably by at least 40%, even more preferably by at least 50%, even more preferably by at least 60%, even more preferably by at least 70%, even more preferably by at least 80%, even more preferably by at least 90%, even more preferably by at least 95% and most preferably by 100% as compared to a subject of anon-immunized control group of the same species. It is in the general knowledge of a person skilled in the art how to measure the reduction of the ciliostasis.

In one aspect of the present invention said subject is avian.

The term "avian" is well known to the person skilled in the art. The term "avian" encompasses all birds including poultry.

In one aspect of the present invention said subject is poultry.

The term "poultry" is well known to the person skilled in the art. The term "poultry" encompasses chickens, turkeys, quails, pheasants, guineafowl, geese, and ducks. Further, the term "chicken" includes broiler, laying hens, and reproductive stocks for both also refeered as breeders.

In one aspect of the present invention said subject is selected from the list consisting of chicken, turkey, quail, or pheasant.

In one aspect of the present invention said subject is chicken.

In one aspect of the present invention the immunogenic composition is administered once.

It is understood, that a single-dose is administered only once. As shown in the Examples the immunogenic composition as provided herein has been proven to be efficacious after the administration of a single dose to a subject of need.

The dose volume per poultry depends on the route of vaccination and the age of the poultry.

Typically, eye drop vaccines are administered in a volume of 1 to 100 μl per dose at any age. Preferably, the single-dose for eye drop vaccines has a total volume between about 5 μl and 70 μl and more preferably between about 20 μl and 50 μl with a single 20 μl, 25 μl, 30 μl, 35 μl, 40 μl, 45 μl or 50 μl dose being preferred. Most preferred, the single-dose for eye drop vaccines has a total volume between between about 30 μl and 50 μl with a single 30 μl, 40 μl, 45 μl or 50 μl dose being preferred.

Spray vaccines may contain the dose in a volume of 25 to 1000 μl for day-old poultry. Preferably, the single-dose for spray vaccines has a total volume between about 50 μl and 5000 more preferably between about 75 μl and 2000 μl, more preferably between about 100 μl and 1000 μl, even more preferably between about 200 μl and 900 μl, even more preferably between about 300 μl and 800 μl and even more preferably between about 400 μl and 700 μl with a single 400μ, 425 μl, 450 μl, 475 μl, 500 μl, 525 μl, 550 μl, 575 μl, 600 μl, 625 μl, 650 μl, 675 μl or 700 μl dose being preferred. Most preferred the single-dose has a total volume of 400 μl, 450 μl, 500 μl, 550 μl, 600 μl, 650 μl or 700 μl.

The vaccine for in ovo vaccination may contain the dose in a volume of 50 to 100 μl, preferably 50 μl. Preferably, the single-dose for in ovo vaccines has a total volume between about 10 μl and 250 μl, more preferably between about 15 μl and 200 μl, even more preferably between about 20 μl and 150 μl, even more preferably between about 30 μl and 100 μl, even more preferably between about 30 μl and 75 μl and with a single 30 μl, 35 μl, 40 μl, 45 μl, 50 μl, 55 μl, 60 μl, 65 μl, 70 μl or 75 μl dose being preferred. Most preferred the single-dose has a total volume of 40 μl, 45 μl, 50 μl, 55 μl or 60 μl.

The vaccine for intramuscular or subcutaneous vaccination or one dose of a drinking water vaccine may contain the dose in a volume of 30 μl to 1000 μl. Preferably, the single-dose has a total volume between about 30 μl and 1000 μl, more preferably between about 50 μl and 500 μl, more preferably between about 75 μl and 250 μl and even more preferably between about 100 μl and 200 μl with a single 100 μl, 110 μl, 120 μl, 125 μl, 130 μl, 135 μl, 140 μl, 145 μl, 150 μl, 160 μl, 170 μl, 175 μl, 180 μl, 190 μl, 155 μl, or 200 μl dose being the most preferred.

In one aspect of the present invention the immunogenic composition is administered at two or more doses.

However, the immunogenic composition can be administered at two or more doses, with a first dose being administered prior to the administration of a second (booster) dose.

In a preferred aspect of the two-time administration regimen, both the first and second doses of the immunogenic composition are administered in the same amount. Preferably, each dose is in the preferred amounts specified above. In addition to the first and second dose regimen, an alternate embodiment comprises further subsequent doses. For example, a third, fourth, or fifth dose could be administered in these aspects. Preferably, subsequent third, fourth, and fifth dose regimens are administered in the same amount as the first dose, with the time frame between the doses being consistent with the timing between the first and second doses mentioned above.

Preferably, the first administration of the vaccine is performed within the first three weeks of age, more preferably within the first week of age and most preferred at one day-of-age by methods as described below. A second administration can be performed within the first 20 weeks of age, preferably within 16-18 weeks of age, more preferably between 6-12 weeks of age. Exemplary, the initial (first) vaccination is performed at 1-10 days of age and the second vaccination (booster) is performed with a live or inactivated vaccine at 6-12 or 16-18 weeks of age. More preferably, the initial (first) vaccination is performed at one day-of-age and the second vaccination (booster) is performed with a live or inactivated vaccine at 6-12 or 16-18 weeks of age.

In case in ovo vaccination is used, preferably the first admiration is performed when embryos are between 15 to 19 days old, preferably at day 17, 18 or 19, most preferably at day 18 of age. A second administration can be performed within the first three weeks of age, preferably within the first 10 days of age.

In one aspect of the present invention said immunogenic composition is administered subcutaneously, intramuscularly, oral, in ovo, via spray, via drinking water or by eye drop.

The immunogenic composition is, preferably, administered topically or systemically. Suitable routes of administration conventionally used are oral or parenteral administration, such as intranasal, intravenous, intradermal, transdermal, intramuscular, intraperitoneal, subcutaneous, as well as inhalation, in ovo, via spray, via drinking water or by eye drop. However, depending on the nature and mode of action of a compound, the immunogenic composition may be administered by other routes as well. For example, such other routes include intracutaneously, intravenously, intravascularly, intraarterially, intraperitnoeally, intrathecally, intratracheally, intracutaneously, intracardially, intralobally, intralobarly, intramedullarly, intrapulmonarily, intrarectally, and intravaginally. However, most preferred the immunogenic composition is administered subcutaneously, intramuscularly, oral, in ovo, via spray, via drinking water or by eye drop.

Live IBV vaccines are preferably administered individually by eye drop, intranasal, intramuscular or subcutaneous.

More preferably, mass application methods, including drinking water and aerosol spray vaccination, are used. Also preferred is the use of vaccines as embryo vaccines (so-called in ovo vaccines) as described further below.

For example, broilers may be vaccinated at one-day of age or at 1-3 weeks of age, particularly for broilers with high levels of MDA. Laying stock or reproduction stock may be vaccinated initially at 1-10 days of age and boosted with the vaccine at 7-12 or 16-18 weeks of age.

In Ovo Administration

As outlined above, the present invention also provides an IBV vaccine that can be safely administered via the in ovo route and at the same time is able to induce a protective immune response. The in ovo administration is well known to the person skilled in the art and the person skilled in the art can perform in ovo administration without further ado. The in ovo administration of the vaccine involves the administration of the vaccine to an avian embryo while contained in the egg (for a review on in ovo vaccination see: Ricks et al., Advances in Vet. Med. 495-515, 1999). The vaccine may be administered to any suitable compartment of the egg (e. g. allantois fluid, yolk sac, amnion, air cell or into the embryo) as described in the art (Sharma; Am. J. Vet. Res. 45 1619-1623, 1984). Preferably the vaccine is administered below the shell (aircell) membrane and chorioallantoic membrane.

Preferably, the vaccine is injected into embryonated eggs during late stages of the embryonation, generally during the final quarter of the incubation period, preferably 3-4 days prior to hatch. Preferably, the administration is performed when embryos are between 15 to 19 days old, preferably at day 17, 18 or 19, most preferably at day 18 of age. Subsequently, the vaccinated embryonated eggs are transferred to an incubator for hatch. The process of in ovo administration can be automated using a robotic injection process as described in the prior art.

Usually conventional vaccines for post-hatch vaccination of poultry cannot be used for in ovo vaccination, because late stage embryos are highly susceptible to infection with most vaccine viruses examined. However, International patent application WO 01/64244 discloses that IBV vaccines can be used for in ovo administration provided it is applied at a very low doses. Further, Wakenell et al. 1986 (Am. J. Vet. Res., 47 933-938) discloses that passaging an IB vaccine virus in tissue culture rendered the virus apathogenic for embryos.

In one aspect of the present invention said immunogenic composition is administered via eye drop.

Typically, the live vaccine for post-hatch administration comprises the attenuated IBV in a concentration of $10^1$ to $10^8$ $EID_{50}$ (50% Egg Infective Dose) per dose, preferably in a concentration of $10^2$ to $10^5$ $EID_{50}$ per dose and, more preferably, in a concentration of $10^2$ to $10^4$ $EID_{50}$ per unit dose and, even more preferably, in a concentration of $10^2$ to $10^3$ $EID_{50}$ per dose.

The live vaccine for in ovo administration typically comprises an amount of the attenuated IBV of $10^2$ to $10^7$ $EID_{50}$/embryo, preferably $10^2$ to $10^3$ $EID_{50}$/embryo in a volume of 50 to 100 μl, preferably 50 μl.

Preferably, the immunogenic composition of the present invention comprises the IBV of the present invention in amounts of about 1 to about 10 $\log_{10}$ EID (egg infective dose)$_{50}$/ml per dose, preferably about 2 to about 8 $\log_{10}$ $EID_{50}$ per dose, preferably in an amount of about 2 to about 7 $\log_{10}$ $EID_{50}$ per dose, more preferably in an amount of about 2 to about 6 $\log_{10}$ $EID_{50}$ per dose, even more preferably in an amount of about 2 to about 5 $\log_{10}$ $EID_{50}$ per dose, even more preferably in an amount of about 2 to about 4 $\log_{10}$ $EID_{50}$ per dose, most preferably in an amount of about 2 to about 3 $\log_{10}$ $EID_{50}$ per dose. More preferably, the immunogenic composition of the present invention comprises the IBV of the present invention in amounts of about 1, 1.5, 2, 2.5, 3, 3.5, 4, 4.5, 5, 5.5, 6, 6.5, 7, 7.5 or $\log_{10}$ $EID_{50}$ per dose.

In one aspect of the present invention the immunogenic composition comprises 1 to 10 $\log_{10}$ $EID_{50}$ per dose of the IBV.

In one aspect of the present invention the immunogenic composition comprises 2 to 5 $\log_{10}$ $EID_{50}$ per dose of the IBV.

In one aspect of the present invention the immunogenic composition comprises 2 to 4 $\log_{10}$ $EID_{50}$ per dose of the IBV.

In one aspect of the present invention the immunogenic composition is administered to subjects within the first week of age, within the first three days of age, within the first two days of age, or within the first day of age.

Preferably, the subject to be immunized is 1, 2, 3, 4, 5, 6, 7, 8, 9, 10, 11, 12, 13, 14, 15, 16, 17, 18, 19, 20 or 21 days of age. More preferably, said subject to be immunized is 1, 2, 3, 4, 5, 6, 7, 8, 9, 10, 11, 12, 13 or 14 days of age. Most preferably, said subject to be immunized is 1, 2, 3, 4, 5, 6 or 7 days of age.

However, it has to be understood that after vaccination of the subject being a few days of age, it does need several days for the immune system of the poultry to build up immunity against an IBV infection. Therefore, preferably, the subjects are immunized within the first 24 h of age.

In one aspect of the present invention the immunogenic composition is administered to subjects within the first day of age. As shown in the Examples the immunogenic composition as provided herein has been proven to be safe and efficacious when administered to 1-day old poultry.

In one aspect of the present invention said method results in an improvement in an efficacy parameter selected from the group consisting of: prevention or reduction of ciliostasis, prevention or reduction of rales, prevention or reduction of egg drop, prevention or reduction of kidney lesions, prevention or reduction of watery diarrhea, prevention or reduction in weight loss, a lower virus load, a reduced viral shedding or combinations thereof, in comparison to a subject of a non-treated control group of the same species.

The terms "treatment and/or prophylaxis" have been defined elsewhere, wherein the terms "prophylaxis" and "preventing" or "prevention" are used interchangeable in this application. Further, the terms "shedding" has been defined elsewhere, too.

The term "reducing", "reduced", "reduction" or "lower" means, that the efficacy parameter (ciliostasis, rales, egg drop, kidney lesions, watery diarrhea, weight loss, virus load, viral shedding) is reduced by at least 10%, preferably by at least 20%, more preferably by at least 30%, even more preferably by at least 40%, even more preferably by at least 50%, even more preferably by at least 60%, even more preferably by at least 70%, even more preferably by at least 80%, even more preferably by at least 90%, even more preferably by at least 95% and most preferably by 100% as compared to a subject of a non-immunized control group of the same species. It is in the general knowledge of a person skilled in the art how to measure the improvement in the efficacy parameters.

The term "virus load" is well known to the person skilled in that art. The term virus load is interchangeable used with the term viral titer herein. The virus load or virus titer is a measure of the severity of an active viral infection, and can be determined by methods known to the person skilled in the art. The determination can be based on the detection of viral proteins such as by antibody binding to the viral proteins and further detection or, alternatively, by detection of viral RNA by amplification methods such as RT-PCR. Monitoring of virion associated viral RNA in plasma by nucleic acid amplification methods is a widely used parameter to assess the status and progression of retroviral disease, and to evaluate the effectiveness of prophylactic and therapeutic interventions. Exemplary, the virus load or virus titer can be calculated by estimating the live amount of virus in an involved body fluid such as a number of RNA copies per milliliter of blood plasma.

The term "ciliostasis" is well known to the person skilled in that art. The surface of the trachea is covered with specialised epithelial cells, which are lined with numerous, motile, hair-like structures called cilia. The term "ciliostasis" encompasses the reduction or loss of cilia and/or loss or partial loss of ciliary activity. Ciliostasis can be determined without further ado by the person skilled in the art.

The term "rales" is well known to the person skilled in that art. However, the term "rales" encompasses tracheal rales and refers to sounds emanating from the bronchi. Rales can be determined without further ado by the person skilled in the art.

The term "egg drop" is well known to the person skilled in that art. The term "egg drop" encompasses a decreased egg production.

In one aspect of the present invention the treatment or prevention results in a prevention or reduction of ciliostasis as compared to subjects of a non-treated control group of the same species.

In one aspect of the present invention the treatment or prevention results in a prevention or reduction of kidney lesions as compared to subjects of a non-treated control group of the same species.

In one aspect of the present invention the treatment or prevention results in a prevention or reduction of egg drop as compared to subjects of a non-treated control group of the same species.

The present invention further provides an IBV or an immunogenic composition as described herein for therapeutic use.

The present invention further provides an IBV or an immunogenic composition as described herein for use as an immunogen or vaccine.

The present invention further provides an IBV or an immunogenic composition as described herein for use as a medicament.

The present invention further provides the use of the IBV or immunogenic composition as described herein for the manufacture of a medicament.

The present invention further provides the use of the IBV or immunogenic composition as described herein for the treatment and/or prophylaxis of IBV infections in a subject.

The present invention further provides an immunogenic composition comprising a 4/91 IBV (infectious bronchitis virus) encoding for a heterologous S (spike) protein or fragment thereof, wherein said 4/91 IBV comprises a Nucleocapsid (N) protein, Envelope (E) protein or Membrane glycoprotein (M) having an amino acid sequence as shown for SEQ ID NO:3, SEQ ID NO:4, SEQ ID NO:5, EU780081 (SEQ ID NO 57), AGY56143 (SEQ ID NO 58), AGY56144 (SEQ ID NO 59) or a sequence having at least 85%, 88%, 90%, 91%, 92%, 93%, 94%, 95%, 96%, 97%, 98%, 99%, 99.2%, 99.5%, 99.6%, 99.7%, 99.8%, 99.9%, 99.95%, 99.98% or 99.99% sequence identity thereto, and, wherein the heterologous S protein or fragment thereof is selected from a list of genotypes or serotypes consisting of Massachusetts, QX, Q1, Arkansas, Variant 2 and Brazil or from an amino acid sequence as shown SEQ ID NO: 6, 7, 8, 9, 10, 11, 12, 13, 14, 15, 16 or 17 or a sequence having at least 90%, 91%, 92%, 93%, 94%, 95%, 96%, 97%, 98%, 99%, 99.2%, 99.5%, 99.6%, 99.7%, 99.8%, 99.9%, 99.95%, 99.98% or 99.99% sequence identity thereto.

In another specific aspect of the immunogenic composition according to the present invention the heterologous S protein is the full length spike protein.

In another specific aspect of the immunogenic composition according to the present invention the fragment of the heterologous S (spike) protein has a length of at least 500, 750, 1000 or 1075 amino acids from the N-Terminus.

In another specific aspect of the immunogenic composition according to the present invention the fragment of the heterologous S (spike) protein is the Ectodomain of the spike protein.

In another specific aspect of the immunogenic composition according to the present invention the IBV is attenuated.

In another specific aspect of the immunogenic composition according to the present invention the 4/91 IBV is selected from a list of genotypes or serotypes consisting of CR88 and 793B.

The present invention further provides a method of preparing an immunogenic composition for the treatment and/or prophylaxis of IBV infections in a subject comprising:

a.) providing a 4/91 IBV comprising a spike (S) protein, nucleocapsid (N) protein, envelope (E) protein or membrane glycoprotein (M) having an amino acid sequence as shown for SEQ ID NO:2, SEQ ID NO:3, SEQ ID NO:4, SEQ ID NO:5, AGY6140 (SEQ ID NO 54), AF093793 (SEQ ID NO 60), EU914938 (SEQ ID NO 55), KM067900 (SEQ ID NO 56), EU780081 (SEQ ID NO 57), AGY56143 (SEQ ID NO 58), AGY56144 (SEQ ID NO 59) or a sequence having at least 85%, 88%, 90%, 91%, 92%, 93%, 94%, 95%, 96%, 97%, 98%, 99%, 99.2%, 99.5%, 99.6%, 99.7%, 99.8%, 99.9%, 99.95%, 99.98% or 99.99% sequence identity thereto; and b.) providing a heterologous S protein or fragment thereof selected from a list of genotypes or serotypes consisting of Massachusetts, QX, Q1, Arkansas, Variant 2 and Brazil or from an amino acid sequence as shown SEQ ID NO: 6, 7, 8, 9, 10, 11, 12, 13, 14, 15, 16 or 17 or a sequence having at least 90%, 91%, 92%, 93%, 94%, 95%, 96%, 97%, 98%, 99%, 99.2%, 99.5%, 99.6%, 99.7%, 99.8%, 99.9%, 99.95%, 99.98% or 99.99% sequence identity thereto; and c.) replacing the spike protein or fragment thereof of 4/91 IBV of a) with said heterologous S (spike) protein or fragment thereof of b) to have a 4/91 IBV with a heterologous S protein or fragment thereof; and d.) obtaining said 4/91 IBV with a heterologous S protein or fragment thereof; and e.) addition of a pharmaceutically acceptable carrier.

The term "obtaining" comprises the harvest, isolation, purification and/or formulation (e.g. finishing, inactivation and/or blending) of said IBV 4/91 with a heterologous S protein or fragment thereof.

The term "harvest" refers to collecting or recovering said said IBV 4/91 with a heterologous S protein or fragment thereof from the transfected or infected cell or cell line. Any conventional method known in the art can be used, e.g. any separation method. Well known methods in the art comprise centrifugation or filtration, such as using a semi-permeable membrane having a certain pore size.

The term "isolation" comprises an isolation step of said IBV 4/91 with a heterologous S protein or fragment thereof. Methods for the isolation from the transfected or infected cell or cell line are known to a person skilled in the art. Those methods comprise physical and/or chemical methods, including but are not limited to freeze thaw cycles, treatment with ultrasound and the alike.

Methods for the "purification" of said said IBV 4/91 with a heterologous S protein or fragment thereof from the isolate are known to a person skilled in the art, for example by those methods described in Protein purification methods—a practical approach (E.L.V. Harris and S. Angel, eds., IRL Press at Oxford University Press). Those methods include, but are not limited to, separation by centrifugation and/or filtration, precipitation, size exclusion (gel filtration) chromatography, affinity chromatography, metal chelate chromatography, ion-exchange chromatography covalent chromatography, hydrophobic interaction chromatography, and the alike. The vector can be obtained in a purified pure form, or free or substantially free of other cellular materials or culture medium etc. After said isolation and/or purification the antigen exhibits a purity of at least 80%, preferably 80%-90%, more preferably 90%-97%, most preferred more than 97% up to an absolute pure form without any contamination.

According to a further aspect, "obtaining" as used herein may also include further finishing steps as part of the final formulation process, like the addition of buffer, inactivation, neutralization steps and the alike.

In another specific aspect of the method of preparing an immunogenic composition according to the present invention the fragment of the heterologous S (spike) protein is the ectodomain of the spike protein.

In another specific aspect of the immunogenic composition according to the present invention said pharmaceutically acceptable carrier is selected from the group consisting of solvents, dispersion media, coatings, stabilizing agents, diluents, preservatives, antibacterial and antifungal agents, isotonic agents, adsorption delaying agents, adjuvants, immune stimulants, and combinations thereof.

In another specific aspect of the method of preparing an immunogenic composition according to the present invention the heterologous S protein is the full length spike protein.

In another specific aspect of the method of preparing an immunogenic composition according to the present invention the 4/91 IBV is selected from a list of strains consisting of Spain/98/328, Spain/92/35, IR-3654-VM, FR-CR88061-88, FR-85131-85, UK-1233-95, UK/3/91, Spain/00/336, UK/4/91, UK/7/91, UK/793B/91, 4/91-pathogenic, 4/91 attenuated, IB4-91 and CR88.

The present invention further concerns a plasmid comprising a nucleic acid encoding a partial 4/91 IBV (infectious bronchitis virus) genome including a heterologous IBV S (spike) protein or fragment thereof, such as pUC57-s CR88 rIBV H52 S donor plasmid (SEQ ID NO:21).

CLAUSES

The following clauses are also described herein:

1. A 4/91 IBV (infectious bronchitis virus) encoding for a heterologous IBV S (spike) protein or fragment thereof.

2. An immunogenic composition comprising a 4/91 IBV (infectious bronchitis virus) encoding for a heterologous S (spike) protein or fragment thereof.

3. An immunogenic composition comprising an IBV (infectious bronchitis virus) of clause 1.

4/91 IBV—Definition by Protein Encoding Sequences

4. The IBV or the immunogenic composition of any one of clauses 1 to 3, wherein the 4/91 IBV has or consists of or comprises a nucleotide sequence as shown for KF377577 (SEQ ID NO 53) or a sequence having at least 90%, 91%, 92%, 93%, 94%, 95%, 96%, 97%, 98%, 99%, 99.2%, 99.5%, 99.6%, 99.7%, 99.8%, 99.9%, 99.95%, 99.98% or 99.99% sequence identity thereto.

5. The IBV or the immunogenic composition of any one of clauses 1 to 4, wherein the 4/91 IBV has or consists of or comprises a nucleotide sequence as shown for SEQ ID NO 1 or a sequence having at least 90%, 91%, 92%, 93%, 94%, 95%, 96%, 97%, 98%, 99%, 99.2%, 99.5%, 99.6%, 99.7%, 99.8%, 99.9%, 99.95%, 99.98% or 99.99% sequence identity thereto.

6. The IBV or the immunogenic composition of any one of clauses 1 to 5, wherein the 4/91 IBV strain has or consists of or comprises a spike (S) protein having an amino acid sequence as shown for AGY56140 (SEQ ID NO 54) or a sequence having at least 90%, 91%, 92%, 93%, 94%, 95%, 96%, 97%, 98%, 99%, 99.2%, 99.5%, 99.6%, 99.7%, 99.8%, 99.9%, 99.95%, 99.98% or 99.99% sequence identity thereto.

7. The IBV or the immunogenic composition of any one of clauses 1 to 6, wherein the 4/91 IBV strain has or consists of or comprises a spike (S1) protein having an amino acid sequence as shown for AF093793 (SEQ ID NO 60) or a sequence having at least 90%, 91%, 92%, 93%, 94%, 95%, 96%, 97%, 98%, 99%, 99.2%, 99.5%, 99.6%, 99.7%, 99.8%, 99.9%, 99.95%, 99.98% or 99.99% sequence identity thereto.

8. The IBV or the immunogenic composition of any one of clauses 1 to 7, wherein the 4/91 IBV strain has or consists of or comprises a spike (S1) protein having an amino acid sequence as shown for EU914938 (SEQ ID NO 55) or a sequence having at least 90%, 91%, 92%, 93%, 94%, 95%, 96%, 97%, 98%, 99%, 99.2%, 99.5%, 99.6%, 99.7%, 99.8%, 99.9%, 99.95%, 99.98% or 99.99% sequence identity thereto.

9. The IBV or the immunogenic composition of any one of clauses 1 to 8, wherein the 4/91 IBV strain has or consists of or comprises a spike (S1) protein having an amino acid sequence as shown for KM067900 (SEQ ID NO 56) or a sequence having at least 90%, 91%, 92%, 93%, 94% 95%, 96%, 97%, 98%, 99%, 99.2%, 99.5%, 99.6%, 99.7%, 99.8%, 99.9%, 99.95%, 99.98% or 99.99% sequence identity thereto.

10. The IBV or the immunogenic composition of any one of clauses 1 to 9, wherein the 4/91 IBV strain has or consists of or comprises a spike (S) protein having an amino acid sequence as shown SEQ ID NO:2 or a sequence having at least 90%, 91%, 92%, 93%, 94%, 95%, 96%, 97%, 98%, 99%, 99.2%, 99.5%, 99.6%, 99.7%, 99.8%, 99.9%, 99.95%, 99.98% or 99.99% sequence identity thereto.

11. The IBV or the immunogenic composition of any one of clauses 1 to 10, wherein the 4/91 IBV has or consists of or comprises a nucleocapsid (N) protein having an amino acid sequence as shown for EU780081 (SEQ ID NO 57) or a sequence having at least 95%, 96%, 97%, 98%, 99%, 99.2%, 99.5%, 99.6%, 99.7%, 99.8%, 99.9%, 99.95%, 99.98% or 99.99% sequence identity to at least one of the above mentioned sequences.

12. The IBV or the immunogenic composition of any one of clauses 1 to 11, wherein the 4/91 IBV has or consists of or comprises a nucleocapsid (N) protein having an amino acid sequence as shown SEQ ID NO:3 or a sequence having at least 95%, 96%, 97%, 98%, 99%, 99.2%, 99.5%, 99.6%, 99.7%, 99.8%, 99.9%, 99.95%, 99.98% or 99.99% sequence identity thereto.

13. The IBV or the immunogenic composition of any one of clauses 1 to 12, wherein the 4/91 IBV has or consists of or comprises an envelope (E) protein having an amino acid sequence as shown for AGY56143 (SEQ ID NO 58) or a sequence having at least least 85%, 88%, 90%, 91%, 92%, 93%, 94%, 95%, 96%, 97%, 98%, 99%, 99.2%, 99.5%, 99.6%, 99.7%, 99.8%, 99.9%, 99.95%, 99.98% or 99.99% sequence identity thereto.

14. The IBV or the immunogenic composition of any one of clauses 1 to 13, wherein the 4/91 IBV has or consists of or comprises an envelope (E) protein having an amino acid sequence as shown in SEQ ID NO:4 or a sequence having at least 95%, 96%, 97%, 98%, 99%, 99.2%, 99.5%, 99.6%, 99.7%, 99.8%, 99.9%, 99.95%, 99.98% or 99.99% sequence identity thereto.

15. The IBV or the immunogenic composition of any one of clauses 1 to 14, wherein the 4/91 IBV has or consists of or comprises a membrane glycoprotein (M) protein having an amino acid sequence as shown for AGY56144 (SEQ ID NO 59) or a sequence having at least 95%, 96%, 97%, 98%, 99%, 99.2%, 99.5%, 99.6%, 99.7%, 99.8%, 99.9%, 99.95%, 99.98% or 99.99% sequence identity thereto.

16. The IBV or the immunogenic composition of any one of clauses 1 to 15, wherein the 4/91 IBV has or consists of or comprises a membrane glycoprotein (M) protein having an amino acid sequence as shown in SEQ ID NO:5 or a sequence having at least 95%, 96%, 97%, 98%, 99%, 99.2%, 99.5%, 99.6%, 99.7%, 99.8%, 99.9%, 99.95%, 99.98% or 99.99% sequence identity thereto.

17. The IBV or the immunogenic composition of any one of clauses 1 to 16, wherein the 4/91 IBV is selected from a list of strains consisting of Spain/98/328, Spain/92/35, IR-3654-VM, FR-CR88061-88, FR-85131-85, UK-1233-95, UK/3/91, Spain/00/336, UK/4/91, UK/7/91, UK/793B/91, 4/91-pathogenic, 4/91 attenuated, IB4-91 and CR88.

Heterologous S Protein

18. The IBV or the immunogenic composition of any one of clauses 1 to 17, wherein the heterologous spike is of a non-4/91 genotype or serotype.

19. The IBV or the immunogenic composition of any one of clauses 1 to 18, wherein the heterologous S protein or fragment thereof is from an IBV with a genotype or serotype selected from a list consisting of: Arkansas (such as Arkansas 99), Brazil (such as BR-1, BR-2, 23/2013, IBV/Brasil/351/1984), California (such as California 1734/04, California 99), Connecticut, Delaware (such as Delaware 98), Dutch (such as D207, D212, D274, D3128, D3896, D8880, D1466), Florida, Georgia (such as Georgia GA-07, GA-08, GA-12, GA-13), Gray, Holte, Iowa (such as Iowa 97 and Iowa 69), Italy (such as Italy 02), JMK, LDT3, Maine (such as Maine 209), Massachusetts (M41, H52, H120), Pennsylvania (such as Pennsylvania 1220/98, Pennsylvania Wolg/98), PL84084, Qu (such as Qu-mv), QX (such as GB341/96), Q1, SE 17 and Variant 2 (such as IS/1494/06, IBV/Ck/EG/CU/4/2014, gammaCoV/Ck/Poland/G052/2016).

20. The IBV or the immunogenic composition of any one of clauses 1 to 19, wherein the heterologous S protein or fragment thereof is from an IBV selected from a list of genotypes or serotypes consisting of Massachusetts, QX, Q1, Italy 02, Arkansas, Conneticut, Georgia, LDT3, PL84084, Variant 2 or Brazil.

21. The IBV or the immunogenic composition of any one of clauses 1 to 20, wherein the heterologous S protein or fragment thereof is from an IBV selected from a list of genotypes or serotypes consisting of Massachusetts, QX, Q1, Arkansas, Variant 2 and Brazil.

22. The IBV or the immunogenic composition of clause 21, wherein the Massachusetts strain is selected from a list consisting of: H120, H52, Spain/98/308, IBMA5-1, SD/97/01, Spain/96/334, M41-M21883.

23. The IBV or the immunogenic composition of clause 21, wherein the QX strain is selected from a list consisting of: FR-L1450T-05, FR-L1450L-05, NL-L1449T-04, NL-L1449K-04, IBV/Ck/SP/170/09, IBV/Ck/SP/79/08, IBV/Ck/SP/248/09, HBN, IBVQX, LX4, BJQ, CK/CH/LGD/03 and GB341/96.

24. The IBV or the immunogenic composition of clause 21, wherein the Q1 strain is selected from a list consisting of: CK/CH/LDL/98I, CK/CH/LSD/08-10, J2, Q1, AR08ER22, AR08BA21 and Chile-295-10.

25. The IBV or the immunogenic composition of clause 21, wherein the Arkansas strain is selected from a list consisting of: Ark99, ArkGA, ArkDPI, AL/5364/00, ARKDPI11, AL/0803/01, AL/7149/00, ArkDPI101, AL/1221/01, AL/1793/01 and AL/4614/98.

26. The IBV or the immunogenic composition of clause 21, wherein the Variant 2 strain is selected from a list consisting of: IS/1494/06, IBV/Ck/EG/CU/4/2014, gammaCoV/Ck/Poland/G052/2016, Eg/CLEVB-2/IBV/012, D1344/2/4/10 EG, TR8 and IB VAR2-06.

27. The IBV or the immunogenic composition of clause 21, wherein the Brazil strain is selected from a list consisting of: BR-1, BR-2, 23/2013 and IBV/Brasil/351/1984.

28. The IBV or the immunogenic composition of any one of clauses 1 to 27, wherein the heterologous S protein or fragment thereof is from Massachusetts genotype or serotype.

29. The IBV or the immunogenic composition of any one of clauses 1 to 28, wherein the heterologous S protein or fragment thereof is from genotype or serotype Massachusetts having at least 90%, 91%, 92%, 93%, 94%, 95%, 96%, 97%, 98%, 99%, 99.2%, 99.5%, 99.6%, 99.7%, 99.8%, 99.9%, 99.95%, 99.98% or 99.99% sequence identity to SEQ ID NO: 6 or 7 or the heterologous S protein or fragment thereof consists of or comprises an amino acid sequence as shown in SEQ ID NO: 6 or 7 or a sequence having at least 90%, 91%, 92%, 93%, 94%, 95%, 96%, 97%, 98%, 99%, 99.2%, 99.5%, 99.6%, 99.7%, 99.8%, 99.9%, 99.95%, 99.98% or 99.99% sequence identity thereto.

30. The IBV or the immunogenic composition of any one of clauses 1 to 29, wherein the heterologous S protein or fragment thereof is from genotype or serotype QX having at least 90%, 91%, 92%, 93%, 94%, 95%, 96%, 97%, 98%, 99%, 99.2%, 99.5%, 99.6%, 99.7%, 99.8%, 99.9%, 99.95%, 99.98% or 99.99% sequence identity to SEQ ID NO: 8 or 9 or the heterologous S protein or fragment thereof consists of or comprises an amino acid sequence as shown in SEQ ID NO: 8 or 9 or a sequence having at least 90%, 91%, 92%, 93%, 94%, 95%, 96%, 97%, 98%, 99%, 99.2%, 99.5%, 99.6%, 99.7%, 99.8%, 99.9%, 99.95%, 99.98% or 99.99% sequence identity thereto.

31. The IBV or the immunogenic composition of any one of clauses 1 to 30, wherein the heterologous S protein or fragment thereof is from genotype or serotype Q1 having at least 90%, 91%, 92%, 93%, 94%, 95%, 96%, 97%, 98%, 99%, 99.2%, 99.5%, 99.6%, 99.7%, 99.8%, 99.9%, 99.95%, 99.98% or 99.99% sequence identity to SEQ ID NO: 10 or 11 or the heterologous S protein or fragment thereof consists of or comprises an amino acid sequence as shown in SEQ ID NO: 10 or 11 or a sequence having at least 90%, 91%, 92%, 93%, 94%, 95%, 96%, 97%, 98%, 99%, 99.2%, 99.5%, 99.6%, 99.7%, 99.8%, 99.9%, 99.95%, 99.98% or 99.99% sequence identity thereto.

32. The IBV or the immunogenic composition of any one of clauses 1 to 31, wherein the heterologous S protein or fragment thereof is from genotype or serotype Arkansas having at least 90%, 91%, 92%, 93%, 94%, 95%, 96%, 97%, 98%, 99%, 99.2%, 99.5%, 99.6%, 99.7%, 99.8%, 99.9%, 99.95%, 99.98% or 99.99% sequence identity to SEQ ID NO: 12 or 13 or the heterologous S protein or fragment thereof consists of or comprises an amino acid sequence as shown in SEQ ID NO: 12 or 13 or a sequence having at least 90%, 91%, 92%, 93%, 94%, 95%, 96%, 97%, 98%, 99%, 99.2%, 99.5%, 99.6%, 99.7%, 99.8%, 99.9%, 99.95%, 99.98% or 99.99% sequence identity thereto.

33. The IBV or the immunogenic composition of any one of clauses 1 to 32, wherein the heterologous S protein or fragment thereof is from genotype or serotype Variant 2 having at least 90%, 91%, 92%, 93%, 94%, 95%, 96%, 97%, 98%, 99%, 99.2%, 99.5%, 99.6%, 99.7%, 99.8%, 99.9%, 99.95%, 99.98% or 99.99% sequence identity to SEQ ID NO: 14 or 15 or the heterologous S protein or fragment thereof consists of or comprises an amino acid sequence as shown in SEQ ID NO: 14 or 15 or a sequence having at least 90%, 91%, 92%, 93%, 94%, 95%, 96%, 97%, 98%, 99%, 99.2%, 99.5%, 99.6%, 99.7%, 99.8%, 99.9%, 99.95%, 99.98% or 99.99% sequence identity thereto.

34. The IBV or the immunogenic composition of any one of clauses 1 to 33, wherein the heterologous S protein or fragment thereof is from genotype or serotype Brazil having at least 90%, 91%, 92%, 93%, 94%, 95%, 96%, 97%, 98%, 99%, 99.2%, 99.5%, 99.6%, 99.7%, 99.8%, 99.9%, 99.95%, 99.98% or 99.99% sequence identity to SEQ ID NO:16 or 17 or the heterologous S protein or fragment thereof consists of or comprises an amino acid sequence as shown in SEQ ID NO: 16 or 17 or a sequence having at least 90%, 91%, 92%, 93%, 94%, 95%, 96%, 97%, 98%, 99%, 99.2%, 99.5%, 99.6%, 99.7%, 99.8%, 99.9%, 99.95%, 99.98% or 99.99% sequence identity thereto.

35. The IBV or the immunogenic composition of any one of clauses 1 to 34, wherein the heterologous S protein or fragment thereof is selected from a list consisting of SEQ ID NO: 6, 7, 8, 9, 10, 11, 12, 13, 14, 15, 16 or 17.

36. The IBV or the immunogenic composition of any one of clauses 1 to 35, wherein the heterologous S protein is the full length spike protein.

37. The IBV or the immunogenic composition of any one of clauses 1 to 36, wherein the fragment of the heterologous S (spike) protein has a length of at least 500, 750, 1000 or 1075 amino acids.

38. The IBV or the immunogenic composition of any one of clauses 1 to 37, wherein the fragment of the heterologous S (spike) protein has a length of at least 500, 750, 1000 or 1075 amino acids from the N-Terminus.

39. The IBV or the immunogenic composition of any one of clauses 1 to 38, wherein the fragment of the heterologous S (spike) protein has a length of at least 1000 amino acids.

40. The IBV or the immunogenic composition of any one of clauses 1 to 39, wherein the fragment of the heterologous S (spike) protein is the ectodomain of the spike protein.

41. The IBV or the immunogenic composition of any one of clauses 1 to 40, wherein the heterologous S (spike) protein or fragment thereof replaces the homologous S protein or fragment thereof.

42. The IBV or the immunogenic composition of any one of clauses 1 to 41, wherein the heterologous S (spike) protein or fragment thereof replaces the natural occurring S protein or fragment thereof.

43. The IBV or the immunogenic composition of any one of clauses 1 to 42, wherein the heterologous S (spike) protein or fragment thereof replaces the S protein or fragment thereof in 4/91.

44. The IBV or the immunogenic composition of any one of clauses 1 to 43, wherein the IBV is attenuated.

45. The IBV or the immunogenic composition of any one of clauses 1 to 43, wherein the IBV is inactivated.

46. The IBV or the immunogenic composition of any one of clauses 1 to 45, wherein the IBV is genetically engineered.

47. The IBV or the immunogenic composition of any one of clauses 1 to 46, wherein the IBV is a recombinant IBV.

48. The immunogenic composition of any one of clauses 2 to 47, wherein the immunogenic composition is a vaccine.

49. The immunogenic composition of any one of clauses 2 to 48, wherein the immunogenic composition comprises a pharmaceutically acceptable carrier.

50. The immunogenic composition of clause 49, wherein the pharmaceutically acceptable carrier is phosphate buffered saline.

51. The immunogenic composition of any one of clauses 2 to 50, wherein the immunogenic composition is effective in the treatment and/or prophylaxis of clinical signs caused by IBV in a subject of need.

52. The immunogenic composition of any one of clauses 2 to 51, wherein the immunogenic composition protects against a challenge with an IBV strain of the genotype or serotype of the heterologous spike protein.

53. The immunogenic composition of any one of clauses 2 to 52, wherein the immunogenic composition protects against a challenge with strains of Massachusetts, QX, Q1, Arkansas Variant 2 or Brazil genotype.

54. The immunogenic composition of any one of clauses 2 to 53, wherein the immunogenic composition protects against a challenge with strains of Massachusetts genotype.

55. The immunogenic composition of any one of clauses 2 to 54, wherein said immunogenic composition is formulated for a single-dose administration.

56. The immunogenic composition of any one of clauses 2 to 55, wherein said immunogenic composition is administered subcutaneously, intramuscularly, oral, in ovo, via spray, via drinking water or by eye drop.

57. The immunogenic composition of any one of clauses 2 to 56, wherein the immunogenic composition comprises 1 to 10 $\log_{10}$ $EID_{50}$ per dose of the IBV.

58. The immunogenic composition of any one of clauses 2 to 57, wherein the immunogenic composition comprises 2 to 5 $\log_{10}$ $EID_{50}$ per dose of the IBV.

59. The immunogenic composition of any one of clauses 2 to 58, wherein the immunogenic composition comprises 2 to 4 $\log_{10}$ $EID_{50}$ per dose of the IBV.

60. A kit comprising the IBV or the immunogenic composition of any one of clauses 1 to 59.

61. The kit according to clause 60, wherein the kit further comprises an instruction letter for the treatment and/or prophylaxis of diseases of avians.

62. The kit according to clause 60, wherein the kit further comprises an instruction letter for the treatment and/or prophylaxis of diseases of poultry.

63. The kit according to clauses 60, wherein the kit further comprises an instruction letter for the treatment and/or prophylaxis of IB.

64. A method for immunizing a subject comprising administering to such subject an immunogenic composition according to any one of clauses 2 to 59.

65. A method of treating or preventing clinical signs caused by IBV in a subject of need, the method comprising administering to the subject a therapeutically effective amount of an immunogenic composition according to any one of clauses 2 to 59.

66. A method of reducing the ciliostasis in a subject of need, in comparison to a subject of a non-immunized control group of the same species, the method comprising administering to the subject a therapeutically effective amount of an immunogenic composition according to any one of clauses 2 to 59.

67. The immunogenic composition according to any one of clauses 2 to 59 for use in a method for immunizing a subject, the method comprising administering to the subject a therapeutically effective amount of said immunogenic composition.

68. The immunogenic composition according to any one of clauses 2 to 59 for use in a method of treating or preventing clinical signs caused by IBV in a subject of need, the method comprising administering to the subject a therapeutically effective amount of said immunogenic composition.

69. The immunogenic composition according to any one of clauses 2 to 59 for use in a method of reducing the ciliostasis in a subject of need, in comparison to a subject of a non-immunized control group of the same species, the method comprising administering to the subject a therapeutically effective amount of said immunogenic composition.

70. The method or use of any one of clauses 64 to 69, wherein said subject is avian.

71. The method or use of any one of clauses 64 to 70, wherein said subject is poultry.

72. The method or use of any one of clauses 64 to 71, wherein said subject is selected from the list consisting of chicken, turkey, quail, or pheasant.

73. The method or use of any one of clauses 64 to 72, wherein said subject is chicken.

74. The method or use of any one of clauses 64 to 73, wherein the immunogenic composition is administered once.

75. The method or use of any one of clauses 64 to 73, wherein the immunogenic composition is administered at two or more doses.

76. The method or use of any one of clauses 64 to 75, wherein said immunogenic composition is administered subcutaneously, intramuscularly, oral, in ovo, via spray, via drinking water or by eye drop.

77. The method or use of any one of clauses 64 to 76, wherein said immunogenic composition is administered via eye drop.

78. The method or use of any one of clauses 64 to 77, wherein the immunogenic composition comprises 1 to 10 $log_{10}$ $EID_{50}$ per dose of the IBV.
79. The method or use of any one of clauses 64 to 78, wherein the immunogenic composition comprises 2 to 5 $log_{10}$ $EID_{50}$ per dose of the IBV.
80. The method or use of any one of clauses 64 to 79, wherein the immunogenic composition comprises 2 to 4 $log_{10}$ $EID_{50}$ per dose of the IBV.
81. The method or use of any one of clauses 64 to 80, wherein the immunogenic composition is administered to subjects within the first week of age, within the first three days of age, within the first two days of age, or within the first day of age.
82. The method or use of any one of clauses 64 to 81, wherein the immunogenic composition is administered to subjects within the first day of age.
83. The method or use of any one of clauses 64 to 82, wherein said method results in an improvement in an efficacy parameter selected from the group consisting of: prevention or reduction of ciliostasis, prevention or reduction of rales, prevention or reduction of egg drop, prevention or reduction of kidney lesions, prevention or reduction of watery diarrhea, prevention or reduction in weight loss, a lower virus load, a reduced viral shedding or combinations thereof, in comparison to a subject of a non-treated control group of the same species.
84. The method or use of any one of clauses 64 to 83, wherein the treatment or prevention results in a prevention or reduction of ciliostasis as compared to subjects of a non-treated control group of the same species.
85. The method or use of any one of clauses 64 to 84, wherein the treatment or prevention results in a prevention or reduction of kidney lesions as compared to subjects of a non-treated control group of the same species.
86. The method or use of any one of clauses 64 to 85, wherein the treatment or prevention results in a prevention or reduction of egg drop as compared to subjects of a non-treated control group of the same species.
87. The IBV or immunogenic composition of any one of clauses 1 to 59 for therapeutic use.
88. The IBV or immunogenic composition of any one of clauses 1 to 59 for use as an immunogen or vaccine.
89. The IBV or immunogenic composition any one of clauses 1 to 59 for use as a medicament.
90. Use of the IBV or immunogenic composition of any one of clauses 1 to 59 for the manufacture of a medicament.
91. Use of the IBV or immunogenic composition of any one of clauses 1 to 59 for the treatment and/or prophylaxis of IBV infections in a subject.
92. An immunogenic composition comprising a 4/91 IBV (infectious bronchitis virus) encoding for a heterologous S (spike) protein or fragment thereof, wherein said 4/91 IBV comprises a Nucleocapsid (N) protein, Envelope (E) protein or Membrane glycoprotein (M) having or consisting of or comprising an amino acid sequence as shown for SEQ ID NO:3, SEQ ID NO:4, SEQ ID NO:5, EU780081 (SEQ ID NO 57), AGY56143 (SEQ ID NO 58), AGY56144 (SEQ ID NO 59) or a sequence having at least 85%, 88%, 90%, 91%, 92%, 93%, 94%, 95%, 96%, 97%, 98%, 99%, 99.2%, 99.5%, 99.6%, 99.7%, 99.8%, 99.9%, 99.95%, 99.98% or 99.99% sequence identity thereto, and, wherein the heterologous S protein or fragment thereof is selected from a list of genotypes or serotypes consisting of Massachusetts, QX, Q1, Arkansas, Variant 2 and Brazil or from an amino acid sequence as shown SEQ ID NO: 6, 7, 8, 9, 10, 11, 12, 13, 14, 15, 16 or 17 or a sequence having at least 90%, 91%, 92%, 93%, 94%, 95%, 96%, 97%, 98%, 99%, 99.2%, 99.5%, 99.6%, 99.7%, 99.8%, 99.9%, 99.95%, 99.98% or 99.99% sequence identity thereto or the heterologous S protein or fragment thereof consists of or comprises an amino acid sequence as shown in SEQ ID NO: 6, 7, 8, 9, 10, 11, 12, 13, 14, 15, 16 or 17 or a sequence having at least 90%, 91%, 92%, 93%, 94%, 95%, 96%, 97%, 98%, 99%, 99.2%, 99.5%, 99.6%, 99.7%, 99.8%, 99.9%, 99.95%, 99.98% or 99.99% sequence identity thereto.
93. The immunogenic composition of clause 92, wherein the heterologous S protein is the full length spike protein.
94. The immunogenic composition of clause 92 or 93, wherein the fragment of the heterologous S (spike) protein has a length of at least 500, 750, 1000 or 1075 amino acids from the N-Terminus.
95. The immunogenic composition of any one of clause 92 to 94, wherein the fragment of the heterologous S (spike) protein is the Ectodomain of the spike protein.
96. The immunogenic composition of any one of clauses 92 to 95, wherein the IBV is attenuated.
97. The immunogenic composition of any one of clauses 92 to 96, wherein the 4/91 IBV is selected from a list of strains consisting of Spain/98/328, Spain/92/35, IR-3654-VM, FR-CR88061-88, FR-85131-85, UK-1233-95, UK/3/91, Spain/00/336, UK/4/91, UK/7/91, UK/793B/91, 4/91-pathogenic, 4/91 attenuated, IB4-91 and CR88.
98. A method of preparing an immunogenic composition for the treatment and/or prophylaxis of IBV infections in a subject comprising:

a.) providing a 4/91 IBV comprising a spike (S) protein, Nucleocapsid (N) protein, Envelope (E) protein or Membrane glycoprotein (M) having or consisting of or comprising an amino acid sequence as shown for SEQ ID NO:2, SEQ ID NO:3, SEQ ID NO:4, SEQ ID NO:5, AGY6140 (SEQ ID NO 54), AF093793 (SEQ ID NO 60), EU914938 (SEQ ID NO 55), KM067900 (SEQ ID NO 56), EU780081 (SEQ ID NO 57), AGY56143 (SEQ ID NO 58), AGY56144 (SEQ ID NO 59) or a sequence having at least 95%, 96%, 97%, 98%, 99%, 99.2%, 99.5%, 99.6%, 99.7%, 99.8%, 99.9%, 99.95%, 99.98% or 99.99% sequence identity thereto; and b.) providing a heterologous S protein or fragment thereof selected from a list of genotypes or serotypes consisting of Massachusetts, QX, Q1, Arkansas, Variant 2 and Brazil or from an amino acid sequence as shown SEQ ID NO: 6, 7, 8, 9, 10, 11, 12, 13, 14, 15, 16 or 17 or a sequence having at least 90%, 91%, 92%, 93%, 94%, 95%, 96%, 97%, 98%, 99%, 99.2%, 99.5%, 99.6%, 99.7%, 99.8%, 99.9%, 99.95%, 99.98% or 99.99% sequence identity thereto or providing a heterologous S protein or fragment thereof consisting of or comprising an amino acid sequence as shown in SEQ ID NO: 6, 7, 8, 9, 10, 11, 12, 13, 14, 15, 16 or 17 or a sequence having at least 90%, 91%, 92%, 93%, 94%, 95%, 96%, 97%, 98%, 99%, 99.2%, 99.5%, 99.6%, 99.7%, 99.8%, 99.9%, 99.95%, 99.98% or 99.99% sequence identity thereto; and c.) replacing the spike protein of 4/91 IBV of a) with said heterologous S (spike) protein or fragment thereof of b) to have a 4/91 IBV with a heterologous S protein or fragment thereof; and d.) obtaining said 4/91 IBV with a heterologous S protein or fragment thereof; and e.) addition of a pharmaceutically acceptable carrier.

99. The method of clause 98, wherein the fragment of the heterologous S (spike) protein is the Ectodomain of the spike protein.

100. The method of clause 98 or 99, wherein said pharmaceutically acceptable carrier is selected from the group consisting of solvents, dispersion media, coatings, stabilizing agents, diluents, preservatives, antibacterial and antifungal agents, isotonic agents, adsorption delaying agents, adjuvants, immune stimulants, and combinations thereof.

101. The method of clause 98 or 100, wherein the heterologous S protein is the full length spike protein.

102. The method of any one of clauses 98 to 101, wherein the 4/91 IBV is selected from a list of strains consisting of Spain/98/328, Spain/92/35, IR-3654-VM, FR-CR88061-88, FR-85131-85, UK-1233-95, UK/3/91, Spain/00/336, UK/4/91, UK/7/91, UK/793B/91, 4/91-pathogenic, 4/91 attenuated, IB4-91 and CR88.

BRIEF DESCRIPTION OF THE DRAWINGS

FIG. 1. In ovo replication kinetics for CR88 rIBV H52 S in comparison to recombinant wild type viruses CR88 and H52. Data points represent the mean of 5 samples per time point. Error bars indicate the standard deviation.

FIG. 2. Summary of ciliostasis scoring. The sum of the 10 individual scores for the 10 rings of one animal is calculated and is represented by one dot in the graph. Maximum ciliostasis corresponds to a score of 40, while absence of ciliostasis is represented by a score of 0. Mean and significance are calculated using GraphPad Prism and an ordinary one-way ANOVA test ($p<0.0001$).

SEQUENCES OVERVIEW

SEQ ID NO:1 CR88 genome

Figure 3:
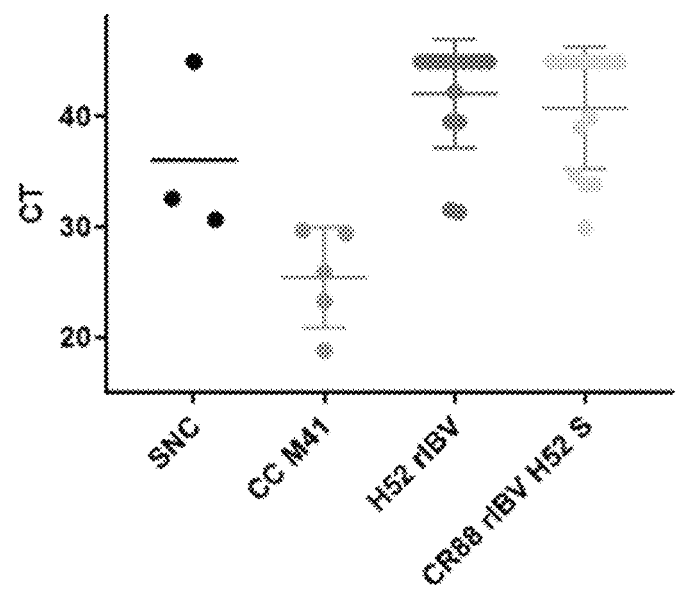
FIG. 3. Summary of RT-qPCR results of kidney tissues. Each individual bird is indicated by one data point.
Figure 4:
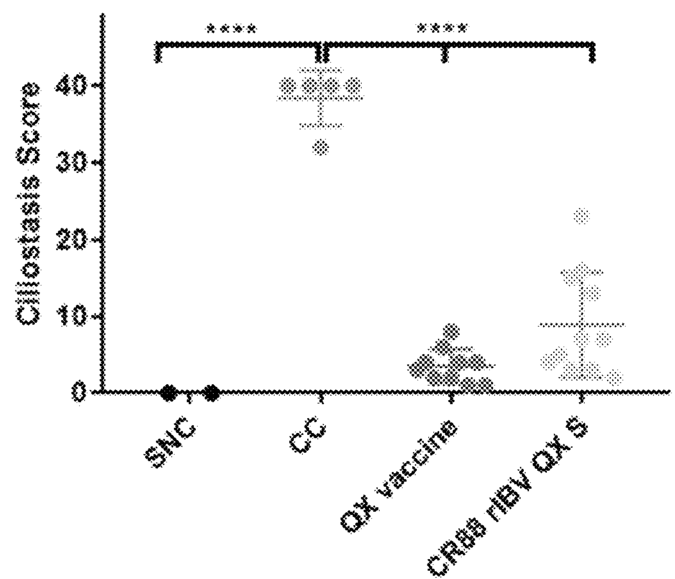
FIG. 4. Summary of ciliostasis scoring. The sum of the 10 individual scores for the 10 rings of one animal is calculated and is represented by one dot in the graph. Maximum ciliostasis corresponds to a score of 40, while absence of ciliostasis is represented by a score of 0. Mean and significance are calculated using GraphPad Prism and an ordinary one-way ANOVA test ($p<0.0001$).

SEQ ID NO:2: CR88 IBV spike (S) protein.

SEQ ID NO:3: CR88 IBV Nucleocapsid (N) protein.

SEQ ID NO:4: CR88 IBV Envelope (E) protein.

SEQ ID NO:5: CR88 IBV Membrane glycoprotein (M) protein.

SEQ ID NO:6 and 7: Heterologous S protein or fragment from genotype or serotype Massachusetts.

SEQ ID NO:8 and 9: Heterologous S protein or fragment thereof from genotype or serotype QX.

SEQ ID NO:10 and 11: Heterologous S protein or fragment thereof from genotype or serotype Q1.

SEQ ID NO:12 and 13: Heterologous S protein or fragment thereof from genotype or serotype Arkansas.

SEQ ID NO:14 and 15: Heterologous S protein or fragment thereof from genotype or serotype Variant 2.

SEQ ID NO:16 and 17: Heterologous S protein or fragment thereof from genotype or serotype Brazil.

SEQ ID NO:18: pUC57-s CR88 mIBV.

SEQ ID NO:19: IBV H52 Spike nucleic acid coding sequence

SEQ ID NO:20: IBV CR88 Spike nucleic acid coding sequence

SEQ ID NO:21 pUC57-s CR88 rIBV donor plasmid.

SEQ ID NO:22: pUC57-s CR88 rIBV H52 S donor plasmid.

SEQ ID NO:23 to SEQ ID NO:52 Primer.

SEQ ID NO:53 KF377577 (4/91 IBV nucleotide sequence)

SEQ ID NO:54 AGY56140 (4/91 IBV Spike protein amino acid sequence)

SEQ ID NO:55 EU914938 (4/91 IBV Spike protein amino acid sequence)

SEQ ID NO:56 KM067900 (4/91 IBV Spike protein amino acid sequence)

SEQ ID NO:57 EU780081 (4/91 IBV Spike protein amino acid sequence)

SEQ ID NO:58 AGY56143 (4/91 IBV E protein amino acid sequence)

SEQ ID NO:59 AGY56144 (4/91 IBV M protein amino acid sequence)

SEQ ID NO:60 AF093793 (4/91 IBV Spike protein amino acid sequence)

SEQ ID NO:61 Primer

EXAMPLES

The following examples are set forth below to illustrate specific embodiments of the present invention. These examples are merely illustrative and are understood not to limit the scope or the underlying principles of the present invention.

Example 1

Generation of Recombinant IBV CR88 in Which the Coding Sequence for the CR88 Spike is Replaced by the Coding Sequence for a Heterologous Spike or Spike Ectodomain Targeted RNA Recombination and Rescue of Recombinant IBV For the generation of recombinant IBV the method of targeted RNA recombination as described by van Beurden et al. (Virol J. 2017; 14(1):109) is applied. A murinized helper virus (mIBV) is generated to enable the targeted recombination of IBV in cell culture.

Construction of an IBV CR88 Murinized Donor Plasmid

To generate the CR88 murinized (m)IBV donor plasmid the donor sequence is synthesized by a commercial supplier: 497 bases of the 5' UTR of the CR88 genome are fused to the 3' part of the lab region (752 bases) and the first 72 bases coding for the CR88 IBV spike, followed by 3753 bases of the MHV spike ectodomain, continuing with the terminal 210 bases of the CR88 IBV spike and the following sequence until the 3' end of the genome. In addition, a SacI restriction site and the sequence of the T7 promoter are added to the 5' end of the donor region, as well as a 100× polyA sequence, followed by a Not I restriction site for linearization at the 3' end. respectively. A silent A to C mutation at position 5634 of the assembled sequence is introduced to generate an XhoI restriction site. The synthesized sequence is inserted into pUC57-simple to yield the pUC57-s CR88 mIBV donor plasmid (SEQ ID NO:18).

Rescue of CR88 mIBV

CR88 mIBV is rescued in analogy to H52 mIBV (van Beurden et al. Virol J. 2017; 14(1):109) with some alterations: The virus allantoic fluid stock is concentrated via ultracentrifugation before isolation of the viral RNA for electroporation. 18 ml of viral allantoic fluid are centrifuged at 50,000×g for 2 hours through a 2 ml 20% Sucrose cushion in TNE (Tris, NaCl, EDTA) buffer. The supernatant is discarded and the pellet resuspended in 150 μl TNE buffer followed by RNA isolation with QIAamp viral RNA mini kit (Qiagen). Further, chicken embryo fibroblasts (CEFs)

instead of BHK cells are used for electroporation (2 pulses 250V/300 μF, 10 sec break) and 1.25% DMSO is added to the electroporation mixture.

Construction of an IBV CR88 Donor Plasmid in which the Coding Sequence for the CR88 Spike is Replaced by the Coding Sequence for a Heterologous Spike or Spike Ectodomain Exemplary the construction for the replacement of the CR88 spike by the H52 spike is described. The IBV H52 spike nucleic acid coding sequence (SEQ ID NO:19) is used as a template to replace the IBV CR88 spike nucleic acid coding sequence (SEQ ID NO:20) in the pUC57-s CR88 rIBV donor plasmid (generated as described above for the mIBV plasmid by keeping the complete CR88 Spike sequence (SEQ ID NO:21)). Bases 1657 to 5151 of SEQ ID NO:21 are replaced with the corresponding IBV H52 spike nucleic acid coding sequence (SEQ ID NO:19). This results in the pUC57-s CR88 rIBV H52 S donor plasmid (SEQ ID NO:22) in which the IBV H52 spike is encoded by bases 1657 to 5145. For this, the H52 spike nucleic acid coding sequence and the pUC57-s CR88 backbone sequence are amplified in two separate PCR reactions with Q5C) High-Fidelity DNA Polymerase (NEB; see table 1 for primers). The PCR products are purified by QIAquick gel extraction kit (QIiagen) and are subsequently used for Gibson assembly with the NEBuilder® HiFi DNA Assembly Cloning Kit (NEB) according to the kit protocol to generate the pUC57-s CR88 rIBV H52 S donor plasmid (SEQ ID NO:22).

TABLE 1

Gibson assembly primers designed with the NEBuilder online tool by NEB and used to generate PCR products to assemble the pUC57-s CR88 rIBV H52 S donor plasmid (SEQ ID NO: 22).

| PCR | Product | Primer |
|---|---|---|
| 1 | CR88 backbone | tgattaaaagtcccacatcttttc taatattattaattcttctttgg (SEQ ID NO: 23) ctcttaccagtaacttaccacact taattaaattaaagactaagtc (SEQ ID NO: 24) |
| 2 | H52 Spike | aagtgtggtaagttactggtaaga gatgttggtaacacctcttttac (SEQ ID NO: 25) agaaaagatgtgggacttttaatc attaaacagactttttaggtctg (SEQ ID NO: 26) |

Targeted RNA Recombination and Rescue of Recombinant IBV

For the rescue of CR88 rIBV with heterologous spike or spike ectodomain, LR7 cells are infected with CR88 mIBV and electroporated with in vitro transcript, generated from the pUC57-s CR88 rIBV H52 S donor plasmid after NotI linearization. Subsequently, cells and supernatant are injected into 8-day old embryonated SPF chicken eggs (VALO BioMedia) which are incubated up to 9 days at 37.5° C. and 60% humidity. The allantoic fluid of eggs with dead embryos is harvested and used for an end-point dilution in 8-day old SPF eggs. Nucleic acids isolation of allantoic fluid samples of the limiting dilution is performed using the MagMAX™ Core Nucleic Acid Purification Kit (ThermoFisher) with the KingFisher™ Duo Prime Purification System (ThermoFisher). Nucleic acids are subsequently analyzed for the presence and relative quantity of rIBV via IBV specific RT-qPCR with a protocol adapted from Callison et al. (J Virol Methods. 2006; 138(1-2):60-5). Briefly, the same primers and probe are used and the thermoprofile is adapted for the use of TaqMan® Fast Virus 1-Step Master Mix (ThermoFisher) and the a StepOnePlus™ Real-Time PCR System (ThermoFisher). Afterwards, the positive-tested allantoic fluid of the egg inoculated with the highest dilution is used for propagation in 8-day old embryonated SPF chicken eggs. The allantoic fluid is diluted 1:100 in 1×PBS and 100 μl are injected per egg. Allantoic fluid is harvested 48 hours post inoculation, cleared from debris and stored at −80° C. and again analyzed by RT-qPCR to confirm stock quality.

To confirm the correct insertion of the spike in the generated rIBV, viral nucleic acid is isolated with the QIAamp viral RNA mini kit followed by the SuperScript III One-Step RT-PCR using the primers listed in table 2, QIAquick PCR purification and subsequent Sanger sequencing performed by a commercial supplier.

TABLE 2

PCR and sequencing primers to confirm the correct insertion and spike sequence in CR88 rIBV H52 S.

| PCR | Name | Sequence | Region | Purpose | Amplicon [bp] |
|---|---|---|---|---|---|
| 1 | PO1565 | caggattgtgcatggtggac (SEQ ID NO: 27) | 1 ab | PCR + Sequencing | 2468 |
| | PO764 | agaaaacctaaaggtcctgc (SEQ ID NO: 28) | S | PCR + Sequencing | |
| | PO618 | taaatggtgatcttgttt (SEQ ID NO: 29) | S | Sequencing | n/a |
| | PO1410 | tttgtatacgagagccatca (SEQ ID NO: 30) | S | Sequencing | |
| 2 | PO1400 | ttgccttcagtatgtttgtg (SEQ ID NO: 31) | S | PCR + Sequencing | 2531 |
| | PO635 | ctgcgacaagacctcctg (SEQ ID NO: 32) | M | PCR + Sequencing | |

TABLE 2-continued

PCR and sequencing primers to confirm the correct insertion and spike sequence in CR88 rIBV H52 S.

| PCR Name | Sequence | Region | Purpose | Amplicon [bp] |
|---|---|---|---|---|
| P0619 | tgctgcttcctttaataag (SEQ ID NO: 33) | S | Sequencing | n/a |
| P01183 | cgctgttgtgacactctatg (SEQ ID NO: 34) | S | Sequencing | |

Generation and Characterization of CR88 Recombinant IBV in Which the Coding Sequence for the CR88 Spike or Spike Ectodomain is Replaced by the Coding Sequence for a Spike From Another IBV Genotype The same methods as described for the generation of CR88 rIBV H52 S are applied to generate and characterize CR88 recombinant IBV in which the CR88 spike coding sequence (bases 1657 to 5151 in SEQ ID NO:21) or CR88 spike ectodomain coding sequence (bases 1711 to 4941 in SEQ ID NO:21) is replaced with the coding sequences for the IBV spike or spike ectodomain of the serotypes and genotypes listed in Table 3.

TABLE 3

Primers used for Gibson assembly of H52 rIBV donor plasmids with heterologous spikes or spike ectodomains.

| spike | PCR | product | primer |
|---|---|---|---|
| H52 S Ecto SEQ ID NO: 6 | 1 | CR88 backbone | tggccttggtatgtgtgg (SEQ ID NO: 35) agcactacatagtgcatac (SEQ ID NO: 36) |
| | 2 | H52 S Ecto | tctttggtatgcactatgtagtgctgcttttgtatgactcgagttc (SEQ ID NO: 37) tggcaagccacacataccaaggccacttaatataagttttgagtattgaaagtttttc (SEQ ID NO: 38) |
| QX S SEQ ID NO: 7 | 1 | CR88 backbone | tgattaaaagtcccacatcttttctaatattattaattcttctttgg (SEQ ID NO: 23) ctcttaccagtaacttaccacacttaattaaattaaagactaagtc (SEQ ID NO: 24) |
| | 2 | QX S | aagtgtggtaagttactggtaagagatgttggtgaagtcactg (SEQ ID NO: 39) agaaaagatgtgggacttttaatcattaaacagactttttaggtctg (SEQ ID NO: 26) |
| QX S Ecto SEQ ID NO: 8 | 1 | CR88 backbone | tggccttggtatgtgtgg (SEQ ID NO: 35) agcactacatagtgcatac (SEQ ID NO: 36) |

TABLE 3-continued

Primers used for Gibson assembly of H52 rIBV donor plasmids with heterologous spikes or spike ectodomains.

| spike | PCR | product | primer |
|---|---|---|---|
| | 2 | QX S Ecto | tctttggtatgcactatgtagtgctaatttgtttgattctgataataattatg (SEQ ID NO: 40) tggcaagccacacataccaaggccacttaatataagttttaattattgaaagttcttc (SEQ ID NO: 41) |
| Q1 S SEQ ID NO: 9 | 1 | CR88 backbone | tgattaaaagtcccacatcttttctaatattattaattcttctttgg (SEQ ID NO: 23) ctcttaccagtaacttaccacacttaattaaattaaagactaagtc (SEQ ID NO: 24) |
| | 2 | Q1 S | aagtgtggtaagttactggtaagagatgttggggaagtcactg (SEQ ID NO: 42) agaaaagatgtgggacttttaatcattaaacagactttttaggtctg (SEQ ID NO: 26) |
| Q1 S Ecto SEQ ID NO: 10 | 1 | CR88 backbone | tggccttggtatgtgtgg (SEQ ID NO: 35) agcactacatagtgcatac (SEQ ID NO: 36) |
| | 2 | Q1 S Ecto | tctttggtatgcactatgtagtgctgcttttgtttgataataatgaaac (SEQ ID NO: 43) tggcaagccacacataccaaggccatttaatataagtcttgagtattgaaag (SEQ ID NO: 44) |
| Ark S SEQ ID NO 11 | 1 | CR88 backbone | ggtaacttaacaatacagacctaaaaagtctg (SEQ ID NO: 61) ctcttaccagtaacttaccacacttaattaaattaaagactaagtc (SEQ ID NO: 24) |

TABLE 3-continued

Primers used for Gibson assembly of H52 rIBV donor plasmids with heterologous spikes or spike ectodomains.

| spike | PCR | product | primer |
|---|---|---|---|
| | 2 | Ark S | aagtgtggtaagttactggtaagagatgttggtgaagtcactg (SEQ ID NO: 39)<br>gtctgtattgttaagttaccacatcgttatc (SEQ ID NO: 45) |
| Ark S Ecto SEQ ID NO 12 | 1 | CR88 backbone | tggccttggtatgtgtgg (SEQ ID NO: 35)<br>agcactacatagtgcatac (SEQ ID NO: 36) |
| | 2 | Ark S Ecto | tctttggtatgcactatgtagtgctaatttatatgacaacgaatcttttg (SEQ ID NO: 46)<br>tggcaagccacacataccaaggccacttaatataagttttgagtattgaaag (SEQ ID NO: 47) |
| Variant 2 S SEQ ID NO 13 | 1 | CR88 backbone | ggtaacttaacaatacagacctaaaaagtctg (SEQ ID NO: 61)<br>ctcttaccagtaacttaccacacttaattaaattaaagactaagtc (SEQ ID NO: 24) |
| | 2 | Variant 2 S | aagtgtggtaagttactggtaagagatgttggtgaagtcactg (SEQ ID NO: 39)<br>gtctgtattgttaagttaccacatcattatcaaaag (SEQ ID NO: 48) |
| Variant 2 S Ecto SEQ ID NO 14 | 1 | CR88 backbone | tggccttggtatgtgtgg (SEQ ID NO: 35)<br>agcactacatagtgcatac (SEQ ID NO: 36) |
| | 2 | Variant 2 S Ecto | tctttggtatgcactatgtagtgctgctctgtttgataataatcag (SEQ ID NO: 49)<br>tggcaagccacacataccaaggccacttaatataagttttaattattgaaagttcttc (SEQ ID NO: 41) |
| Brazil S SEQ ID NO 15 | 1 | CR88 backbone | tgattaaaagtcccacatcttttctaatattattaattcttctttgg (SEQ ID NO: 23)<br>ctcttaccagtaacttaccacacttaattaaattaaagactaagtc (SEQ ID NO: 24) |
| | 2 | Brazil S | aagtgtggtaagttactggtaagagatgttggttcaacctctttt |

TABLE 3-continued

Primers used for Gibson assembly of H52 rIBV donor plasmids with heterologous spikes or spike ectodomains.

| spike | PCR | product | primer |
|---|---|---|---|
| | | | ac (SEQ ID NO: 50)<br>agaaaagatgtgggacttttaatcattaaacagactttttaggtctg (SEQ ID NO: 26) |
| Brazil S Ecto SEQ ID NO 16 | 1 | CR88 backbone | tggccttggtatgtgtgg (SEQ ID NO: 35)<br>agcactacatagtgcatac (SEQ ID NO: 36) |
| | 2 | Brazil S Ecto | tctttggtatgcactatgtagtgcttcttttgtacaataatgatagctatg (SEQ ID NO: 51)<br>tggcaagccacacataccaaggccatttaatataagttttaaaatagaaagtgtttc (SEQ ID NO: 52) |

Primers for characterization and identification of the different spike sequences in the recombinant IBV are adapted to the respective spike sequence if necessary.

Example 2

In Ovo Replication Kinetics

Eight Eight day-old embryonated chicken eggs are inoculated with $10^2$ 50% embryo infectious dose ($EID_{50}$) of the recombinant IBV and appropriate controls. Eggs are incubated at 37.5° C., 60% humidity and candled daily after 0, 8, 24, 34, 48 and 72 hours of incubation and embryo mortality is recorded. Five preselected eggs per sample and time point are removed and transferred to 4° C. for at least 2 hours. Subsequently, the allantoic fluid is harvested and stored at −80° C. For analysis, samples are thawed and diluted 1:10 in 1×PBS without Ca and Mg and nucleic acids are extracted with the QIAamp DNA Blood Mini kit (Qiagen) with addition of carrier RNA using the Hamilton Starlet pipet robot. Extracted nucleic acids are analyzed by RT-qPCR for the relative amount of IBV RNA with a protocol adapted from Callison et al. (J Virol Methods. 2006; 138(1-2):60-5). Briefly, the same primers and probe are used and the thermoprofile is adapted for the use of TaqMan® Fast Virus 1-Step Master Mix (ThermoFisher) and the ABI™ 7900HT Fast Real-Time PCR System (Thermo Fisher Scientific). All nucleic acid samples are analyzed in triplicates using a 10-fold dilution series of IBV H52 as reference.

Figures 1, 2:
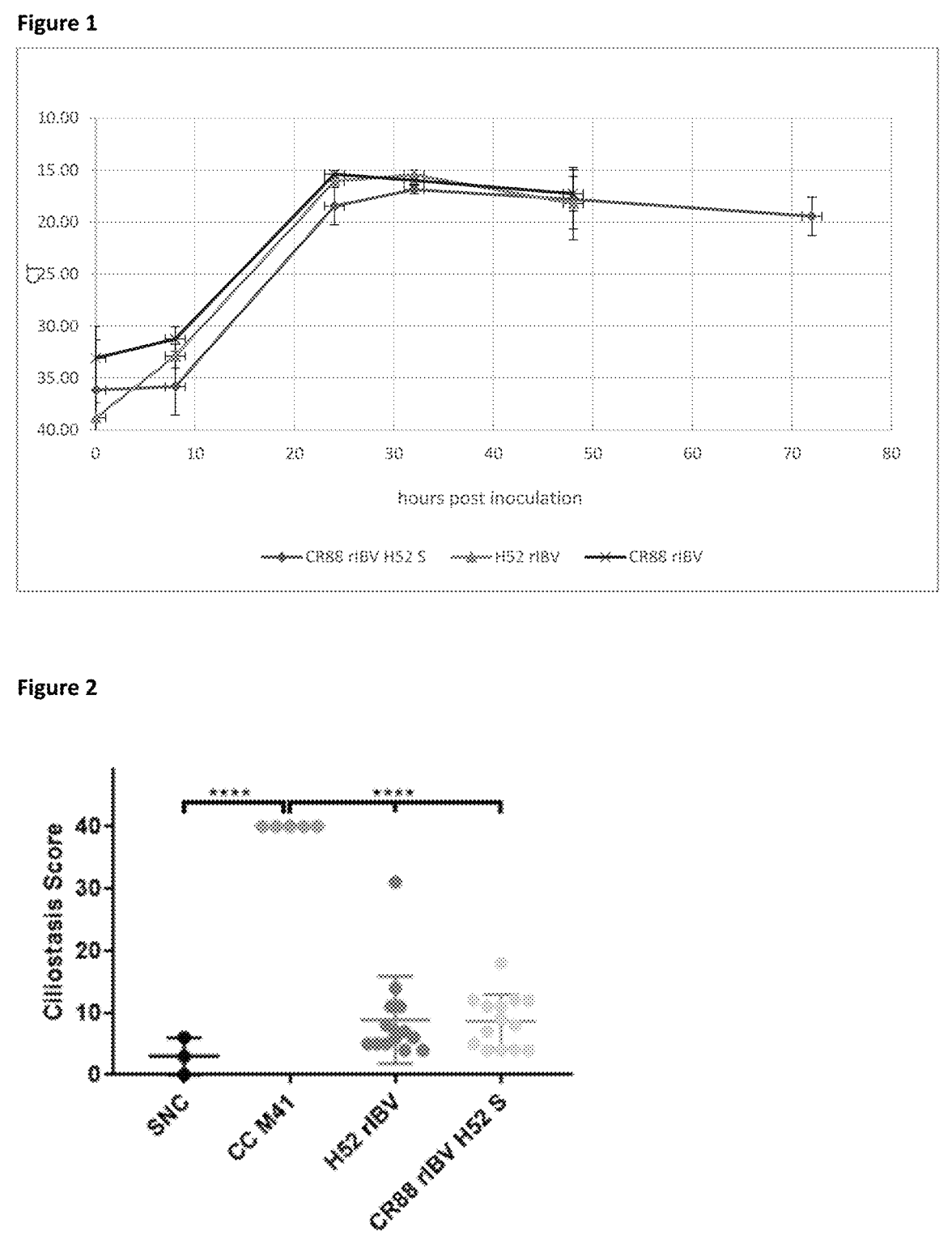

Replication of CR88 rIBV H52 S in comparison to the recombinant wild type viruses CR88 and H52 is analyzed by injecting 8 day old SPF eggs with 100 $EID_{50}$ at time point 0. Slightly different replication kinetics are observed at early time points. However, after 32 hours all viruses reach comparable ct values. All embryos are alive at 32 hours post inoculation, while at time point 48 hours post infection all remaining embryos for the wild type controls are dead. In contrast, 60 to 80% of the embryos infected with CR88 rIBV H52 S were still alive at time points 48 and 72 hours post inoculation. The replication of CR88 rIBV H52 S is considered equally efficient compared to the wild type viruses as all viruses reach the a plateau after 32 hours (see FIG. 1).

Example 3

Preparation of Vaccine and Challenge Virus

To demonstrate the efficacy of the CR88 rIBV with heterologous spike or spike ectodomain in chickens, an aliquot of the virus stock is thawed and 10-fold diluted in 1×PBS to determine the 50% embryo infectious dose ($EID_{50}$) by inoculation of 100 µl into five 8-day old embryonated chicken eggs per dilution. Eggs are incubated at 37.5° C., 60% humidity until 7 days post inoculation. Eggs with dead embryos after 24 hours are excluded from the experiment. All other eggs with dead embryos at 7 days post inoculation are considered positive. All eggs with living embryos are candled from the bottom at 7 days post inoculation to identify dwarfs, which are considered positive. The $EID_{50}$/ml is calculated with the formula of Reed and Muench (Am J Epidemiol, 1938; 27(3):493-497). For vaccination the virus stock is diluted in 1×PBS to obtain a titer of $10^{43}$ $EID_{50}$/ml ($10^{3}$ $EID_{50}$ per chicken in 50 µl).

The challenge viruses M41, QX, Q1, Ark, Variant 2 and Brazil are propagated in 10-day-old embryonated SPF eggs. 24 hours post inoculation the eggs are transferred to 4° C. for at least 2 hours. The allantoic fluid is harvested, aliquoted and stored at −80° C. The virus titer is determined as described above. The titer is set to $10^{43}$ to $10^{53}$ $EID_{50}$/ml by dilution with 1×PBS ($10^{3}$ to $10^{4}$ $EID_{50}$ per chicken in 50 µl).

Example 4

Determination of Vaccine Efficacy

Fertilized SPF eggs are incubated for 18 days in an egg setter at 99.7° F. and 50% humidity with 1 turn per hour. At day 18 of incubation the eggs are candled and fertile eggs are transferred to the hatcher and incubated at 99° F. and 70% humidity until hatch. Chicks without clinical signs or deformation are randomly distributed into respective treatment groups and transferred into separate isolators. At least two chicks serve as strict negative control (SNC) group, five chicks are enrolled in the challenge control (CC) group and at least 10 in groups which are vaccinated with the recombinant IBV with heterologous spike or spike ectodomain and and subsequently challenged. Animals are kept under housing conditions in compliance to local and national requirements for animal welfare recommendations. The light regime is adjusted to 16 hours light per day. Feed and water are provided ad libitum. After transfer to the isolator, chicks are vaccinated (1-day old) with $10^{3}$ $EID_{50}$ per chicken via eye drop (total volume 50 µl, 25 µl per eye) while the SNC and CC groups remain untreated. At 21 days post vaccination chickens of the CC and vaccinated groups are challenged with $10^{3}$ to $10^{4}$ $EID_{50}$ per chicken of the respective spike-homologous challenge strain (M41, QX, Q1, Ark, Variant 2 or Brazil) via eye drop (total volume 50 µl, 25 µl per eye). At 7 days post challenge all chickens are euthanized, choanal swabs are taken and kidneys are removed and stored in RNAlater Stabilization Solution (ThermoFisher) at 4° C. for IBV-specific RT-qPCR analysis. In addition, tracheas are removed and transferred into 50 ml tubes with warm cell culture medium. Afterwards, tracheas are cleaned from connective tissues and flushed with cell culture medium. The tracheas are cut into tracheal rings using the McIlwain tissue chopper set to 0.6-0.8 mm slice thickness. Per trachea three rings of the upper part, four rings of the middle part and three rings of the lower part are analyzed for ciliar beating by light microscopy and scored for ciliostasis (see table 4). A ring is recorded as normal if more than 50% of the internal ring shows vigorous ciliar movement (Score 2 and lower). A ring is recorded as positive for ciliostasis if less than 50% of the cilia are beating (Score 3 and 4).

For IBV-specific RT-qPCR analysis kidney tissue pieces are warmed up to room temperature and transferred to separate 2 ml Precellys tubes, which are filled with medium and PBS, respectively. Kidneys are homogenized with the Precellys® tissue homogenizer (Bertin Instruments) for 1×20 sec at 6800 rpm. Choanal swabs are eluted in 2 ml 1×PBS. Nucleic acids are isolated from 200 µl eluate and tissue homogenate respectively using the MagMAX™ Core Nucleic Acid Purification Kit (ThermoFisher) and the KingFisher™ Duo Prime Purification System (ThermoFisher). RT-qPCR is performed as described for the in ovo kinetics above, except for using a StepOnePlus™ Real-Time PCR System (ThermoFisher) for analysis in duplicates.

TABLE 5

Scoring of ciliostasis in tracheal rings.

| Ciliar activity [%] | Ciliostasis score |
|---|---|
| 100 | 0 |
| <100-75 | 1 |
| <75-50 | 2 |
| <50-25 | 3 |
| <25-0 | 4 |

Example 5

Efficacy Of Recombinant IBV 4/91 Encoding a Heterologous Spike or Spike Ectodomain The objective of the studies is to demonstrate that vaccination with a recombinant IBV CR88 (4/91 genotype and serotype) encoding a heterologous spike or fragment thereof is able to confer protection against challenge with a spike-homologous challenge strain.

It is analyzed if the recombinant IBV CR88 (4/91 genotype) encoding the spike ectodomain of IBV H52 (Mass genotype) is able to confer protection against challenge with a virulent M41 strain (Mass genotype), considered as homologous challenge for the encoded IBV H52 spike and as heterologous challenge considering the IBV CR88 backbone. All chickens are observed daily for clinical signs. No clinical signs are recorded after vaccination or challenge. Back titrations for the vaccination with CR88 rIBV H52 S and the H52 rIBV wild type at 1-day of age determine a titer of $10^{4.38}$ $EID_{50}$/ml and $10^{45}$ $EID_{50}$/ml, respectively (target $10^{43}$ $EID_{50}$/ml) as well as $10^{4.32}$ $EID_{50}$/ml (target $10^{43}$ $EID_{50}$/ml) for the M41 challenge virus applied at 21 days post vaccination. Ciliostasis is scored as described above and results are depicted in and summarized in table 5.

TABLE 5

Summary of ciliostasis scoring for protection at 28 days post vaccination and 7 days post challenge. The mean ciliostasis score per group is calculated by adding up the sum score of the individual chickens per group and dividing the group sum by the number of animals (highest possible score 40, lowest possible score 0). An animal is considered not affected if not fewer than 9 out of 10 rings show normal ciliar activity.

| Group | Vaccine | Challenge | Mean Ciliostasis Score | Not affected [%] |
|---|---|---|---|---|
| 1 | — | — | 3.0 | 100 |
| 2 | — | M41 | 40.0 | 0 |
| 3 | H52 | M41 | 8.9 | 93 |
| 4 | CR88 rIBV H52 S | M41 | 8.6 | 93 |

All animals of the strict negative control show normal ciliar movement while all animals of the challenge control group are positive for ciliostasis. In contrast, 93% of the animals vaccinated with CR88 rIBV H52 S or H52 rIBV wild type are protected. In addition, the viral load in the kidneys of animals vaccinated with CR88 rIBV H52 S is reduced compared to the animals of the challenge control (FIG. 3).

Further, it is analyzed if the recombinant IBV CR88 encoding the spike of IBV QX is able to confer protection against challenge with a virulent D388 QX strain, considered as homologous challenge for the encoded IBV QX spike and as heterologous challenge considering the IBV CR88 backbone. All chickens are observed daily for clinical signs. No clinical signs are recorded after vaccination or challenge. Back titrations for the vaccination with CR88 rIBV QX S and the QX vaccine at 1-day of age determine titers that exceeded $10^{5}$ $EID_{50}$/ml (target $10^{43}$ $EID_{50}$/ml) as well as $10^{4.83}$ $EID_{50}$/ml (target $10^{43}$ $EID_{50}$/ml) for the D388 QX challenge virus applied at 21 days post vaccination, respectively. Ciliostasis is scored as described above and results are depicted in and summarized in Table 6 Summary of ciliostasis scoring for protection at 28 days post vaccination and 7 days post challenge. The mean ciliostasis score per group is calculated by adding up the sum score of the individual chickens per group and dividing the group sum by the number of animals (highest possible score 40, lowest possible score 0).

TABLE 6

Summary of ciliostasis scoring for protection at 28 days post vaccination and 7 days post challenge. The mean ciliostasis score per group is calculated by adding up the sum score of the individual chickens per group and dividing the group sum by the number of animals (highest possible score 40, lowest possible score 0). An animal is considered not affected if not fewer than 9 out of 10 rings show normal ciliar activity.

| Group | Vaccine | Challenge | Mean Ciliostasis Score | Not affected [%] |
|---|---|---|---|---|
| 1 | — | — | 0 | 100 |
| 2 | — | D388 QX | 38.4 | 0 |
| 3 | QX vaccine | D388 QX | 3.5 | 100 |
| 3 | CR88 rIBV QX S | D388 QX | 8.9 | 100 |

All animals of the strict negative control show normal ciliar movement while all animals of the challenge control group are positive for ciliostasis. In contrast, 100% of the animals vaccinated with CR88 rIBV QX S or the QX vaccine are protected.

Similar results are obtained with the other CR88 rIBV with heterologous spikes or spike ectodomains.

The results highlight the suitability of IBV H52 as a potent backbone for the generation of recombinant IBV with heterologous spike and show excellent results, in particular, when compared to prior art data for the IBV Beaudette backbone.

The invention claimed is:

1. A genetically engineered 4/91 infectious bronchitis virus (IBV) encoding for a heterologous IBV spike protein (S protein) or fragment thereof, wherein the heterologous IBV S protein or fragment thereof comprises an amino acid sequence having at least 90% sequence identity to at least one of SEQ ID NOs: 6, 7, 8, 9, 10, 11, 12, 13, 14, 15, 16, or 17.

2. The 4/91 IBV of claim 1, wherein the heterologous IBV S protein or fragment thereof is from an IBV with a genotype or serotype selected from: Arkansas, Brazil, California, Connecticut, Delaware, Dutch, Florida, Georgia, Gray, Holte, Iowa, Italy, JMK, LDT3, Maine, Massachusetts, Pennsylvania, PL84084, Qu, QX, Q1, SE 17, and Variant 2.

3. The 4/91 IBV of claim 1, wherein the heterologous IBV S protein or fragment thereof is from an IBV with a genotype or serotype selected from: Massachusetts, QX, Q1, Arkansas, Variant 2, and Brazil.

4. The 4/91 IBV of claim 1, wherein the heterologous IBV S protein or fragment thereof comprises 500 amino acids.

5. The 4/91 IBV of claim 1, wherein the genetically engineered 4/91 IBV is attenuated.

6. A method for immunizing a subject, comprising:

administering to the subject an immunogenic composition comprising a genetically engineered 4/91 IBV encoding for a heterologous IBV S protein or fragment thereof, wherein the heterologous IBV S protein or fragment thereof comprises an amino acid sequence having at least 90% sequence identity to at least one of SEQ ID NOs: 6, 7, 8, 9, 10, 11, 12, 13, 14, 15, 16, or 17.

7. The method of claim 6, wherein a protective immune response effective to reduce or eliminate subsequent IBV-infection clinical signs in the subject, relative to a non-vaccinated control subject of the same species, is elicited by administration of the immunogenic composition.

8. The method of claim 6, wherein a protective immune response effective to reduce ciliostasis risk in the subject, relative to a non-vaccinated control subject of the same species, is elicited by administration of the immunogenic composition.

9. The method of claim 6, wherein the subject is a poultry.

10. The method of claim 6, wherein the method is effective to prevent or reduce ciliostasis, rales, egg drop, kidney lesions, watery diarrhea, weight loss, viral load, and/or viral shedding in the subject relative to a non-vaccinated control subject of the same species if the subject is subsequently infected with IBV.

11. An immunogenic composition comprising a genetically engineered 4/91 IBV encoding for a heterologous IBV S protein or fragment thereof in a pharmaceutically-acceptable carrier, wherein the heterologous IBV S protein or fragment thereof comprises an amino acid sequence having at least 90% sequence identity to at least one of SEQ ID NOs: 6, 7, 8, 9, 10, 11, 12, 13, 14, 15, 16, or 17.

12. The immunogenic composition of claim 11, wherein the heterologous IBV S protein or fragment thereof is from an IBV with a genotype or serotype selected from: Arkansas, Brazil, California, Connecticut, Delaware, Dutch, Florida, Georgia, Gray, Holte, Iowa, Italy, JMK, LDT3, Maine, Massachusetts, Pennsylvania, PL84084, Qu, QX, Q1, SE 17, and Variant 2.

13. The immunogenic composition of claim 11, wherein the heterologous IBV S protein or fragment thereof is from an IBV with a genotype or serotype selected from: Massachusetts, QX, Q1, Arkansas, Variant 2, and Brazil.

14. The immunogenic composition of claim 11, wherein the heterologous IBV S protein or fragment thereof comprises 500 amino acids.

15. The immunogenic composition of claim 11, wherein the 4/91 IBV is attenuated.

16. The immunogenic composition of claim 11, wherein the immunogenic composition is a vaccine.

17. The immunogenic composition of claim 11, wherein the immunogenic composition is part of a kit.

* * * * *

UNITED STATES PATENT AND TRADEMARK OFFICE

CERTIFICATE OF CORRECTION

PATENT NO. : 11,224,649 B2
APPLICATION NO. : 16/665434
DATED : January 18, 2022
INVENTOR(S) : Kraemer-Kuehl et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 27 days.

Signed and Sealed this
Twenty-ninth Day of November, 2022

Katherine Kelly Vidal

Katherine Kelly Vidal
*Director of the United States Patent and Trademark Office*